US012624038B2

(12) United States Patent
Min et al.

(10) Patent No.: US 12,624,038 B2
(45) Date of Patent: May 12, 2026

(54) MOLECULES AND METHODS RELATED TO TREATMENT OF UNCONTROLLED CELLULAR PROLIFERATION

(71) Applicant: ST. JUDE CHILDREN'S RESEARCH HOSPITAL, Memphis, TN (US)

(72) Inventors: Jaeki Min, Memphis, TN (US); Jamie Jarusiewicz, Memphis, TN (US); Marcelo Actis, Bartlett, TN (US); Yunchao Chang, Memphis, TN (US); Kathryn Roberts, Memphis, TN (US); Charles Mullighan, Memphis, TN (US); Zoran Rankovic, Memphis, TN (US)

(73) Assignee: St. Jude Children's Research Hospital, Inc., Memphis, TN (US)

( * ) Notice: Subject to any disclaimer, the term of this patent is extended or adjusted under 35 U.S.C. 154(b) by 1076 days.

(21) Appl. No.: 17/629,268

(22) PCT Filed: Jul. 30, 2020

(86) PCT No.: PCT/US2020/044317
§ 371 (c)(1),
(2) Date: Jan. 21, 2022

(87) PCT Pub. No.: WO2021/022076
PCT Pub. Date: Feb. 4, 2021

(65) Prior Publication Data

US 2022/0251097 A1 Aug. 11, 2022

Related U.S. Application Data

(60) Provisional application No. 62/881,774, filed on Aug. 1, 2019.

(51) Int. Cl.
*C07D 487/04* (2006.01)
*A61P 35/00* (2006.01)
*A61P 35/02* (2006.01)

(52) U.S. Cl.
CPC ............ *C07D 487/04* (2013.01); *A61P 35/00* (2018.01); *A61P 35/02* (2018.01)

(58) Field of Classification Search
CPC .. C07D 401/04; C07D 401/14; A61K 31/454; A61K 31/5377; A61K 45/06
See application file for complete search history.

(56) References Cited

U.S. PATENT DOCUMENTS 8,765,920 B2 * 7/2014 Barbas, III ........... C07D 249/12 548/263.6
2007/0135461 A1 6/2007 Rogers et al.
(Continued)

FOREIGN PATENT DOCUMENTS

WO WO-2018237026 A1 * 12/2018 ........... C07D 487/04
WO WO 2019/042442 3/2019
(Continued)

OTHER PUBLICATIONS

Yao et al., Bioorganic & Medicinal Chemistry Letters 28 (2018) 2636-2640 (Year: 2018).*
(Continued)

*Primary Examiner* — Clinton A Brooks
*Assistant Examiner* — Izabela Schmidt
(74) *Attorney, Agent, or Firm* — Ballard Spahr LLP

(57) ABSTRACT

The present disclosure relates to chemical compounds that modulate cellular proliferation for the treatment of uncontrolled cellular proliferation disorders (such as cancer), pharmaceutical compositions containing such compounds, and their use in treatment. This abstract is intended as a
(Continued)

scanning tool for purposes of searching in the particular art and is not intended to be limiting of the present invention.

19 Claims, 28 Drawing Sheets

Specification includes a Sequence Listing.

(56) References Cited

U.S. PATENT DOCUMENTS

| | | | | |
|---|---|---|---|---|
| 2017/0121321 | A1* | 5/2017 | Crews | A61K 47/55 |
| 2017/0121339 | A1 | 5/2017 | Sprengeler et al. | |
| 2017/0233395 | A1* | 8/2017 | Lan | A61K 31/5377 424/133.1 |

FOREIGN PATENT DOCUMENTS

| | | | | |
|---|---|---|---|---|
| WO | WO-2019042442 | A1 * | 3/2019 | A61K 31/519 |
| WO | PCT/US2020/044317 | | 7/2020 | |
| WO | WO 2021/022076 | | 2/2021 | |
| WO | PCT/US2021/064157 | | 12/2021 | |
| WO | WO 2022/133285 | | 6/2022 | |

OTHER PUBLICATIONS

Yao (Yao et al., Bioorganic & Medicinal Chemistry Letters 28 (2018) 2636-2640) (Year: 2018).*

Shah, et al. (2020) "Hi-JAK-ing the Ubiquitin System: the Design and Physicochemical Optimisation of JAK PROTACs," *Bioorganic & Medicinal Chemistry* 28: 115326, 10 pgs.

Ferrajoli et al. (2006) "The JAK-STAT pathway: a therapeutic target in hematological malignancies" *Curr Cancer Drug Targets*. 6(8):671-679.

Moriggl et al. (1999) "Stat5 activation is uniquely associated with cytokine signaling in peripheral T cells" *Immunity*. 11(2):225-230.

Friedrich et al. (1999) "Activation of STAT5 by IL-4 relies on Janus kinase function but not on receptor tyrosine phosphorylation, and can contribute to both cell proliferation and gene regulation" *Int Immunol.* 11(8):1283-1294.

Bradley et al. (2002) "Cell intrinsic defects in cytokine responsiveness of STAT5-deficient hematopoietic stem cells" *Blood*. 100(12):3983-3989.

Bunting et al. (2002) "Reduced lymphomyeloid repopulating activity from adult bone marrow and fetal liver of mice lacking expression of STAT5" *Blood*. 99(2):479-487).

Schwartz et al. (2016) "Type I/II cytokines, JAKs, and new strategies for treating autoimmune diseases" *Nat Rev Rheumatol* 12: 25-36.

Singh et al. (2016) "Biologics or tofacitinib for rheumatoid arthritis in incomplete responders to methotrexate or other traditional disease-modifying anti-rheumatic drugs: a systematic review and network meta-analysis" *Cochrane Database Syst Rev*, CD012183.

U.S. Appl. No. 62/881,774, filed Aug. 1, 2019, Jaeki Min (St. Jude Children's Research Hospital).

U.S. Appl. No. 63/127,677, filed Dec. 18, 2020, Jaeki Min (St. Jude Children's Research Hospital).

* cited by examiner cmpd (3)

cmpd (4)

A

B

B

3

4

C

5

6

7

8

56

61

53

59

80

E

F

H

G

```
                         SEQUENCE LISTING


<160> NUMBER OF SEQ ID NOS: 3

<210> SEQ ID NO 1
<211> LENGTH: 20
<212> TYPE: RNA
<213> ORGANISM: Artificial sequence
<220> FEATURE:
<223> OTHER INFORMATION: synthetic construct

<400> SEQUENCE: 1

uguaugugau gucggcagac                                            20


<210> SEQ ID NO 2
<211> LENGTH: 23
<212> TYPE: PRT
<213> ORGANISM: Artificial sequence
<220> FEATURE:
<223> OTHER INFORMATION: synthetic construct; primer

<400> SEQUENCE: 2

Gly Cys Ala Gly Ala Gly Ala Gly Thr Gly Ala Gly Gly Ala Ala Gly
1               5                   10                  15

Ala Ala Gly Ala Thr Gly Ala
            20


<210> SEQ ID NO 3
<211> LENGTH: 20
<212> TYPE: PRT
<213> ORGANISM: Artificial sequence
<220> FEATURE:
<223> OTHER INFORMATION: synthetic construct; primer
```

-continued

```
<400> SEQUENCE: 3

Gly Cys Cys Cys Ala Thr Gly Thr Cys Cys Thr Cys Ala Thr Cys Cys
1               5                   10                  15

Ala Cys Ala Ala
            20
```

MOLECULES AND METHODS RELATED TO TREATMENT OF UNCONTROLLED CELLULAR PROLIFERATION

CROSS-REFERENCE TO RELATED APPLICATIONS

This Application is a national phase application under 35 U.S.C. § 371 of International Application No. PCT/US2020/044317, filed on Jul. 30, 2020, which claims the benefit of U.S. Application No. 62/881,774, filed on Aug. 1, 2019, the contents of which are hereby incorporated by reference in their entireties entirety.

STATEMENT REGARDING FEDERALLY FUNDED RESEARCH

This invention was made with government support under grant number CA197695 awarded by the National Institutes of Health. The government has certain rights in the invention.

REFERENCE TO SEQUENCE LISTING

The Sequence Listing submitted Jan. 21, 2022 as a text filed named "19116_0044U2_ST25.txt," created on Jan. 20, 2022, and having a size of 1.279 bytes 1,235 bytes is hereby incorporated by reference pursuant to 37 C.F.R. § 1.52 (e)(5).

BACKGROUND

Cancer is a disease characterized primarily by an uncontrolled division of abnormal cells (uncontrolled cellular proliferation) derived from a given normal tissue and the invasion of adjacent tissues by these malignant cells. Blood or lymphatic transportation can spread cancer cells to other parts of the body leading to regional lymph nodes and to distant sites (metastasis). Cancer is a complex, multistep process that begins with minor preneoplastic changes, which may under certain conditions progress to neoplasia. There are more than 100 different types of cancer, which can be grouped into broader categories. The main categories include carcinoma, sarcoma, leukemia, lymphoma and myeloma, and central nervous system cancers. The incidence of cancer continues to climb as the general population ages, as new cancers develop, and as susceptible populations (e.g., people infected with AIDS or excessively exposed to sunlight) grow. A tremendous demand therefore exists for new methods and compositions that can be used to treat patients with cancer.

Hematologic or hematopoietic malignancies are cancers of the blood or bone marrow, including leukemia and lymphoma. Leukemia is a type of cancer of the blood characterized by abnormal accumulation of immature white blood cells. There are four types of leukemia: acute lymphocytic leukemia (ALL), acute myelogenous leukemia (AML), chronic lymphocytic leukemia (CLL), and chronic myelogenous leukemia (CML). Acute leukemia is a rapidly progressing disease that results in the accumulation of immature, functionless cells in the marrow and blood. The marrow often stops producing enough normal red cells, which include cells and platelets. On the other hand, chronic leukemia progresses more slowly and allows greater numbers of more mature, functional cells to be made.

Leukemia can affect people at any age. The cause of most cases of leukemia is not known. Extraordinary doses of radiation and certain cancer therapies are possible causes. About 90% of leukemia cases are diagnosed in adults. Cases of chronic leukemia account for 4.5 percent more cases that acute leukemia.

The dramatic improvement in blood cancer treatment in the latter part of the twentieth century is largely the result of chemotherapy. In addition, there are more than fifty drugs individually used to treat these disorders and a number of potential new therapies are under investigation in clinical trials.

Thus, there remains a need for treat a disorder of uncontrolled cellular proliferation. The following disclosure describes a group of such compounds, as well as methods for making and using them.

SUMMARY

In accordance with the purpose(s) of the invention, as embodied and broadly described herein, the invention, in one aspect, relates to compositions and methods for use in the prevention and treatment of disorders associated with uncontrolled cellular proliferation, such as cancer.

Disclosed are compounds having a structure represented by a formula:

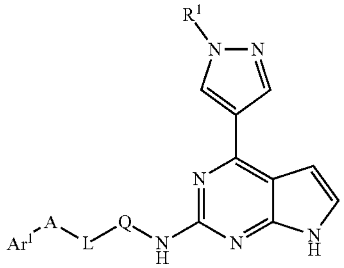

wherein A is selected from —O—, —S—, —NH—, —$CH_2$—, —O—(C1-C4 alkyl)-C(O)NH—, and a structure

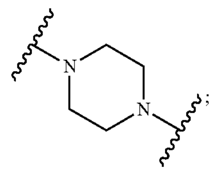

wherein L is selected from C2-C15 alkyl and —($CH_2CH_2O$)$_n$(C1-C4 alkyl)-; wherein n is selected from 1, 2, 3, 4, 5, 6, 7, and 8; wherein Q is selected from —NHC(O)($C_6H_4$)— and —C(O)NH($C_6H_4$)—; wherein $R^1$ is selected from C1-C8 alkyl, C1-C8 hydroxyalkyl, C1-C8 cyanoalkyl, C1-C8 aminoalkyl, and a structure selected from:

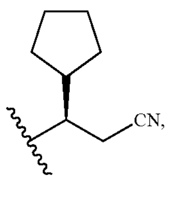 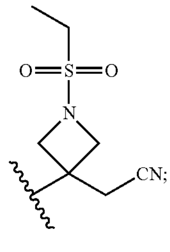 and 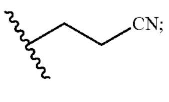

and wherein $Ar^1$ is a structure selected from:

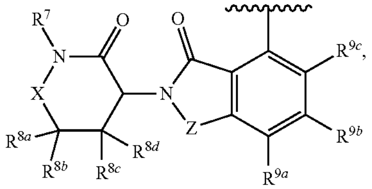

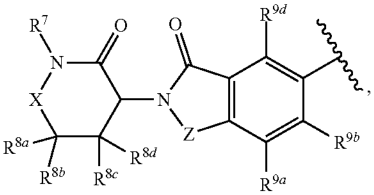

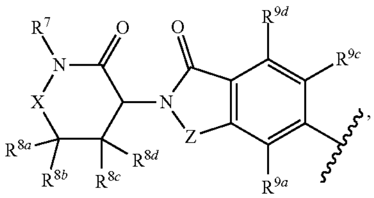

and

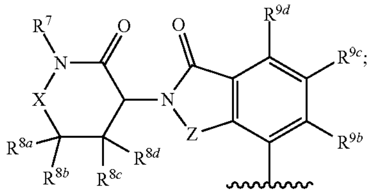

wherein X is selected from —C(O)— and —$CH_2$—; wherein Z is selected from —$CH_2$— and C(O); wherein $R^7$ is selected from hydrogen and C1-C8 alkyl; wherein each of $R^{8a}$, $R^{8b}$, $R^{8c}$, and $R^{8d}$ is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{9a}$, $R^{9b}$, $R^{9c}$, and $R^{9d}$, when present, is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

Also disclosed are compounds having a structure represented by a formula:

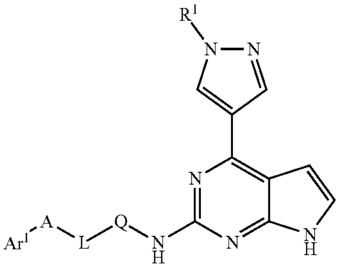

wherein A is selected from —O—, —S—, —NH—, and —$CH_2$—; wherein L is selected from C2-C15 alkyl and —$(CH_2CH_2O)_n$(C1-C4 alkyl)-; wherein n is selected from 1, 2, 3, 4, 5, 6, 7, and 8; wherein Q is selected from —NHC(O)($C_6H_4$)— and —C(O)NH($C_6H_4$)—; wherein $R^1$ is selected from C1-C8 alkyl, C1-C8 hydroxyalkyl, C1-C8 cyanoalkyl, C1-C8 aminoalkyl, and a structure selected from:

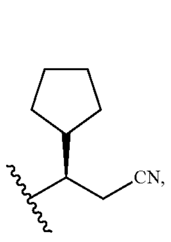

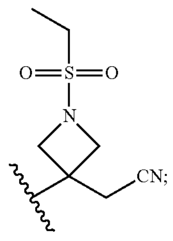

and

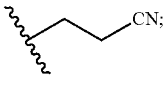

and wherein $Ar^1$ is a structure selected from:

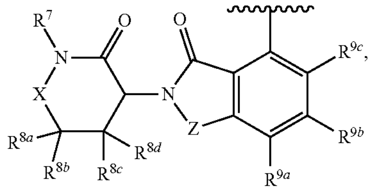

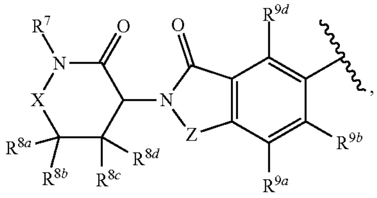

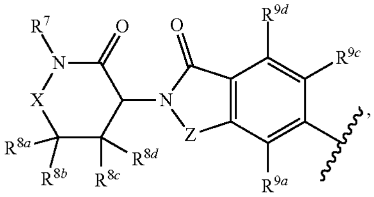

and

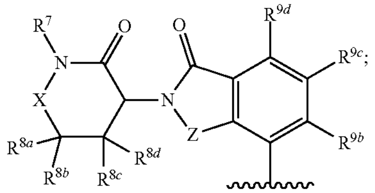

wherein X is selected from —C(O)— and —$CH_2$—; wherein Z is selected from —$CH_2$— and C(O); wherein $R^7$ is selected from hydrogen and C1-C8 alkyl; wherein each of $R^{8a}$, $R^{8b}$, $R^{8c}$, and $R^{8d}$ is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{9a}$, $R^{9b}$, $R^{9c}$, and $R^{9d}$, when present, is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

Also disclosed are methods of making a disclosed compound.

Also disclosed are pharmaceutical compositions comprising a therapeutically effective amount of at least one disclosed compound and a pharmaceutically acceptable carrier.

Also disclosed are methods of treating a disorder of uncontrolled cellular proliferation in a subject, the method comprising the step of administering to the subject an effective amount of a compound disclosed herein.

Also disclosed are kits comprising a compound disclosed herein, and one or more of: a) an agent known to treat a disorder of uncontrolled cellular proliferation; b) instructions for administering the compound in connection with treating a disorder of uncontrolled cellular proliferation; and c) instructions for treating a disorder of uncontrolled cellular proliferation.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1A:
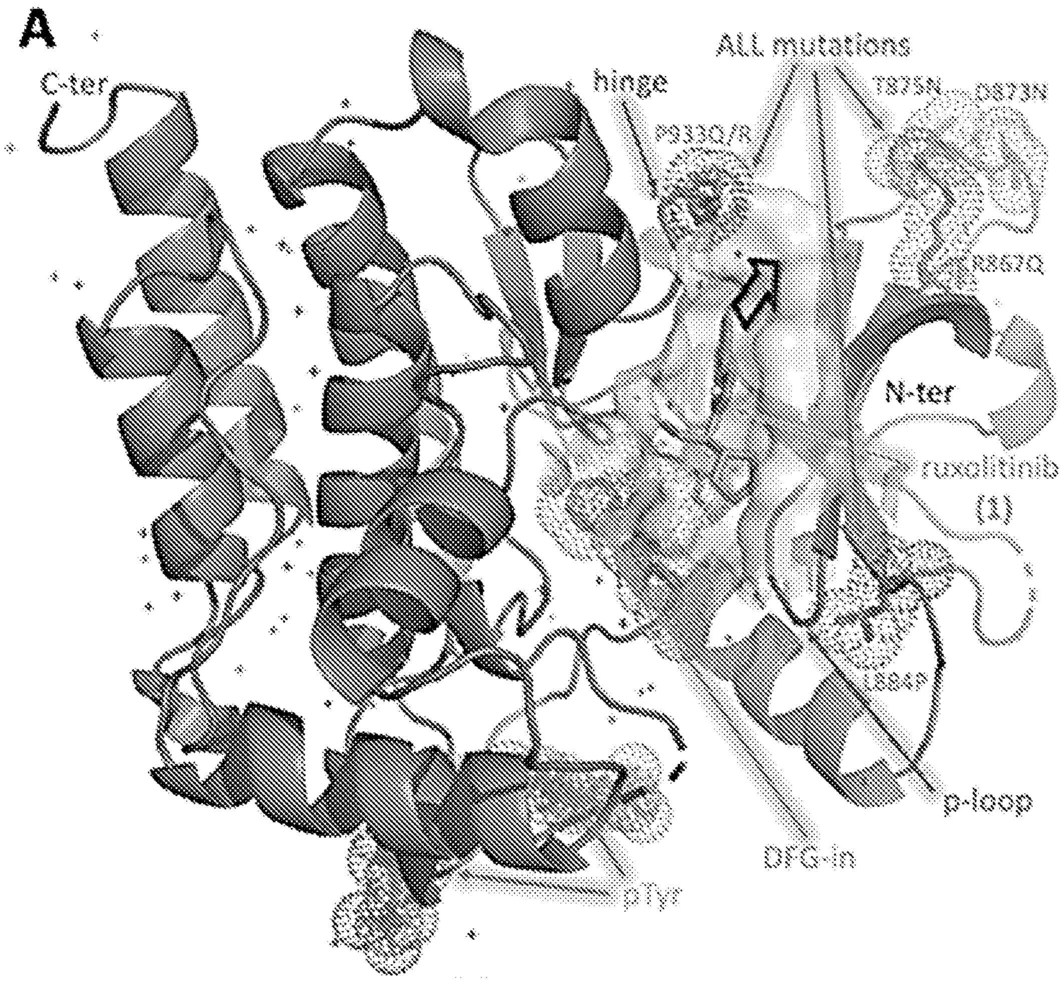
FIG. 1A-E show representative data illustrating a structural analysis of JAK inhibitors and PROTACsbound to JAK2.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

As used in the specification and the appended claims, the singular forms “a,” “an” and “the” include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage form can comprise a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and cosolvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more $—OCH_2CH_2O—$ units in the polyester, regardless of whether ethylene glycol was used to prepare the polyester. Similarly, a sebacic acid residue in a polyester refers to one or more $—CO(CH_2)_8CO—$ moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. In a further aspect, the alkyl group can be substituted. For example, the alkyl group can be substituted with one or more groups including, but not limited to, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. In a further aspect, the cycloalkyl group and heterocycloalkyl group can be substituted. For example, the cycloalkyl group and heterocycloalkyl group can be substituted with 0, 1, 2, 3, or 4 groups independently selected from C1-C4 alkyl, C3-C7 cycloalkyl, C1-C4 alkoxy, $-NH_2$, (C1-C4) alkylamino, (C1-C4)(C1-C4) dialkylamino, ether, halogen, —OH, C1-C4 hydroxyalkyl, $-NO_2$, silyl, sulfo-oxo, —SH, and C1-C4 thioalkyl, as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C{=}C(A^3A^4)$ are intended to include both the E and Z isomers. This can be presumed in structural formulae herein wherein an asymmetric alkene is present, or it can be explicitly indicated by the bond symbol C=C. In a further aspect, the alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. In a further aspect, the cycloalkenyl group and heterocycloalkenyl group can be substituted. For example, the cycloalkenyl group and heterocycloalkenyl group can be substituted with 0, 1, 2, 3, or 4 groups independently selected from C1-C4 alkyl, C3-C7 cycloalkyl, C1-C4 alkoxy, C2-C4 alkenyl, C3-C6 cycloalkenyl, C2-C4 alkynyl, aryl, heteroaryl, aldehyde, $-NH_2$, (C1-C4) alkylamino, (C1-C4)(C1-C4) dialkylamino, carboxylic acid, ester, ether, halogen, —OH, C1-C4 hydroxyalkyl, ketone, azide, $-NO_2$, silyl, sulfo-oxo, —SH, and C1-C4 thioalkyl, as described herein.

The term "alkynyl" as used herein is a hydrocarbon group of 2 to 24 carbon atoms with a structural formula containing at least one carbon-carbon triple bond. In a further aspect, the alkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. In a further aspect, the cycloalkynyl group and heterocycloalkynyl group can be substituted. For example, the cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. In a further aspect, the aryl group can be substituted. For example, the aryl group can be substituted with one or more groups including, but not limited to, alkyl, cycloalkyl, alkoxy, alkenyl, cycloalkenyl, alkynyl, cycloalkynyl, aryl, heteroaryl, aldehyde, $—NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" or "CO" is a short hand notation for a carbonyl group, i.e., C═O.

The terms "amine" or "amino" as used herein are represented by the formula $—NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is $—NH_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula $—N(\text{-alkyl})_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula $—OC(O)A^1$ or $—C(O)OA^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula $-(A^1O(O)C\text{-}A^2\text{-}C(O)O)_a—$ or $-(A^1O(O)C\text{-}A^2\text{-}OC(O))_a—$, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula $-(A^1O\text{-}A^2O)_a—$, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. In a further aspect, the heteroaryl group can be substituted. For example, the heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxy" or "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula $—N_3$.

The term "nitro" as used herein is represented by the formula $—NO_2$.

The term "nitrile" or "cyano" as used herein is represented by the formula —CN or —C≡N.

The term "silyl" as used herein is represented by the formula $—SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas $—S(O)A^1$, $—S(O)_2A^1$, $—OS(O)_2A^1$, or $—OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S═O. The term "sulfonyl" is used herein to refer to the sulfo-oxo group represented by the formula $—S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $—(CH_2)_{0-4}R^o$; $—(CH_2)_{0-4}OR^o$; $—O(CH_2)_{0-4}R^o$, $—O—(CH_2)_{0-4}C(O)OR^o$; $—(CH_2)_{0-4}CH(OR^o)_2$; $—(CH_2)_{0-4}SR^o$; $—(CH_2)_{0-4}Ph$, which may be substituted with $R^o$; $—(CH_2)_{0-4}O(CH_2)_{0-1}Ph$ which may be substituted with $R^o$; —CH═CHPh, which may be substituted with $R^o$; $—(CH_2)_{0-4}O(CH_2)_{0-1}$-pyridyl which may be substituted with $R^o$; $—NO_2$; —CN; $—N_3$; $—(CH_2)_{0-4}$ $N(R^{\circ})_2$; —$(CH_2)_{0-4}N(R^{\circ})C(O)R^{\circ}$; —$N(R^{\circ})C(S)R^{\circ}$; —$(CH_2)_{0-4}N(R^{\circ})C(O)NR^{\circ}_2$; —$N(R^{\circ})C(S)NR^{\circ}_2$; —$(CH_2)_{0-4}N(R^{\circ})C(O)OR^{\circ}$; —$N(R^{\circ})N(R^{\circ})C(O)R^{\circ}$; —$N(R^{\circ})N(R^{\circ})C(O)NR^{\circ}_2$; —$N(R^{\circ})N(R^{\circ})C(O)OR^{\circ}$; —$(CH_2)_{0-4}C(O)R^{\circ}$; —$C(S)R^{\circ}$; —$(CH_2)_{0-4}C(O)OR^{\circ}$; —$(CH_2)_{0-4}C(O)SR^{\circ}$; —$(CH_2)_{0-4}C(O)OSiR^{\circ}_3$; —$(CH_2)_{0-4}OC(O)R^{\circ}$; —$OC(O)(CH_2)_{0-4}SR$—, $SC(S)SR^{\circ}$; —$(CH_2)_{0-4}SC(O)R^{\circ}$; —$(CH_2)_{0-4}C(O)NR^{\circ}_2$; —$C(S)NR^{\circ}_2$; —$C(S)SR^{\circ}$; —$(CH_2)_{0-4}OC(O)NR^{\circ}_2$; —$C(O)N(OR^{\circ})R^{\circ}$; —$C(O)C(O)R^{\circ}$; —$C(O)CH_2C(O)R^{\circ}$; —$C(NOR^{\circ})R^{\circ}$; —$(CH_2)_{0-4}SSR^{\circ}$; —$(CH_2)_{0-4}S(O)_2R^{\circ}$; —$(CH_2)_{0-4}S(O)_2OR^{\circ}$; —$(CH_2)_{0-4}OS(O)_2R^{\circ}$; —$S(O)_2NR^{\circ}_2$; —$(CH_2)_{0-4}S(O)R^{\circ}$; —$N(R^{\circ})S(O)_2NR^{\circ}_2$; —$N(R^{\circ})S(O)_2R^{\circ}$; —$N(OR^{\circ})R^{\circ}$; —$C(NH)NR^{\circ}_2$; —$P(O)_2R^{\circ}$; —$P(O)R^{\circ}_2$; —$OP(O)R^{\circ}_2$; —$OP(O)(OR^{\circ})_2$; $SiR^{\circ}_3$; —($C_{1-4}$ straight or branched)alkylene)O—$N(R^{\circ})_2$; or —($C_{1-4}$ straight or branched)alkylene)C(O)O—$N(R^{\circ})_2$, wherein each $R^{\circ}$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^{\circ}$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^{\circ}$ (or the ring formed by taking two independent occurrences of $R^{\circ}$ together with their intervening atoms), are independently halogen, —$(CH_2)_{0-2}R^{574}$ , —(halo$R^{\bullet}$), —$(CH_2)_{0-2}OH$, —$(CH_2)_{0-2}$ $OR^{574}$ , —$(CH_2)_{0-2}CH(OR^{574})_2$; —O(halo$R_{574}$) —CN, —$N_3$, —$(CH_2)_{0-2}C(O)R^{\bullet}$, —$(CH_2)_{0-2}C(O)OR^{\bullet}$, —$(CH_2)_{0-2}SR^{\bullet}$, —$(CH_2)SH$, —$(CH_2)_{0-2}NH_2$, —$(CH_2)_{0-2}NHR^{\bullet}$, —$(CH_2)_{0-2}NR^{\bullet}_{0-2}$, —$NO^2$, —$SiR^{\bullet}_3$, —$OSiR^{\bullet}_3$, —$C(O)SR^{\bullet}$, —$C_{1-4}$ straight or branched alkylene)$C(O)OR^{\bullet}$, or $SSR^{\bullet}$wherein each $R^{\bullet}$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^{\circ}$ include ═O and ═S.

Suitable divalent substituents on a saturated carbon atom of an "optionally substituted" group include the following: ═O, ═S, ═$NNR^*_2$, ═$NNHC(O)R^*$, ═$NNHC(O)OR^*$, ═$NNHS(O)_2R^*$, ═$NR^*$, ═$NOR^*$, —$O(C(R^*_2))_{2-3}O$—, or —$S(C(R^*_2))_{2-3}S$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, —$R^{\bullet}$, —(halo$R^{\bullet}$), —OH, —$OR^{\bullet}$, —O(halo$R^{\bullet}$)m —CN, —C(O)OH, —$C(O)OR^{\bullet}$, —$NH_2$, 13 $NHR^{\bullet}$, $NR^{\bullet}_2$, or —$NO_2$ wherein each $R^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^{\dagger}$, —$NR^{\dagger}_2$, —$C(O)R^{\dagger}$, —$C(O)OR^{\dagger}$, —$C(O)C(O)R^{\dagger}$, —$C(O)CH_2C(O)R^{\dagger}$, —$S(O)_2R^{\dagger}$, —$S(O)_2NR^{\dagger}_2$, —$C(S)NR^{\dagger}_2$, —$C(NH)NR^{\dagger}_2$, or —$N(R^{\dagger})S(O)_2R^{\dagger}$; wherein each $R^{\dagger}$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^{\dagger}$ are independently halogen, —$R^{\bullet}$, —(halo$R^{\bullet}$), —OH, —$OR^{\bullet}$, —O(halo$R^{\bullet}$)m —CN, —C(O)OH, —$C(O)OR^{\bullet}$, —$NH_2$, 13 $NHR^{\bullet}$, $NR^{\bullet}_2$, or —$NO_2$ wherein each $R^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

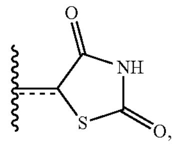

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}C$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

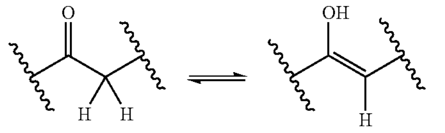

keto form enol form

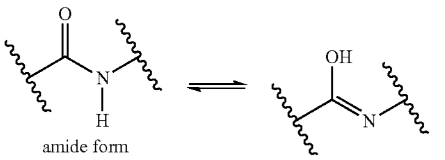

amide form imidic acid form

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

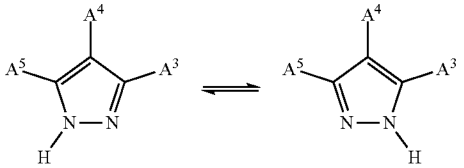

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

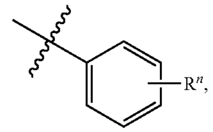

which is understood to be equivalent to a formula:

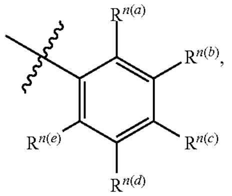

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, disclosed are compounds useful in treating or preventing a disorder associated with uncontrolled cellular proliferation such as, for example, cancer, for example, CRLF2-rearranged (CRLF2r) and JAK-STAT signaling driven acute lymphocytic leukemia. CRLF2-rearranged ALL comprises up to 60% of Philadelphia-like (Ph-like, BCR ABL1-like) acute lymphoblastic leukemia (ALL), and up to 15% of B-ALL overall, and is associated with high risk features and poor outcome. In a further aspect, the disclosed compounds exhibit modulation of uncontrolled cellular proliferation. In still a further aspect, the disclosed compounds exhibit inhibition of uncontrolled cellular proliferation.

In one aspect, the compounds of the invention are useful in the treatment or prevention of disorders associated with uncontrolled cellular proliferation, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula:

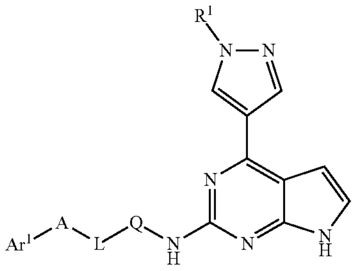

wherein A is selected from —O—, —S—, —NH—, —$CH_2$—, —O—(C1-C4 alkyl)-C(O)NH—, and a structure

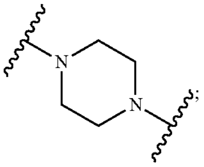

wherein L is selected from C2-C15 alkyl and —($CH_2CH_2O$)$_n$(C1-C4 alkyl)-; wherein n is selected from 1, 2, 3, 4, 5, 6, 7, and 8; wherein Q is selected from —NHC(O)($C_6H_4$)— and —C(O)NH($C_6H_4$)—; wherein $R^1$ is selected from C1-C8 alkyl, C1-C8 hydroxyalkyl, C1-C8 cyanoalkyl, C1-C8 aminoalkyl, and a structure selected from:

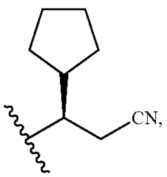

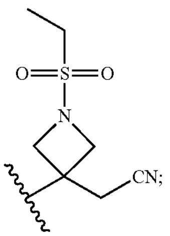

and

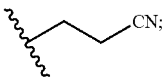

and wherein $Ar^1$ is a structure selected from:

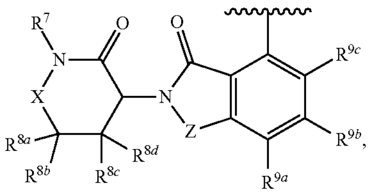

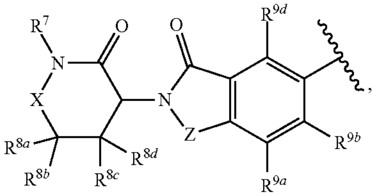

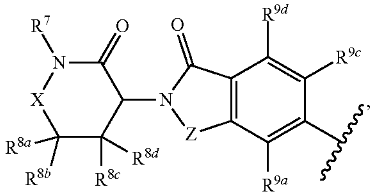

and

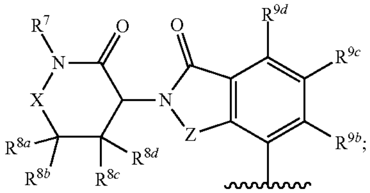

wherein X is selected from —C(O)— and —$CH_2$—; wherein Z is selected from —$CH_2$— and C(O); wherein $R^7$ is selected from hydrogen and C1-C8 alkyl; wherein each of $R^{8a}$, $R^{8b}$, $R^{8c}$, and $R^{8d}$ is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{9a}$, $R^{9b}$, $R^{9c}$, and $R^{9d}$, when present, is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

In one aspect, disclosed are compounds having a structure represented by a formula:

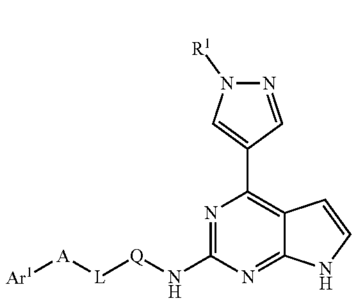

wherein A is selected from —O—, —S—, —NH—, and —$CH_2$—; wherein L is selected from C2-C15 alkyl and —$(CH_2CH_2O)_n$(C1-C4 alkyl)-; wherein n is selected from 1, 2, 3, 4, 5, 6, 7, and 8; wherein Q is selected from —NHC(O)($C_6H_4$)— and —C(O)NH($C_6H_4$)—; wherein $R^1$ is selected from C1-C8 alkyl, C1-C8 hydroxyalkyl, C1-C8 cyanoalkyl, C1-C8 aminoalkyl, and a structure selected from:

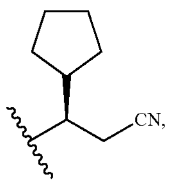

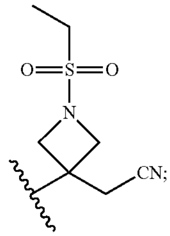

and

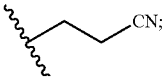

and wherein $Ar^1$ is a structure selected from:

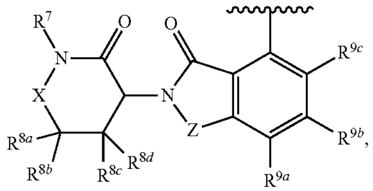

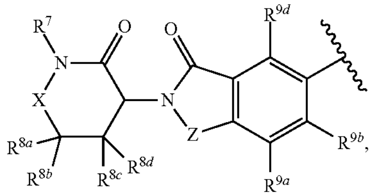

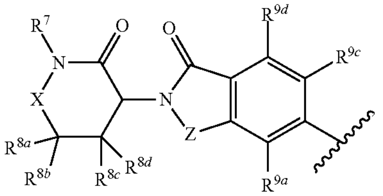

and

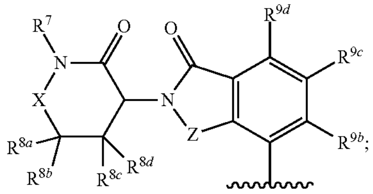

wherein X is selected from —C(O)— and —$CH_2$—; wherein Z is selected from —$CH_2$— and C(O); wherein $R^7$ is selected from hydrogen and C1-C8 alkyl; wherein each of $R^{8a}$, $R^{8b}$, $R^{8c}$, and $R^{8d}$ is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{9a}$, $R^{9b}$, $R^{9c}$, and $R^{9d}$, when present, is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

In a further aspect, the compound has a structure represented by a formula:

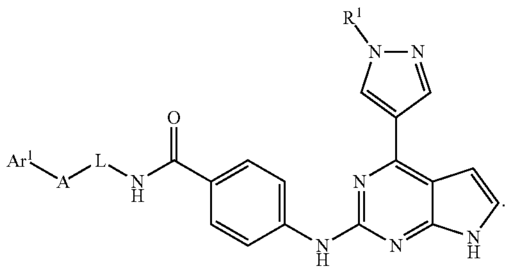

In a further aspect, the compound has a structure represented by a formula:

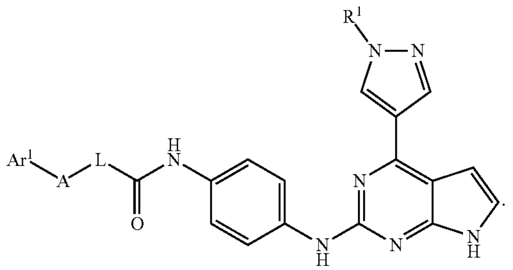

In a further aspect, the compound has a structure represented by a formula:

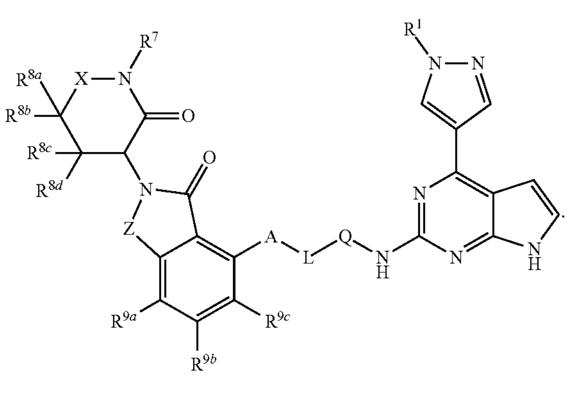

In a further aspect, the compound has a structure represented by a formula:

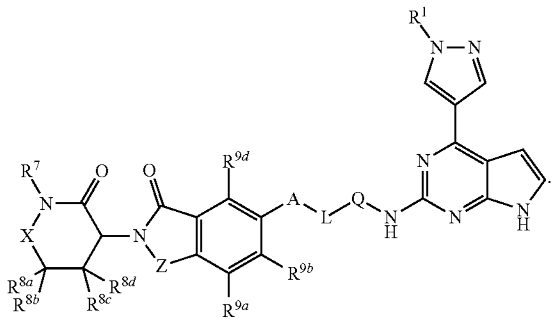

In a further aspect, the compound has a structure represented by a formula:

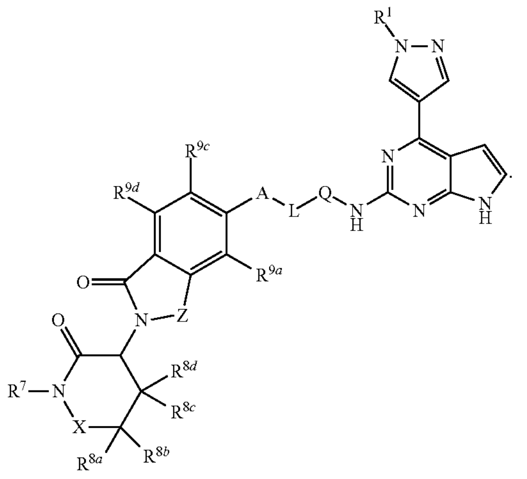

In a further aspect, the compound has a structure represented by a formula:

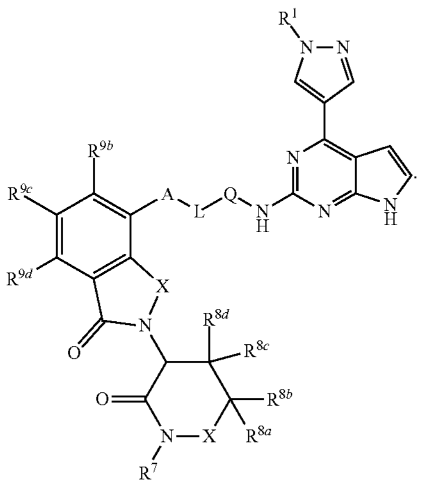

In a further aspect, n, when present, is selected from 1, 2, 3, 4, 5, 6, 7, and 8. In a still further aspect, n is selected from 1, 2, 3, 4, 5, 6, and 7. In yet a further aspect, n, when present, is selected from 1, 2, 3, 4, 5, and 6. In a still further aspect, n, when present, is selected from 1, 2, 3, 4, and 5. In yet a further aspect, n, when present, is selected from 1, 2, 3, and 4. In an even further aspect, n, when present is selected from 1, 2, and 3. In a still further aspect, n, when present is selected from 1 and 2. In yet a further aspect, n, when present, is 1.

In one aspect, disclosed are compounds having a structure selected from:

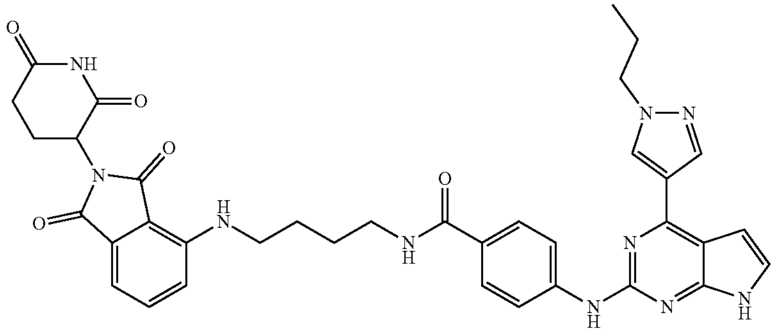

,

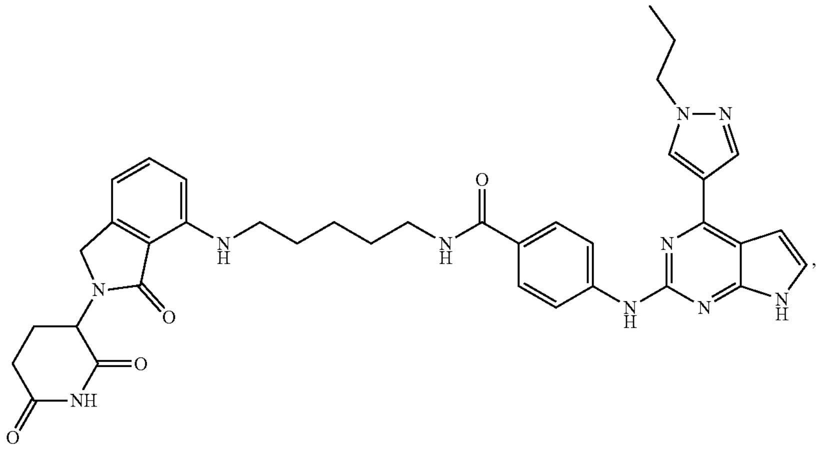

,

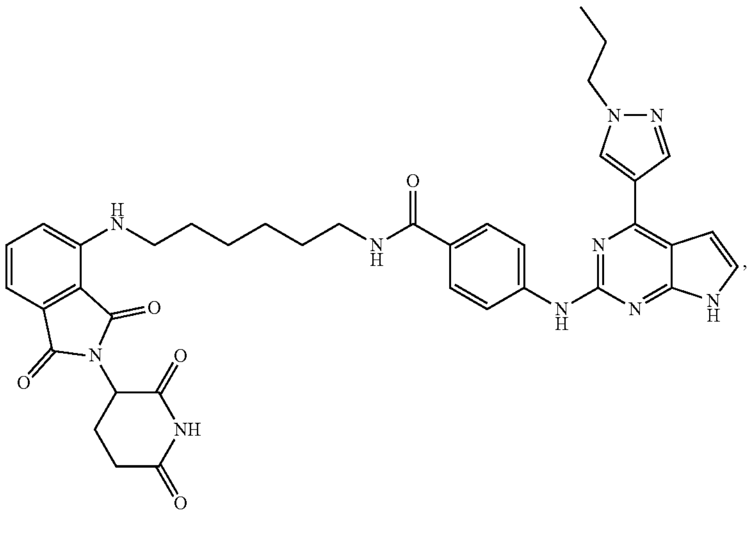

,

-continued
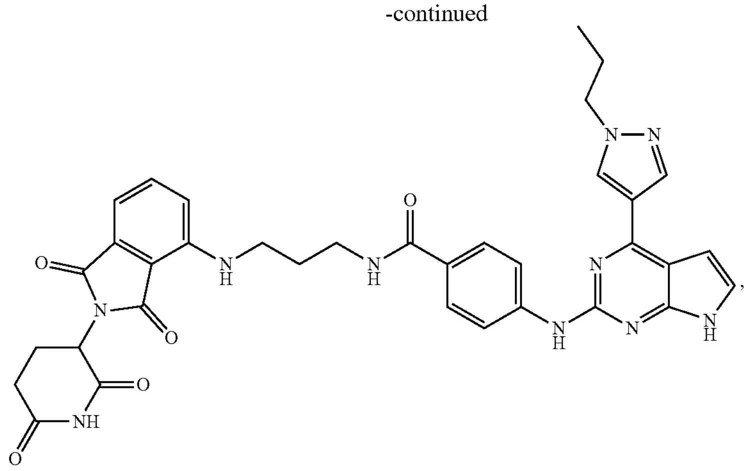
,
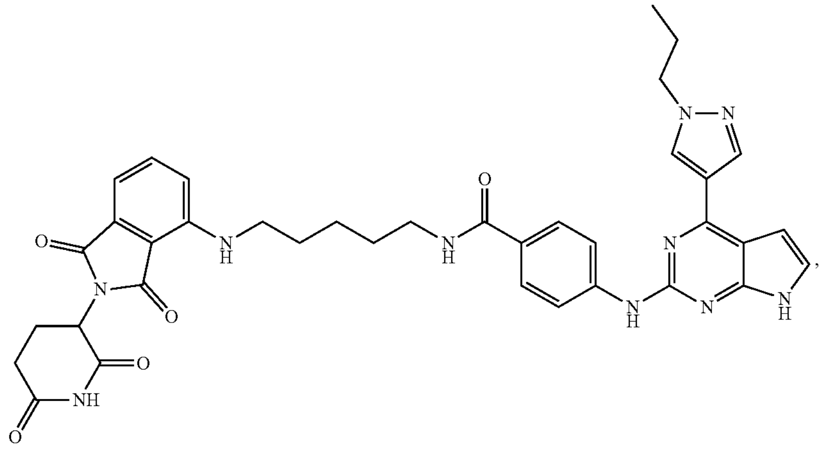
,
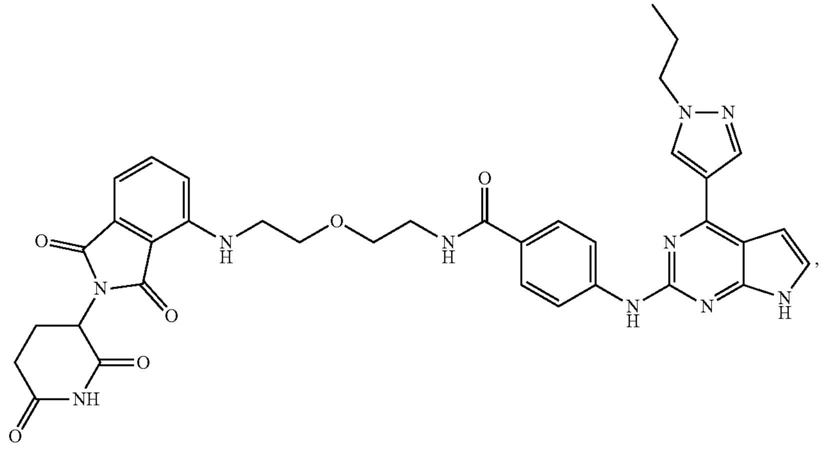
,

-continued
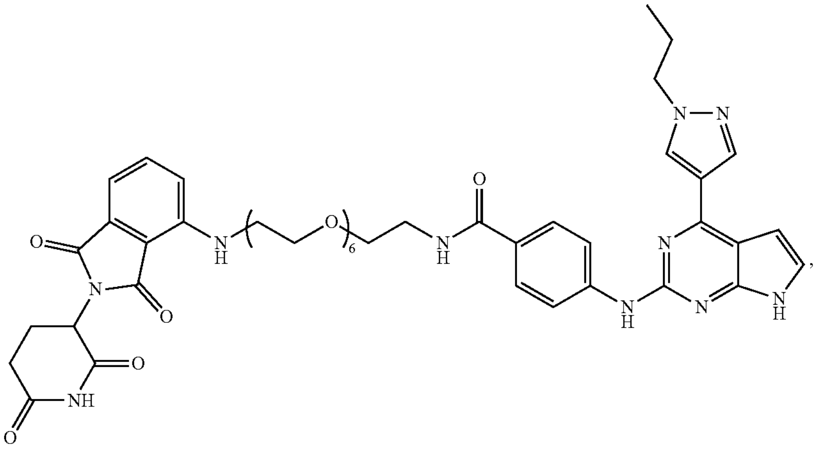
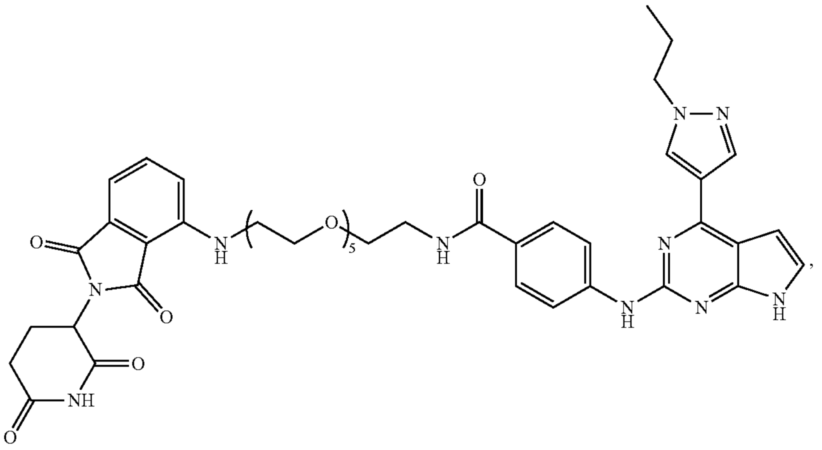
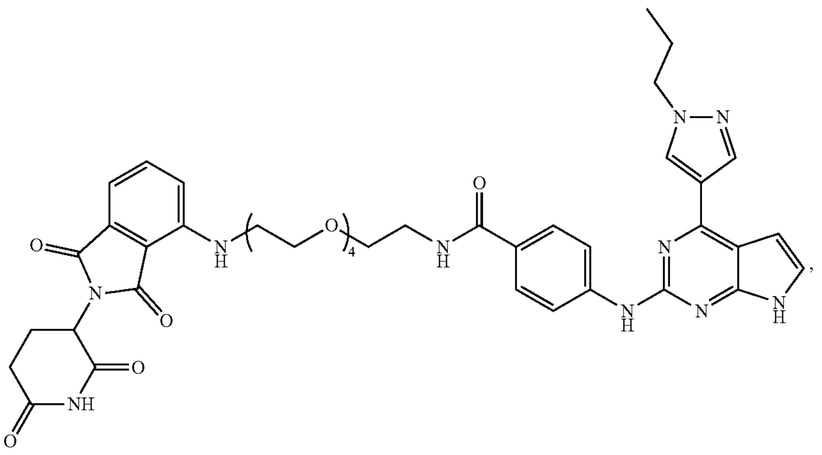

-continued
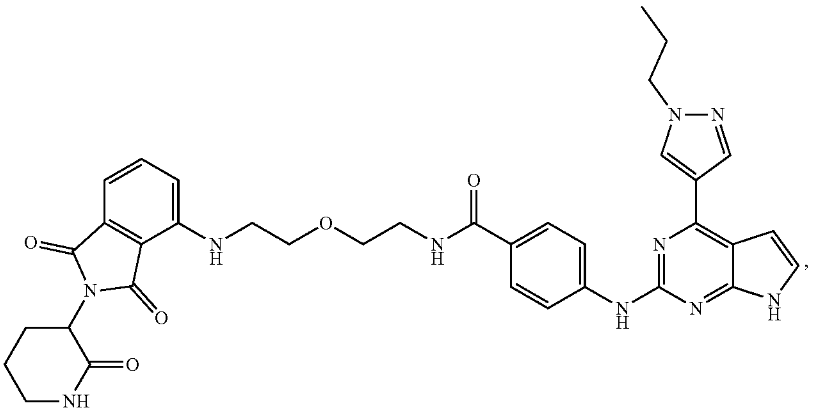
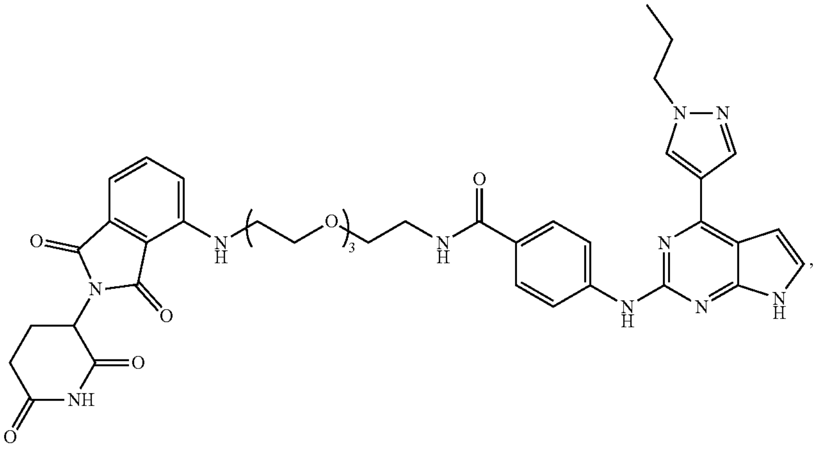
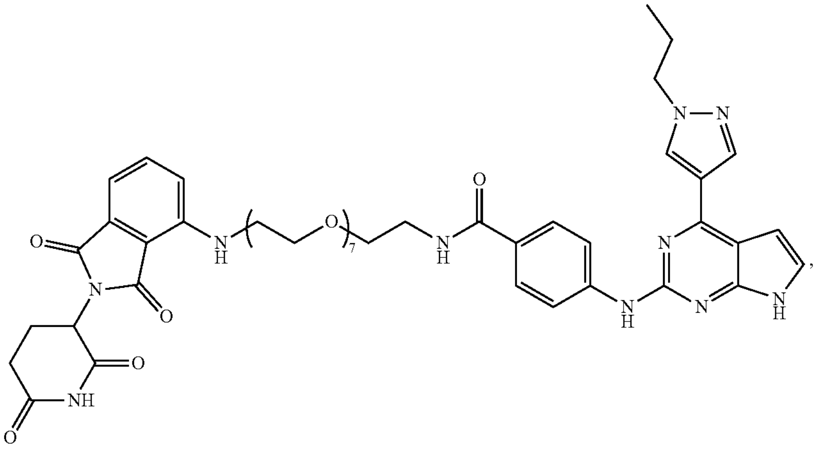

-continued
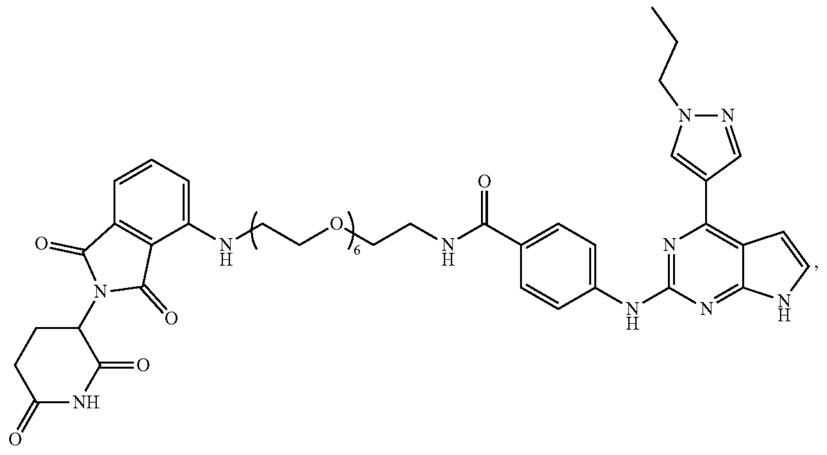
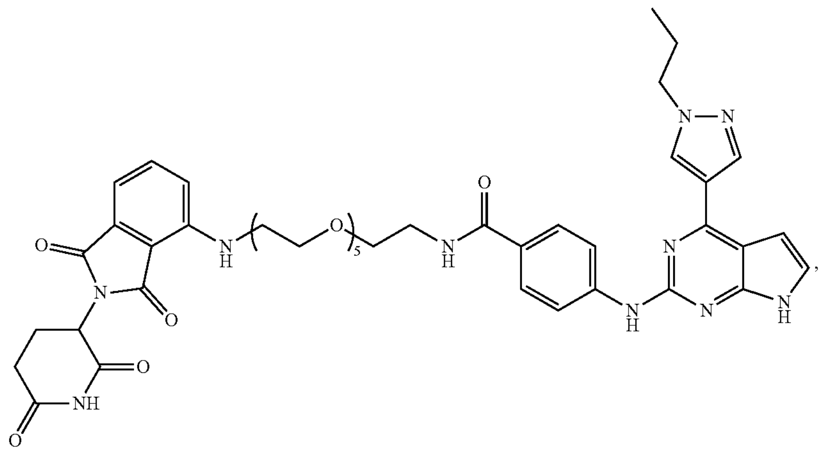
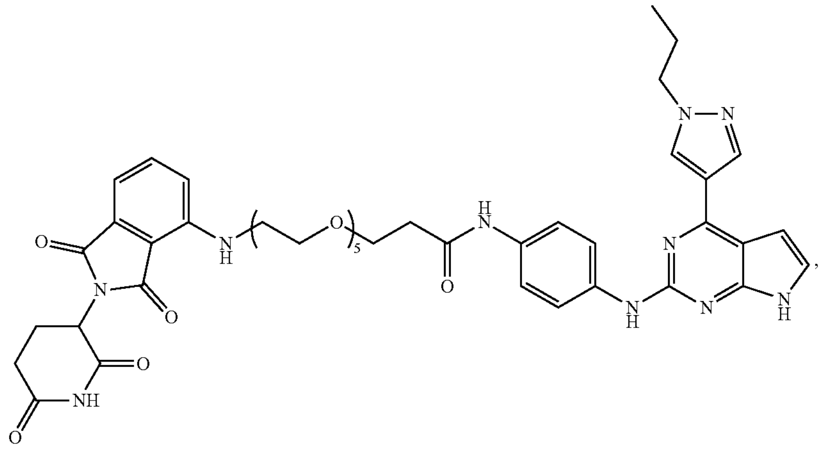

-continued
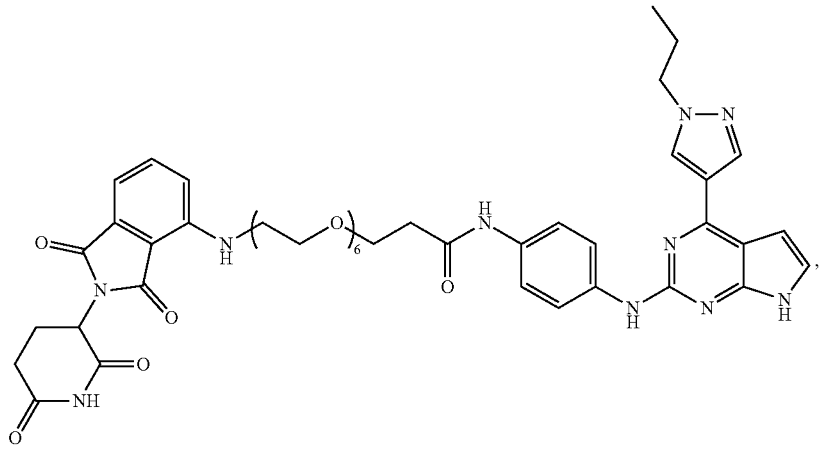
,
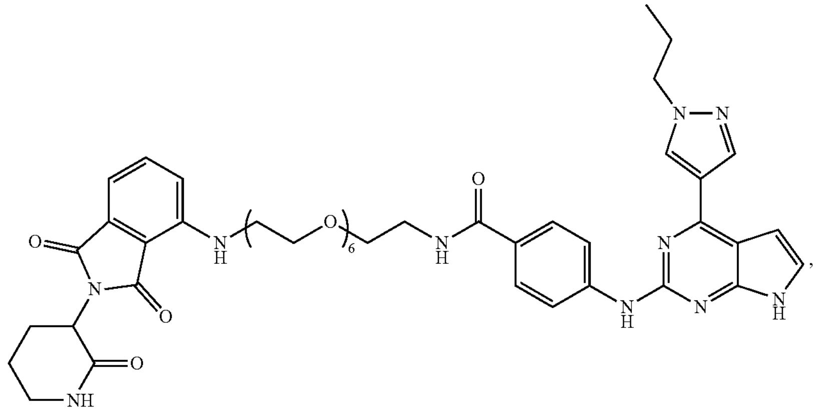
,
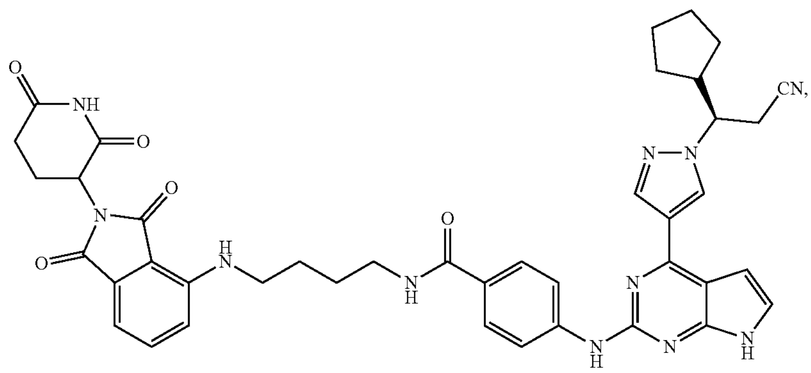
,
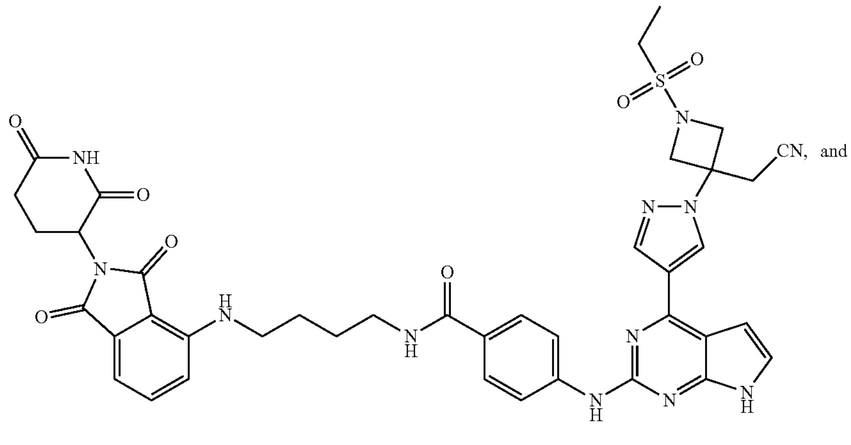
and

-continued
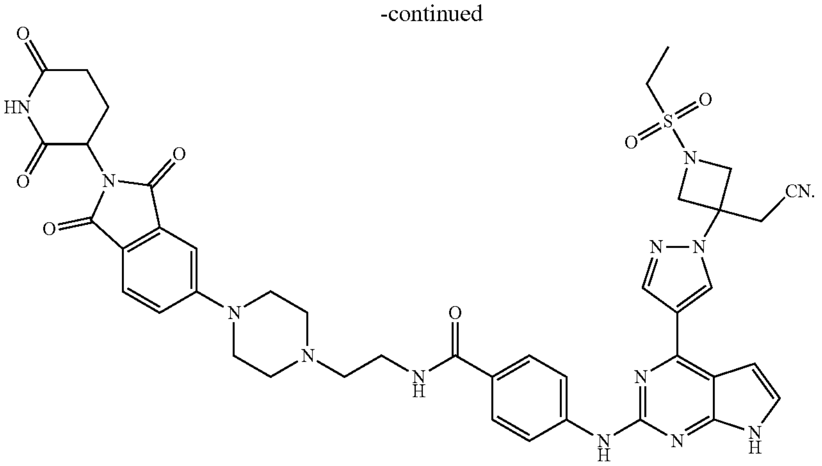
or a pharmaceutically acceptable salt thereof.
In one aspect, disclosed are compounds having a structure selected from:
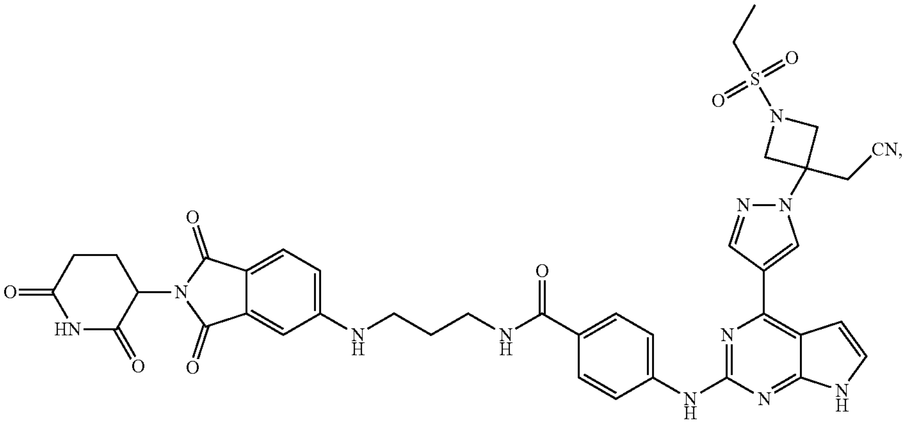
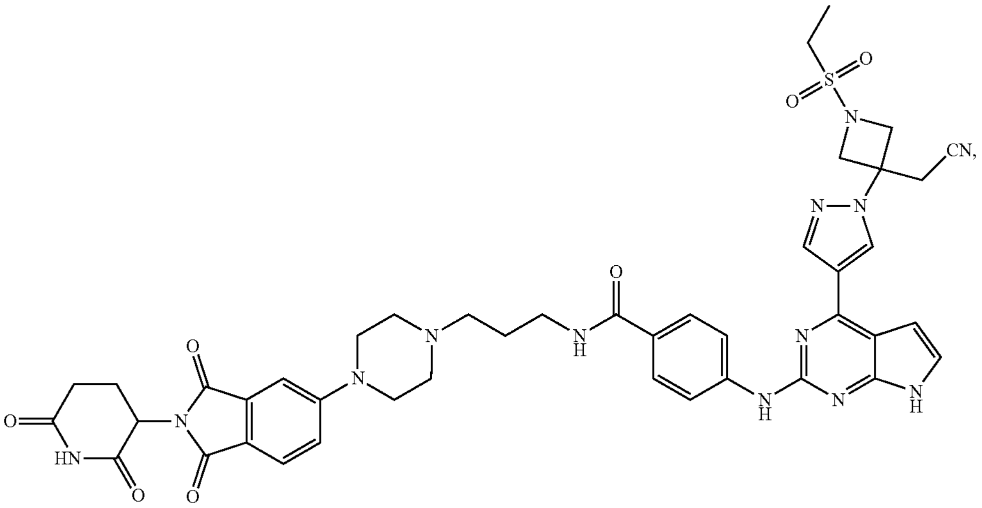

-continued
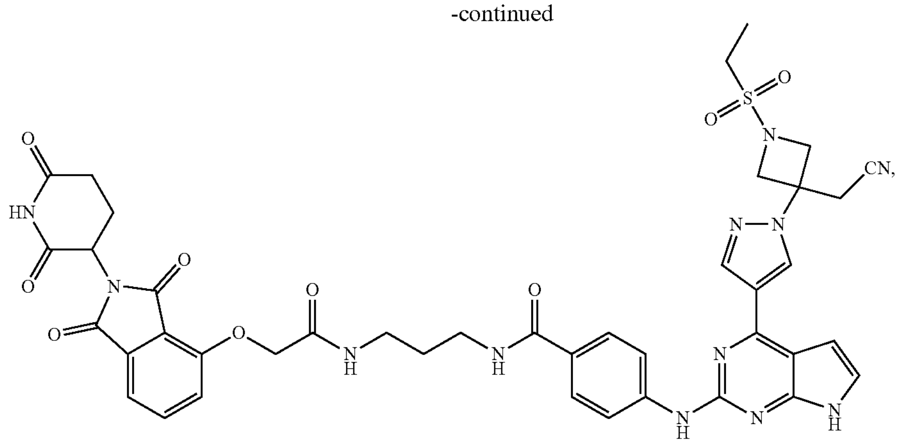
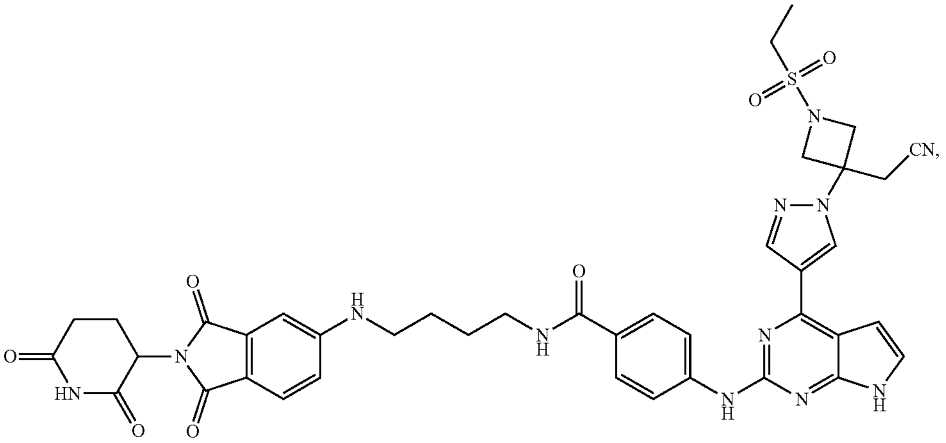
and
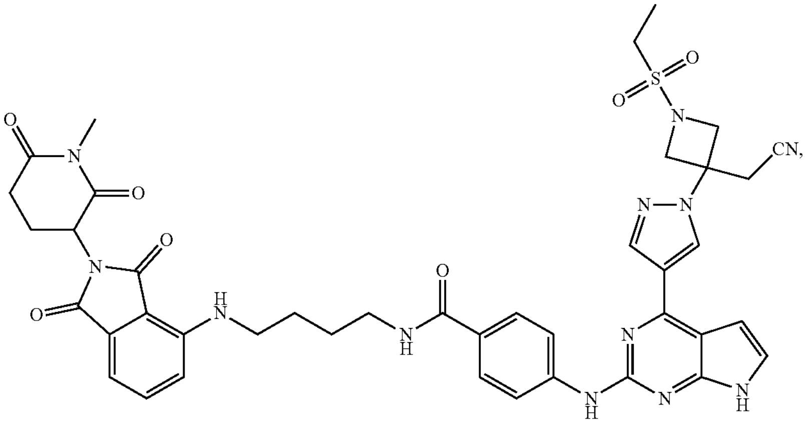
or a pharmaceutically acceptable salt thereof.
a. A Groups
In one aspect, A is selected from —O—, —S—, —NH—, —$CH_2$—, —O—(C1-C4 alkyl)-C(O)NH—, and a structure
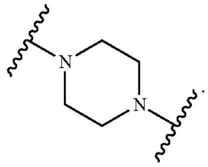 [SMILES: *N1CCN(*)CC1]
In a further aspect, A is selected from —O—, —S—, —O—(C1-C4 alkyl)-C(O)NH—, and a structure
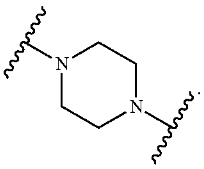 [SMILES: *N1CCN(*)CC1]

In a still further aspect, A is selected from —O—(C1-C4 alkyl)-C(O)NH—, and a structure

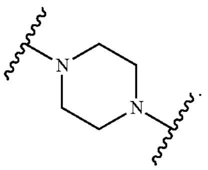 [SMILES: *N1CCN(*)CC1]

In yet a further aspect, A is —O—(C1-C4 alkyl)-C(O)NH—. In an even further aspect, A is a structure

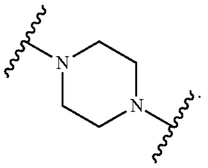 [SMILES: *N1CCN(*)CC1]

In one aspect, A is selected from —O—, —S—, —NH—, and —$CH_2$—. In a further aspect, A is selected from —O—, —S—, and —NH—. In a still further aspect, A is selected from —O—, —S—, and —$CH_2$—. In yet a further aspect, A is selected from —S—, —NH—, and —$CH_2$—. In an even further aspect, A is selected from —O—, —NH—, and —$CH_2$—.

In a further aspect, A is selected from —O— and —S—. In a further aspect, A is selected from is selected from —NH— and —$CH_2$—. In a further aspect, A is selected from —O— and —NH—. In a further aspect, A is selected from —O— and —$CH_2$—. In a further aspect, A is selected from —S— and —NH—. In a further aspect, A is selected from —S— and —$CH_2$—.

In one aspect, A is —O—. In one aspect, A is —S—. In one aspect, A is —NH—. In one aspect, A is —$CH_2$—.

b. L Groups

In one aspect, L is selected from C2-C15 alkyl and —$(CH_2CH_2O)_n$(C1-C4 alkyl)-, wherein n is selected from 1, 2, 3, 4, 5, 6, 7, and 8.

Thus, in one aspect, L is selected from C2-C15 alkyl and —$(CH_2CH_2O)_n$(C1-C4 alkyl)-. In a further aspect, L is selected from C2-C10 alkyl and —$(CH_2CH_2O)_n$(C1-C4 alkyl)-. In a still further aspect, L is selected from C2-C8 alkyl and —$(CH_2CH_2O)_n$(C1-C4 alkyl)-. In yet a further aspect, L is selected from C2-C4 alkyl and —$(CH_2CH_2O)_n$(C1-C4 alkyl)-. In an even further aspect, L is selected from ethyl, n-propyl, isopropyl, and —$(CH_2CH_2O)_n$(C1-C4 alkyl)-. In a still further aspect, L is selected from ethyl and —$(CH_2CH_2O)_n$(C1-C4 alkyl)-.

In one aspect, L is C2-C15 alkyl. In a further aspect, L is C2-C12 alkyl. In a further aspect, L is C2-C8 alkyl. In a further aspect, L is C2-C6 alkyl. In a further aspect, L is C2-C4 alkyl. In a further aspect, L is C4-C6 alkyl. In a further aspect, L is selected from ethyl, n-propyl, and isopropyl. In a further aspect, L is ethyl.

In a further aspect, L is C5 alkyl. In a still further aspect, L is selected from n-pentyl and neopentyl. In yet a further aspect, L is n-pentyl.

In one aspect, L is —$(CH_2CH_2O)_n$(C1-C4 alkyl)-, wherein n is selected from 1, 2, 3, 4, 5, 6, 7, and 8. In a further aspect, L is —$(CH_2CH_2O)_n$(C1-C4 alkyl)-, wherein n is 1. In a further aspect, L is —$(CH_2CH_2O)_n$(C1-C4 alkyl)-, wherein n is 2. In a further aspect, L is —$(CH_2CH_2O)_n$(C1-C4 alkyl)-, wherein n is 3. In a further aspect, L is —$(CH_2CH_2O)_n$(C1-C4 alkyl)-, wherein n is 4. In a further aspect, L is —$(CH_2CH_2O)_n$(C1-C4 alkyl)-, wherein n is 5. In a further aspect, L is —$(CH_2CH_2O)_n$(C1-C4 alkyl)-, wherein n is 6. In a further aspect, L is —$(CH_2CH_2O)_n$(C1-C4 alkyl)-, wherein n is 7. In a further aspect, L is —$(CH_2CH_2O)_n$(C1-C4 alkyl)-, wherein n is 8.

In one aspect, L is —$(CH_2CH_2O)_n$(C1 alkyl)-, wherein n is selected from 1, 2, 3, 4, 5, 6, 7, and 8. In one aspect, L is —$(CH_2CH_2O)_n$(C2 alkyl)-, wherein n is selected from 1, 2, 3, 4, 5, 6, 7, and 8. In one aspect, L is —$(CH_2CH_2O)_n$(C3 alkyl)-, wherein n is selected from 1, 2, 3, 4, 5, 6, 7, and 8. In one aspect, L is —$(CH_2CH_2O)_n$(C4 alkyl)-, wherein n is selected from 1, 2, 3, 4, 5, 6, 7, and 8. In a further aspect, L is —$CH_2CH_2OCH_2CH_2$—.

In a further aspect, L is —$(CH_2CH_2O)_n$(C1-C4 alkyl)-. In a still further aspect, L is —$(CH_2CH_2O)_{1-6}$(C1-C4 alkyl)-. In yet a further aspect, L is —$(CH_2CH_2O)_{1-4}$(C1-C4 alkyl)-. In an even further aspect, L is —$(CH_2CH_2O)_{1-2}$(C1-C4 alkyl)-. In a still further aspect, L is —$(CH_2CH_2O)$(C1-C4 alkyl)-.

In a further aspect, L is selected from —$(CH_2CH_2O)_n(CH_2)$—, —$(CH_2CH_2O)_n(CH_2CH_2)$—, —$(CH_2CH_2O)_n(CH_2CH_2CH_2)$—, and —$(CH_2CH_2O)_n(CH(CH_3)CH_2)$—. In a still further aspect, L is selected from —$(CH_2CH_2O)_n(CH_2)$— and —$(CH_2CH_2O)_n(CH_2CH_2)$—. In yet a further aspect, L is —$(CH_2CH_2O)_n(CH_2)$—. In an even further aspect, L is —$(CH_2CH_2O)_n(CH_2CH_2)$—.

In a further aspect, L is selected from —$(CH_2CH_2O)_3(CH_2CH_2)$—, —$(CH_2CH_2O)_4(CH_2CH_2)$—, —$(CH_2CH_2O)_5(CH_2CH_2)$—, and —$(CH_2CH_2O)_6(CH_2CH_2)$—. In a still further aspect, L is —$CH_2CH_2OCH_2CH_2$—.

c. Q Groups

In one aspect, Q is selected from —$NHC(O)(C_6H_4)$— and —$C(O)NH(C_6H_4)$—. In a further aspect, Q is —$NHC(O)(C_6H_4)$—. In a further aspect, Q is —$C(O)NH(C_6H_4)$—.

In one aspect, Q has a structure:

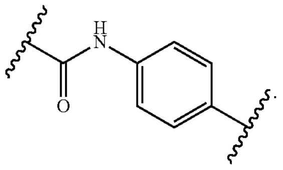 [SMILES: *C(=O)Nc1ccc(*)cc1]

In one aspect, Q has a structure:

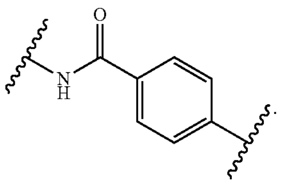 [SMILES: *NC(=O)c1ccc(*)cc1]

d. X Groups

In one aspect, X is selected from —C(O)— and —$CH_2$—. In a further aspect, X is —$CH_2$—. In a further aspect, X is —C(O)—.

e. Z Groups

In one aspect, Z is selected from —$CH_2$— and —C(O)—. In a further aspect, Z is —$CH_2$—. In a further aspect, Z is —C(O)—.

f. $R^1$ Groups

In one aspect, $R^1$ is selected from C1-C8 alkyl, C1-C8 hydroxyalkyl, C1-C8 cyanoalkyl, C1-C8 aminoalkyl, and a structure selected from:

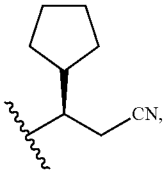 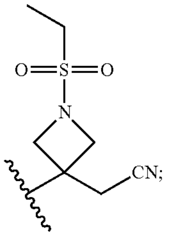 and 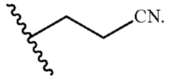

In a further aspect, $R^1$ is selected from C1-C8 alkyl, C1-C8 hydroxyalkyl, C1-C8 cyanoalkyl, and C1-C8 aminoalkyl. In a still further aspect, $R^1$ is selected from C1-C4 alkyl, C1-C4 hydroxyalkyl, C1-C4 cyanoalkyl, and C1-C4 aminoalkyl. In yet a further aspect, $R^1$ is selected from methyl, ethyl, n-propyl, isopropyl, —$CH_2OH$, —$CH_2CH_2OH$, —$CH_2CH_2CH_2OH$, —$CH(CH_3)CH_2OH$, —$CH_2CN$, —$CH_2CH_2CN$, —$CH_2CH_2CH_2CN$, —$CH(CH_3)CH_2CN$, —$CH_2NH_2$, —$CH_2CH_2NH_2$, —$CH_2CH_2CH_2NH_2$, and —$CH(CH_3)CH_2NH_2$. In a still further aspect, $R^1$ is selected from methyl, ethyl, —$CH_2OH$, —$CH_2CH_2OH$, —$CH_2CN$, —$CH_2CH_2CN$, —$CH_2NH_2$, and —$CH_2CH_2NH_2$. In yet a further aspect, $R^1$ is selected from methyl, —$CH_2OH$, —$CH_2CN$, and —$CH_2NH_2$.

In a further aspect, $R^1$ is selected from n-C1-C8 alkyl, n-C1-C8 hydroxyalkyl, n-C1-C8 cyanoalkyl, n-C1-C8 aminoalkyl, and a structure selected from:

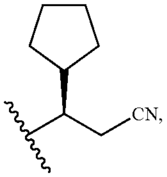 [SMILES: *[C@H](CC#N)C1CCCC1] 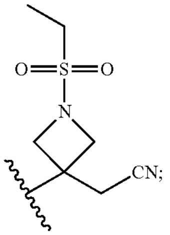 [SMILES: *C1(CC#N)CN(S(=O)(=O)CC)C1] and 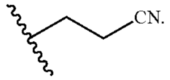 [SMILES: *CCC#N]

In a further aspect, $R^1$ is C1-C8 alkyl. In a further aspect, $R^1$ is C1-C4 alkyl. In a further aspect, $R^1$ is n-C3-C8 alkyl. In a further aspect, $R^1$ is n-C3-C5 alkyl. In a further aspect, $R^1$ is n-propyl. In a still further aspect, $R^1$ is selected from methyl, ethyl, n-propyl, and isopropyl. In yet a further aspect, $R^1$ is selected from methyl and ethyl. In an even further aspect, $R^1$ is methyl.

In a further aspect, $R^1$ is C1-C8 hydroxyalkyl. In a further aspect, $R^1$ is C1-C4 hydroxyalkyl. In a further aspect, $R^1$ is n-C3-C8 hydroxyalkyl. In a further aspect, $R^1$ is n-C3-C5 hydroxyalkyl. In a still further aspect, $R^1$ is selected from —$CH_2OH$, —$CH_2CH_2OH$, —$CH_2CH_2CH_2OH$, and —$CH(CH_3)CH_2OH$. In yet a further aspect, $R^1$ is selected from —$CH_2OH$, and —$CH_2CH_2OH$. In an even further aspect, $R^1$ is —$CH_2OH$.

In a further aspect, $R^1$ is C1-C8 cyanoalkyl. In a further aspect, $R^1$ is C1-C4 cyanoalkyl. In a further aspect, $R^1$ is n-C3-C8 cyanoalkyl. In a further aspect, $R^1$ is n-C3-C5 cyanoalkyl. In a still further aspect, $R^1$ is selected from —$CH_2CN$, —$CH_2CH_2CN$, —$CH_2CH_2CH_2CN$, and —$CH(CH_3)CH_2CN$. In yet a further aspect, $R^1$ is selected from —$CH_2CN$, and —$CH_2CH_2CN$. In an even further aspect, $R^1$ is —$CH_2CN$.

In a further aspect, $R^1$ is C1-C8 aminoalkyl. In a further aspect, $R^1$ is C1-C4 aminoalkyl. In a further aspect, $R^1$ is n-C3-C8 aminoalkyl. In a further aspect, $R^1$ is n-C3-C5 aminoalkyl. In a still further aspect, $R^1$ is selected from —$CH_2NH_2$, —$CH_2CH_2NH_2$, —$CH_2CH_2CH_2NH_2$, and —$CH(CH_3)CH_2NH_2$. In yet a further aspect, $R^1$ is selected from —$CH_2NH_2$, and —$CH_2CH_2NH_2$. In an even further aspect, $R^1$ is —$CH_2NH_2$.

In a further aspect, $R^1$ is a structure selected from:

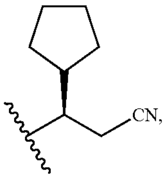 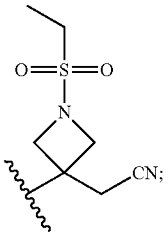 and 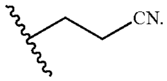

In a further aspect, $R^1$ is

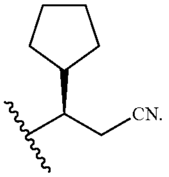

In a further aspect, $R^1$ is

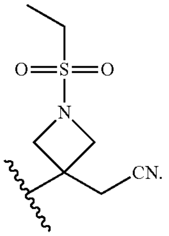

In a further aspect, $R^1$ is

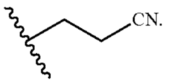

g. $R^7$ Groups

In one aspect, $R^7$ is selected from hydrogen and C1-C8 alkyl. In a further aspect, $R^7$ is selected from hydrogen and C1-C4 alkyl. In a still further aspect, $R^7$ is selected from hydrogen, methyl, ethyl, n-propyl, and isopropyl. In yet a further aspect, $R^7$ is selected from hydrogen, methyl, and ethyl. In an even further aspect, $R^7$ is selected from hydrogen and ethyl. In a still further aspect, $R^7$ is selected from hydrogen and methyl. In yet a further aspect, $R^7$ is hydrogen.

In a further aspect, $R^7$ is C1-C8 alkyl. In a further aspect, $R^7$ is C1-C4 alkyl. In a further aspect, $R^7$ is C3-C8 alkyl. In a further aspect, $R^7$ is C3-C5 alkyl. In a further aspect, $R^7$ is selected from methyl, ethyl, n-propyl, and isopropyl. In a further aspect, $R^7$ is selected from methyl and ethyl. In a still further aspect, $R^7$ is ethyl. In yet a further aspect, $R^7$ is methyl.

h. $R^{8A}$, $R^{8B}$, $R^{8C}$, and $R^{8D}$ Groups

In one aspect, each of $R^{8a}$, $R^{8b}$, $R^{8c}$, and $R^{8d}$ is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each of $R^{8a}$, $R^{8b}$, $R^{8c}$, and $R^{8d}$ is independently selected from hydrogen, —F, —Cl, —$NH_2$, —OH, —$NO_2$, —CN, methyl, ethyl, n-propyl, isopropyl, ethenyl, n-propenyl, isopropenyl, —$CH_2F$, —$CHF_2$, —$CF_3$, —$CH_2CH_2F$, —$CH_2CH_2CH_2F$, —$CH(CH_3)CH_2F$, —$CH_2CN$, —$CH_2CH_2CN$, —$CH_2CH_2CH_2CN$, —$CH(CH_3)CH_2CN$, —$CH_2OH$, —$CH_2CH_2OH$, —$CH_2CH_2CH_2OH$, —$CH(CH_3)CH_2OH$, —$OCH_2F$, —$OCHF_2$, —$OCF_3$, —$OCH_2CH_2F$, —$OCH_2CH_2CH_2F$, —$OCH(CH_3)CH_2F$, —$OCH_3$, —$OCH_2CH_3$, —$OCH_2CH_2CH_3$, —$OCH(CH_3)_2$, —$NHCH_3$, —$NHCH_2CH_3$, —$NHCH_2CH_2CH_3$, —$NHCH(CH_3)_2$, —$N(CH_3)_2$, —$N(CH_3)CH_2CH_3$, —$N(CH_2CH_3)$, —$N(CH_3)CH_2CH_2CH_3$, —$N(CH_3)CH(CH_3)_2$, —$CH_2NH_2$, —$CH_2CH_2NH_2$, —$CH_2CH_2CH_2NH_2$, and —$CH(CH_3)CH_2NH_2$. In a still further aspect, each of $R^{8a}$, $R^{8b}$, $R^{8c}$, and $R^{8d}$ is independently selected from hydrogen, —F, —Cl, —$NH_2$, —OH, —$NO_2$, —CN, methyl, ethyl, ethenyl, —$CH_2F$, —$CHF_2$, —$CF_3$, —$CH_2CH_2F$, —$CH_2CN$, —$CH_2CH_2CN$, —$CH_2OH$, —$CH_2CH_2OH$, —$OCH_2F$, —$OCHF_2$, —$OCF_3$, —$OCH_2CH_2F$, —$OCH_3$, —$OCH_2CH_3$, —$NHCH_3$, —$NHCH_2CH_3$, —$N(CH_3)_2$, —$N(CH_3)CH_2CH_3$, —$N(CH_2CH_3)$, —$CH_2NH_2$, and —$CH_2CH_2NH_2$. In yet a further aspect, each of $R^{8a}$, $R^{8b}$, $R^{8c}$, $R^{8d}$ is independently selected from hydrogen, —F, —Cl, —$NH_2$, —OH, —$NO_2$, —CN, methyl, —$CH_2F$, —$CHF_2$, —$CF_3$, —$CH_2CN$, —$CH_2OH$, —$OCH_2F$, —$OCHF_2$, —$OCF_3$, —$OCH_3$, —$NHCH_3$, —$N(CH_3)_2$, and —$CH_2NH_2$.

In a further aspect, each of $R^{8a}$, $R^{8b}$, $R^{8c}$, and $R^{8d}$ is hydrogen.

In a further aspect, each of $R^{8a}$, $R^{8b}$, $R^{8c}$, and $R^{8d}$ is independently hydrogen. In a further aspect, each of $R^{8a}$, $R^{8b}$, $R^{8c}$, and $R^{8d}$ is independently selected from hydrogen and C1-C4 alkyl. In a further aspect, each of $R^{8a}$, $R^{8b}$, $R^{8c}$, and $R^{8d}$ is independently selected from hydrogen, halogen, —$NH_2$, —OH, —$NO_2$, and —CN. In a further aspect, each of $R^{8a}$, $R^{8b}$, $R^{8c}$, and $R^{8d}$ is independently selected from C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In a further aspect, three of $R^{8a}$, $R^{8b}$, $R^{8c}$, and $R^{8d}$ is hydrogen and one of $R^{8a}$, $R^{8b}$, $R^{8c}$, and $R^{8d}$ is selected from halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. For example, $R^{8b}$, $R^{8c}$, and $R^{8d}$ can be hydrogen and $R^{8a}$ is selected from halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In another example, $R^{8a}$, $R^{8b}$, and $R^{8d}$ can be hydrogen and $R^{8c}$ is selected from halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In a further aspect, two of $R^{8a}$, $R^{8b}$, $R^{8c}$, and $R^{8d}$ is hydrogen and two of $R^{8a}$, $R^{8b}$, $R^{8c}$, and $R^{8d}$ is independently selected from halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. For example, $R^{8a}$ and $R^{8c}$ can be hydrogen and each of $R^{8b}$ and $R^{8d}$ is independently selected from halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In various aspects, each of $R^{8a}$, $R^{8b}$, $R^{8c}$, and $R^{8d}$ is independently selected from hydrogen, halogen, —$NH_2$, —OH, —$NO_2$, —CN, C1-C4 alkyl, and C2-C4 alkenyl. In a further aspect, each of $R^{8a}$, $R^{8b}$, $R^{8c}$, and $R^{8d}$ is independently selected from hydrogen, —F, —Cl, —$NH_2$, —OH, —$NO_2$, —CN, methyl, ethyl, n-propyl, isopropyl, ethenyl, n-propenyl, and isopropenyl. In a still further aspect, each of $R^{8a}$, $R^{8b}$, $R^{8c}$, and $R^{8d}$ is independently selected from hydrogen, —F, —Cl, —$NH_2$, —OH, —$NO_2$, —CN, methyl, ethyl, and ethenyl. In yet a further aspect, each of $R^{8a}$, $R^{8b}$, $R^{8c}$, and $R^{8d}$ is independently selected from hydrogen, —F, —Cl, —$NH_2$, —OH, —$NO_2$, —CN, and methyl.

In various aspects, each of $R^{8a}$, $R^{8b}$, $R^{8c}$, and $R^{8d}$ is independently selected from hydrogen, halogen, —$NH_2$, —OH, —$NO_2$, —CN, C1-C4 haloalkyl, and C1-C4 cyanoalkyl. In a further aspect, each of $R^{8a}$, $R^{8b}$, $R^{8c}$, and $R^{8d}$ is independently selected from hydrogen, —F, —Cl, —$NH_2$, —OH, —$NO_2$, —CN, —$CH_2F$, —$CHF_2$, —$CF_3$, —$CH_2CH_2F$, —$CH_2CH_2CH_2F$, —$CH(CH_3)CH_2F$, —$CH_2CN$, —$CH_2CH_2CN$, —$CH_2CH_2CH_2CN$, and —$CH(CH_3)CH_2CN$. In a still further aspect, each of $R^{8a}$, $R^{8b}$, $R^{8c}$, and $R^{8d}$ is independently selected from hydrogen, —F, —Cl, —$NH_2$, —OH, —$NO_2$, —CN, —$CH_2F$, —$CHF_2$, —$CF_3$, —$CH_2CH_2F$, —$CH_2CN$, and —$CH_2CH_2CN$. In yet a further aspect, each of $R^{8a}$, $R^{8b}$, $R^{8c}$, and $R^{8d}$ is independently selected from hydrogen, —F, —Cl, —$NH_2$, —OH, —$NO_2$, —CN, —$CH_2F$, —$CHF_2$, —$CF_3$, and —$CH_2CN$.

In various aspects, each of $R^{8a}$, $R^{8b}$, $R^{8c}$, and $R^{8d}$ is independently selected from hydrogen, halogen, —$NH_2$, —OH, —$NO_2$, —CN, C1-C4 hydroxyalkyl, C1-C4 haloalkoxy, and C1-C4 alkoxy. In a further aspect, each of $R^{8a}$, $R^{8b}$, $R^{8c}$, and $R^{8d}$ is independently selected from hydrogen, —F, —Cl, —$NH_2$, —OH, —$NO_2$, —CN, —$CH_2OH$, —$CH_2CH_2OH$, —$CH_2CH_2CH_2OH$, —$CH(CH_3)CH_2OH$, —$OCH_2F$, —$OCHF_2$, —$OCF_3$, —$OCH_2CH_2F$, —$OCH_2CH_2CH_2F$, —$OCH(CH_3)CH_2F$, —$OCH_3$, —$OCH_2CH_3$, —$OCH_2CH_2CH_3$, and —$OCH(CH_3)_2$. In a still further aspect, each of $R^{8a}$, $R^{8b}$, $R^{8c}$, and $R^{8d}$ is independently selected from hydrogen, —F, —Cl, —$NH_2$, —OH, —$NO_2$, —CN, —$CH_2OH$, —$CH_2CH_2OH$, —$OCH_2F$, —$OCHF_2$, —$OCF_3$, —$OCH_2CH_2F$, —$OCH_3$, and —$OCH_2CH_3$. In yet a further aspect, each of $R^{8a}$, $R^{8b}$, $R^{8c}$, and $R^{8d}$ is independently selected from hydrogen, —F, —Cl, —$NH_2$, —OH, —$NO_2$, —CN, —$CH_2OH$, —$OCH_2F$, —$OCHF_2$, —$OCF_3$, and —$OCH_3$.

In various aspects, each of $R^{8a}$, $R^{8b}$, $R^{8c}$, and $R^{8d}$ is independently selected from hydrogen, halogen, —$NH_2$, —OH, —$NO_2$, —CN, C1-C4 alkylamino, (C1-C4)(C1-C4) dialkylamino, and C1-C4 aminoalkyl. In a further aspect, each of $R^{8a}$, $R^{8b}$, $R^{8c}$, and $R^{8d}$ is independently selected from hydrogen, —F, —Cl, —$NH_2$, —OH, —$NO_2$, —CN, —$NHCH_3$, —$NHCH_2CH_3$, —$NHCH_2CH_2CH_3$, —$NHCH(CH_3)_2$, —$N(CH_3)_2$, —$N(CH_3)CH_2CH_3$, —$N(CH_2CH_3)$, —$N(CH_3)CH_2CH_2CH_3$, —$N(CH_3)CH(CH_3)_2$, —$CH_2NH_2$, —$CH_2CH_2NH_2$, —$CH_2CH_2CH_2NH_2$, and —$CH(CH_3)CH_2NH_2$. In a still further aspect, each of $R^{8a}$, $R^{8b}$, $R^{8c}$, and $R^{8d}$ is independently selected from hydrogen, —F, —Cl, —$NH_2$, —OH, —$NO_2$, —CN, —$NHCH_3$, —$NHCH_2CH_3$, —$N(CH_3)_2$, —$N(CH_3)CH_2CH_3$, —$N(CH_2CH_3)$, —$CH_2NH_2$, and —$CH_2CH_2NH_2$. In yet a further aspect, each of $R^{8a}$, $R^{8b}$, $R^{8c}$, and $R^{8d}$ is independently selected from hydrogen, —F, —Cl, —$NH_2$, —OH, —$NO_2$, —CN, —$NHCH_3$, —$N(CH_3)_2$, and —$CH_2NH_2$.

In various aspects, each of $R^{8a}$, $R^{8b}$, $R^{8c}$, and $R^{8d}$ is independently selected from hydrogen, C1-C4 alkyl, and C2-C4 alkenyl. In a further aspect, each of $R^{8a}$, $R^{8b}$, $R^{8c}$, and $R^{8d}$ is independently selected from hydrogen, methyl, ethyl, n-propyl, isopropyl, ethenyl, n-propenyl, and isopropenyl. In a still further aspect, each of $R^{8a}$, $R^{8b}$, $R^{8c}$, and $R^{8d}$ is independently selected from hydrogen, methyl, ethyl, and ethenyl. In yet a further aspect, each of $R^{8a}$, $R^{8b}$, $R^{8c}$, and $R^{8d}$ is independently selected from hydrogen and methyl.

i. $R^{9a}$, $R^{9b}$, $R^{9c}$, and $R^{9d}$ Groups

In one aspect, each of $R^{9a}$, $R^{9b}$, $R^{9c}$, and $R^{9d}$ is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each of $R^{9a}$, $R^{9b}$, $R^{9c}$, and $R^{9d}$ is independently selected from hydrogen, —F, —Cl, —$NH_2$, —OH, —$NO_2$, —CN, methyl, ethyl, n-propyl, isopropyl, ethenyl, n-propenyl, isopropenyl, —$CH_2F$, —$CHF_2$, —$CF_3$, —$CH_2CH_2F$, —$CH_2CH_2CH_2F$, —$CH(CH_3)CH_2F$, —$CH_2CN$, —$CH_2CH_2CN$, —$CH_2CH_2CH_2CN$, —$CH(CH_3)CH_2CN$, —$CH_2OH$, —$CH_2CH_2OH$, —$CH_2CH_2CH_2OH$, —$CH(CH_3)CH_2OH$, —$OCH_2F$, —$OCHF_2$, —$OCH_2CH_2F$, —$OCH_2CH_2CH_2F$, —$OCH(CH_3)CH_2F$, —$OCH_3$, —$OCH_2CH_3$, —$OCH_2CH_2CH_3$, —$OCH(CH_3)_2$, —$NHCH_3$, —$NHCH_2CH_3$, —$NHCH_2CH_2CH_3$, —$NHCH(CH_3)_2$, —$N(CH_3)_2$, —$N(CH_3)CH_2CH_3$, —$N(CH_2CH_3)$, —$N(CH_3)CH_2CH_2CH_3$, —$N(CH_3)CH(CH_3)_2$, —$CH_2NH_2$, —$CH_2CH_2NH_2$, —$CH_2CH_2CH_2NH_2$, and —$CH(CH_3)CH_2NH_2$. In a still further aspect, each of $R^{9a}$, $R^{9b}$, $R^{9c}$, and $R^{9d}$ is independently selected from hydrogen, —F, —Cl, —$NH_2$, —OH, —$NO_2$, —CN, methyl, ethyl, ethenyl, —$CH_2F$, —$CHF_2$, —$CF_3$, —$CH_2CH_2F$, —$CH_2CN$, —$CH_2CH_2CN$, —$CH_2OH$, —$CH_2CH_2OH$, —$OCH_2F$, —$OCHF_2$, —$OCF_3$, —$OCH_2CH_2F$, —$OCH_3$, —$OCH_2CH_3$, —$NHCH_3$, —$NHCH_2CH_3$, —$N(CH_3)_2$, —$N(CH_3)CH_2CH_3$, —$N(CH_2CH_3)$, —$CH_2NH_2$, and —$CH_2CH_2NH_2$. In yet a further aspect, each of $R^{9a}$, $R^{9b}$, $R^{9c}$, and $R^{9d}$ is independently selected from hydrogen, —F, —Cl, —$NH_2$, —OH, —$NO_2$, —CN, methyl, —$CH_2F$, —$CHF_2$, —$CF_3$, —$CH_2CN$, —$CH_2OH$, —$OCH_2F$, —$OCHF_2$, —$OCH_3$, —$NHCH_3$, —$N(CH_3)_2$, and —$CH_2NH_2$.

In a further aspect, each of $R^{9a}$, $R^{9b}$, $R^{9c}$, and $R^{9d}$ is hydrogen. It is understood that in the structure $Ar^1$ only three of $R^{9a}$, $R^{9b}$, $R^{9c}$, and $R^{9d}$ are present at the same time. For example, $R^{9a}$, $R^{9b}$, and $R^{9c}$ can be present at the same time. In another example, $R^{9a}$, $R^{9b}$, and $R^{9d}$ can be present at the same time. In yet another example, $R^{9a}$, $R^{9c}$, and $R^{9d}$ can be present at the same time. In yet another example, $R^{9b}$, $R^{9c}$, and $R^{9d}$ can be present at the same time.

In a further aspect, each of $R^{9a}$, $R^{9b}$, and $R^{9c}$ is independently hydrogen. In a further aspect, each of $R^{9a}$, $R^{9b}$, and $R^{9d}$ is independently hydrogen. In a further aspect, each of $R^{9a}$, $R^{9c}$, and $R^{9d}$ is independently hydrogen. In a further aspect, each of $R^{9b}$, $R^{9c}$, and $R^{9d}$ is independently hydrogen. In a further aspect, each of $R^{9a}$, $R^{9b}$, $R^{9c}$, and $R^{9d}$ is independently selected from hydrogen and C1-C4 alkyl. In a further aspect, each of $R^{9a}$, $R^{9b}$, $R^{9c}$, and $R^{9d}$ is independently selected from hydrogen, halogen, —$NH_2$, —OH, —$NO_2$, and —CN. In a further aspect, each of $R^{9a}$, $R^{9b}$, $R^{9c}$, and $R^{9d}$ is independently selected from C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In a further aspect, two of $R^{9a}$, $R^{9b}$, $R^{9c}$, and $R^{9d}$ is hydrogen and one of $R^{9a}$, $R^{9b}$, $R^{9c}$, and $R^{9d}$ is selected from halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. For example, $R^{9a}$ and $R^{9b}$ can be hydrogen and $R^{9c}$ is selected from halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In another example, $R^{9b}$ and $R^{9c}$ can be hydrogen and $R^{9a}$ is selected from halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In another example, $R^{9a}$ and $R^{9c}$ can be hydrogen and $R^{9b}$ is selected from halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In various aspects, each of $R^{9a}$, $R^{9b}$, $R^{9c}$, and $R^{9d}$ is independently selected from hydrogen, halogen, —$NH_2$, —OH, —$NO_2$, —CN, C1-C4 alkyl, and C2-C4 alkenyl. In a further aspect, each of $R^{9a}$, $R^{9b}$, $R^{9c}$, and $R^{9d}$ is independently selected from hydrogen, —F, —Cl, —$NH_2$, —OH, —$NO_2$, —CN, methyl, ethyl, n-propyl, isopropyl, ethenyl, n-propenyl, and isopropenyl. In a still further aspect, each of $R^{9a}$, $R^{9b}$, $R^{9c}$, and $R^{9d}$ is independently selected from hydrogen, —F, —Cl, —$NH_2$, —OH, —$NO_2$, —CN, methyl, ethyl, and ethenyl. In yet a further aspect, each of $R^{9a}$, $R^{9b}$, $R^{9c}$, and $R^{9d}$ is independently selected from hydrogen, —F, —Cl, —$NH_2$, —OH, —$NO_2$, —CN, and methyl.

In various aspects, each of $R^{9a}$, $R^{9b}$, $R^{9c}$, and $R^{9d}$ is independently selected from hydrogen, halogen, —$NH_2$, —OH, —$NO_2$, —CN, C1-C4 haloalkyl, and C1-C4 cyanoalkyl. In a further aspect, each of $R^{9a}$, $R^{9b}$, $R^{9c}$, and $R^{9d}$ is independently selected from hydrogen, —F, —Cl, —$NH_2$, —OH, —$NO_2$, —CN, —$CH_2F$, —$CHF_2$, —$CF_3$, —$CH_2CH_2F$, —$CH_2CH_2CH_2F$, —$CH(CH_3)CH_2F$, —$CH_2CN$, —$CH_2CH_2CN$, —$CH_2CH_2CH_2CN$, and —$CH(CH_3)CH_2CN$. In a still further aspect, each of $R^{9a}$, $R^{9b}$, $R^{9c}$, and $R^{9d}$ is independently selected from hydrogen, —F, —Cl, —$NH_2$, —OH, —$NO_2$, —CN, —$CH_2F$, —$CHF_2$, —$CF_3$, —$CH_2CH_2F$, —$CH_2CN$, and —$CH_2CH_2CN$. In yet a further aspect, each of $R^{9a}$, $R^{9b}$, $R^{9c}$, and $R^{9d}$ is independently selected from hydrogen, —F, —Cl, —$NH_2$, —OH, —$NO_2$, —CN, —$CH_2F$, —$CHF_2$, —$CF_3$, and —$CH_2CN$.

In various aspects, each of $R^{9a}$, $R^{9b}$, $R^{9c}$, and $R^{9d}$ is independently selected from hydrogen, halogen, —$NH_2$, —OH, —$NO_2$, —CN, C1-C4 hydroxyalkyl, C1-C4 haloalkoxy, and C1-C4 alkoxy. In a further aspect, each of $R^{9a}$, $R^{9b}$, $R^{9c}$, and $R^{9d}$ is independently selected from hydrogen, —F, —Cl, —$NH_2$, —OH, —$NO_2$, —CN, —$CH_2OH$, —$CH_2CH_2OH$, —$CH_2CH_2CH_2OH$, —$CH(CH_3)CH_2OH$, —$OCH_2F$, —$OCHF_2$, —$OCF_3$, —$OCH_2CH_2F$, —$OCH_2CH_2CH_2F$, —$OCH(CH_3)CH_2F$, —$OCH_3$, —$OCH_2CH_3$, —$OCH_2CH_2CH_3$, and —$OCH(CH_3)_2$. In a still further aspect, each of $R^{9a}$, $R^{9b}$, $R^{9c}$, and $R^{9d}$ is independently selected from hydrogen, —F, —Cl, —$NH_2$, —OH, —$NO_2$, —CN, —$CH_2OH$, —$CH_2CH_2OH$, —$OCH_2F$, —$OCHF_2$, —$OCF_3$, —$OCH_2CH_2F$, —$OCH_3$, and —$OCH_2CH_3$. In yet a further aspect, each of $R^{9a}$, $R^{9b}$, $R^{9c}$, and $R^{9d}$ is independently selected from hydrogen, —F, —Cl, —$NH_2$, —OH, —$NO_2$, —CN, —$CH_2OH$, —$OCH_2F$, —$OCHF_2$, —$OCF_3$, and —$OCH_3$.

In various aspects, each of $R^{9a}$, $R^{9b}$, $R^{9c}$, and $R^{9d}$ is independently selected from hydrogen, halogen, —$NH_2$, —OH, —$NO_2$, —CN, C1-C4 alkylamino, (C1-C4)(C1-C4) dialkylamino, and C1-C4 aminoalkyl. In a further aspect, each of $R^{9a}$, $R^{9b}$, $R^{9c}$, and $R^{9d}$ is independently selected from hydrogen, —F, —Cl, —$NH_2$, —OH, —$NO_2$, —CN, —$NHCH_3$, —$NHCH_2CH_3$, —$NHCH_2CH_2CH_3$, —$NHCH(CH_3)_2$, —$N(CH_3)_2$, —$N(CH_3)CH_2CH_3$, —$N(CH_2CH_3)$, —$N(CH_3)CH_2CH_2CH_3$, —$N(CH_3)CH(CH_3)_2$, —$CH_2NH_2$, —$CH_2CH_2NH_2$, —$CH_2CH_2CH_2NH_2$, and —$CH(CH_3)CH_2NH_2$. In a still further aspect, each of $R^{9a}$, $R^{9b}$, $R^{9c}$, and $R^{9d}$ is independently selected from hydrogen, —F, —Cl, —$NH_2$, —OH, —$NO_2$, —CN, —$NHCH_3$, —$NHCH_2CH_3$, —$N(CH_3)_2$, —$N(CH_3)CH_2CH_3$, —$N(CH_2CH_3)$, —$CH_2NH_2$, and —$CH_2CH_2NH_2$. In yet a further aspect, each of $R^{9a}$, $R^{9b}$, $R^{9c}$, and $R^{9d}$ is independently selected from hydrogen, —F, —Cl, —$NH_2$, —OH, —$NO_2$, —CN, —$NHCH_3$, —$N(CH_3)_2$, and —$CH_2NH_2$.

In various aspects, each of $R^{9a}$, $R^{9b}$, $R^{9c}$, and $R^{9d}$ is independently selected from hydrogen, C1-C4 alkyl, and C2-C4 alkenyl. In a further aspect, each of $R^{9a}$, $R^{9b}$, $R^{9c}$, and $R^{9d}$ is independently selected from hydrogen, methyl, ethyl, n-propyl, isopropyl, ethenyl, n-propenyl, and isopropenyl. In a still further aspect, each of $R^{9a}$, $R^{9b}$, $R^{9c}$, and $R^{9d}$ is independently selected from hydrogen, methyl, ethyl, and ethenyl. In yet a further aspect, each of $R^{9a}$, $R^{9b}$, $R^{9c}$, and $R^{9d}$ is independently selected from hydrogen and methyl.

j. $Ar^1$ Groups

In one aspect, $Ar^1$ is a structure represented by a formula selected from:

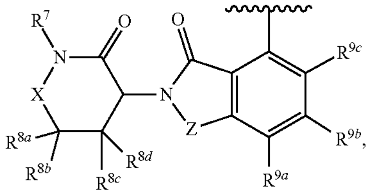

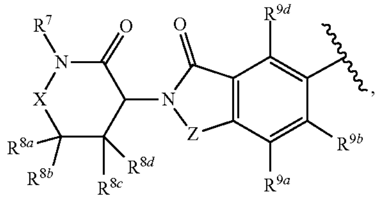

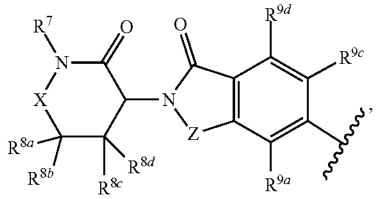

and

-continued

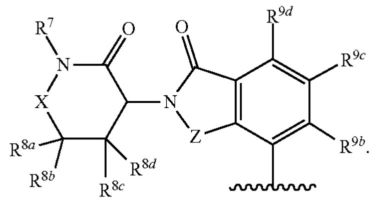

In a further aspect, $Ar^1$ is a structure represented by a formula:

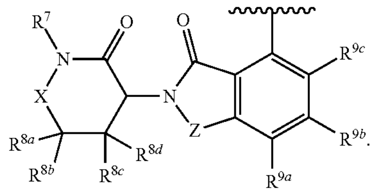

In a further aspect, $Ar^1$ is a structure represented by a formula:

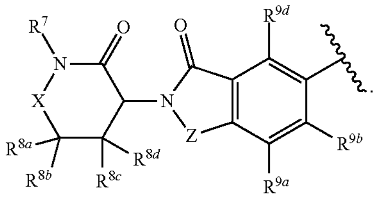

In a further aspect, $Ar^1$ is a structure represented by a formula:

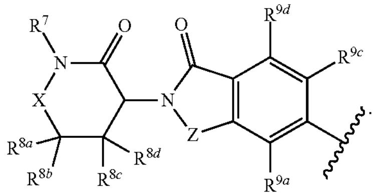

In a further aspect, $Ar^1$ is a structure represented by a formula:

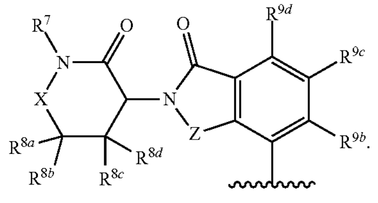

In a further aspect, $Ar^1$ is a structure represented by a formula selected from:
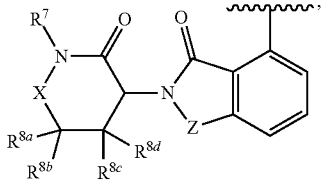
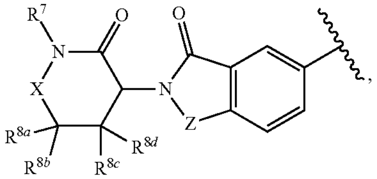
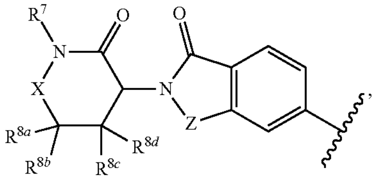
and
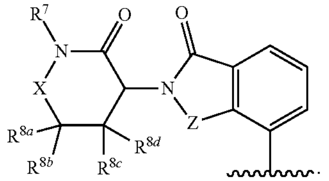
In a further aspect, $Ar^1$ is a structure represented by a formula selected from:
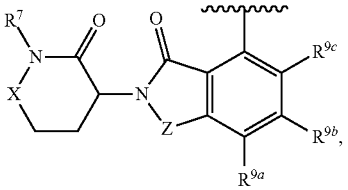
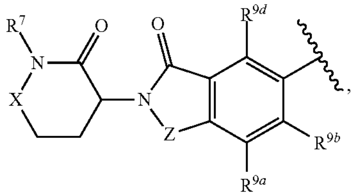
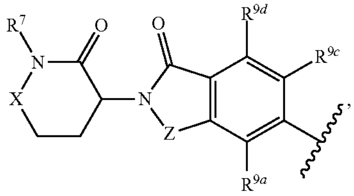
and
-continued
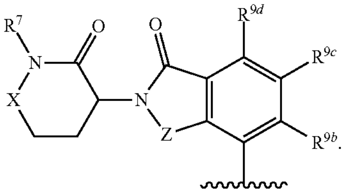
In one aspect, $Ar^1$ is a structure represented by a formula selected from:
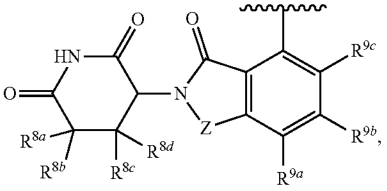
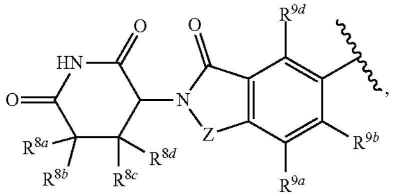
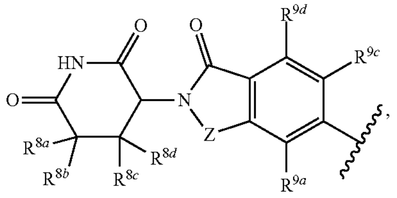
and
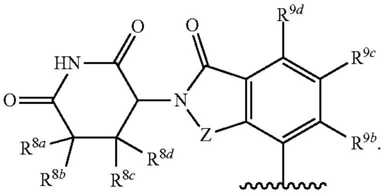
In one aspect, $Ar^1$ is a structure represented by a formula selected from:
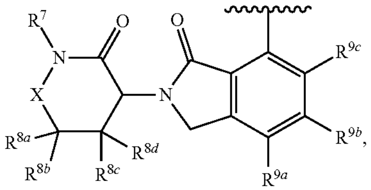
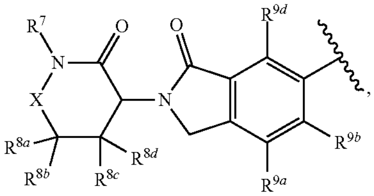

-continued
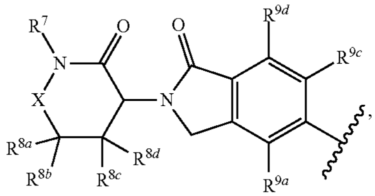
and
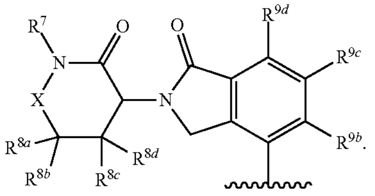
In a further aspect, $Ar^1$ is a structure represented by a formula selected from:
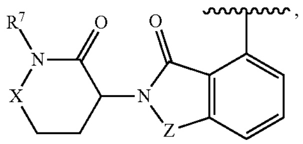
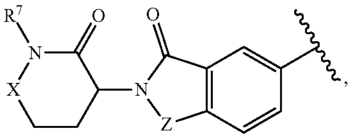
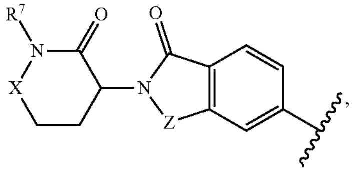
and
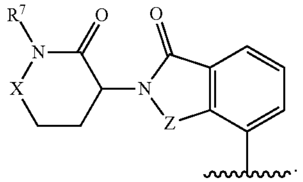
In a further aspect, $Ar^1$ is a structure represented by a formula selected from:
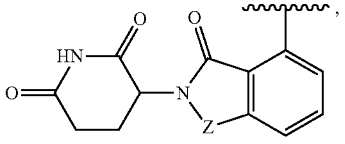
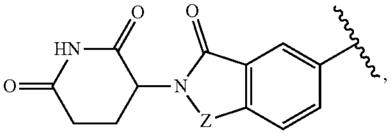
-continued
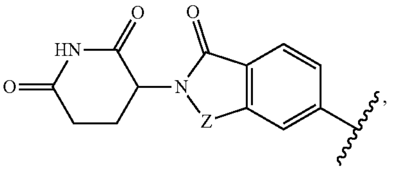
and
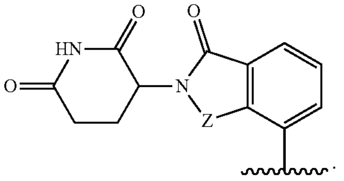
In a further aspect, $Ar^1$ is a structure represented by a formula selected from:
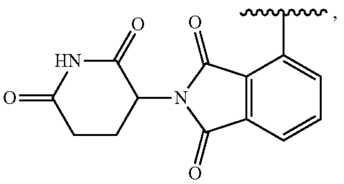
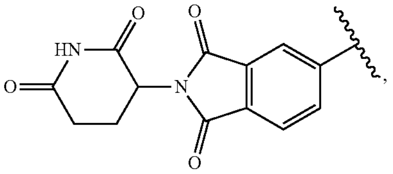 [SMILES: *c1ccc2c(c1)C(=O)N(C1CCC(=O)NC1=O)C2=O]
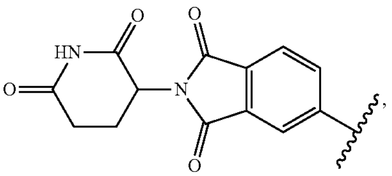
and
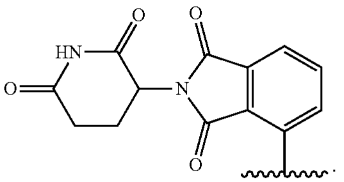
In a further aspect, $Ar^1$ is a structure represented by a formula selected from:
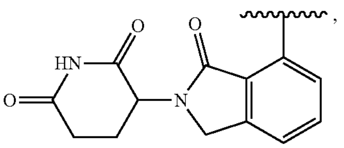
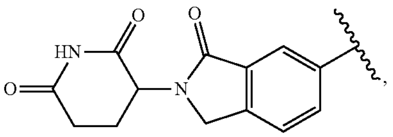 [SMILES: *c1ccc2c(c1)C(=O)N(C1CCC(=O)NC1=O)C2]

-continued

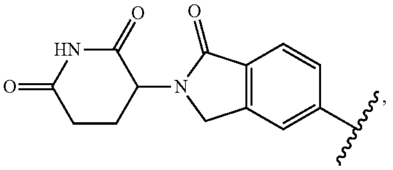

and

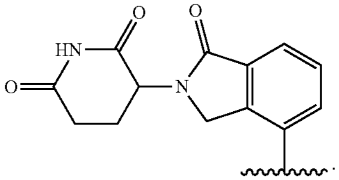

In a further aspect, $Ar^1$ is a structure represented by a formula:

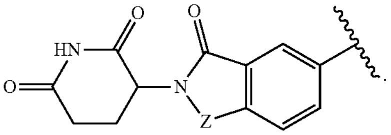

In a further aspect, $Ar^1$ is a structure represented by a formula:

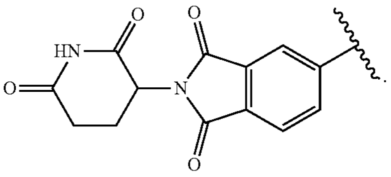

In a further aspect, $Ar^1$ is a structure represented by a formula:

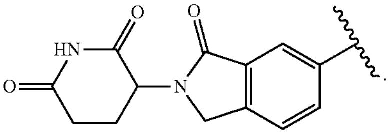

In a further aspect, $Ar^1$ is a structure represented by a formula:

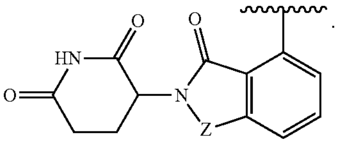

In a further aspect, $Ar^1$ is a structure represented by a formula:

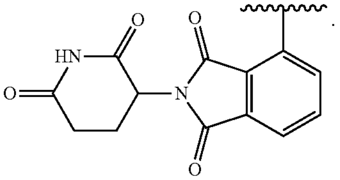 [SMILES: *c1cccc2c1C(=O)N(C1CCC(=O)NC1=O)C2=O]

In a further aspect, $Ar^1$ is a structure represented by a formula:

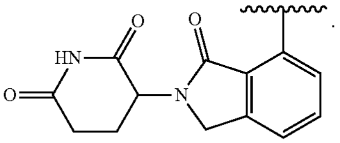 [SMILES: *c1cccc2c1C(=O)N(C1CCC(=O)NC1=O)C2]

2. Example Compounds

In one aspect, a compound can be present as one or more of the following structures:

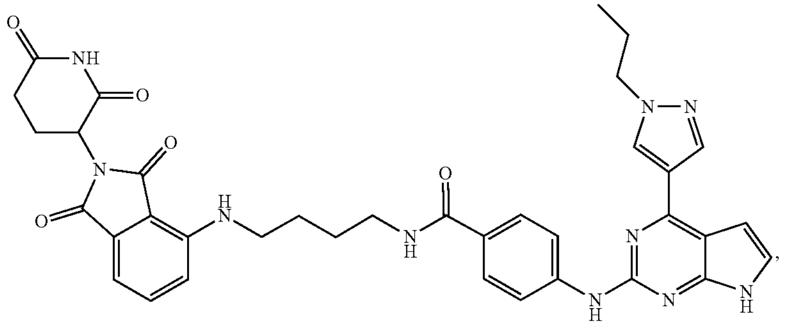

-continued
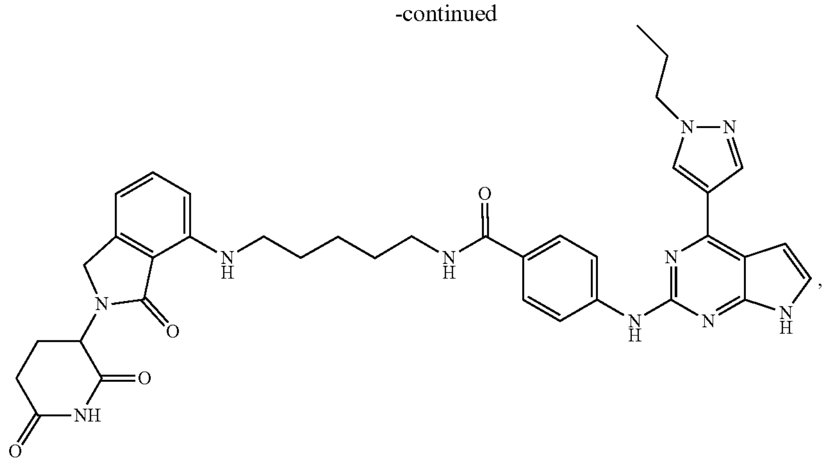
,
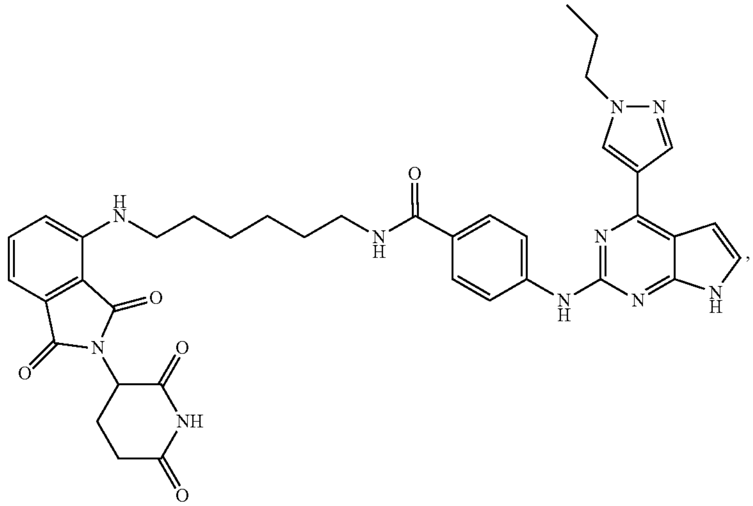
,
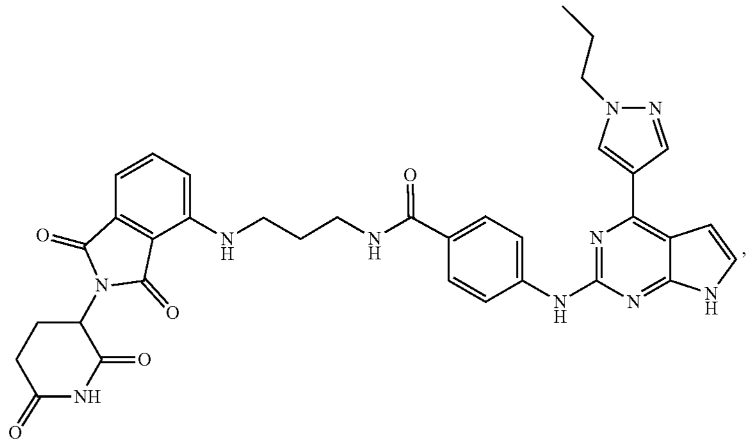
,

-continued
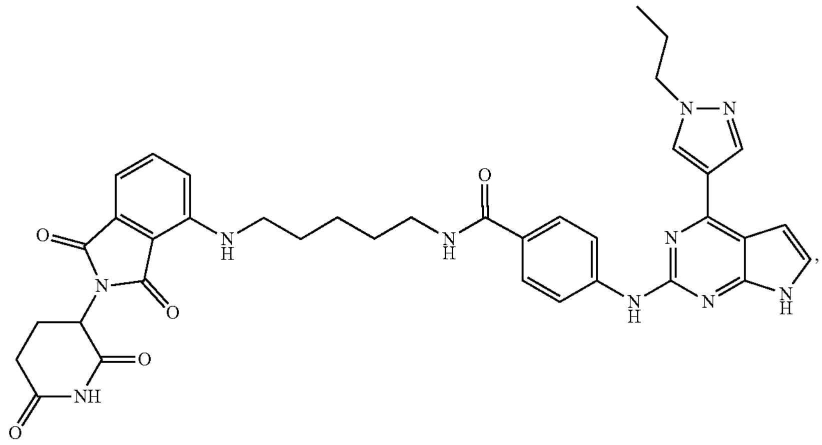
,
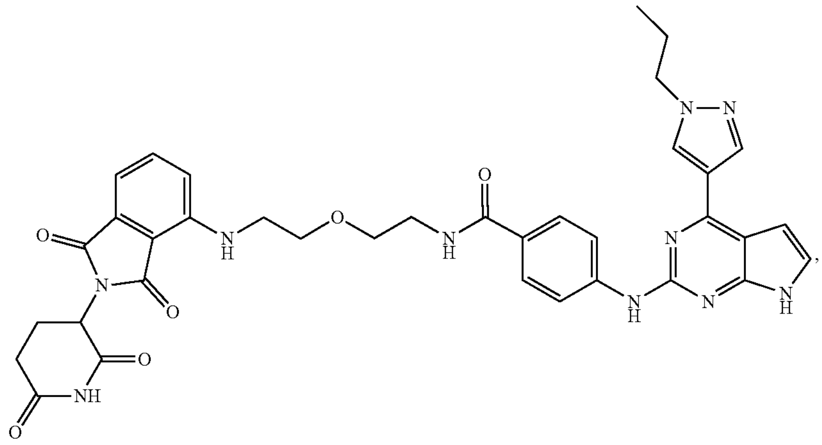 [SMILES: CCCn1cc(-c2nc(Nc3ccc(C(=O)NCCCCCNc4cccc5c4C(=O)N(C4CCC(=O)NC4=O)C5=O)cc3)nc3[nH]ccc23)cn1]
,
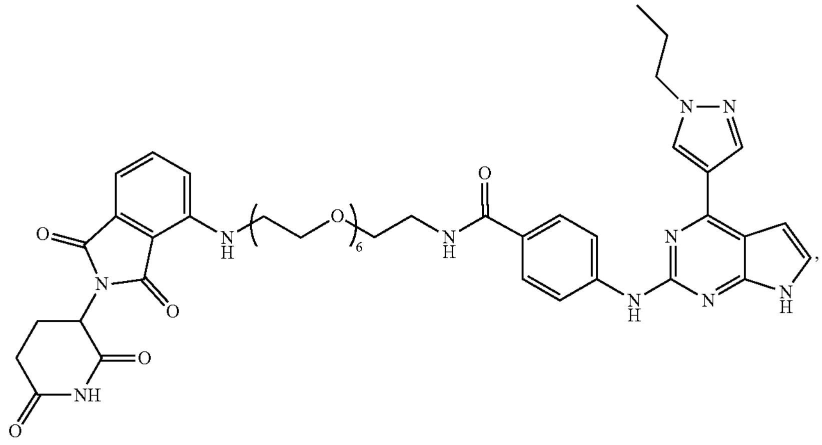
,

-continued
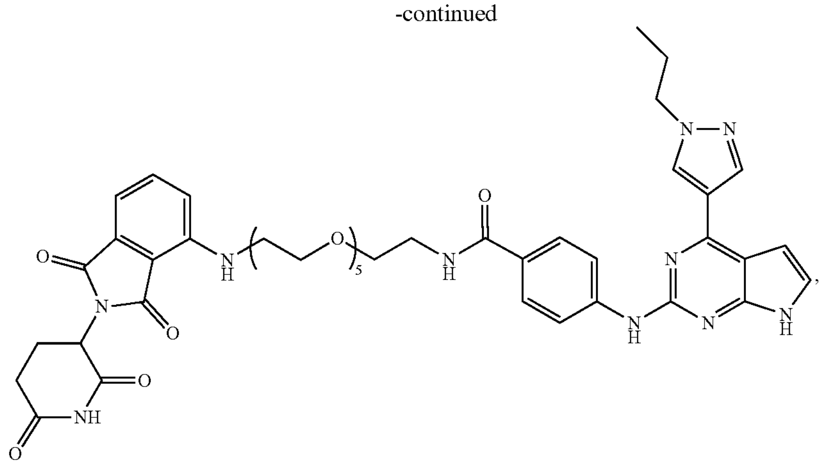
,
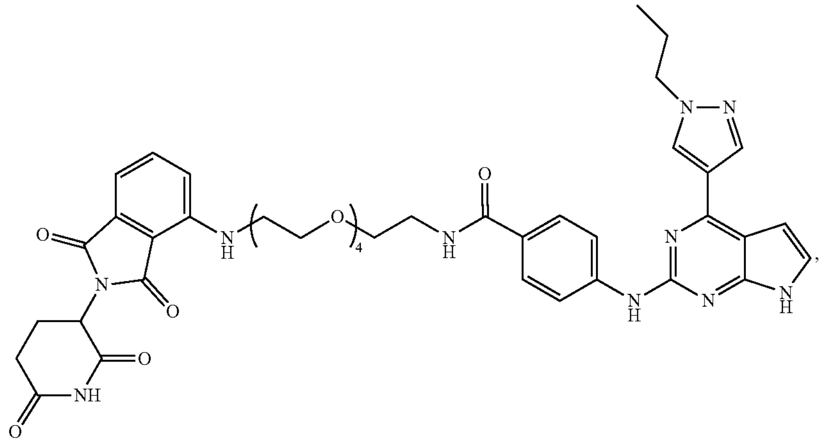
,
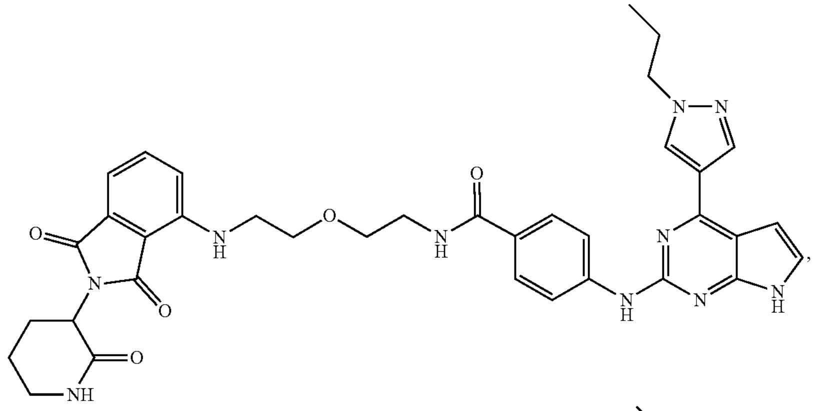
,
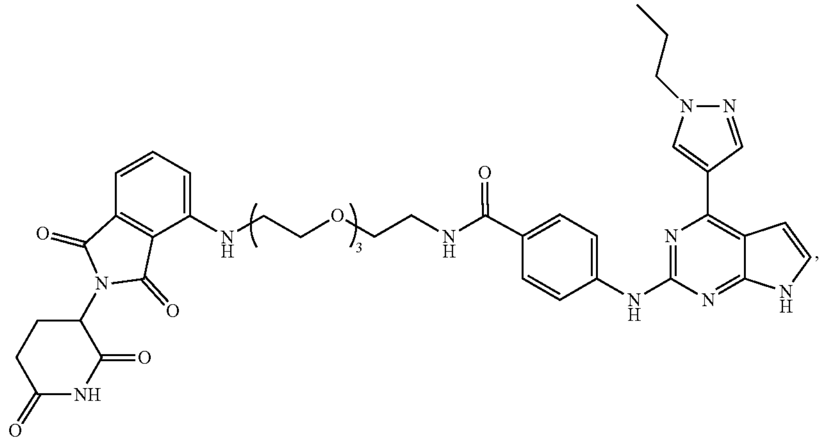
,

-continued
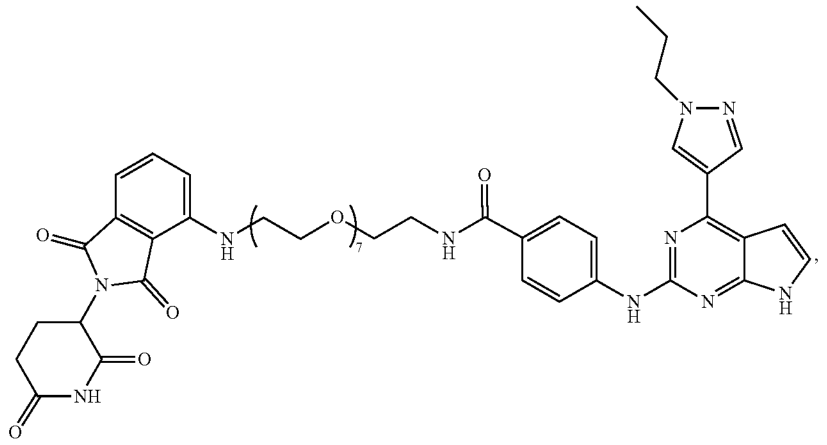
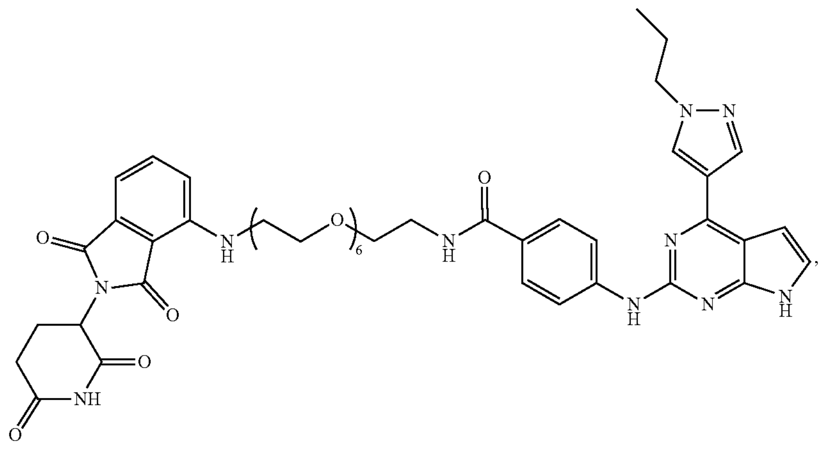
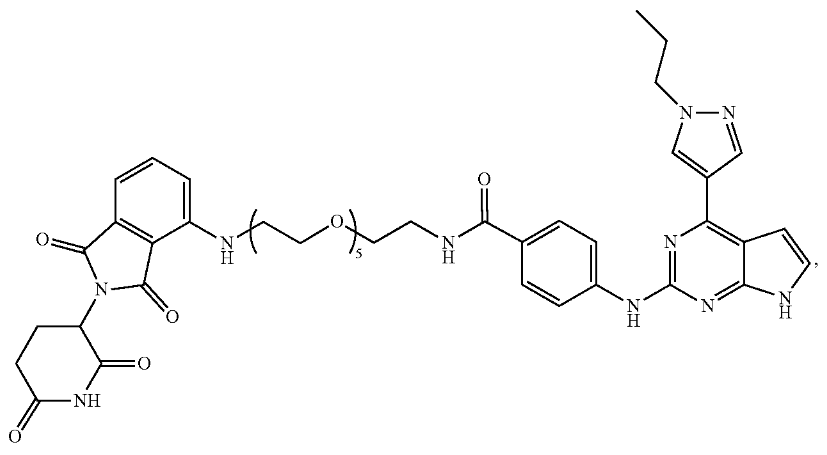

-continued
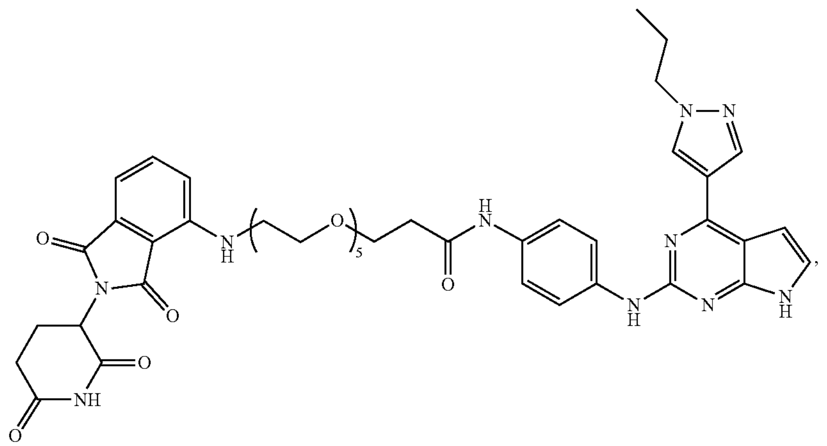
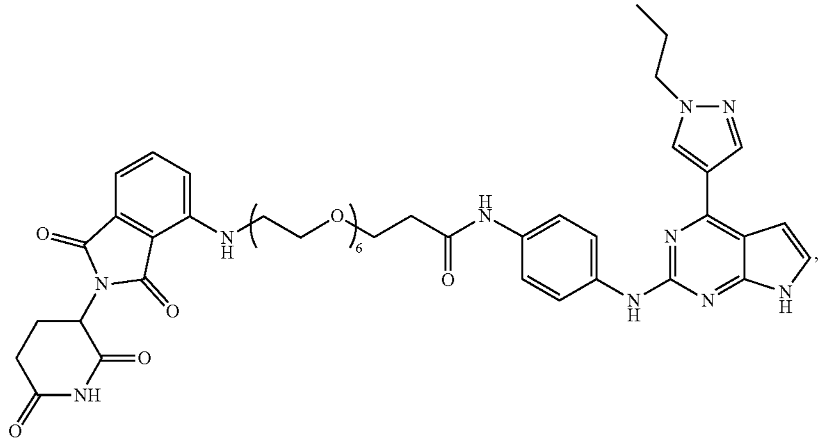
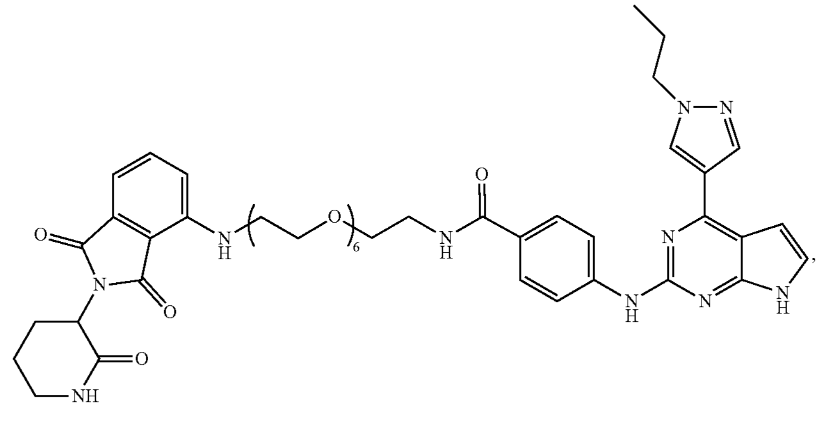
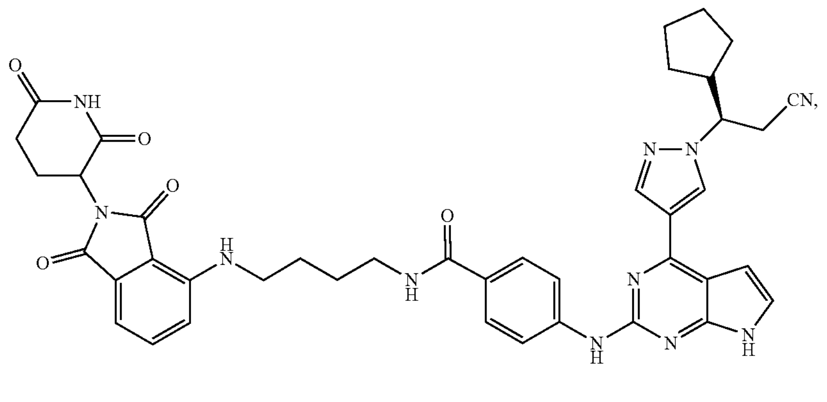

-continued
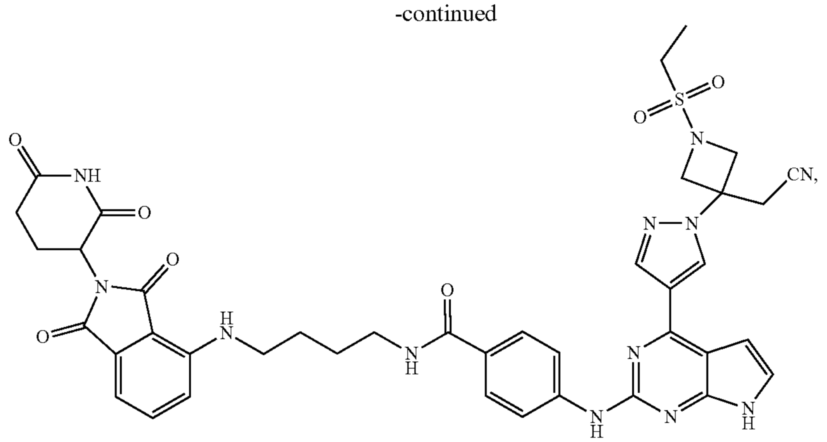
and
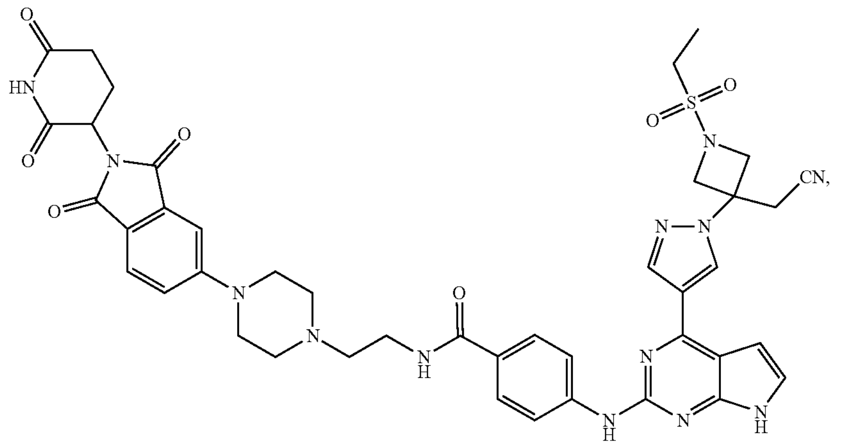
or a pharmaceutically acceptable salt thereof.
In one aspect, a compound can be present as one or more of the following structures:
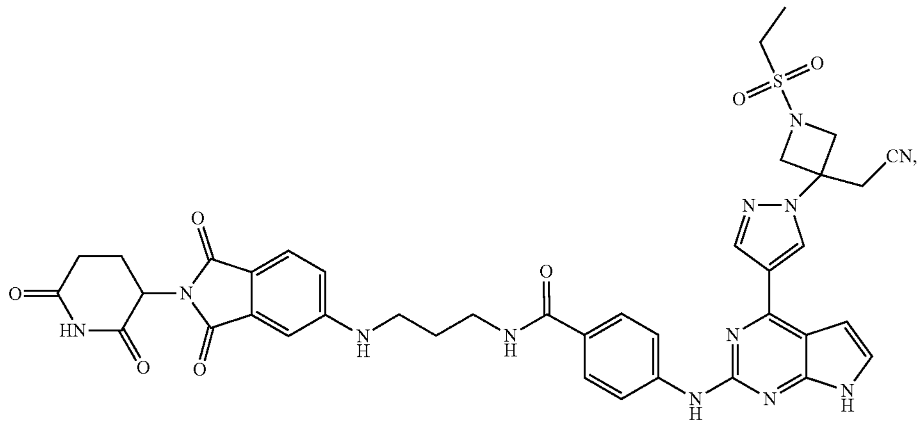

-continued
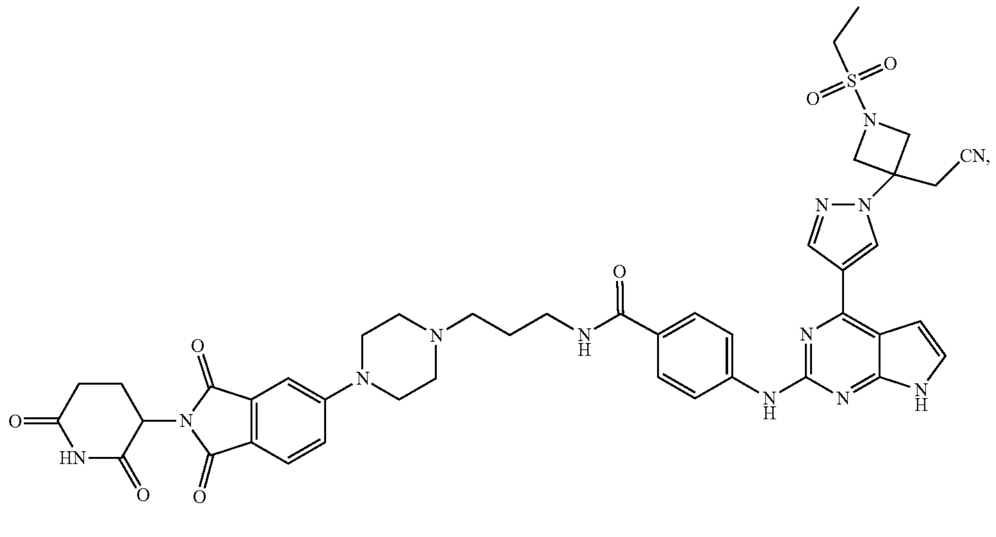
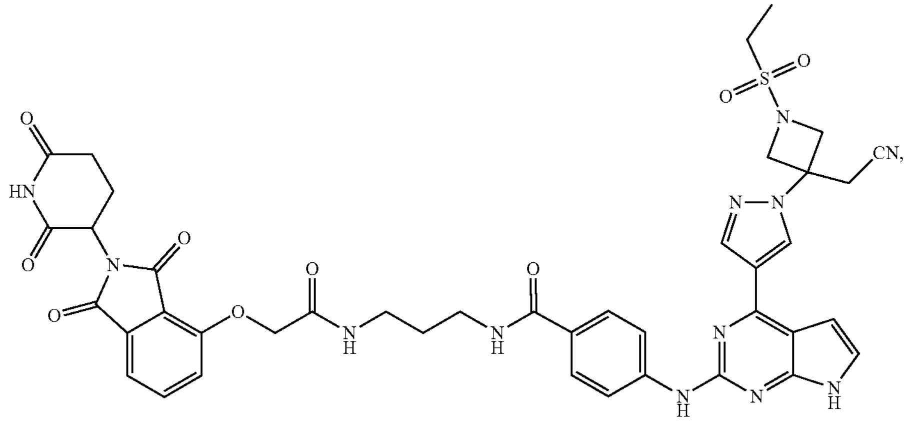
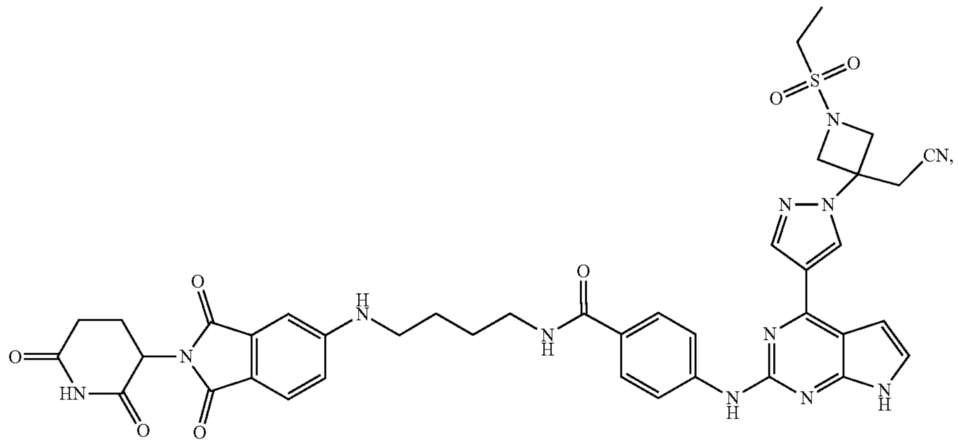
and

-continued

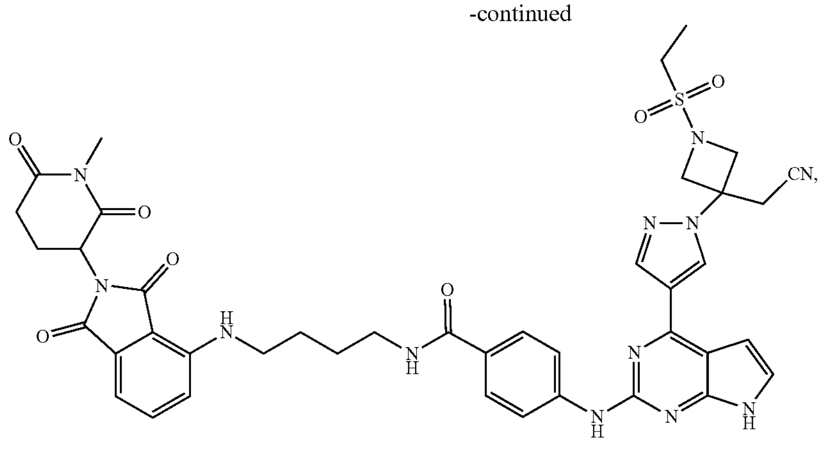

or a pharmaceutically acceptable salt thereof.

C. METHODS OF MAKING A COMPOUND

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Routes I-V, as described and exemplified below. The following examples are provided so that the invention might be more fully understood, are illustrative only, and should not be construed as limiting.

1. Route I

In one aspect, the compounds disclosed herein can be prepared as shown below.

SCHEME 1A.

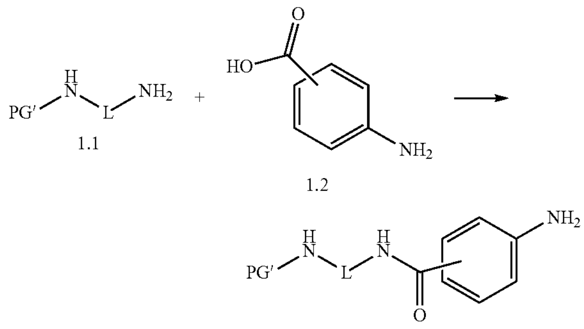

1.1 1.2 1.3

Compounds are represented in generic form, where PG' is an amine protecting group, and with other substituents as noted in compound descriptions elsewhere herein. A more specific example is set forth below.

SCHEME 1B.

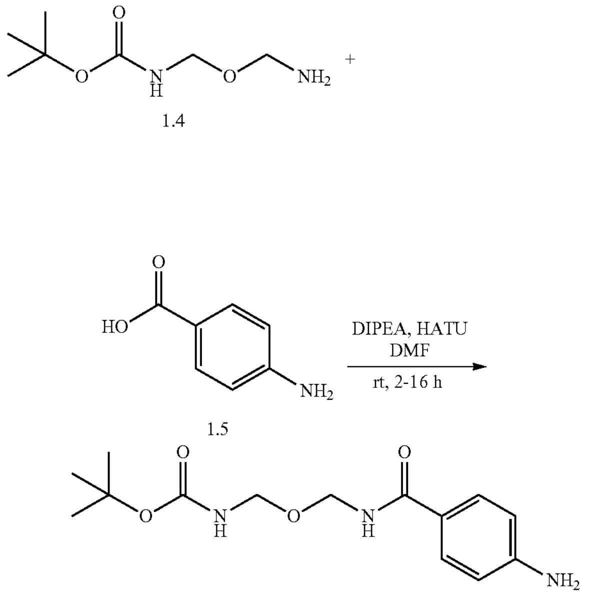

1.4 1.5 1.6

In one aspect, compounds of type 1.6, and similar compounds, can be prepared according to reaction Scheme 1B above. Thus, compounds of type 1.6 can be prepared by a coupling reaction between an appropriate amine, e.g., 1.4 as shown above, and an appropriate carboxylic acid, e.g., 1.5 as shown above. Appropriate amines and appropriate carboxylic acids are commercially available or prepared by methods known to one skilled in the art. The coupling reaction is carried out in the presence of an appropriate coupling agent, e.g., 1-[bis(dimethylamino)methylene]-1H-1,2,3-triazolo[4,5-b]pyridinium 3-oxid hexafluorophosphate (HATU), and an appropriate base, e.g., diisopropylethylamine (DIPEA), in an appropriate solvent, e.g., dimethylformamide, for an appropriate period of time, e.g., 2 to 16 hours. As can be appreciated by one skilled in the art, the above reaction provides an example of a generalized approach wherein compounds similar in structure to the specific reactants above (compounds similar to compounds of type 1.1 and 1.2), can be substituted in the reaction to provide amide derivatives similar to Formula 1.6.

2. Route II
In one aspect, the compounds disclosed herein can be prepared as shown below.
SCHEME 2A.
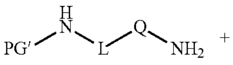
2.1
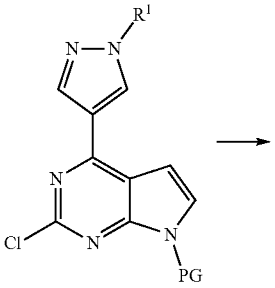
2.2
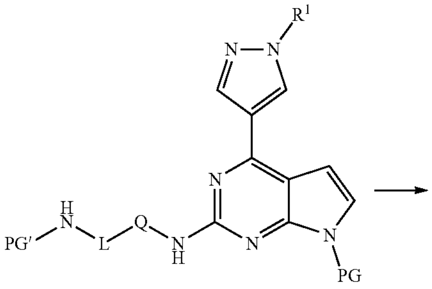
2.3
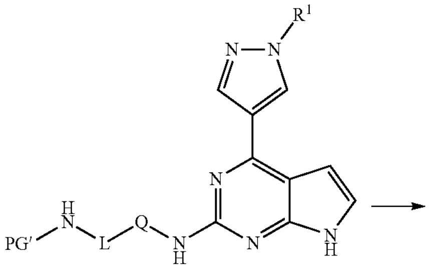
2.4
-continued
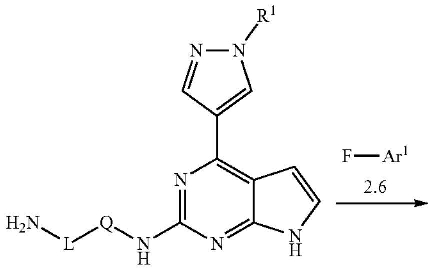
2.5
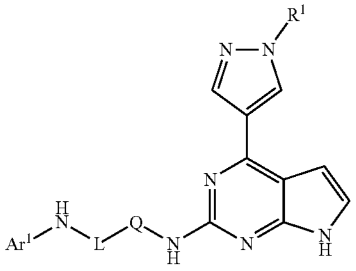
2.7
Compounds are represented in generic form, where PG and PG' are independently amine protecting groups, and with other substituents as noted in compound descriptions elsewhere herein. A more specific example is set forth below.
SCHEME 2B.
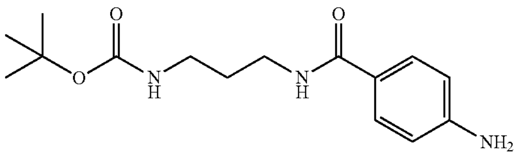
2.8
+
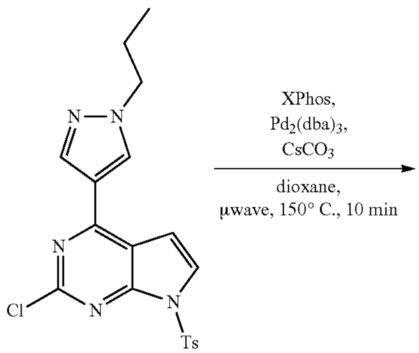
2.9

-continued

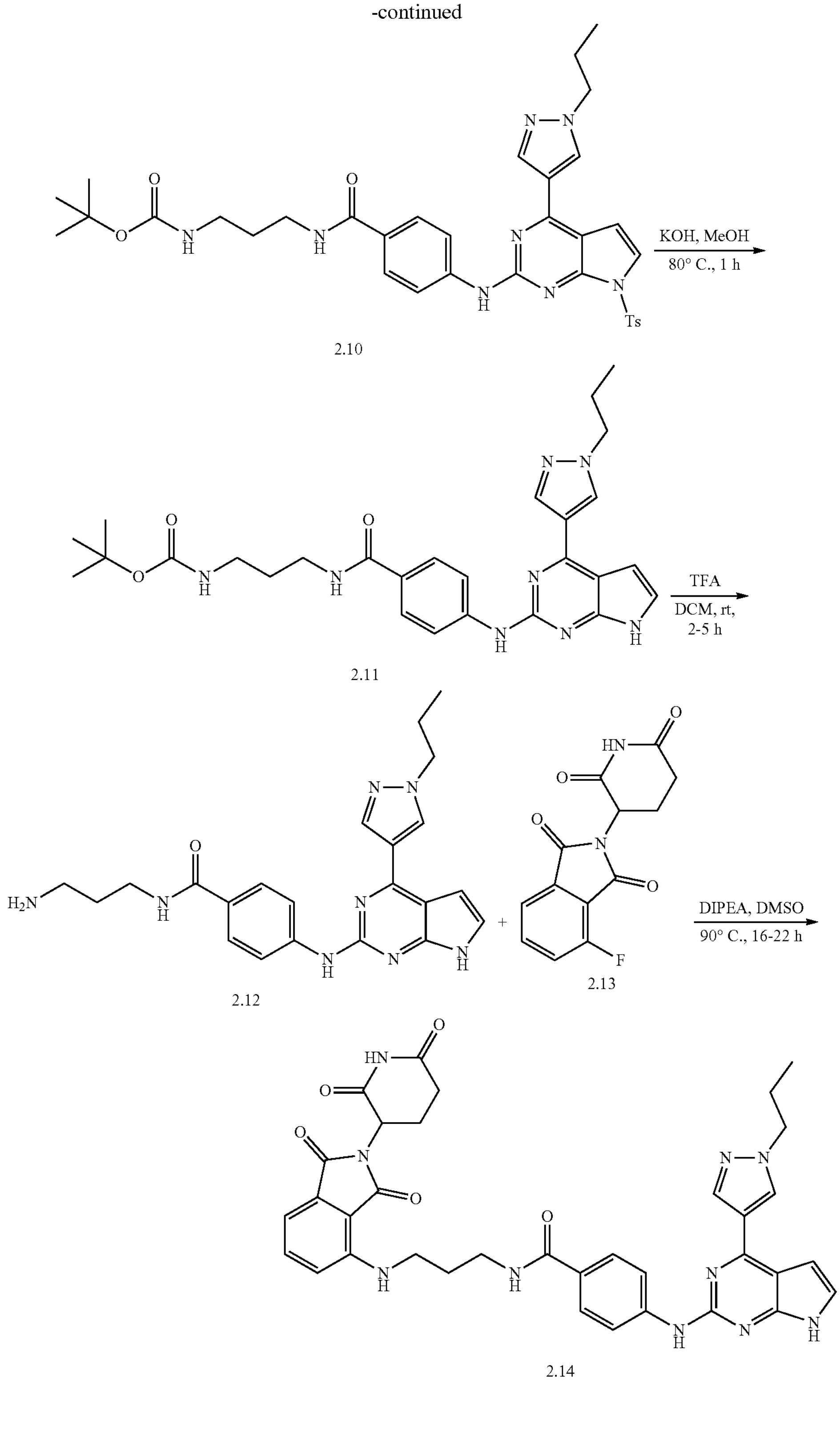

2.10, 2.11, 2.12, 2.13, 2.14

In one aspect, compounds of type 2.14, and similar compounds, can be prepared according to reaction Scheme 2B above. Thus, compounds of type 2.10 can be prepared by a coupling reaction between an appropriate amine, e.g., 2.8 as shown above, and an appropriate aryl halide, e.g., 2.9 as shown above. Appropriate aryl halides are commercially available or prepared by methods known to one skilled in the art. The coupling reaction is carried out in the presence of an appropriate catalyst, e.g., tris(dibenzylideneacetone)dipalladium(0), an appropriate ligand, e.g., 2-dicyclohexylphosphino-2',4',6'-triisopropylbiphenyl (XPhos), and an appropriate base, e.g., cesium carbonate, in an appropriate solvent, e.g., dioxane, at an appropriate temperature, e.g., 150° C., for an appropriate period of time, e.g., 10 minutes under microwave irradiation. Compounds of type 2.11 can be prepared by deprotection of an appropriate protected secondary amine, e.g., 2.10 as shown above. The deprotection is carried out in the presence of an appropriate deprotecting agent, e.g., a base such as potassium hydroxide, in an appropriate solvent, e.g., methanol, at an appropriate temperature, e.g., 80° C., for an appropriate period of time, e.g., 1 hour. Compounds of type 2.12 can be prepared by deprotection of an appropriate protected primary amine, e.g., 2.11 as shown above. The deprotection is carried out in the presence of an appropriate deprotecting agent, e.g., an acid such as trifluoroacetic acid, in an appropriate solvent, e.g., dichloromethane, for an appropriate period of time, e.g., 2 to 5 hours. Compounds of type 2.14 can be prepared by by a coupling reaction between an appropriate amine, e.g., 2.12 as shown above, and an appropriate aryl halide, e.g., 2.13 as shown above. Appropriate aryl halides are commercially available or prepared by methods known to one skilled in the art. The coupling reaction is carried out in the presence of an appropriate base, e.g., diisopropylethylamine (DIPEA), in an appropriate solvent, e.g., dimethylsulfoxide, at an appropriate temperature, e.g., 90° C., for an appropriate period of time, e.g., 16 to 22 hours. As can be appreciated by one skilled in the art, the above reaction provides an example of a generalized approach wherein compounds similar in structure to the specific reactants above (compounds similar to compounds of type 2.1, 2.2, 2.3, 2.4, and 2.5), can be substituted in the reaction to provide substituted PROTAC derivatives similar to Formula 2.6.

3. Route III

In one aspect, the compounds disclosed herein can be prepared as shown below.

SCHEME 3A.

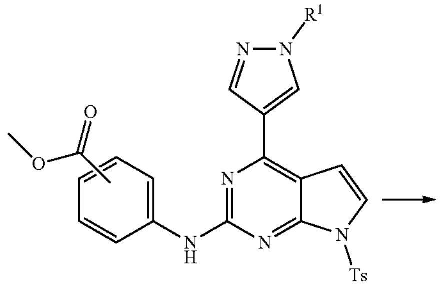

3.1

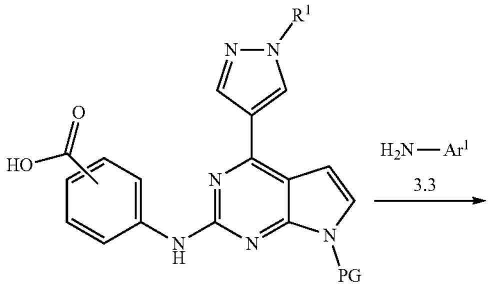

3.2

-continued

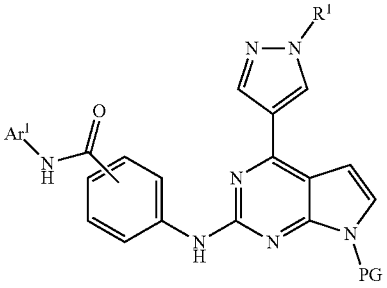

3.4

Compounds are represented in generic form, where PG is an amine protecting group, and with other substituents as noted in compound descriptions elsewhere herein. A more specific example is set forth below.

SCHEME 3B.

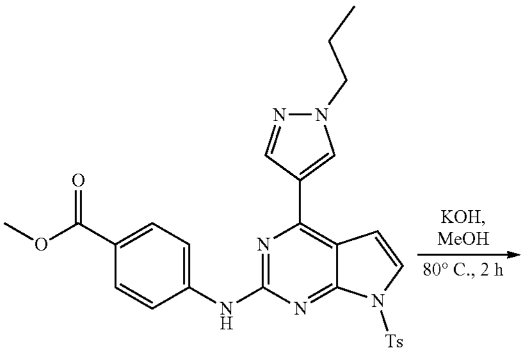

3.5

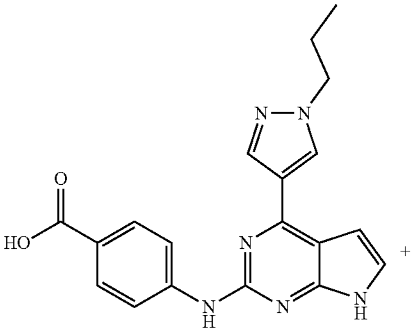

3.6

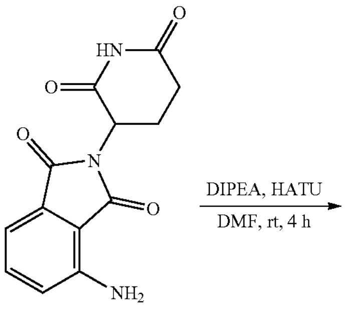

3.7

-continued

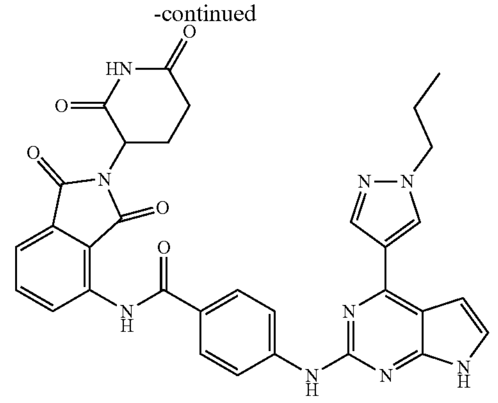

3.8

In one aspect, compounds of type 3.8, and similar compounds, can be prepared according to reaction Scheme 3B above. Thus, compounds of type 3.6 can be prepared by saponification of an appropriate ester, e.g., 3.5 as shown above. Appropriate esters are commercially available or prepared by methods known to one skilled in the art. The saponification is carried out in the presence of an appropriate base, e.g., potassium hydroxide, in an appropriate solvent, e.g., methanol, at an appropriate temperature, e.g., 80° C., for an appropriate period of time, e.g., 2 hours. Compounds of type 3.8 can be prepared by a coupling reaction between an appropriate carboxylic acid, e.g., 3.6 as shown above, and an appropriate amine, e.g., 3.7 as shown above. Appropriate amines are commercially available or prepared by methods known to one skilled in the art. The coupling reaction is carried out in the presence of an appropriate coupling agent, e.g., 1-[bis(dimethylamino)methylene]-1H-1,2,3-triazolo[4,5-b]pyridinium 3-oxid hexafluorophosphate (HATU), and an appropriate base, e.g., diisopropylethylamine (DIPEA), in an appropriate solvent, e.g., dimethylformamide, for an appropriate period of time, e.g., 4 hours. As can be appreciated by one skilled in the art, the above reaction provides an example of a generalized approach wherein compounds similar in structure to the specific reactants above (compounds similar to compounds of type 3.1, 3.2, and 3.3), can be substituted in the reaction to provide substituted PROTAC derivatives similar to Formula 3.4.

4. Route IV

In one aspect, the compounds disclosed herein can be prepared as shown below.

SCHEME 4A.

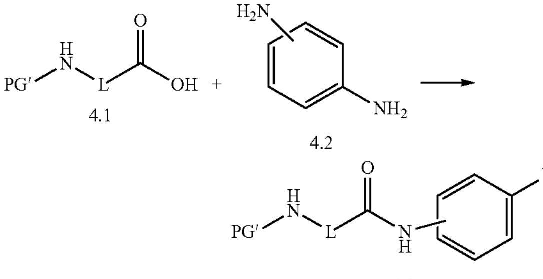

4.1 4.2 4.3

Compounds are represented in generic form, where PG' is an amine protecting group, and with other substituents as noted in compound descriptions elsewhere herein. A more specific example is set forth below.

SCHEME 4B.

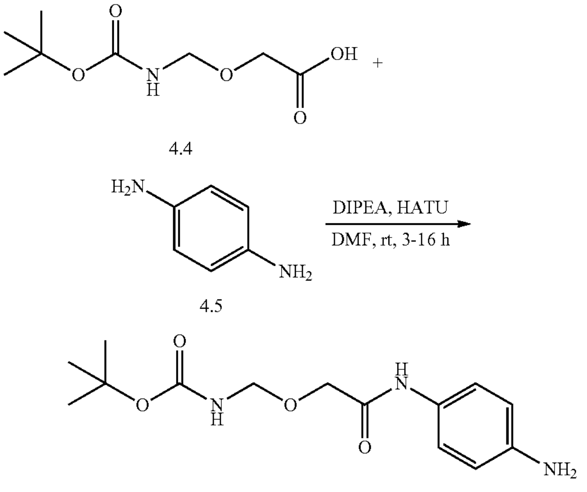

4.4 4.5 4.6

In one aspect, compounds of type 1.6, and similar compounds, can be prepared according to reaction Scheme 4B above. Thus, compounds of type 4.6 can be prepared by a coupling reaction between an appropriate carboxylic acid, e.g., 4.4 as shown above, and an appropriate amine, e.g., 4.5 as shown above. Appropriate amines and appropriate carboxylic acids are commercially available or prepared by methods known to one skilled in the art. The coupling reaction is carried out in the presence of an appropriate coupling agent, e.g., 1-[bis(dimethylamino)methylene]-1H-1,2,3-triazolo[4,5-b]pyridinium 3-oxid hexafluorophosphate (HATU), and an appropriate base, e.g., diisopropylethylamine (DIPEA), in an appropriate solvent, e.g., dimethylformamide, for an appropriate period of time, e.g., 3 to 16 hours. As can be appreciated by one skilled in the art, the above reaction provides an example of a generalized approach wherein compounds similar in structure to the specific reactants above (compounds similar to compounds of type 4.1 and 4.2), can be substituted in the reaction to provide amide derivatives similar to Formula 4.6.

5. Route V

In one aspect, the compounds disclosed herein can be prepared as shown below.

SCHEME 5A.

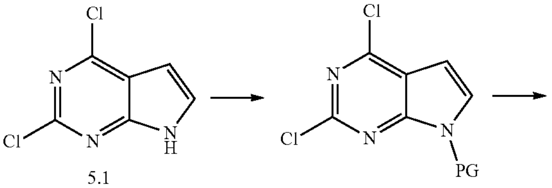

5.1 5.2

-continued
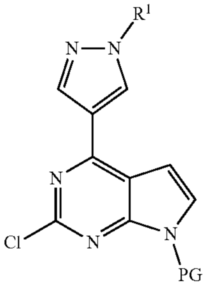
5.3
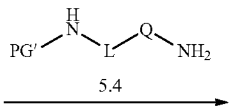
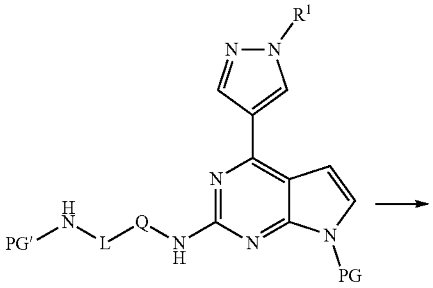
5.5
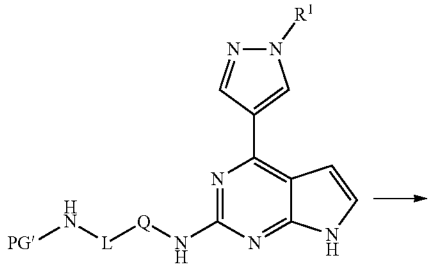
5.6
-continued
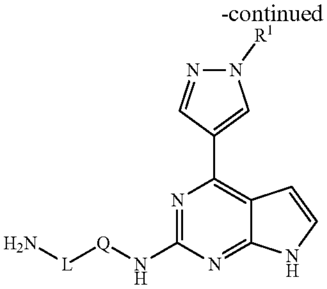
5.7
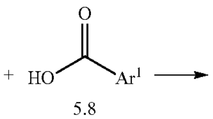
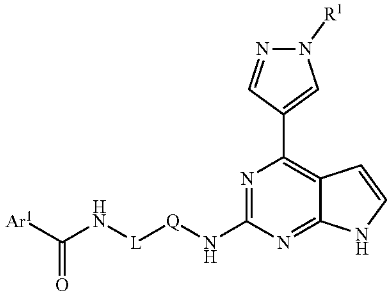
5.9
Compounds are represented in generic form, where PG is an amine protecting group, and with other substituents as noted in compound descriptions elsewhere herein. A more specific example is set forth below.
SCHEME 5B.
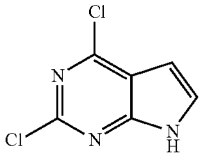
5.10
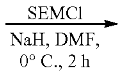
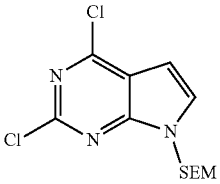
5.11
+
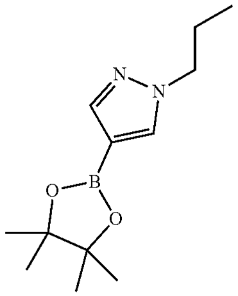
5.12
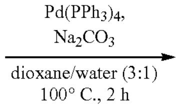

-continued
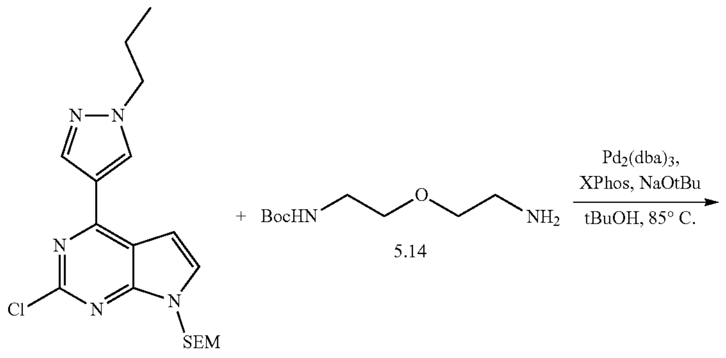
5.13 5.14
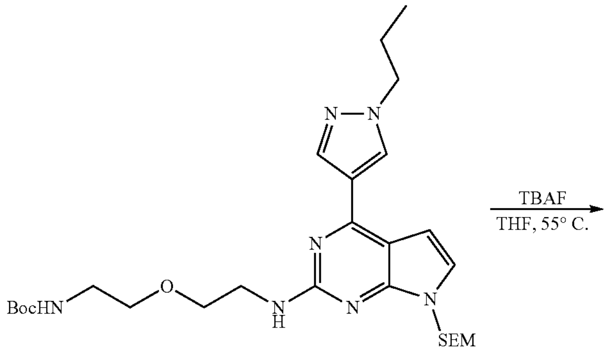
5.15
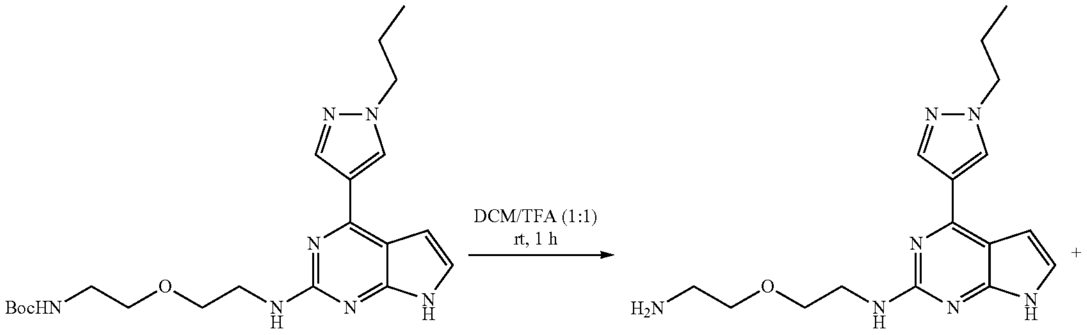
5.16 5.17
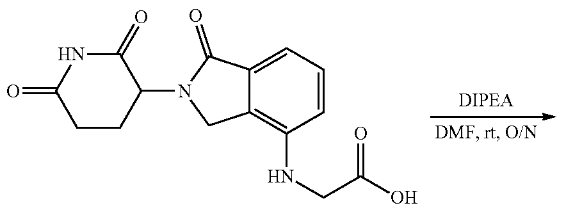
5.18

-continued

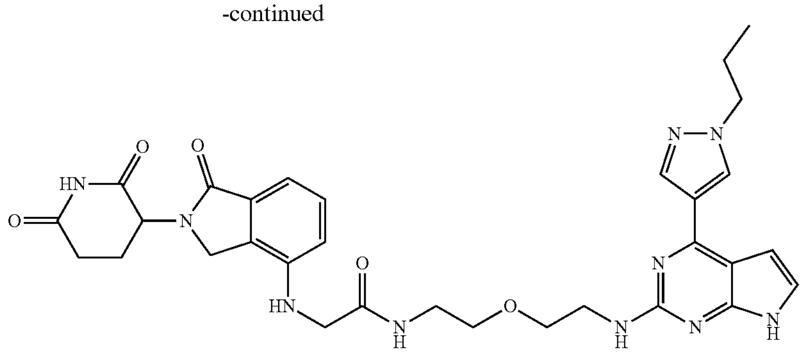

5.19

In one aspect, compounds of type 5.19, and similar compounds, can be prepared according to reaction Scheme 5B above. Thus, compounds of type 5.11 can be prepared by protection of an appropriate pyrrolopyrimidine, e.g., 5.10 as shown above. Appropriate pyrrolopyrimidines are commercially available or prepared by methods known to one skilled in the art. The protection can be carried out in the presence of an appropriate protecting agent, e.g., 2-(trimethylsilyl) ethoxymethyl chloride (SEMC1), and an appropriate base, e.g., sodium hydride, in an appropriate solvent, e.g., dimethylformamide, at an appropriate temperature, e.g., 0° C., for an appropriate period of time, e.g., 2 hours. Compounds of type 5.13 can be prepared by an appropriate coupling reaction between an appropriate aryl halide, e.g., 5.11 as shown above, and an appropriate boronic ester, e.g., 5.12 as shown above. Appropriate boronic esters are commercially available or prepared by methods known to one skilled in the art. The coupling reaction is carried out in the presence of an appropriate catalyst, e.g., tetrakis(triphenylphosphine)palladium(0), and an appropriate base, e.g., sodium carbonate, in an appropriate solvent system, e.g., dioxane:water (3:1), at an appropriate temperature, e.g., 100° C., for an appropriate period of time, 2 hours. Compounds of type 5.15 can be prepared by an appropriate coupling reaction between an appropriate aryl halide, e.g., 5.13 as shown above, and an appropriate amine, e.g., 5.14 as shown above. Appropriate amines are commercially available or prepared by methods known to one skilled in the art. The coupling reaction is carried out in the presence of an appropriate catalyst, e.g., tris(dibenzylideneacetone)dipalladium(0), an appropriate ligand, e.g., 2-dicyclohexylphosphino-2',4',6'-triisopropylbiphenyl (XPhos), and an appropriate base, e.g., sodium tert-butoxide, in an appropriate solvent, e.g., tert-butanol, at an appropriate temperature, e.g., 85° C. Compounds of type 5.16 can be prepared by deprotection of an appropriate protected secondary amine, e.g., 5.15 as shown above. The deprotection is carried out in the presence of an appropriate deprotecting agent, e.g., tetrabutylammonium fluoride (TBAF), in an appropriate solvent, e.g., tetrahydrofuran, at an appropriate temperature, e.g., 55° C. Compounds of type 5.17 can be prepared by deprotection of an appropriate protected primary amine, e.g., 5.16 as shown above. The deprotection is carried out in the presence of an appropriate deprotecting agent, e.g., dichloromethane/trifluoroacetic acid (1:1), for an appropriate period of time, e.g., 1 hour. Compounds of type 5.19 can be prepared by a coupling reaction between an appropriate amine, e.g., 5.17 as shown above, and an appropriate carboxylic acid, e.g., 5.18 as shown above. Appropriate carboxylic acids are commercially available or prepared by methods known to one skilled in the art. The coupling reaction is carried out in the presence of an appropriate base, e.g., diisopropylethylamine (DIPEA), in an appropriate solvent, e.g., dimethylformamide. As can be appreciated by one skilled in the art, the above reaction provides an example of a generalized approach wherein compounds similar in structure to the specific reactants above (compounds similar to compounds of type 5.1, 5.2, 5.3, 5.4, 5.5, 5.6, 5.7, and 5.8), can be substituted in the reaction to provide substituted PROTAC derivatives similar to Formula 5.9.

D. PHARMACEUTICAL COMPOSITIONS

In one aspect, disclosed are pharmaceutical compositions comprising a disclosed compound, or a pharmaceutically acceptable salt thereof and a pharmaceutically acceptable carrier.

Thus, in one aspect, disclosed are pharmaceutical compositions comprising a therapeutically effective amount of at least one compound having a structure represented by a formula:

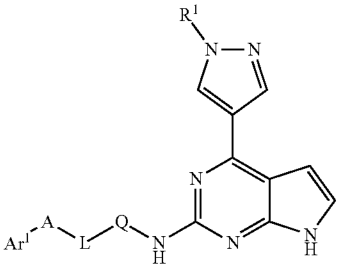

wherein A is selected from —O—, —S—, —NH—, —$CH_2$—, —O—(C1-C4 alkyl)-C(O)NH—, and a structure

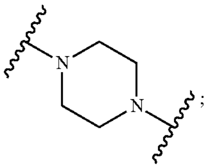

;

wherein L is selected from C2-C15 alkyl and —($CH_2CH_2O$)$_n$(C1-C4 alkyl)-; wherein n is selected from 1, 2, 3, 4, 5, 6, 7, and 8; wherein Q is selected from —NHC(O)($C_6H_4$)— and —C(O)NH($C_6H_4$)—; wherein $R^1$ is selected from C1-C8 alkyl, C1-C8 hydroxyalkyl, C1-C8 cyanoalkyl, C1-C8 aminoalkyl, and a structure selected from:

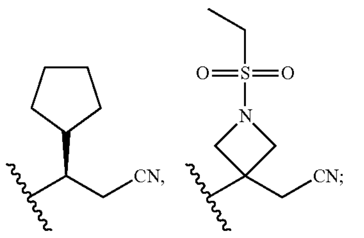
and
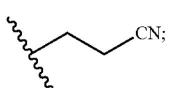

and wherein $Ar^1$ is a structure selected from:

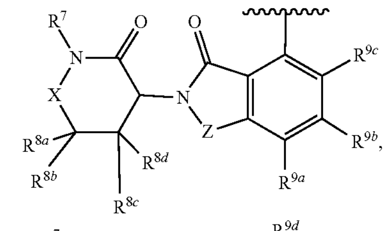
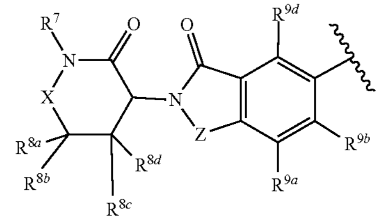
,
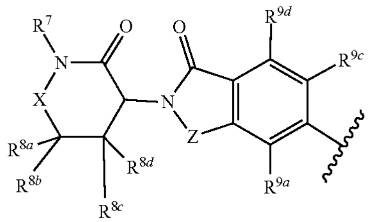
, and
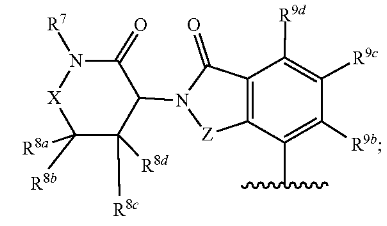

wherein X is selected from —C(O)— and —$CH_2$—; wherein Z is selected from —$CH_2$— and C(O); wherein $R^7$ is selected from hydrogen and C1-C8 alkyl; wherein each of $R^{8a}$, $R^{8b}$, $R^{8c}$, and $R^{8d}$ is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{9a}$, $R^{9b}$, $R^{9c}$, and $R^{9d}$, when present, is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

Also disclosed are pharmaceutical compositions comprising a therapeutically effective amount of at least one compound having a structure represented by a formula:

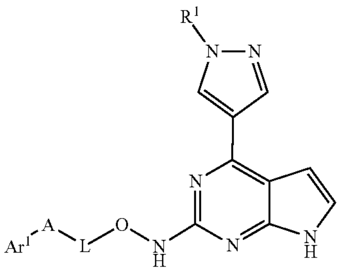

wherein A is selected from —O—, —S—, —NH—, and —$CH_2$—; wherein L is selected from C2-C15 alkyl and —$(CH_2CH_2O)_n$(C1-C4 alkyl)-; wherein n is selected from 1, 2, 3, 4, 5, 6, 7, and 8; wherein Q is selected from —NHC(O)($C_6H_4$)— and —C(O)NH($C_6H_4$)—; wherein $R^1$ is selected from C1-C8 alkyl, C1-C8 hydroxyalkyl, C1-C8 cyanoalkyl, C1-C8 aminoalkyl, and a structure selected from:

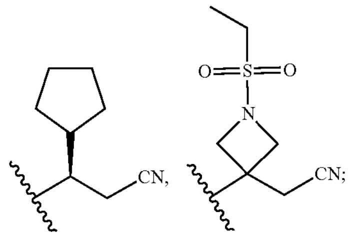
and
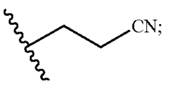

and wherein $Ar^1$ is a structure selected from:

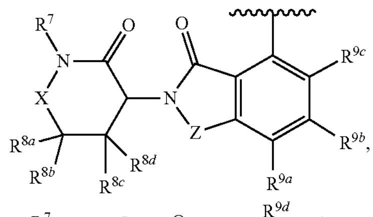
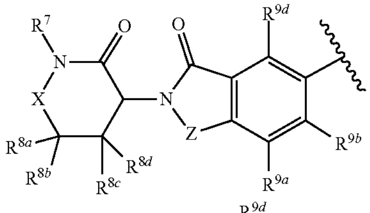
,
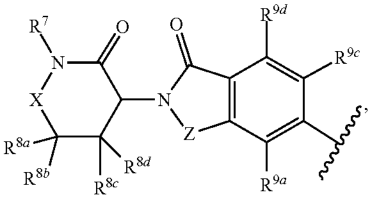
, and

-continued

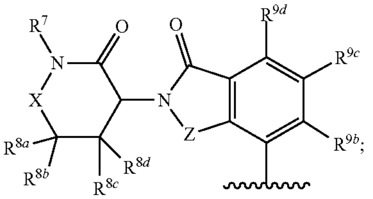

wherein X is selected from —C(O)— and —$CH_2$—; wherein Z is selected from —$CH_2$— and C(O); wherein $R^7$ is selected from hydrogen and C1-C8 alkyl; wherein each of $R^{8a}$, $R^{8b}$, $R^{8c}$, and $R^{8d}$ is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{9a}$, $R^{9b}$, $R^{9c}$, and $R^{9d}$, when present, is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, and a pharmaceutically acceptable carrier.

In one aspect, disclosed are pharmaceutical compositions comprising a therapeutically effective amount of at least one compound having a structure selected from:

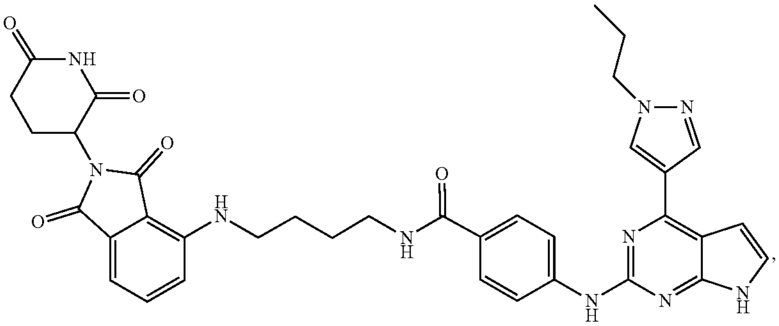

,

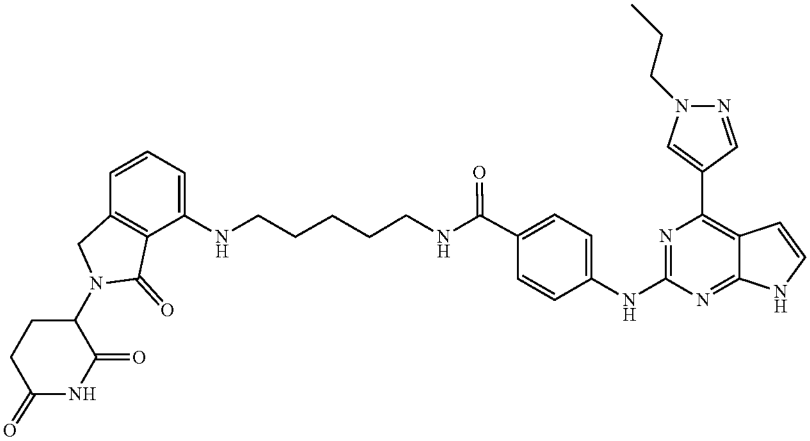

,

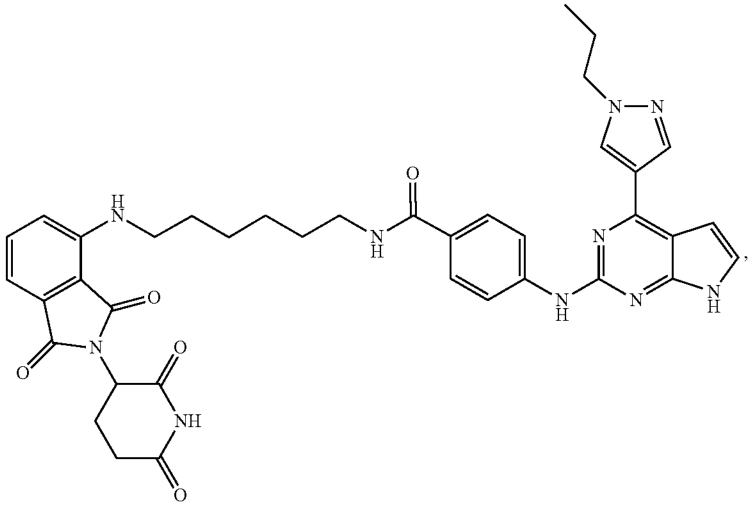

,

-continued
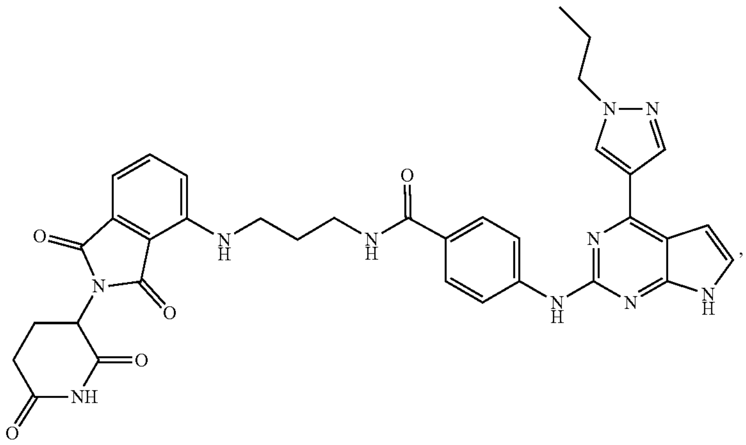
,
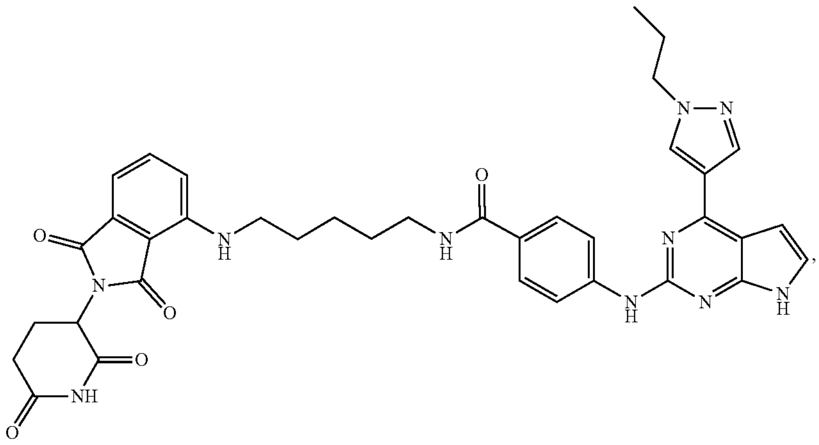 [SMILES: CCCn1cc(-c2nc(Nc3ccc(C(=O)NCCCCCNc4cccc5c4C(=O)N(C4CCC(=O)NC4=O)C5=O)cc3)nc3[nH]ccc23)cn1]
,
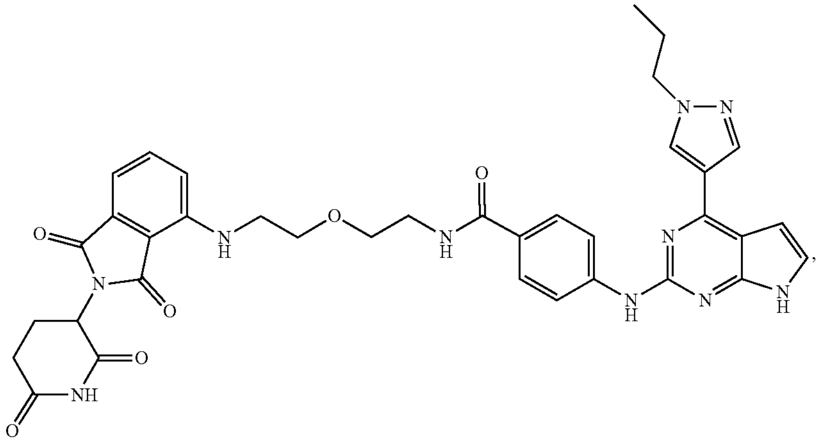
,

-continued
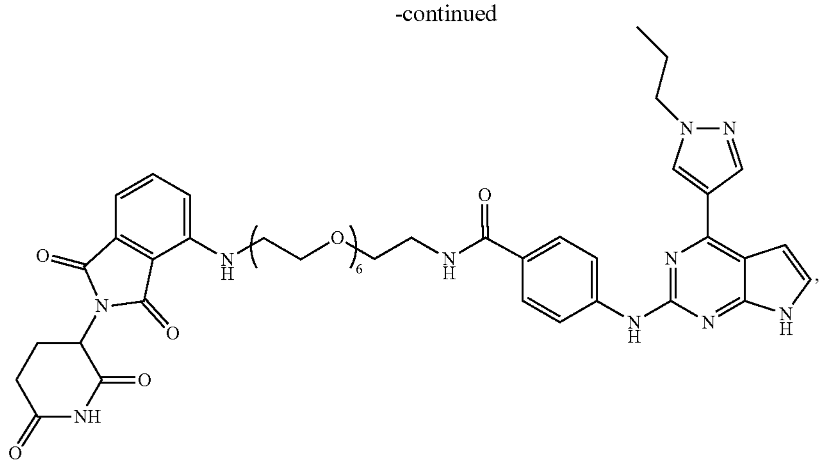
,
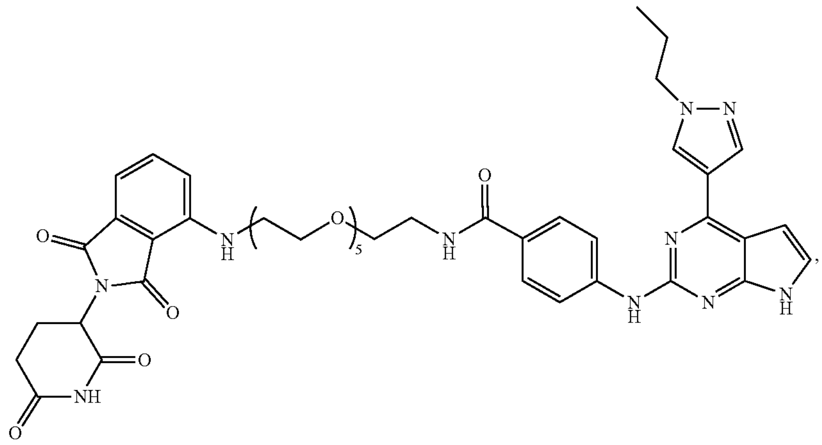
,
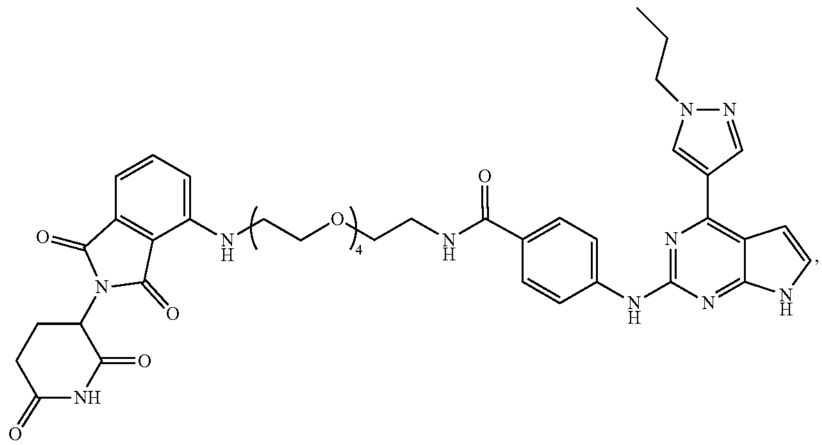
,
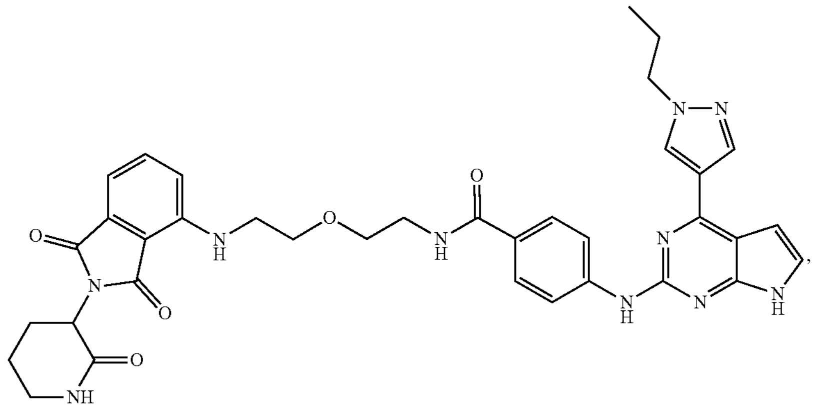
,

-continued
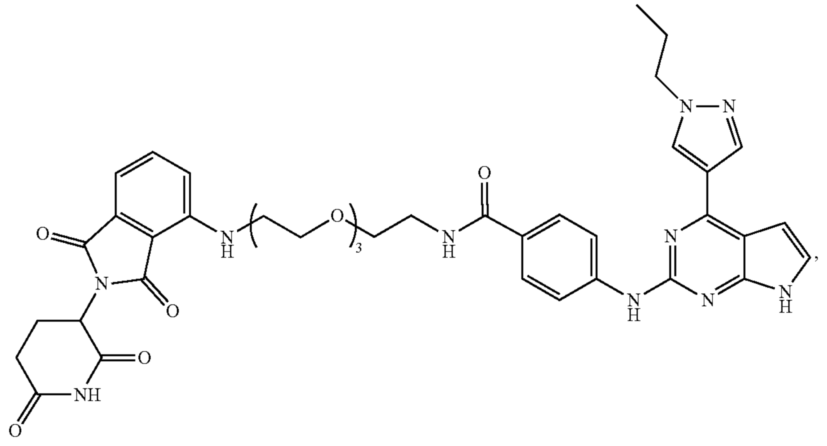
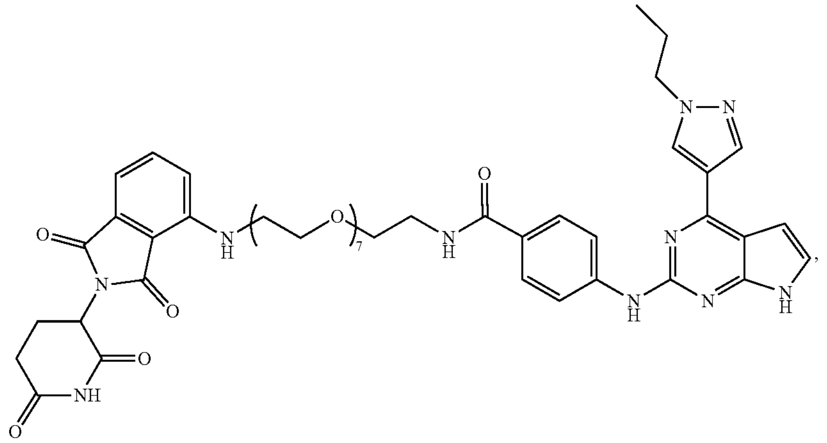
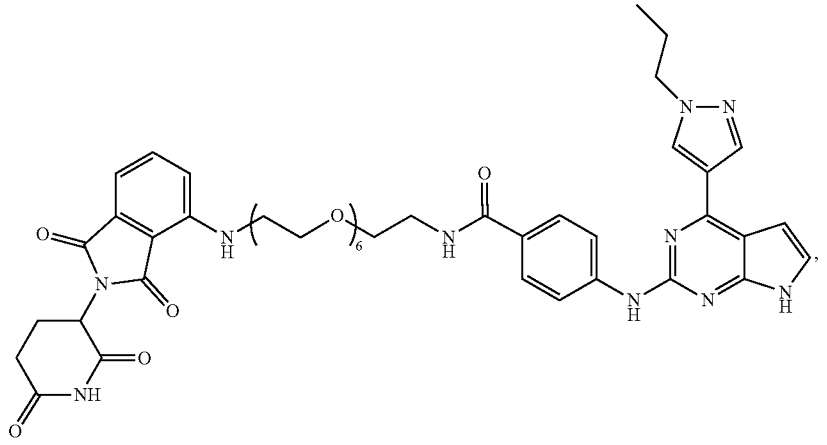

-continued
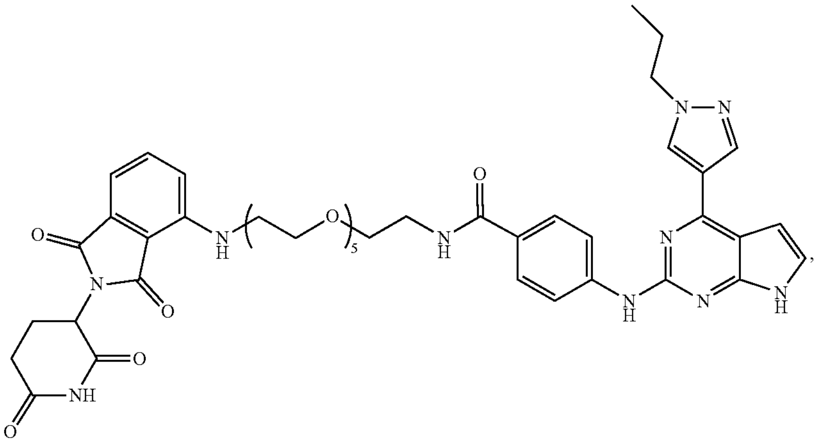
,
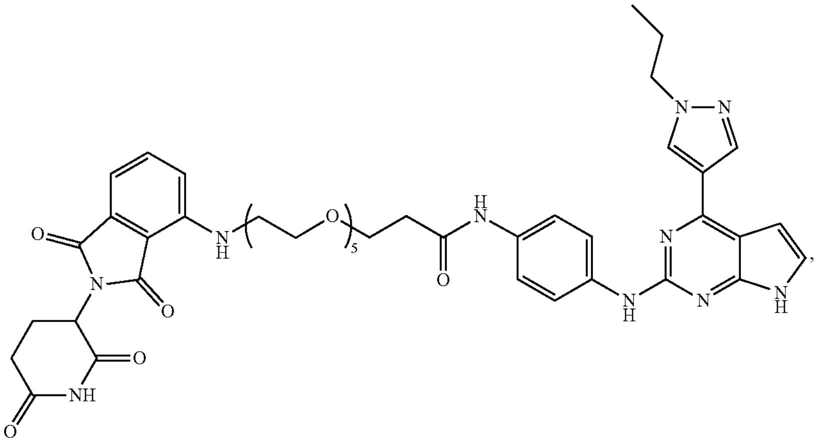
,
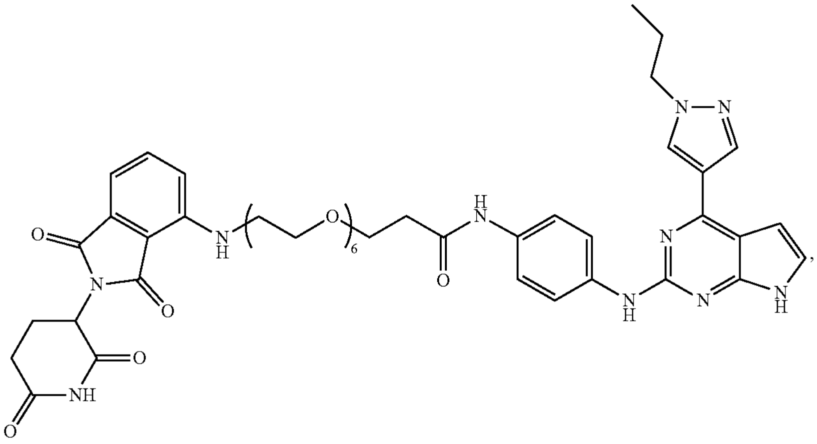
,

-continued
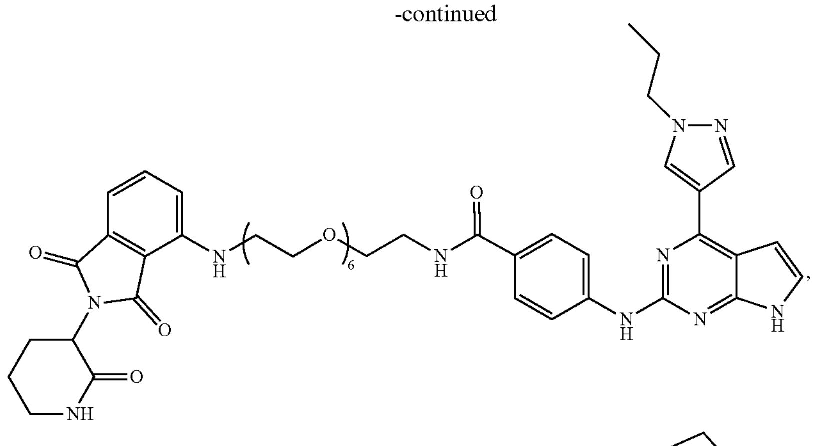
,
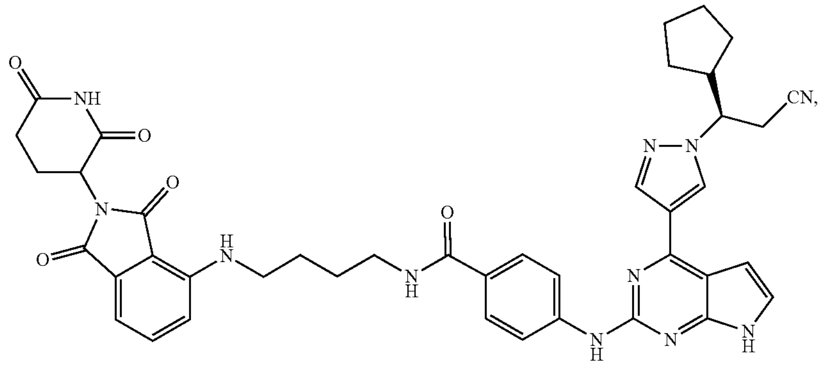
,
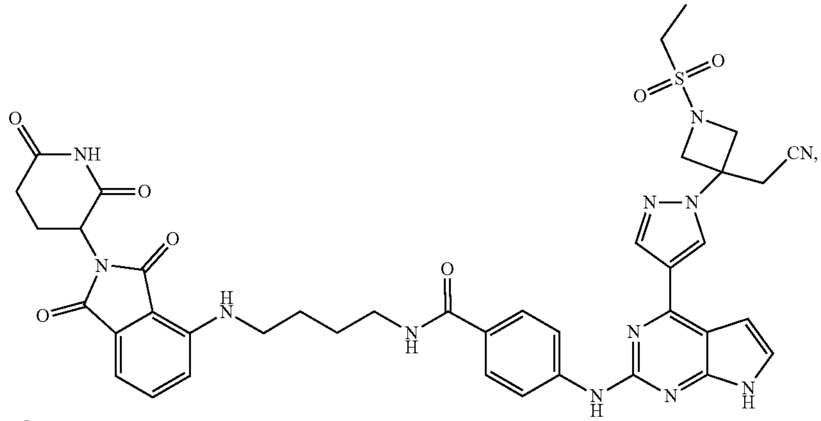
, and
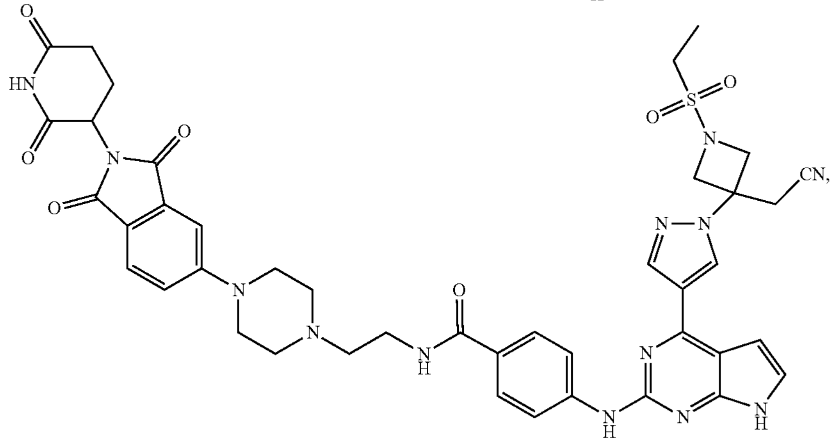
,
or a pharmaceutically acceptable salt thereof, and a pharmaceutically acceptable carrier.

In one aspect, disclosed are pharmaceutical composition comprising a therapeutically effective amount of at least one compound having a structure selected from:
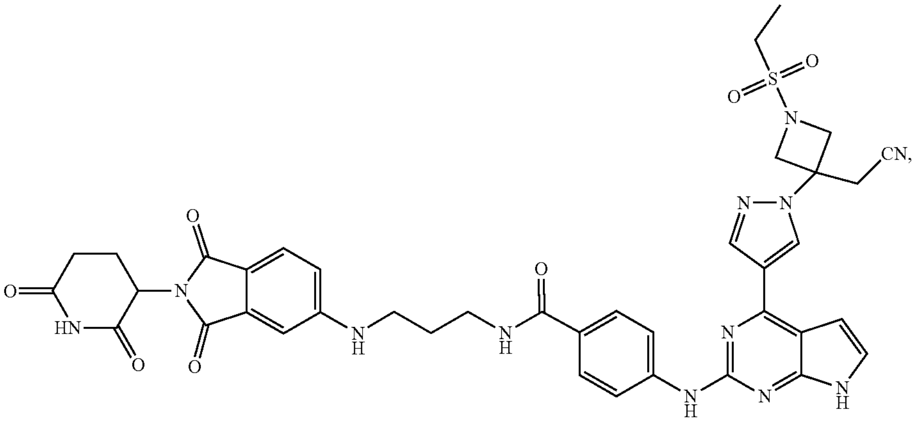
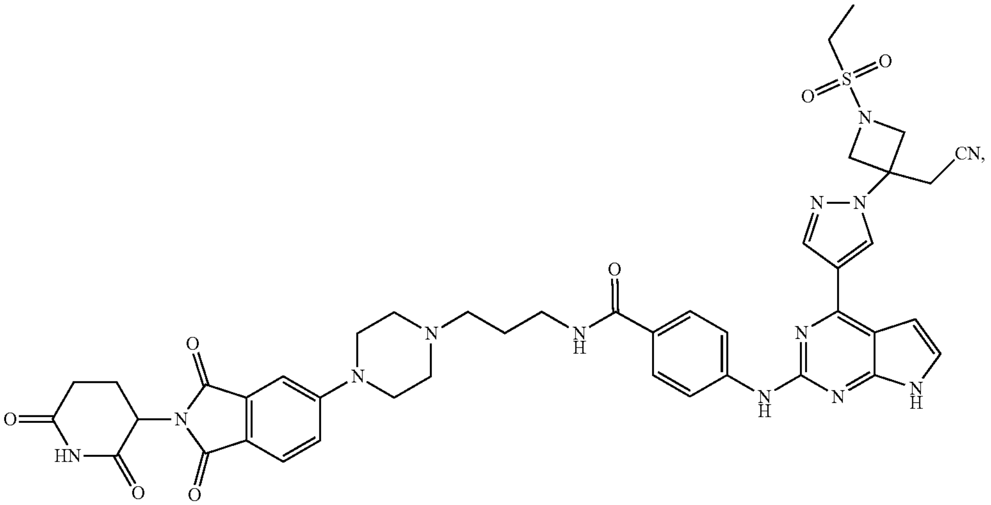
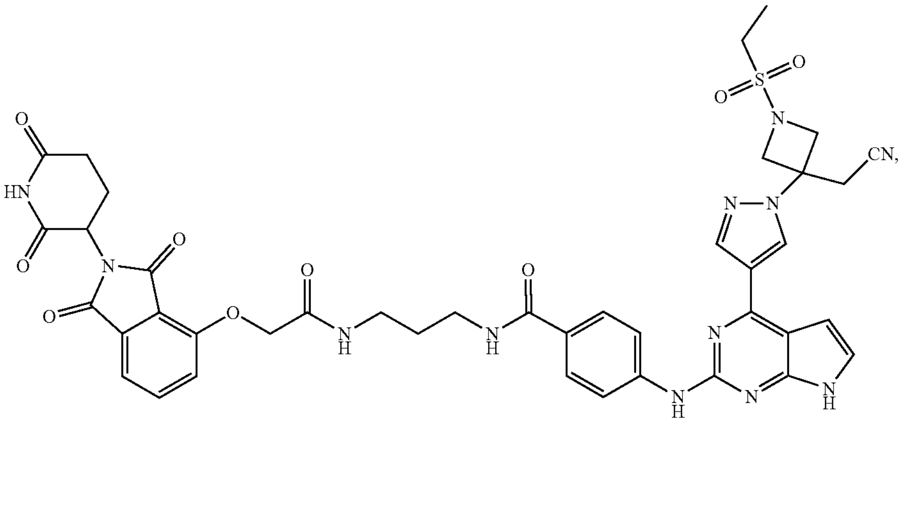

-continued

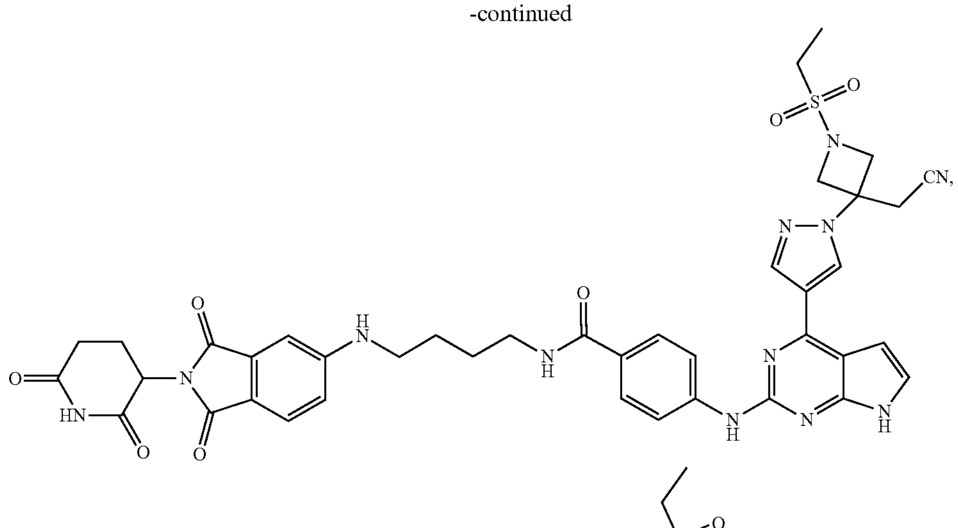

and

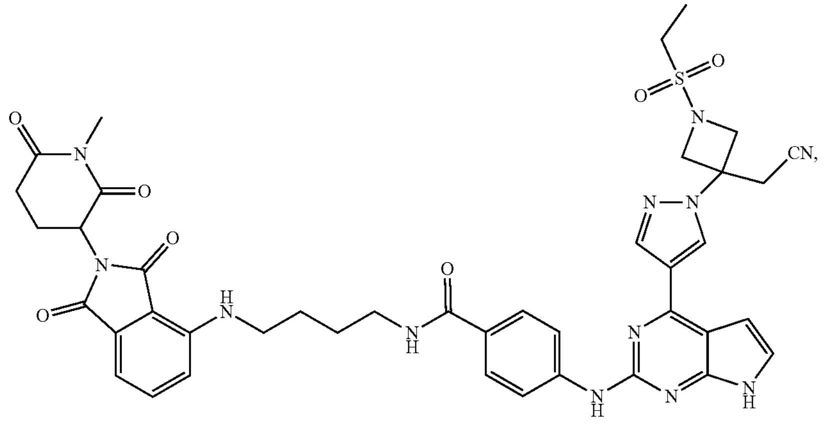

or a pharmaceutically acceptable salt thereof, and a pharmaceutically acceptable carrier.

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, PA 1990.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, an effective amount is a therapeutically effective amount. In a still further aspect, an effective amount is a prophylactically effective amount.

In a further aspect, the pharmaceutical composition is administered to a mammal. In a still further aspect, the mammal is a human. In an even further aspect, the human is a patient.

In a further aspect, the pharmaceutical composition is used to treat a disorder associated with uncontrolled cellular proliferation such as, for example, cancer, such as for example, sarcoma, a carcinoma, a hematological cancer, a solid tumor, breast cancer, cervical cancer, gastrointestinal cancer, colorectal cancer, brain cancer, skin cancer, prostate cancer, ovarian cancer, non-small cell lung carcinoma, thyroid cancer, testicular cancer, pancreatic cancer, liver cancer, endometrial cancer, melanoma, glioma, leukemia, lymphoma, chronic myeloproliferative disorder, myelodysplastic syndrome, myeloproliferative neoplasm, and plasma cell neoplasm (myeloma). In one aspect, the cancer is acute lymphoblastic leukemia.

It is understood that the disclosed compositions can be prepared from the disclosed compounds. It is also understood that the disclosed compositions can be employed in the disclosed methods of using.

E. METHODS OF TREATING A DISORDER ASSOCIATED WITH UNCONTROLLED CELLULAR PROLIFERATION

In various aspects, the compounds and compositions disclosed herein are useful for treating, preventing, ameliorating, controlling or reducing the risk of a variety of disorders associated with uncontrolled cellular proliferation, such as for example cancer, for example acute lymphoblastic leukemia. Thus, in one aspect, disclosed are methods of treating a disorder associated with uncontrolled cellular proliferation activity in a subject, the method comprising administering to the subject an effective amount of at least one disclosed compound or a pharmaceutically acceptable salt thereof.

Thus, in one aspect, disclosed are methods of treating a disorder associated with uncontrolled cellular proliferation, such as for example cancer, sarcoma, a carcinoma, a hematological cancer, a solid tumor, breast cancer, cervical cancer, gastrointestinal cancer, colorectal cancer, brain cancer, skin cancer, prostate cancer, ovarian cancer, non-small cell lung carcinoma, thyroid cancer, testicular cancer, pancreatic cancer, liver cancer, endometrial cancer, melanoma, glioma, leukemia, lymphoma, chronic myeloproliferative disorder, myelodysplastic syndrome, myeloproliferative neoplasm, and plasma cell neoplasm (myeloma), in another example acute lymphoblastic leukemia activity in a subject, the method comprising administering to the subject an effective amount of at least one compound having a structure represented by a formula:

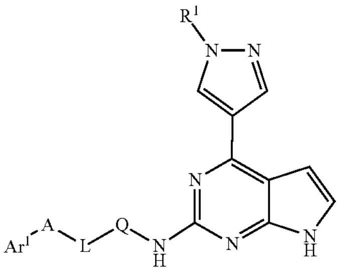

wherein A is selected from —O—, —S—, —NH—, —$CH_2$—, —O—(C1-C4 alkyl)-C(O)NH—, and a structure

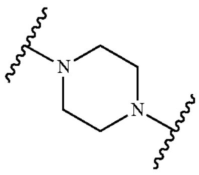

;

wherein L is selected from C2-C15 alkyl and —($CH_2CH_2O$)$_n$(C1-C4 alkyl)-; wherein n is selected from 1, 2, 3, 4, 5, 6, 7, and 8; wherein Q is selected from —NHC(O)($C_6H_4$)— and —C(O)NH($C_6H_4$)—; wherein $R^1$ is selected from C1-C8 alkyl, C1-C8 hydroxyalkyl, C1-C8 cyanoalkyl, C1-C8 aminoalkyl, and a structure selected from:

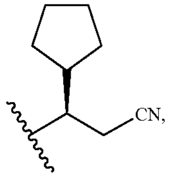

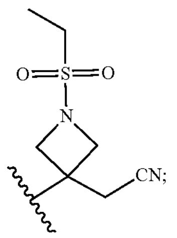

and

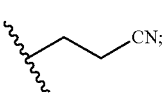

and wherein $Ar^1$ is a structure selected from:

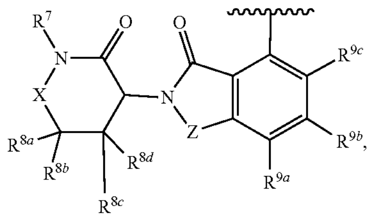

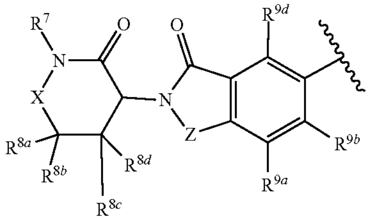

,

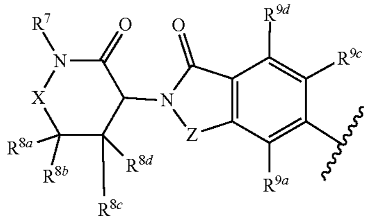

, and

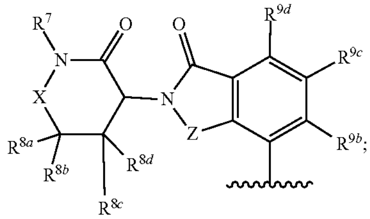

wherein X is selected from —C(O)— and —$CH_2$—; wherein Z is selected from —$CH_2$— and C(O); wherein $R^7$ is selected from hydrogen and C1-C8 alkyl; wherein each of $R^{8a}$, $R^{8b}$, $R^{8c}$, and $R^{8d}$ is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{9a}$, $R^{9b}$, $R^{9c}$, and $R^{9d}$, when present, is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

In one aspect, disclosed are methods of treating a disorder associated with uncontrolled cellular proliferation, such as for example cancer, sarcoma, a carcinoma, a hematological cancer, a solid tumor, breast cancer, cervical cancer, gastrointestinal cancer, colorectal cancer, brain cancer, skin cancer, prostate cancer, ovarian cancer, non-small cell lung carcinoma, thyroid cancer, testicular cancer, pancreatic cancer, liver cancer, endometrial cancer, melanoma, glioma, leukemia, lymphoma, chronic myeloproliferative disorder, myelodysplastic syndrome, myeloproliferative neoplasm, and plasma cell neoplasm (myeloma), in another example acute lymphoblastic leukemia, activity in a subject, the method comprising administering to the subject an effective amount of at least one compound having a structure selected from:

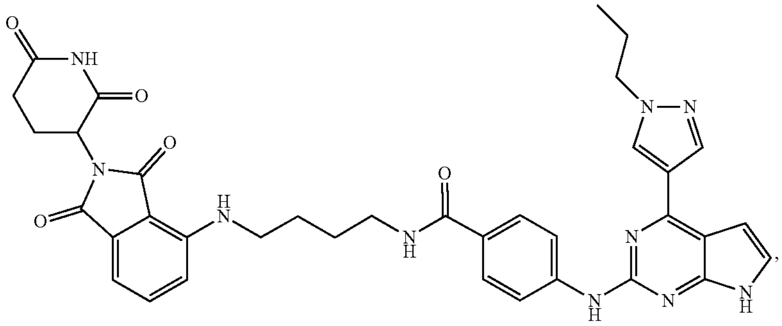
,
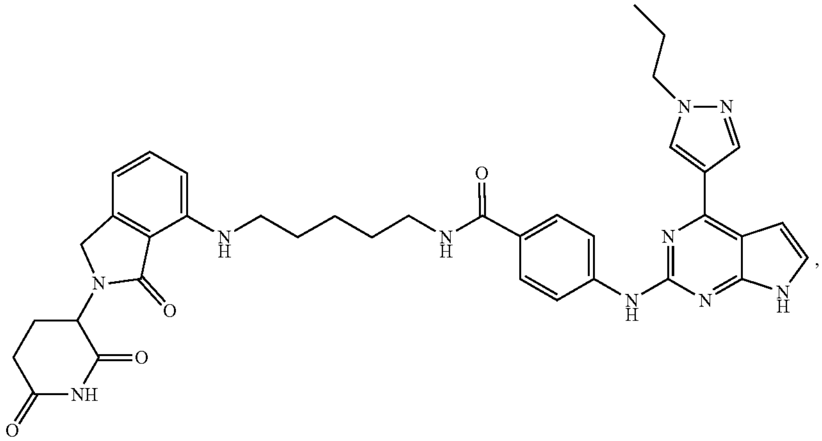
,
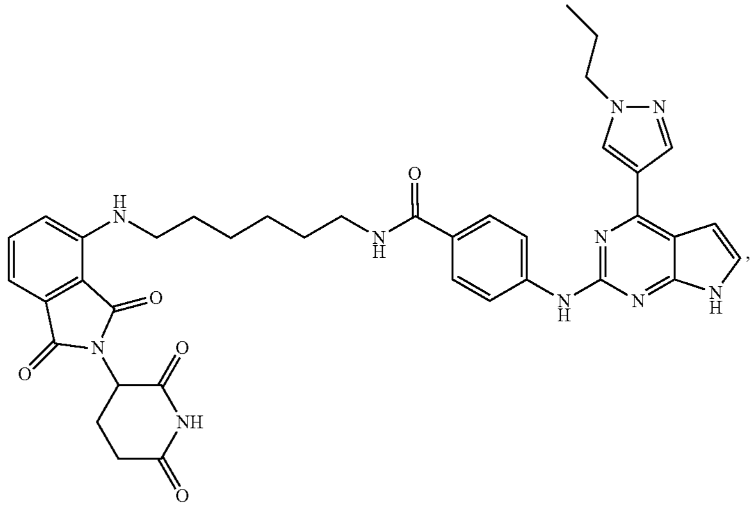
,
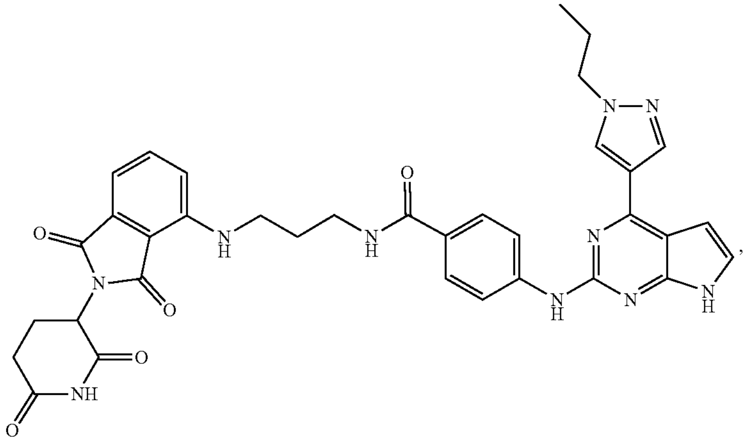
,

-continued
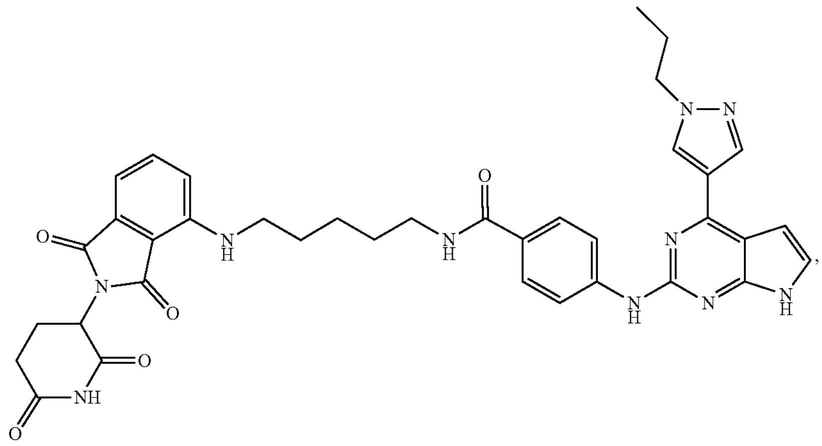
,
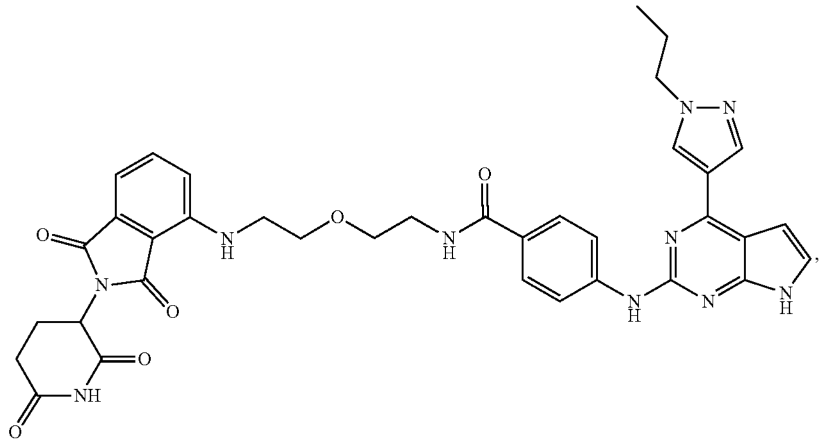 [SMILES: CCCn1cc(-c2nc(Nc3ccc(C(=O)NCCCCCNc4cccc5c4C(=O)N(C4CCC(=O)NC4=O)C5=O)cc3)nc3[nH]ccc23)cn1]
,
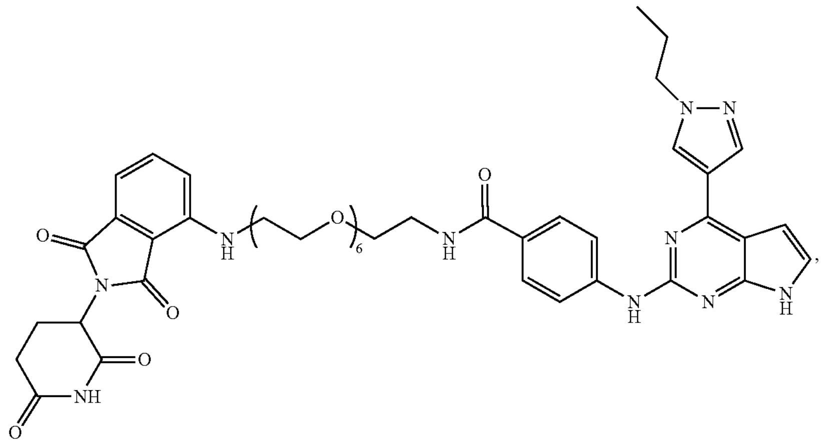
,

-continued
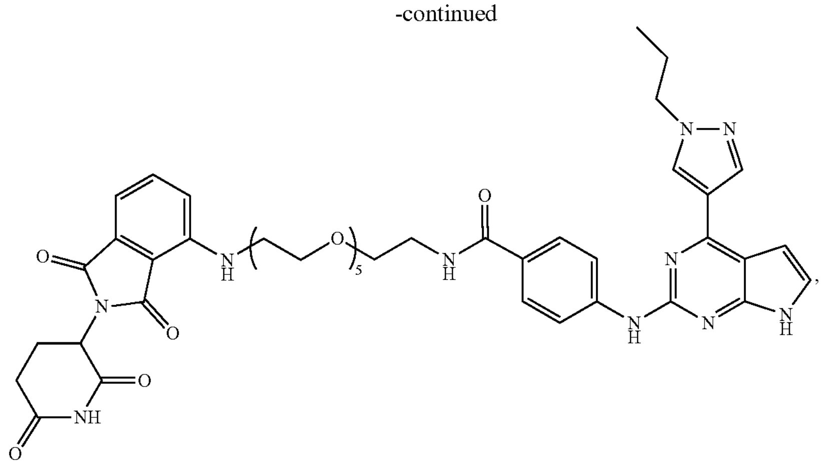
,
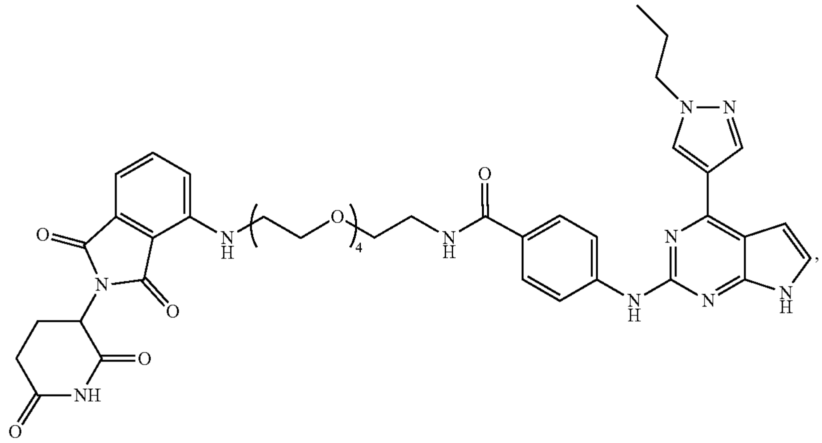
,
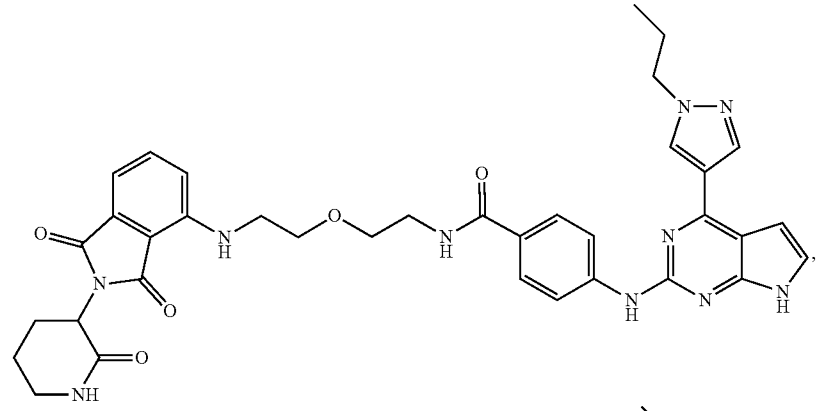
,
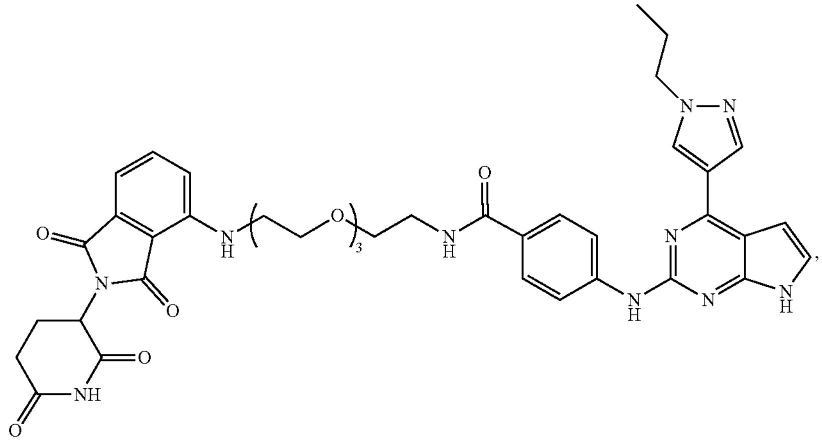
,

-continued
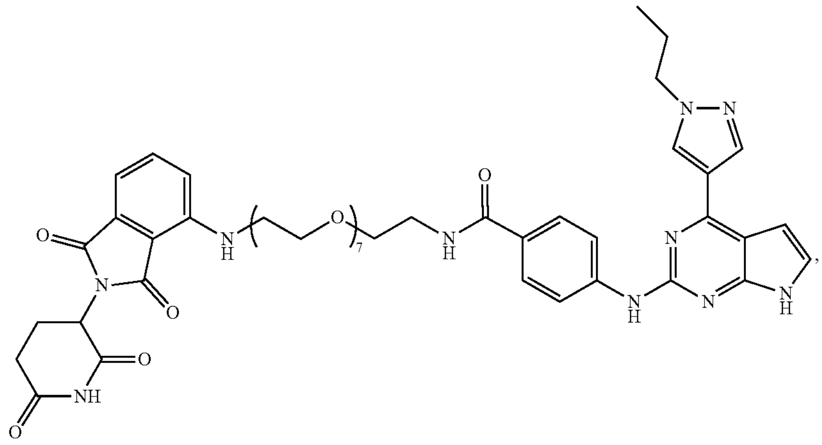
,
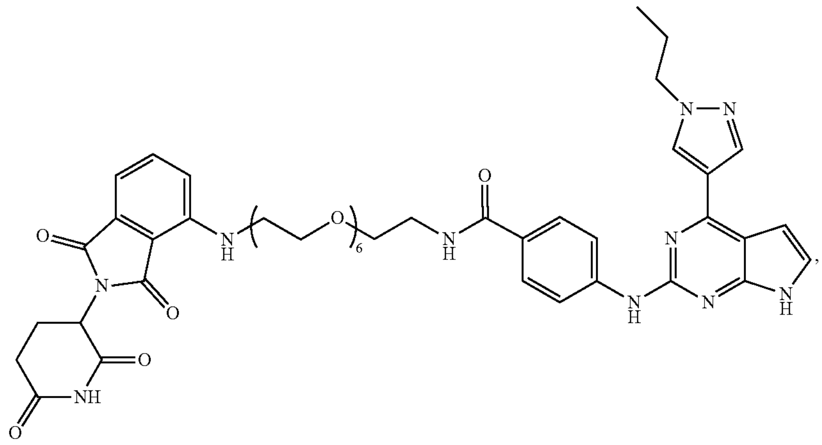
,
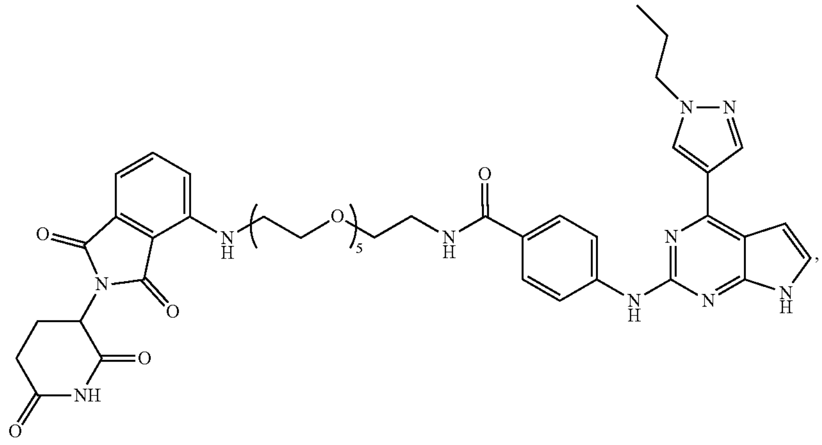
,

-continued
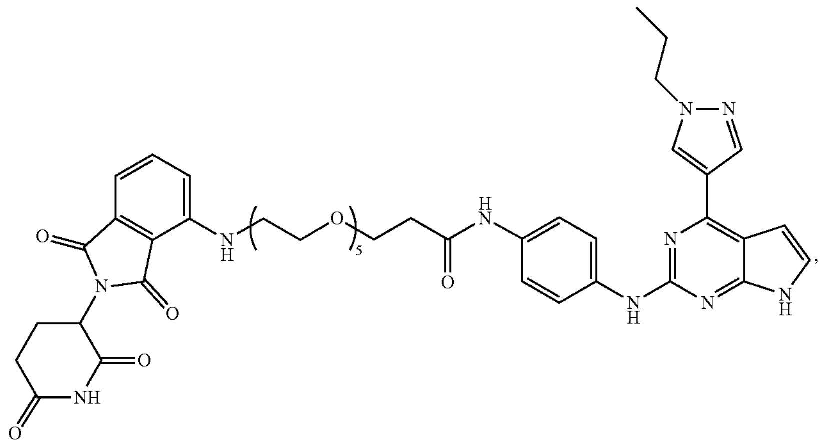
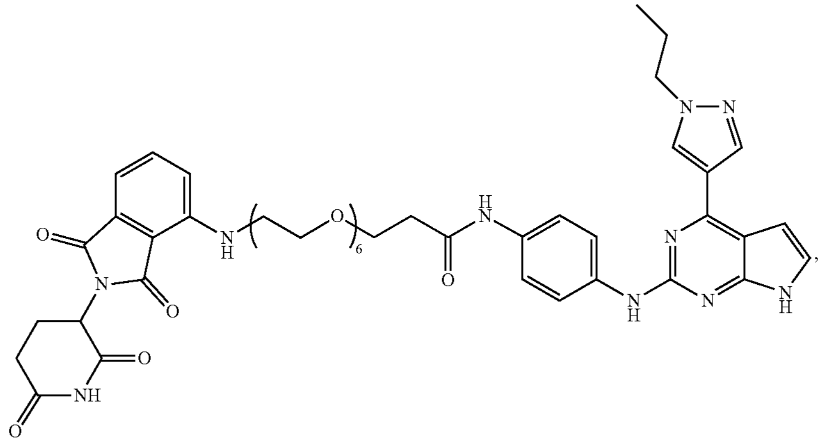
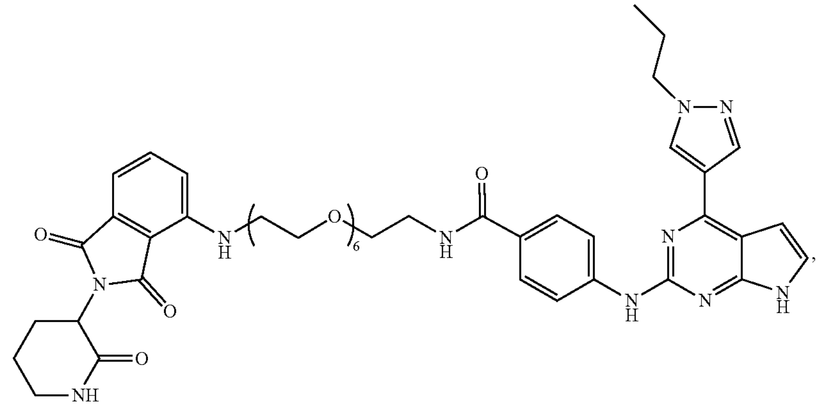
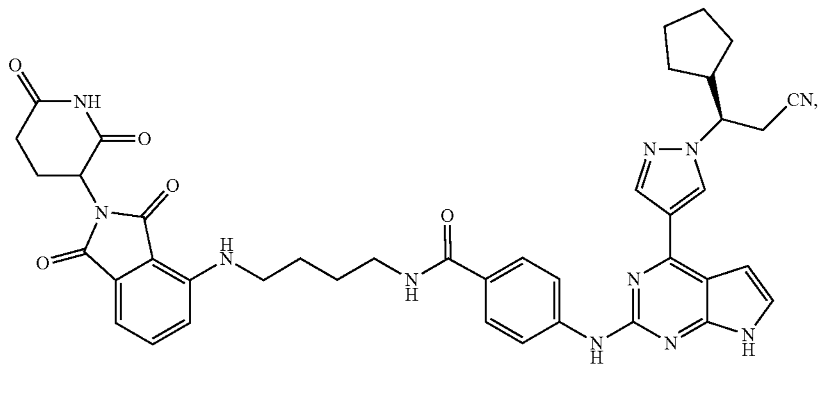

-continued

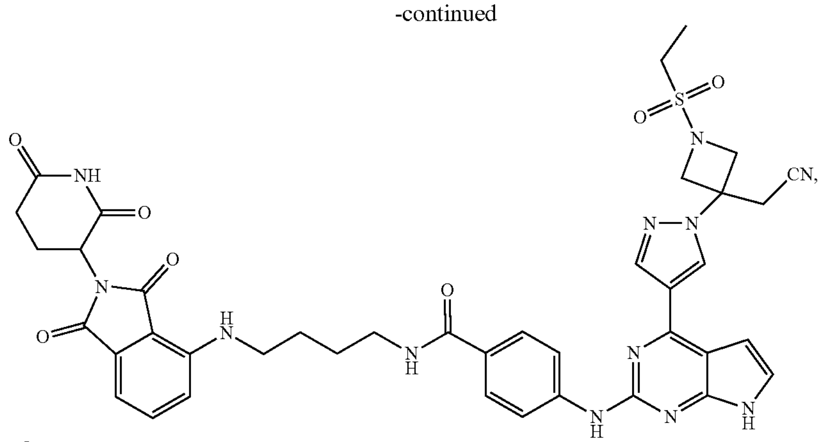

CN, and

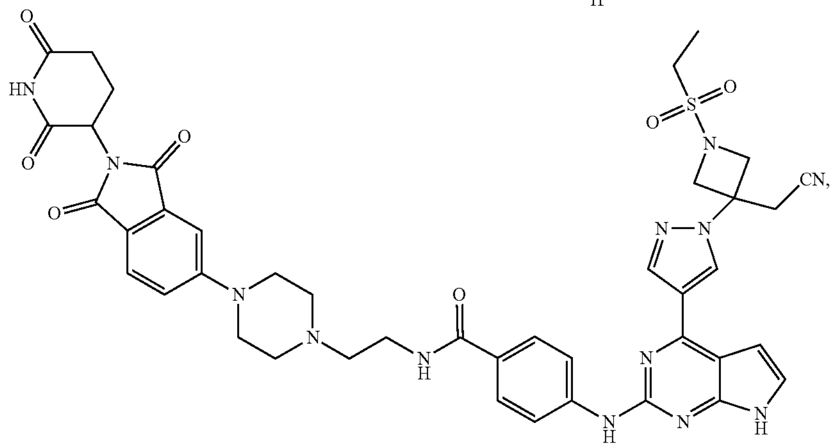

CN, or a pharmaceutical acceptable salt thereof.

In one aspect, disclosed are methods of treating a disorder associated with uncontrolled cellular proliferation, such as for example cancer, sarcoma, a carcinoma, a hematological cancer, a solid tumor, breast cancer, cervical cancer, gastro-intestinal cancer, colorectal cancer, brain cancer, skin cancer, prostate cancer, ovarian cancer, non-small cell lung carcinoma, thyroid cancer, testicular cancer, pancreatic cancer, liver cancer, endometrial cancer, melanoma, glioma, leukemia, lymphoma, chronic myeloproliferative disorder, myelodysplastic syndrome, myeloproliferative neoplasm, and plasma cell neoplasm (myeloma), in another example acute lymphoblastic leukemia, activity in a subject, the method comprising administering to the subject an effective amount of at least one compound having a structure selected from:

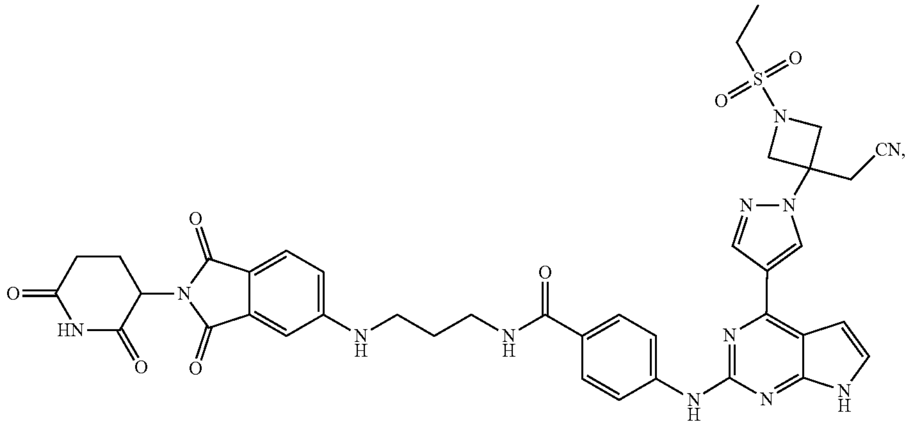

CN,

-continued
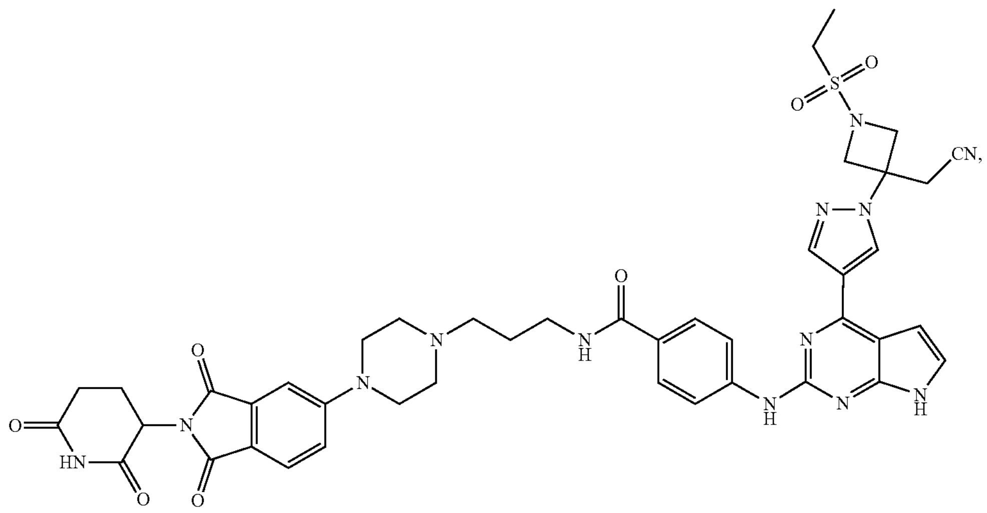
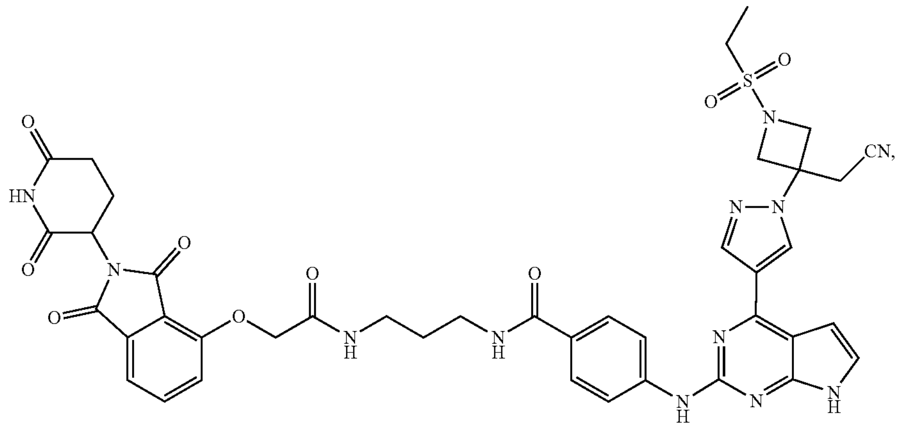
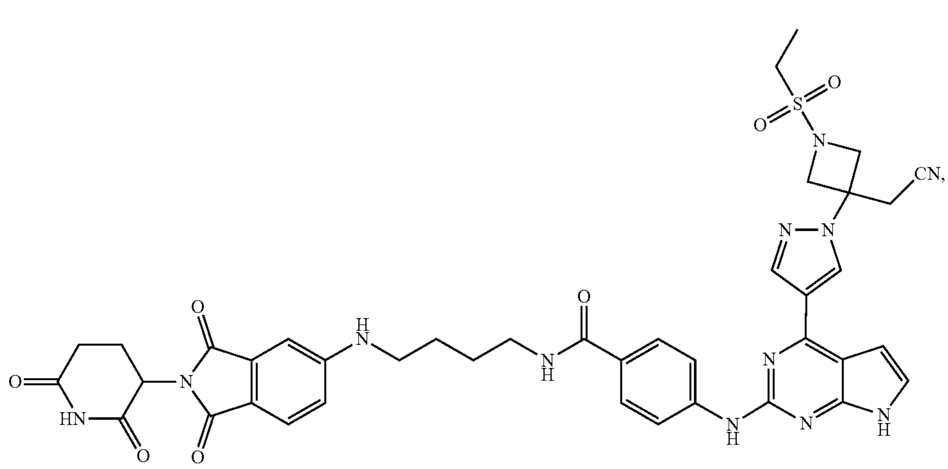
and

-continued

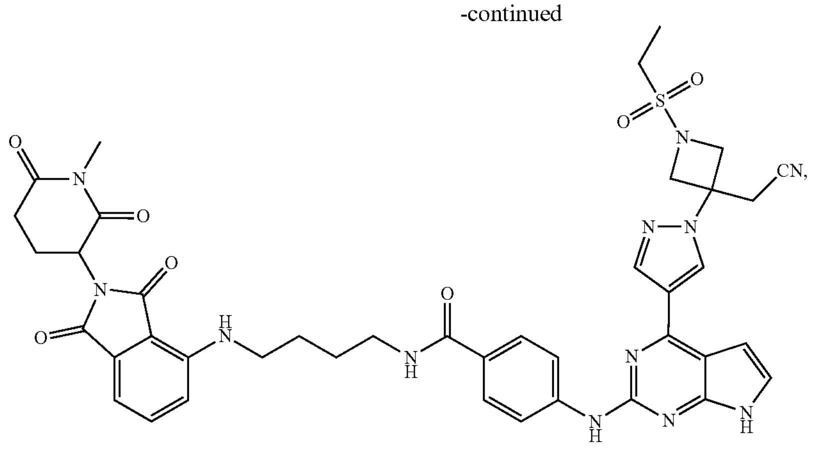

or a pharmaceutically acceptable salt thereof.

In various aspects, the disclosed compounds can be used in combination with one or more other drugs in the treatment, prevention, control, amelioration, or reduction of risk of disorders associated with uncontrolled cellular proliferation, such as for example cancer, sarcoma, a carcinoma, a hematological cancer, a solid tumor, breast cancer, cervical cancer, gastrointestinal cancer, colorectal cancer, brain cancer, skin cancer, prostate cancer, ovarian cancer, non-small cell lung carcinoma, thyroid cancer, testicular cancer, pancreatic cancer, liver cancer, endometrial cancer, melanoma, glioma, leukemia, lymphoma, chronic myeloproliferative disorder, myelodysplastic syndrome, myeloproliferative neoplasm, and plasma cell neoplasm (myeloma), in another example acute lymphoblastic leukemia, activity for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly. Accordingly, the pharmaceutical compositions include those that contain one or more other active ingredients, in addition to a compound of the present invention.

In one aspect, the one or more other active ingredients is a chemotherapeutic agent. The chemotherapeutic agent can be selected from an alkylating agent, an antimetabolite agent, an antineoplastic antibiotic agent, a mitotic inhibitor agent, and a mTor inhibitor agent. In one aspect, the one or more other active ingredients is an antineoplastic antibiotic agent selected from doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof. In a further aspect, the one or more other active ingredients is an antimetabolite agent selected from gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof. In a further aspect, the one or more other active ingredients is an alkylating agent selected from carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt thereof. In a further aspect, the one or more other active ingredients is a mitotic inhibitor agent selected from irinotecan, topotecan, rubitecan, cabazitaxel, docetaxel, paclitaxel, etopside, vincristine, ixabepilone, vinorelbine, vinblastine, and teniposide, or a pharmaceutically acceptable salt thereof. In a further aspect, the one or more other active ingredients is an mTor inhibitor agent selected from everolimus, siroliumus, and temsirolimus, or a pharmaceutically acceptable salt, hydrate, solvate, or polymorph thereof.

In a further aspect, the compound exhibits inhibition of uncontrolled cellular proliferation, such as for example cancer, sarcoma, a carcinoma, a hematological cancer, a solid tumor, breast cancer, cervical cancer, gastrointestinal cancer, colorectal cancer, brain cancer, skin cancer, prostate cancer, ovarian cancer, non-small cell lung carcinoma, thyroid cancer, testicular cancer, pancreatic cancer, liver cancer, endometrial cancer, melanoma, glioma, leukemia, lymphoma, chronic myeloproliferative disorder, myelodysplastic syndrome, myeloproliferative neoplasm, and plasma cell neoplasm (myeloma), in another example acute lymphoblastic leukemia, activity. In a still further aspect, the compound exhibits a decrease in uncontrolled cellular proliferation, such as for example cancer, sarcoma, a carcinoma, a hematological cancer, a solid tumor, breast cancer, cervical cancer, gastrointestinal cancer, colorectal cancer, brain cancer, skin cancer, prostate cancer, ovarian cancer, non-small cell lung carcinoma, thyroid cancer, testicular cancer, pancreatic cancer, liver cancer, endometrial cancer, melanoma, glioma, leukemia, lymphoma, chronic myeloproliferative disorder, myelodysplastic syndrome, myeloproliferative neoplasm, and plasma cell neoplasm (myeloma), in another example acute lymphoblastic leukemia, activity.

In another aspect, disclosed herein is a method of treating a JAK-associated disease or disorder in an subject comprising administering to the subject an effective amount of at least one compound disclosed herein. The JAK-associated disease can include any disease, disorder or condition that is directly or indirectly linked to expression or activity of the JAK, including overexpression and/or abnormal activity levels. A JAK-associated disease can also include any disease, disorder or condition that can be prevented, ameliorated, or cured by modulating JAK activity.

In another aspect, JAK-associated diseases include diseases involving the immune system including, for example, organ transplant rejection (e.g., allograft rejection and graft versus host disease).

In another aspect, JAK-associated diseases include autoimmune diseases such as multiple sclerosis, rheumatoid arthritis, juvenile arthritis, psoriatic arthritis, type I diabetes, lupus, psoriasis, inflammatory bowel disease, ulcerative colitis, Crohn's disease, myasthenia gravis, immunoglobulin nephropathies, autoimmune thyroid disorders, and the like. In some embodiments, the autoimmune disease is an autoimmune bullous skin disorder such as pemphigus vulgaris (PV) or bullous pemphigoid (BP).

In another example, JAK-associated diseases include allergic conditions such as asthma, food allergies, atopic dermatitis and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV). Further examples of JAK-associated diseases or conditions include skin disorders such as psoriasis (for example, psoriasis vulgaris), atopic dermatitis, skin rash, skin irritation, skin sensitization (e.g., contact dermatitis or allergic contact dermatitis).

In a further aspect, the compound exhibits inhibition of uncontrolled cellular proliferation activity with an $IC_{50}$ of from about 0.001 μM to about 25 μM. In a still further aspect, the compound exhibits inhibition of uncontrolled cellular proliferation activity with an $IC_{50}$ of from about 0.001 μM to about 15 μM. In yet a further aspect, the compound exhibits inhibition of uncontrolled cellular proliferation activity with an $IC_{50}$ of from about 0.001 μM to about 10 μM. In an even further aspect, the compound exhibits inhibition of uncontrolled cellular proliferation activity with an $IC_{50}$ of from about 0.001 μM to about 5 μM. In a still further aspect, the compound exhibits inhibition of uncontrolled cellular proliferation activity with an $IC_{50}$ of from about 0.001 μM to about 1 μM. In yet a further aspect, the compound exhibits inhibition of uncontrolled cellular proliferation activity with an $IC_{50}$ of from about 0.001 μM to about 0.5 μM. In an even further aspect, the compound exhibits inhibition of uncontrolled cellular proliferation activity with an $IC_{50}$ of from about 0.001 μM to about 0.1 μM. In a still further aspect, the compound exhibits inhibition of uncontrolled cellular proliferation activity with an $IC_{50}$ of from about 0.001 μM to about 0.05 μM. In yet a further aspect, the compound exhibits inhibition of uncontrolled cellular proliferation activity with an $IC_{50}$ of from about 0.001 μM to about 0.01 μM. In an even further aspect, the compound exhibits inhibition of uncontrolled cellular proliferation activity with an $IC_{50}$ of from about 0.001 μM to about 0.005 μM. In a still further aspect, the compound exhibits inhibition of uncontrolled cellular proliferation activity with an $IC_{50}$ of from about 0.005 μM to about 25 μM. In yet a further aspect, the compound exhibits inhibition of uncontrolled cellular proliferation activity with an $IC_{50}$ of from about 0.01 μM to about 25 μM. In an even further aspect, the compound exhibits inhibition of uncontrolled cellular proliferation activity with an $IC_{50}$ of from about 0.05 μM to about 25 μM. In a still further aspect, the compound exhibits inhibition of uncontrolled cellular proliferation activity with an $IC_{50}$ of from about 0.1 μM to about 25 μM. In yet a further aspect, the compound exhibits inhibition of uncontrolled cellular proliferation activity with an $IC_{50}$ of from about 0.5 μM to about 25 μM. In an even further aspect, the compound exhibits inhibition of uncontrolled cellular proliferation activity with an $IC_{50}$ of from about 1 μM to about 25 μM. In a still further aspect, the compound exhibits inhibition of uncontrolled cellular proliferation activity with an $IC_{50}$ of from about 5 μM to about 25 μM. In yet a further aspect, the compound exhibits inhibition of uncontrolled cellular proliferation activity with an $IC_{50}$ of from about 10 μM to about 25 μM. In an even further aspect, the compound exhibits inhibition of uncontrolled cellular proliferation activity with an $IC_{50}$ of from about 15 μM to about 25 μM.

In a further aspect, the subject is a mammal. In a still further aspect, the mammal is human.

In a further aspect, the subject has been diagnosed with a need for treatment of the disorder prior to the administering step. In a still further aspect, the subject is at risk for developing the disorder prior to the administering step.

In a further aspect, the method further comprises identifying a subject at risk for developing the disorder prior to the administering step.

In a further aspect, the disorder associated with uncontrolled cellular proliferation is cancer, for example a cancer selected from sarcoma, a carcinoma, a hematological cancer, a solid tumor, breast cancer, cervical cancer, gastrointestinal cancer, colorectal cancer, brain cancer, skin cancer, prostate cancer, ovarian cancer, non-small cell lung carcinoma, thyroid cancer, testicular cancer, pancreatic cancer, liver cancer, endometrial cancer, melanoma, glioma, leukemia, lymphoma, chronic myeloproliferative disorder, myelodysplastic syndrome, myeloproliferative neoplasm, and plasma cell neoplasm (myeloma), in another example acute lymphoblastic leukemia.

F. METHODS OF MODULATING CELLULAR PROLIFERATION ACTIVITY IN A SUBJECT

In one aspect, disclosed are methods of modulating cellular proliferation activity in a subject, the method comprising administering to the subject an effective amount of at least one disclosed compound, or a pharmaceutically acceptable salt thereof. In a further aspect, modulating is inhibiting.

Thus, in one aspect, disclosed are methods of modulating cellular proliferation activity in a subject, the method comprising administering to the subject an effective amount of at least one compound having a structure represented by a formula:

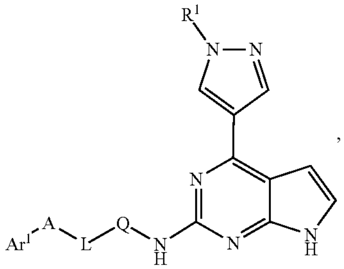
, wherein A is selected from —O—, —S—, —NH—, —$CH_2$—, —O—(C1-C4 alkyl)-C(O)NH—, and a structure

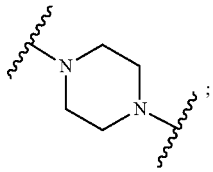

;

wherein L is selected from C2-C15 alkyl and —($CH_2CH_2O$)$_n$(C1-C4 alkyl)-; wherein n is selected from 1, 2, 3, 4, 5, 6, 7, and 8; wherein Q is selected from —NHC(O)($C_6H_4$)— and —C(O)NH($C_6H_4$)—; wherein $R^1$ is selected from C1-C8 alkyl, C1-C8 hydroxyalkyl, C1-C8 cyanoalkyl, C1-C8 aminoalkyl, and a structure selected from:

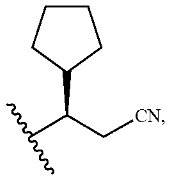

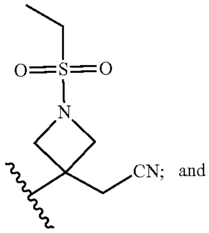

and

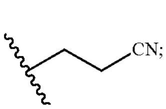

and wherein $Ar^1$ is a structure selected from:

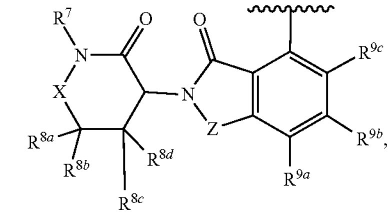

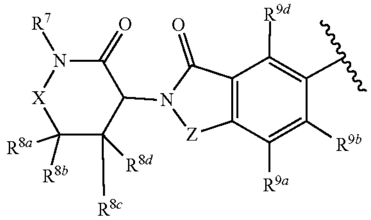

,

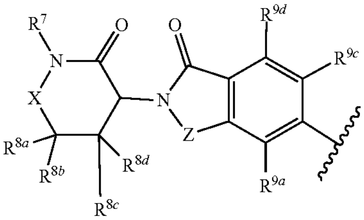

, and

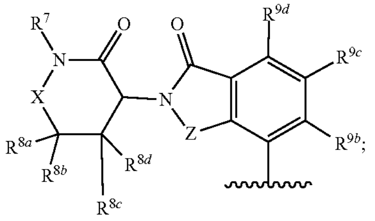

wherein X is selected from —C(O)— and —$CH_2$—; wherein Z is selected from —$CH_2$— and C(O); wherein $R^7$ is selected from hydrogen and C1-C8 alkyl; wherein each of $R^{8a}$, $R^{8b}$, $R^{8c}$, and $R^{8d}$ is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{9a}$, $R^{9b}$, $R^{9c}$, and $R^{9d}$, when present, is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

Also disclosed are disclosed are methods of treating a disorder associated with uncontrolled cellular proliferation, such as for example cancer, sarcoma, a carcinoma, a hematological cancer, a solid tumor, breast cancer, cervical cancer, gastrointestinal cancer, colorectal cancer, brain cancer, skin cancer, prostate cancer, ovarian cancer, non-small cell lung carcinoma, thyroid cancer, testicular cancer, pancreatic cancer, liver cancer, endometrial cancer, melanoma, glioma, leukemia, lymphoma, chronic myeloproliferative disorder, myelodysplastic syndrome, myeloproliferative neoplasm, and plasma cell neoplasm (myeloma), in another example acute lymphoblastic leukemia activity in a subject, the method comprising administering to the subject an effective amount of at least one compound having a structure represented by a formula:

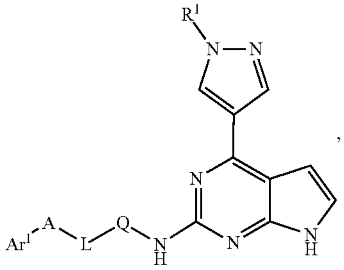

, wherein A is selected from —O—, —S—, —NH—, and —$CH_2$—; wherein L is selected from C2-C15 alkyl and —($CH_2CH_2O$)$_n$(C1-C4 alkyl)-; wherein n is selected from 1, 2, 3, 4, 5, 6, 7, and 8; wherein Q is selected from —NHC(O)($C_6H_4$)— and —C(O)NH($C_6H_4$)—; wherein $R^1$ is selected from C1-C8 alkyl, C1-C8 hydroxyalkyl, C1-C8 cyanoalkyl, C1-C8 aminoalkyl, and a structure selected from:

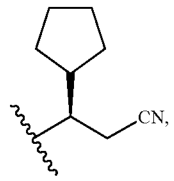

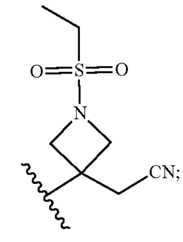

and

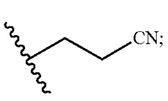

and wherein $Ar^1$ is a structure selected from:

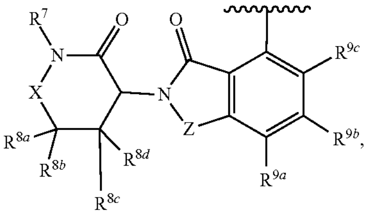

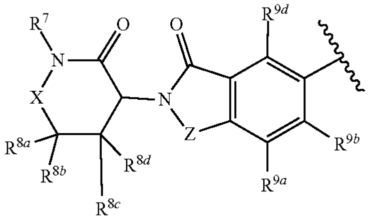

,

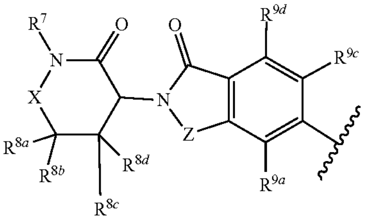

, and

-continued

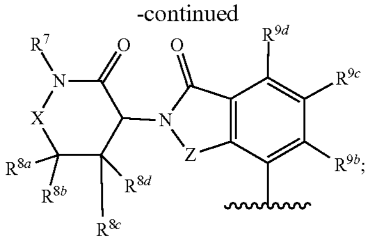

wherein X is selected from —C(O)— and —$CH_2$—; wherein Z is selected from —$CH_2$— and C(O); wherein $R^7$ is selected from hydrogen and C1-C8 alkyl; wherein each of $R^{8a}$, $R^{8b}$, $R^{8c}$, and $R^{8d}$ is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{9a}$, $R^{9b}$, $R^{9c}$, and $R^{9d}$, when present, is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

In one aspect, disclosed are methods of modulating cellular proliferation activity in a subject, the method comprising administering to the subject an effective amount of at least one compound having a structure selected from:

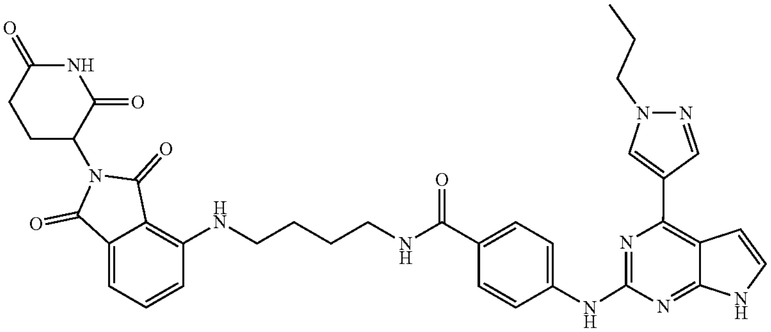

,

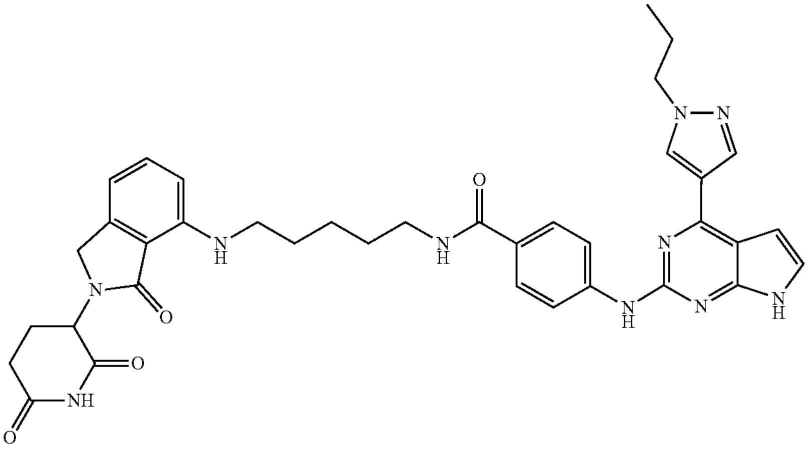

,

-continued
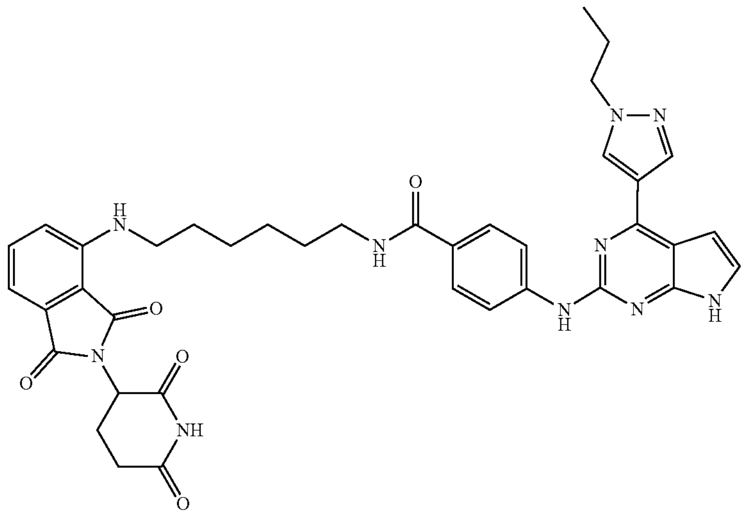
,
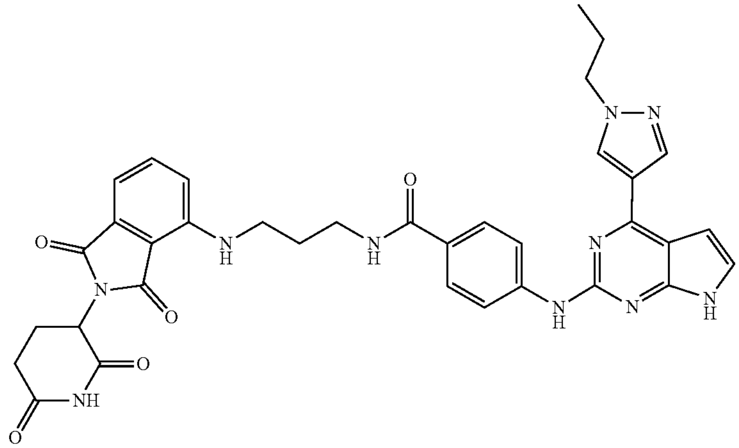
,
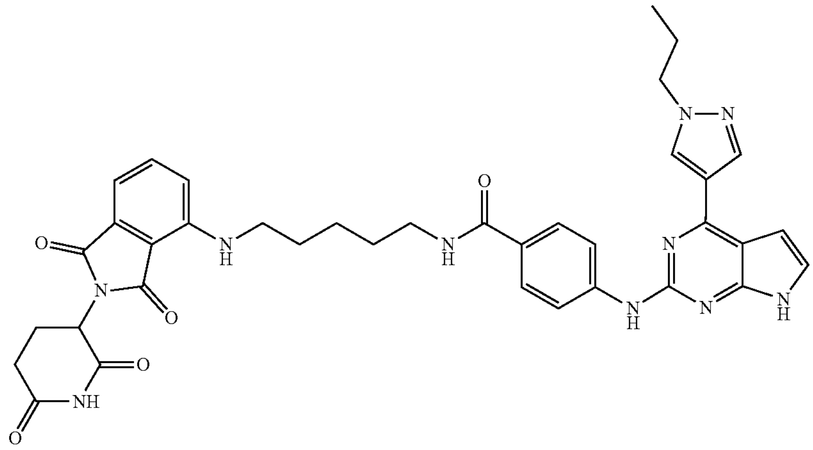
,

-continued
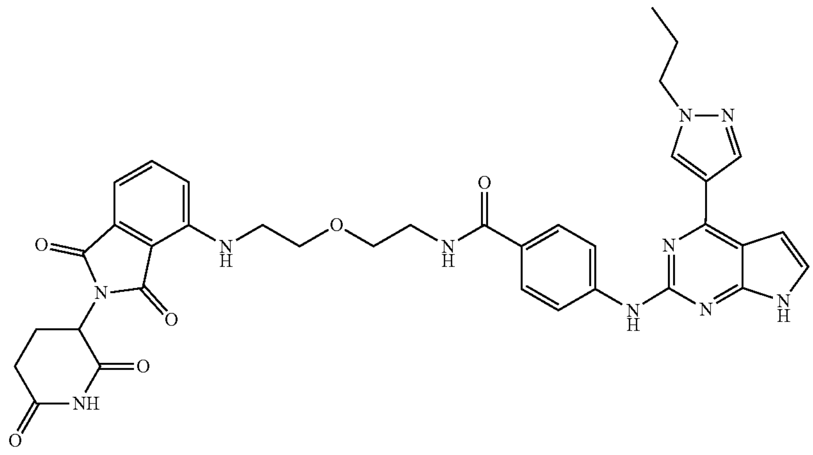
,
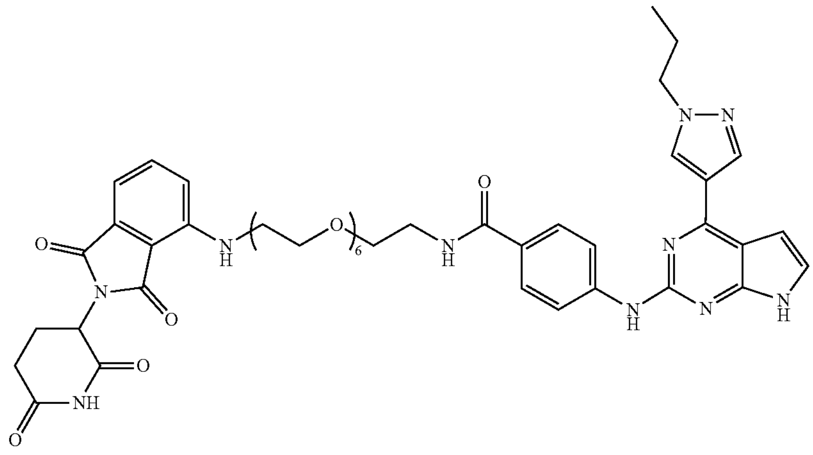
,
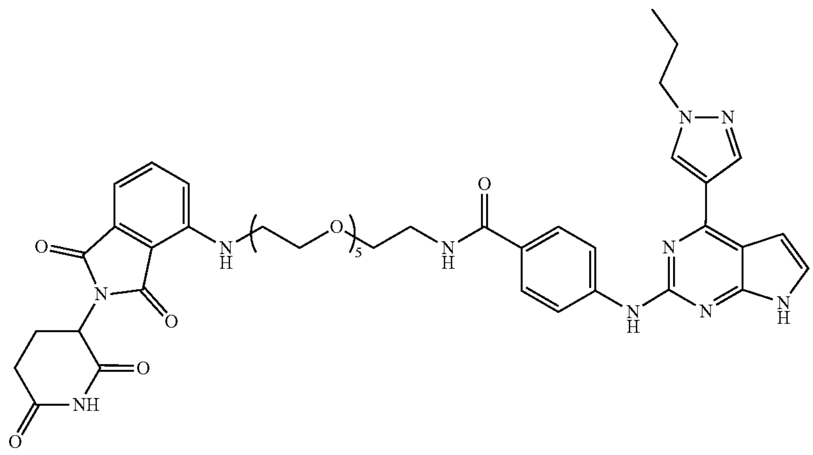
,

-continued
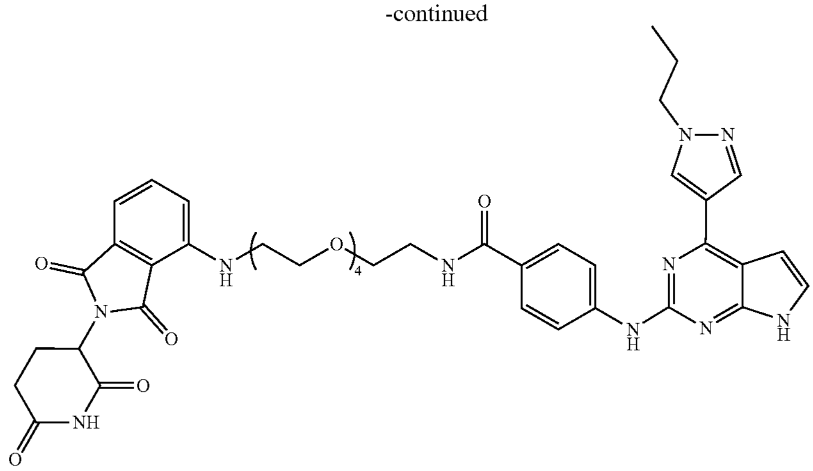
,
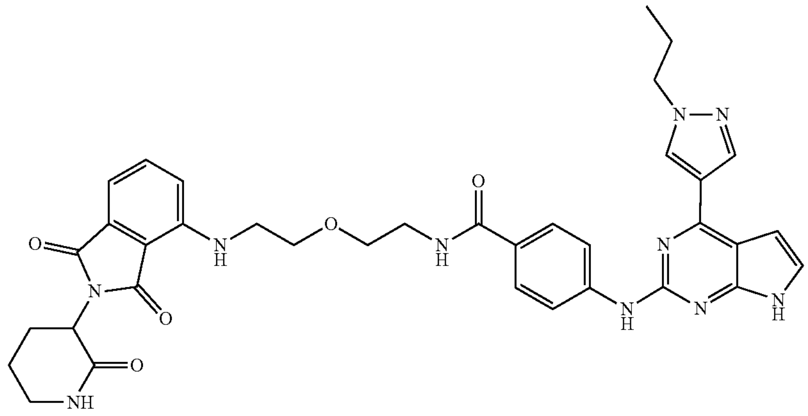
,
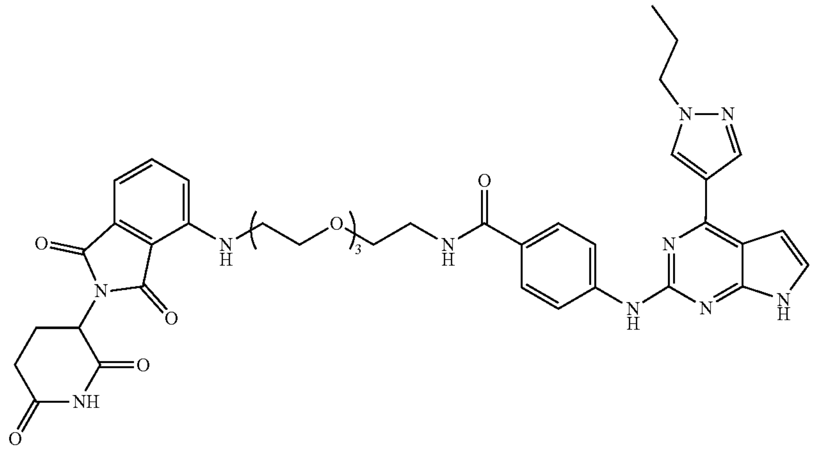
,

-continued
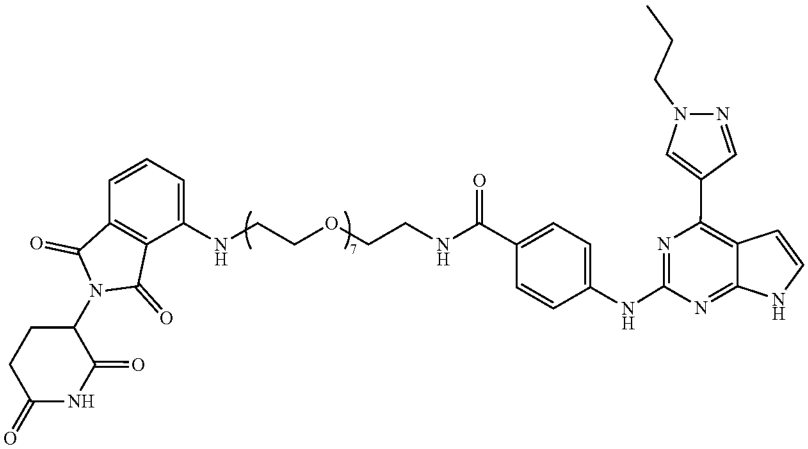
,
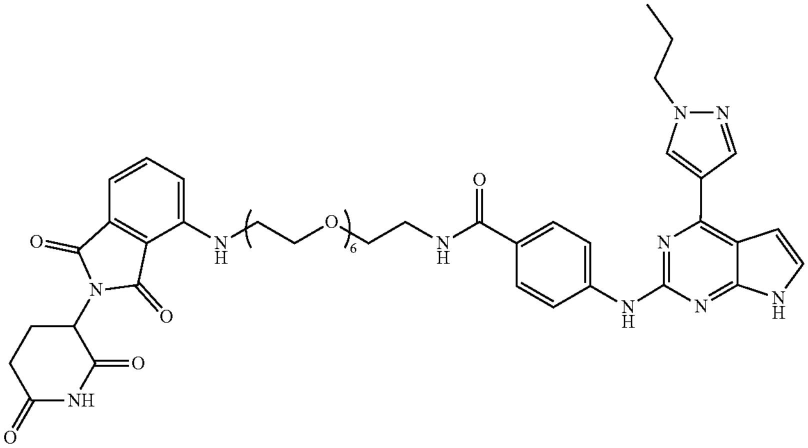
,
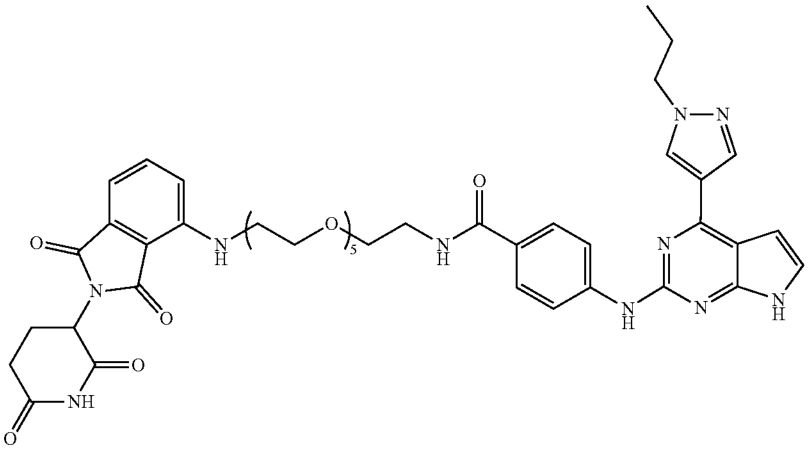
,

-continued
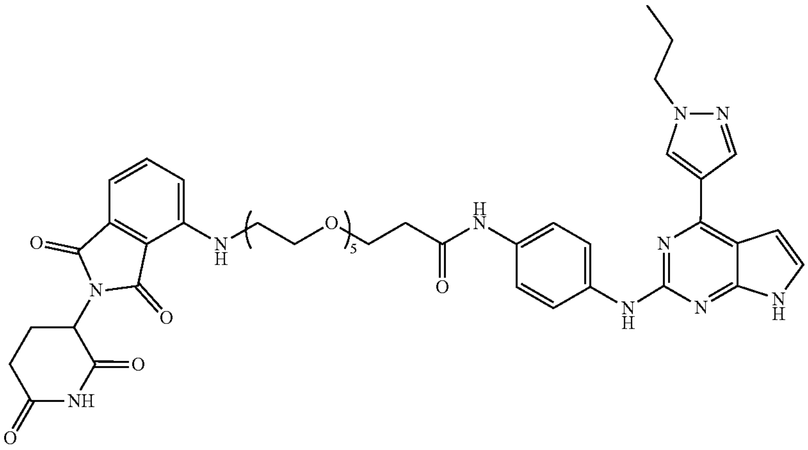
,
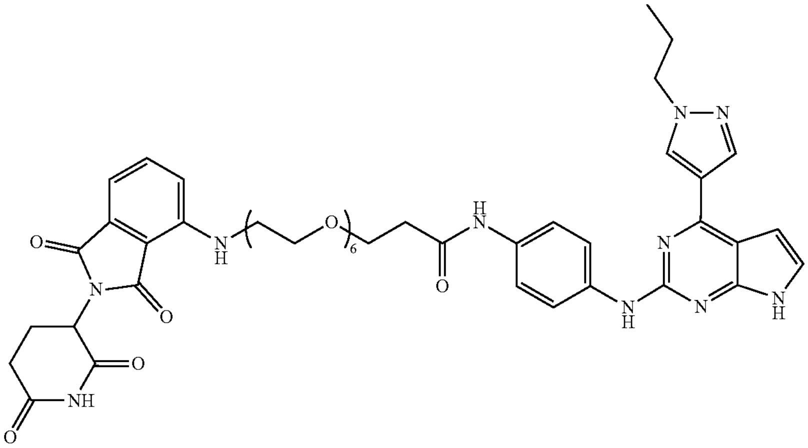
,
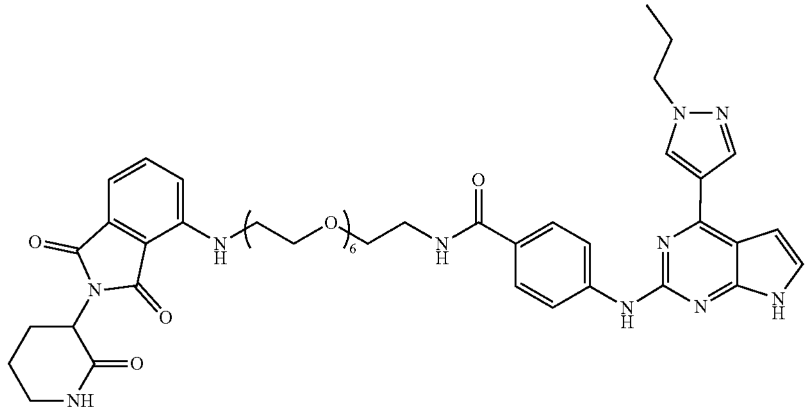
,
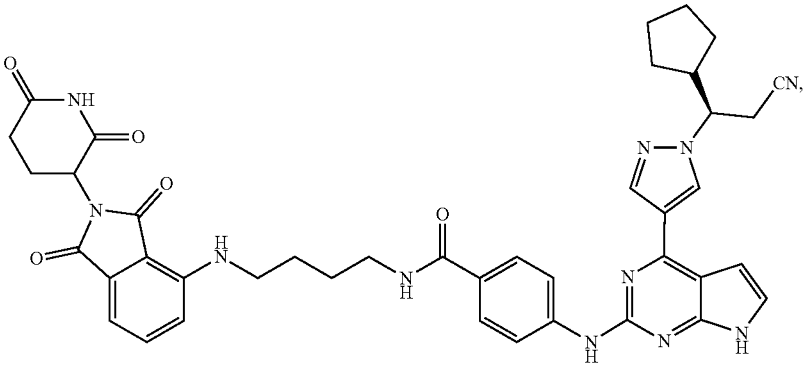
CN,

-continued
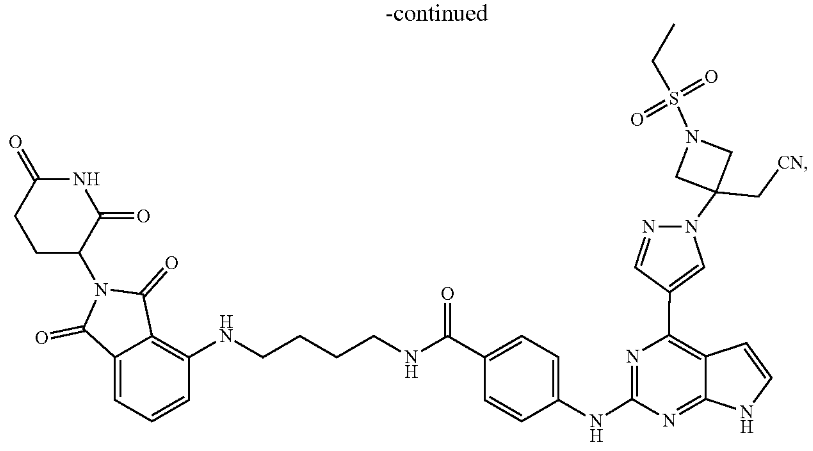
and
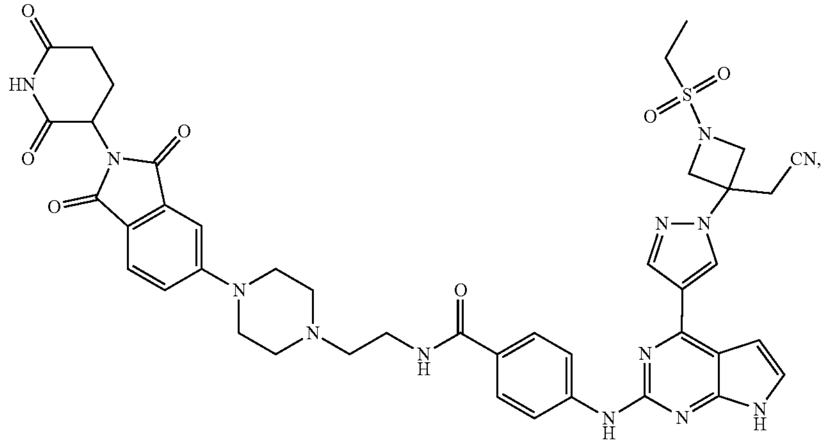 [SMILES: CCS(=O)(=O)N1CC(CC#N)(n2cc(-c3nc(Nc4ccc(C(=O)NCCN5CCN(c6ccc7c(c6)C(=O)N(C6CCC(=O)NC6=O)C7=O)CC5)cc4)nc4[nH]ccc34)cn2)C1]
or a pharmaceutically acceptable salt thereof.
In one aspect, disclosed are methods of modulating cellular proliferation activity in a subject, the method comprising administering to the subject an effective amount of at least one compound having a structure selected from:
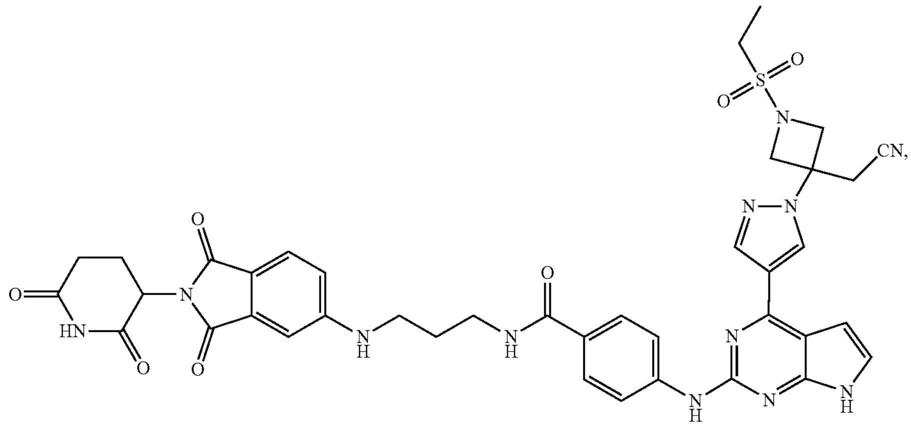

-continued
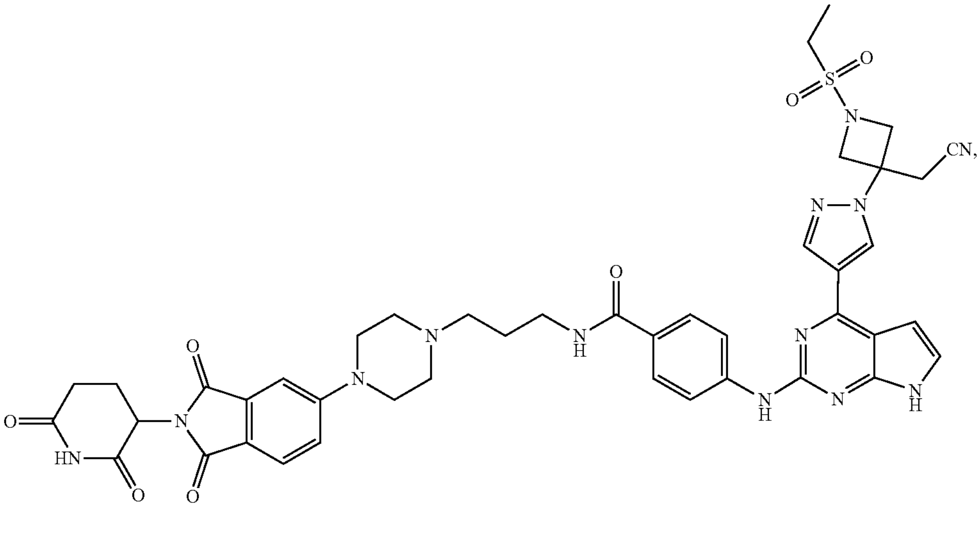
,
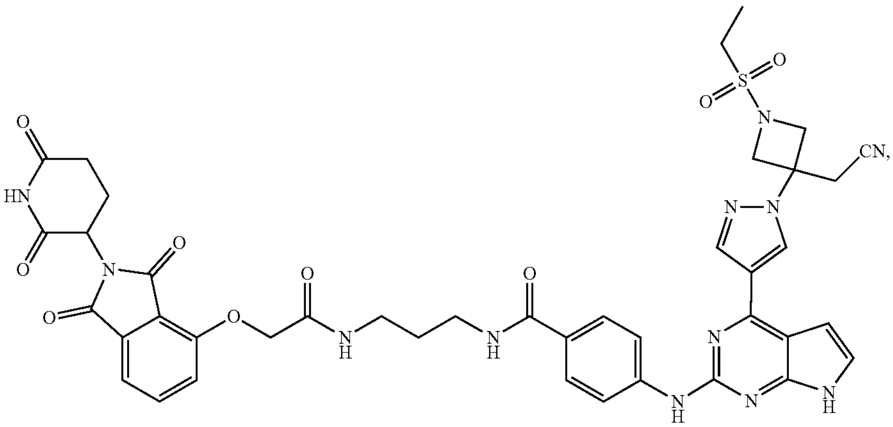
,
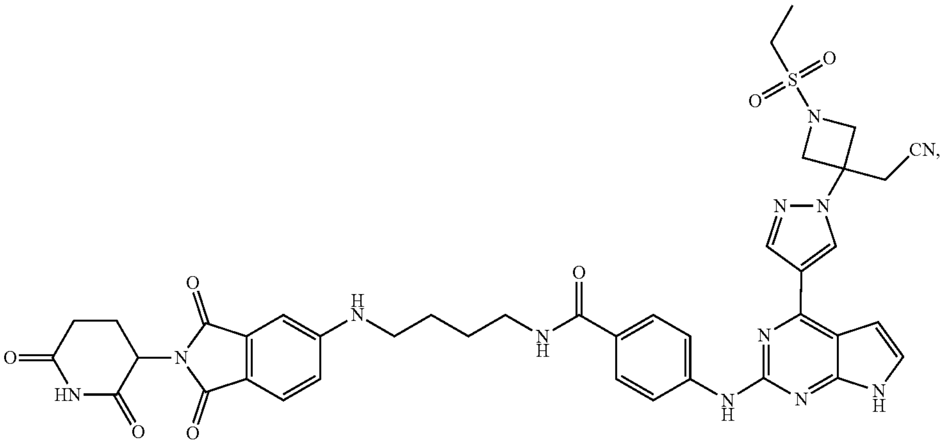
, and

-continued

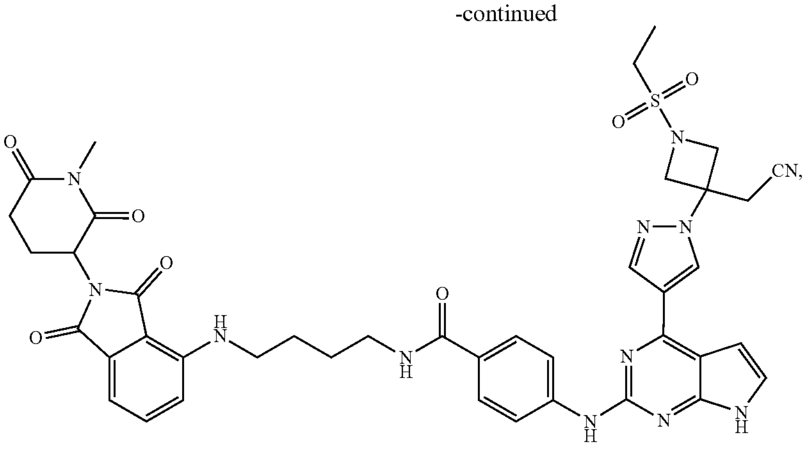

or a pharmaceutically acceptable salt thereof.

In a further aspect, modifying is decreasing. In a still further aspect, modifying is inhibiting.

In a further aspect, the subject has been diagnosed with a disorder of uncontrolled cellular proliferation prior to the administering step.

In a further aspect, the subject has been diagnosed with a need for modifying cellular proliferation prior to the administering step.

In a further aspect, the method further comprises the step of identifying a subject in need of treatment of a disorder associated with cellular proliferation dysfunction.

In a further aspect, the subject has been diagnosed with a need for treatment of a disorder associated with cellular activity prior to the administering step. In a still further aspect, the disorder associated with cellular proliferation activity is cancer, for example a cancer selected from for example a cancer selected from sarcoma, a carcinoma, a hematological cancer, a solid tumor, breast cancer, cervical cancer, gastrointestinal cancer, colorectal cancer, brain cancer, skin cancer, prostate cancer, ovarian cancer, non-small cell lung carcinoma, thyroid cancer, testicular cancer, pancreatic cancer, liver cancer, endometrial cancer, melanoma, glioma, leukemia, lymphoma, chronic myeloproliferative disorder, myelodysplastic syndrome, myeloproliferative neoplasm, and plasma cell neoplasm (myeloma), and in another example acute lymphoblastic leukemia.

In a further aspect, the subject has been diagnosed with a need for modulating cellular proliferation activity prior to the administering step.

G. METHODS OF MODULATING CELLULAR PROLIFERATION ACTIVITY IN AT LEAST ONE CELL

In one aspect, disclosed are methods of cellular proliferation activity in at least one cell, the method comprising the step of contacting the at least one cell with an effective amount of at least one disclosed compound, or a pharmaceutically acceptable salt thereof. In a further aspect, modulating is inhibiting.

Thus, in one aspect, disclosed are methods of modulating cellular proliferation activity in at least one cell, the method comprising the step of contacting the at least one cell with an effective amount of at least one compound having a structure represented by a formula:

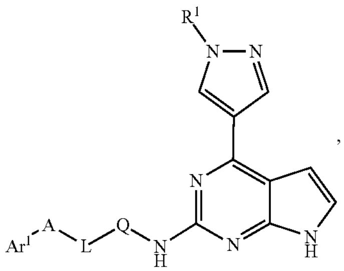

, wherein A is selected from —O—, —S—, —NH—, —$CH_2$—, —O—(C1-C4 alkyl)-C(O)NH—, and a structure

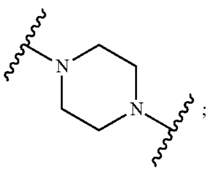

;

wherein L is selected from C2-C15 alkyl and —$(CH_2CH_2O)_n$(C1-C4 alkyl)-; wherein n is selected from 1, 2, 3, 4, 5, 6, 7, and 8; wherein Q is selected from —NHC(O)$(C_6H_4)$— and —C(O)NH$(C_6H_4)$—; wherein $R^1$ is selected from C1-C8 alkyl, C1-C8 hydroxyalkyl, C1-C8 cyanoalkyl, C1-C8 aminoalkyl, and a structure selected from:

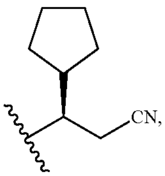

,

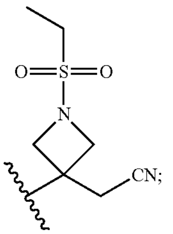

; and

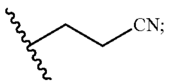

;

and wherein $Ar^1$ is a structure selected from:

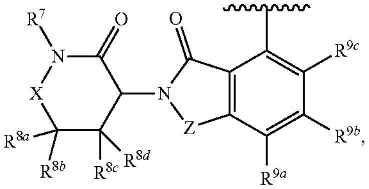

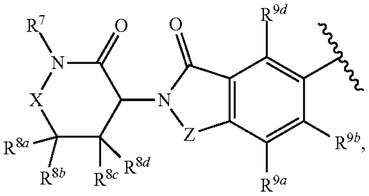

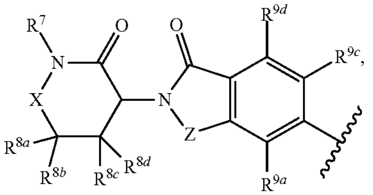

and

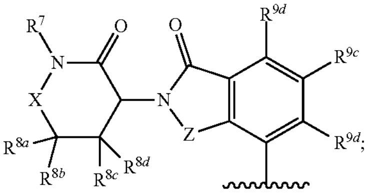

wherein X is selected from —C(O)— and —$CH_2$—; wherein Z is selected from —$CH_2$— and C(O); wherein $R^7$ is selected from hydrogen and C1-C8 alkyl; wherein each of $R^{8a}$, $R^{8b}$, $R^{8c}$, and $R^{8d}$ is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{9a}$, $R^{9b}$, $R^{9c}$, and $R^{9d}$, when present, is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

Also disclosed are disclosed are methods of treating a disorder associated with uncontrolled cellular proliferation, such as for example cancer, sarcoma, a carcinoma, a hematological cancer, a solid tumor, breast cancer, cervical cancer, gastrointestinal cancer, colorectal cancer, brain cancer, skin cancer, prostate cancer, ovarian cancer, non-small cell lung carcinoma, thyroid cancer, testicular cancer, pancreatic cancer, liver cancer, endometrial cancer, melanoma, glioma, leukemia, lymphoma, chronic myeloproliferative disorder, myelodysplastic syndrome, myeloproliferative neoplasm, and plasma cell neoplasm (myeloma), in another example acute lymphoblastic leukemia activity in a subject, the method comprising administering to the subject an effective amount of at least one compound having a structure represented by a formula:

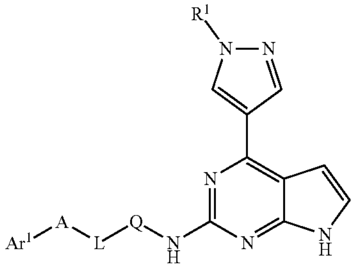

wherein A is selected from —O—, —S—, —NH—, and —$CH_2$—; wherein L is selected from C2-C15 alkyl and —$(CH_2CH_2O)_n$(C1-C4 alkyl)-; wherein n is selected from 1, 2, 3, 4, 5, 6, 7, and 8; wherein Q is selected from —NHC(O)($C_6H_4$)— and —C(O)NH($C_6H_4$)—; wherein $R^1$ is selected from C1-C8 alkyl, C1-C8 hydroxyalkyl, C1-C8 cyanoalkyl, C1-C8 aminoalkyl, and a structure selected from:

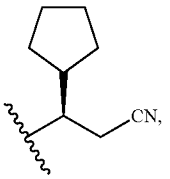

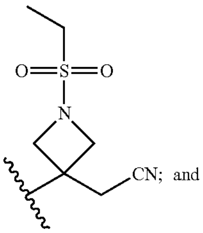

and

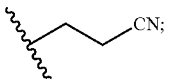

and wherein $Ar^1$ is a structure selected from:

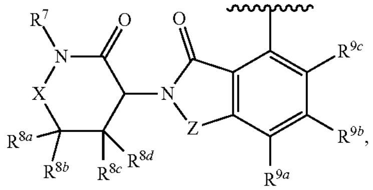

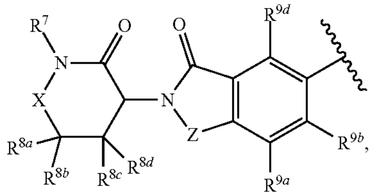

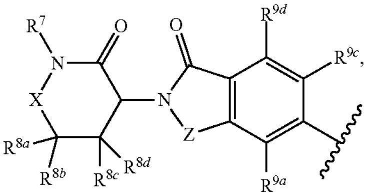

and

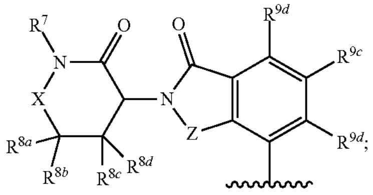

wherein X is selected from —C(O)— and —$CH_2$—; wherein Z is selected from —$CH_2$— and C(O); wherein $R^7$ is selected from hydrogen and C1-C8 alkyl; wherein each of $R^{8a}$, $R^{8b}$, $R^{8c}$, and $R^{8d}$ is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{9a}$, $R^{9b}$, $R^{9c}$, and $R^{9d}$, when present, is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

In one aspect, disclosed are methods of cellular proliferation activity in at least one cell, the method comprising the step of contacting the at least one cell with an effective amount of at least one compound having a structure selected from:

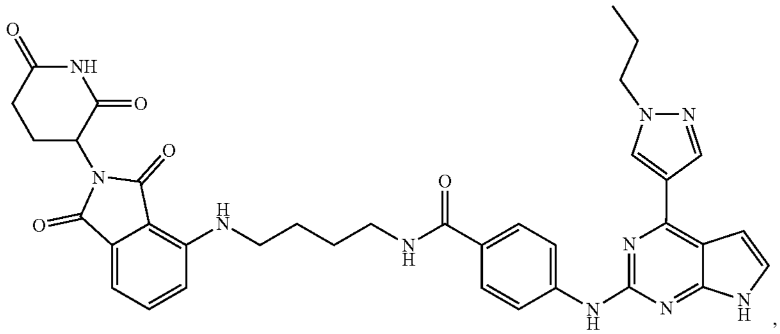
,

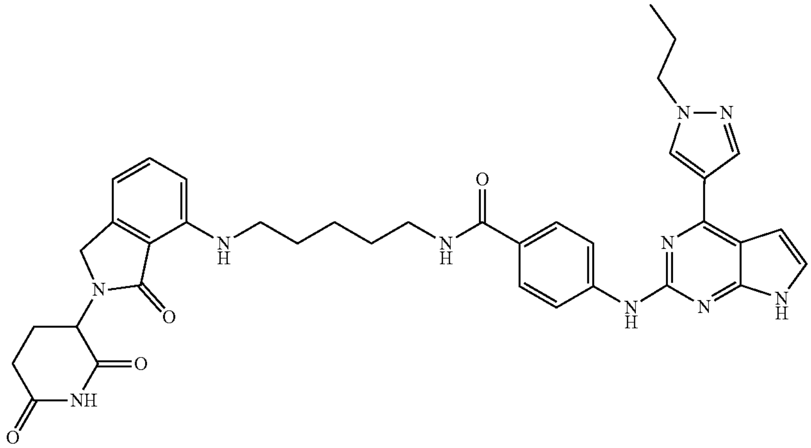
,

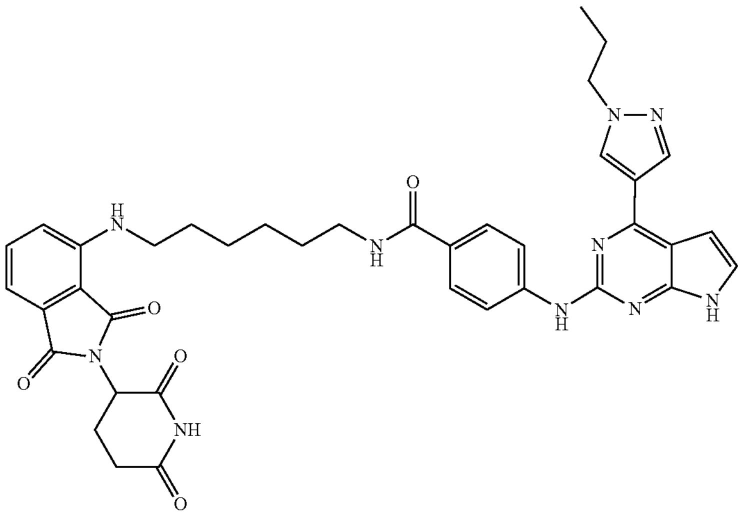
,

-continued
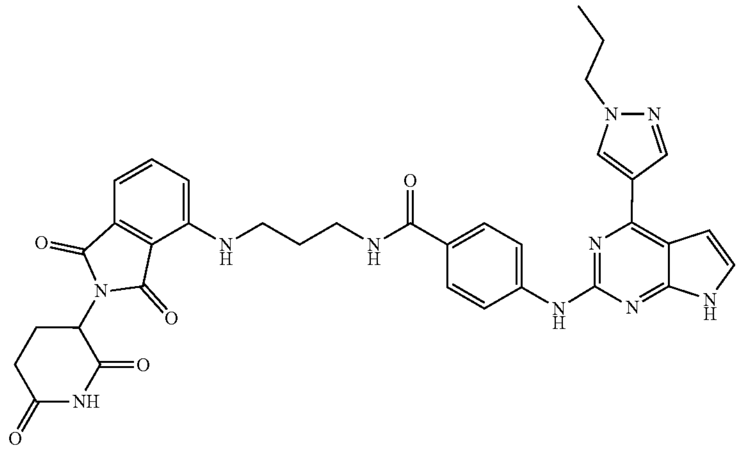
,
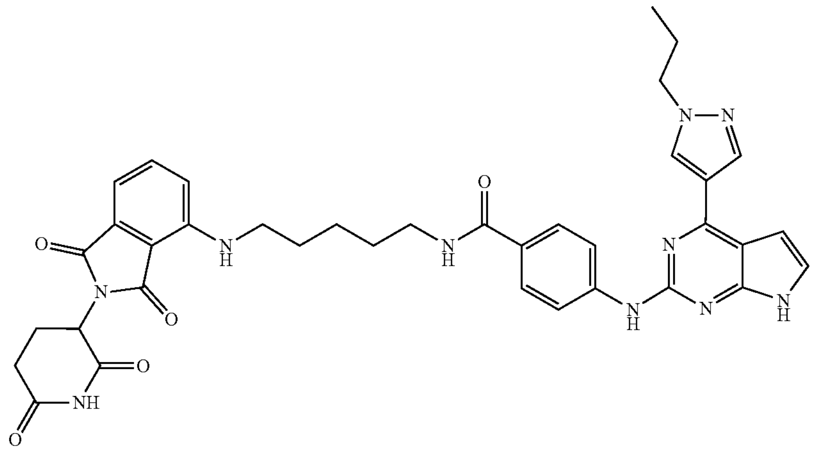
,
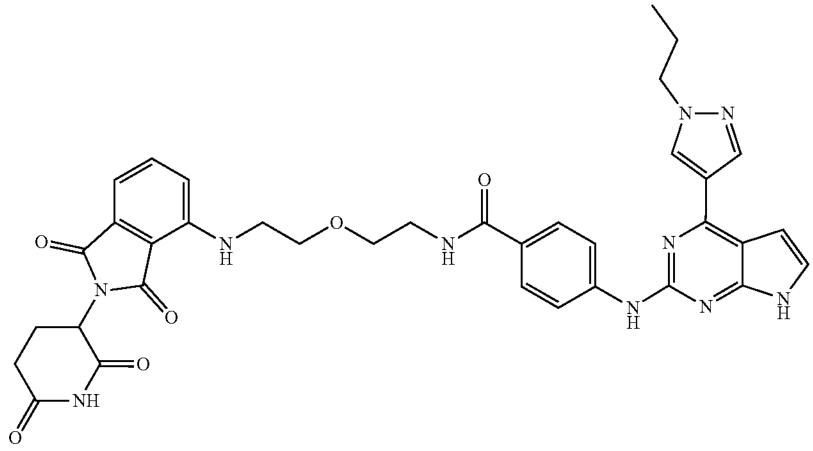
,

-continued
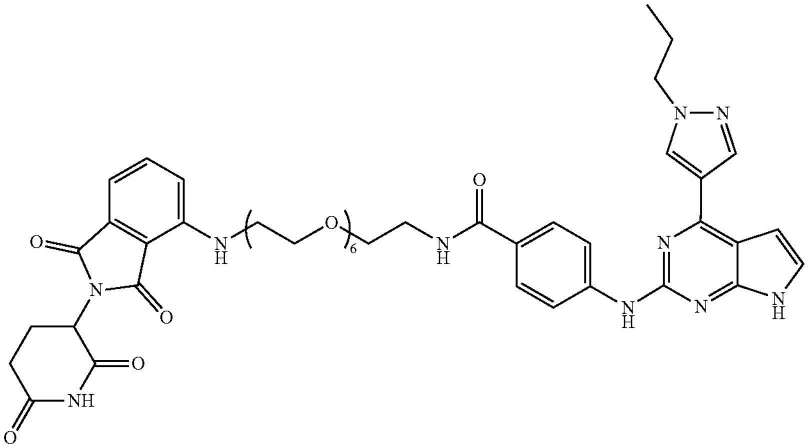
,
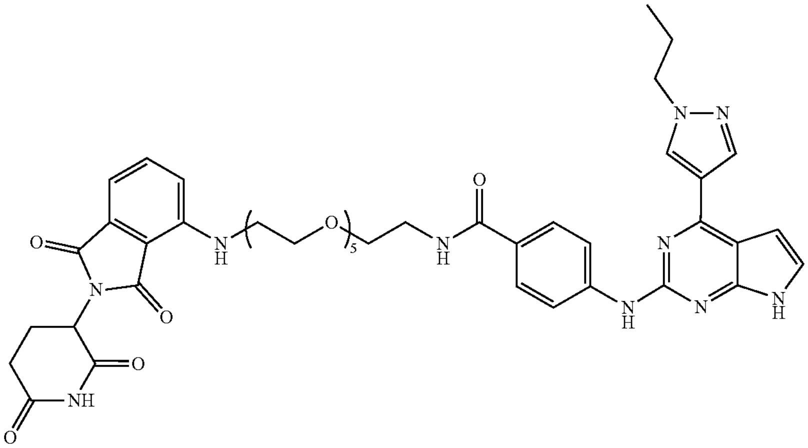
,
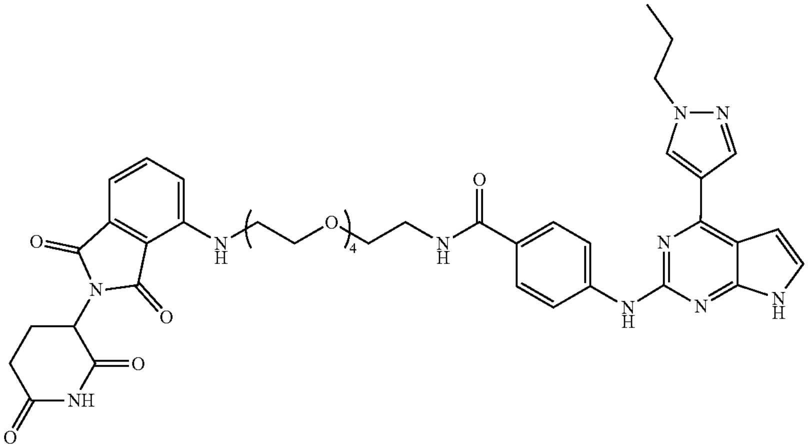
,

-continued
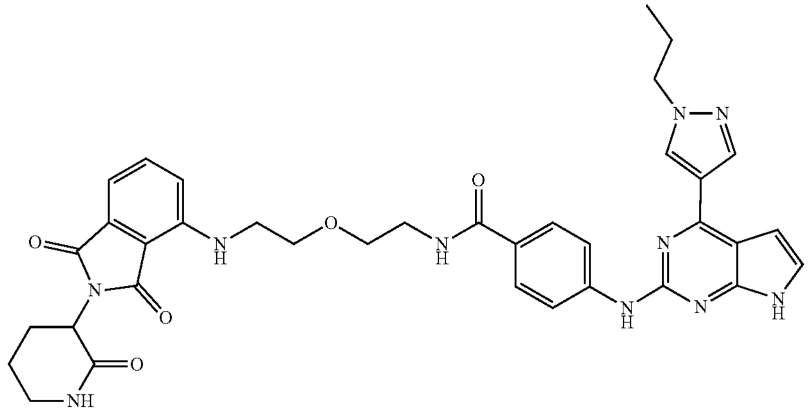
,
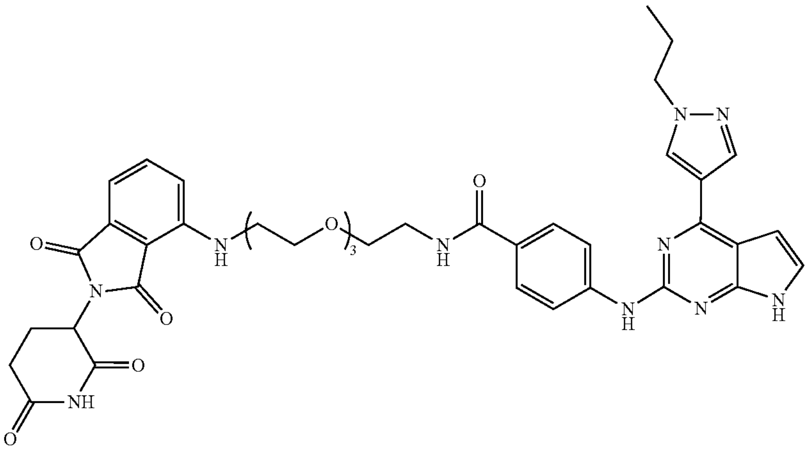
,
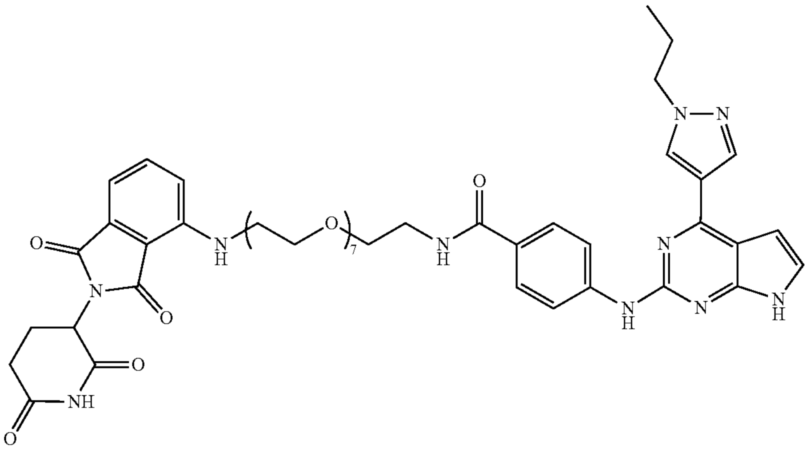
,

-continued
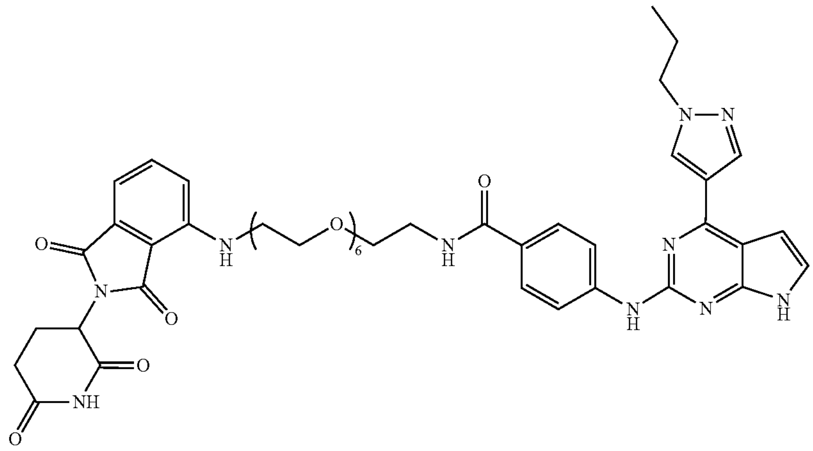
,
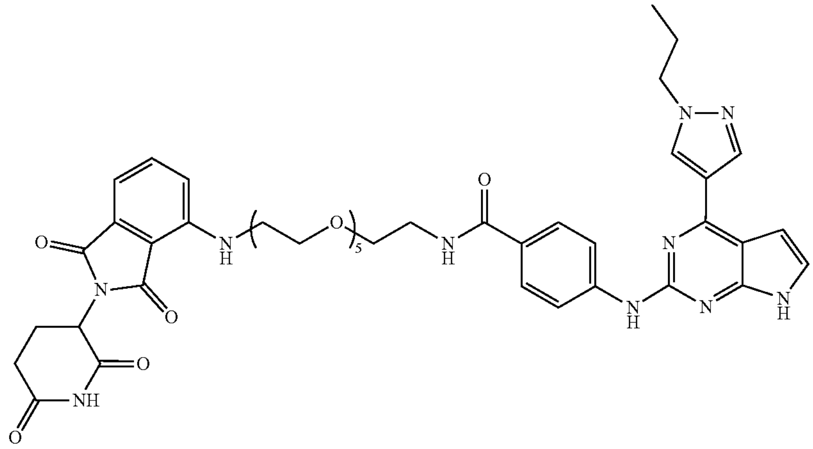
,
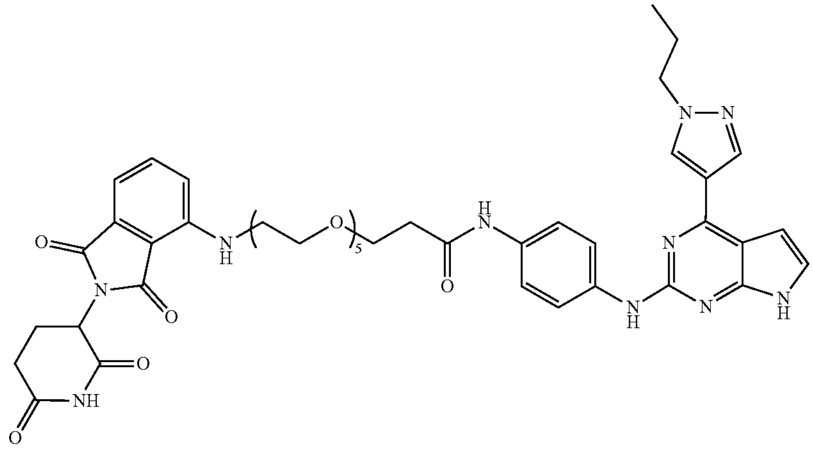
,

-continued
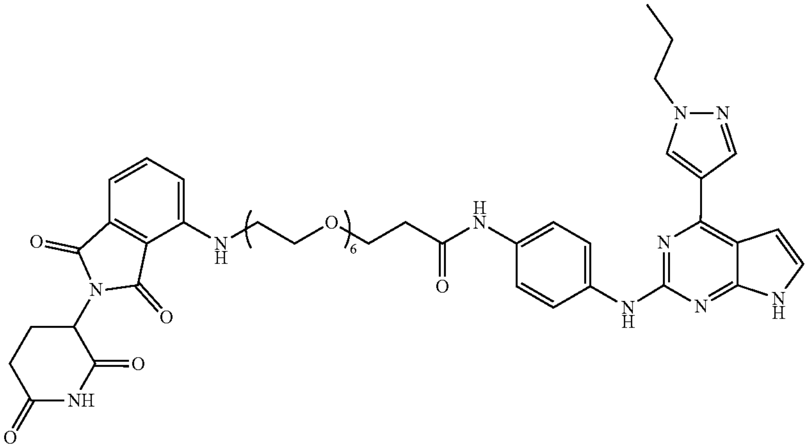
,
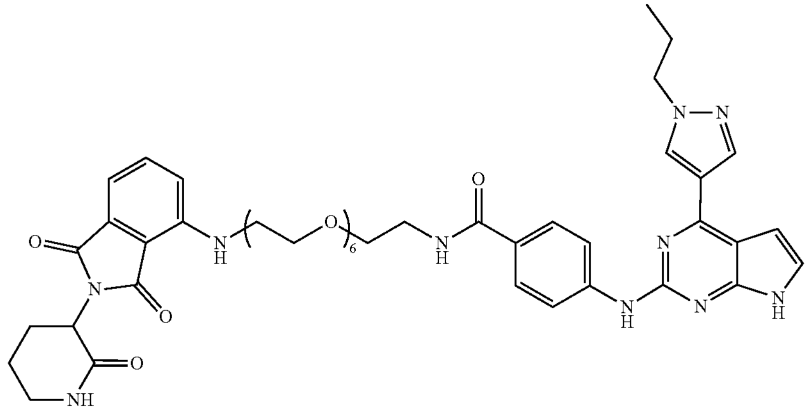
,
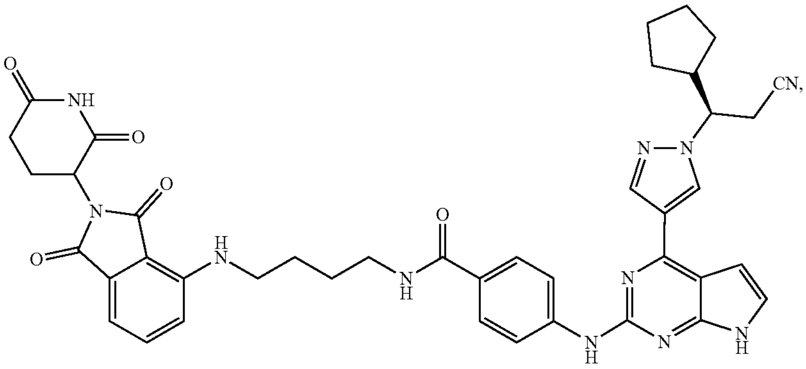
CN,
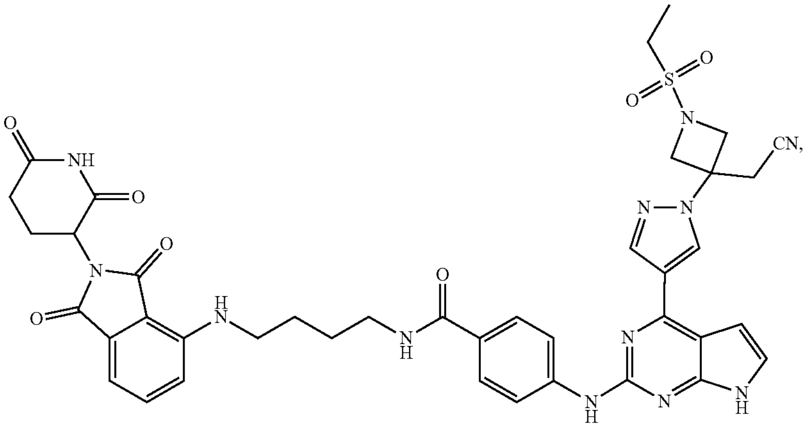
CN, and

-continued
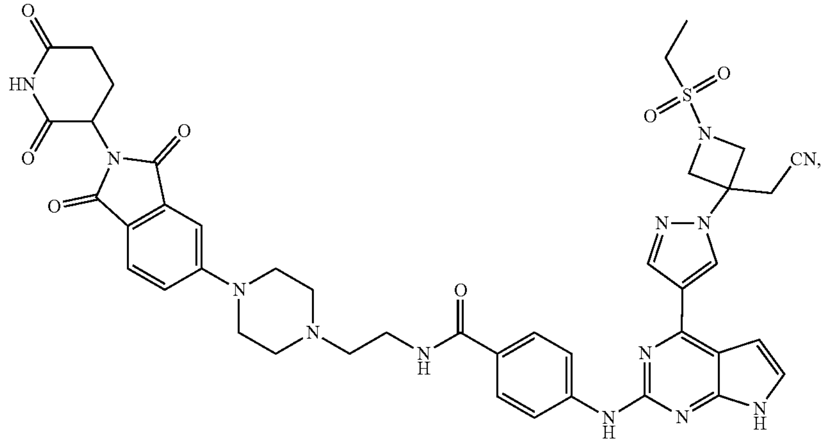 [SMILES: CCS(=O)(=O)N1CC(CC#N)(n2cc(-c3nc(Nc4ccc(C(=O)NCCN5CCN(c6ccc7c(c6)C(=O)N(C6CCC(=O)NC6=O)C7=O)CC5)cc4)nc4[nH]ccc34)cn2)C1]
or a pharmaceutically acceptable salt thereof.
In one aspect, disclosed are methods of cellular proliferation activity in at least one cell, the method comprising the step of contacting the at least one cell with an effective amount of at least one compound having a structure selected from:
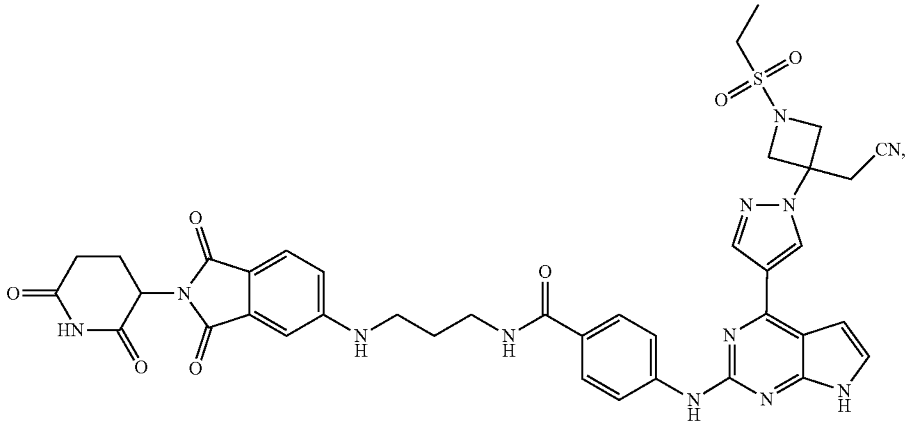
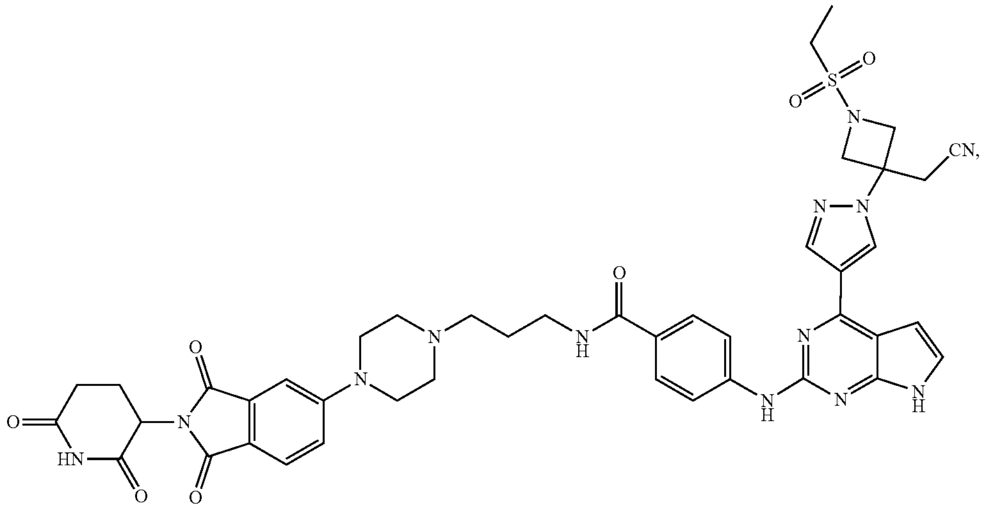

-continued

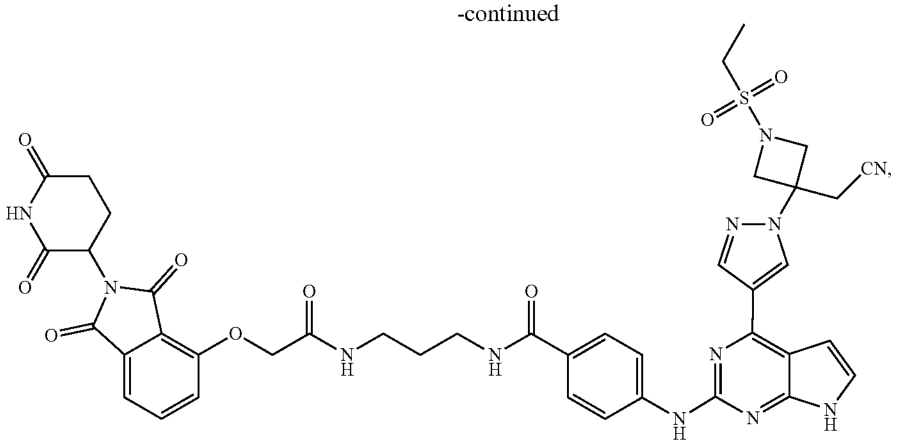

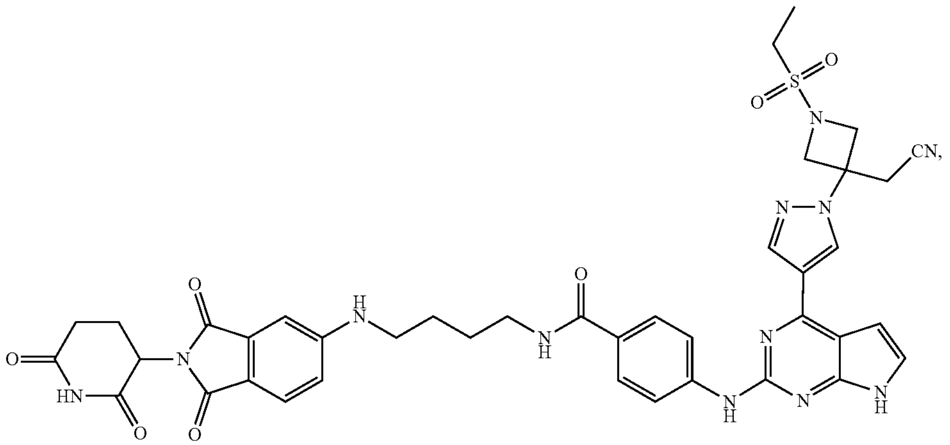

and

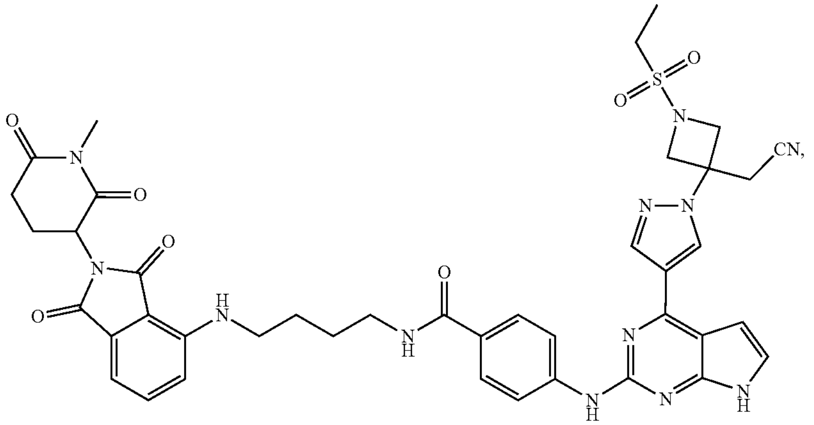

or a pharmaceutically acceptable salt thereof.

In a further aspect, the cell is mammalian. In a still further aspect, the cell is human. In yet a further aspect, the cell has been isolated from a mammal prior to the contacting step.

In a further aspect, contacting is via administration to a mammal.

In a further aspect, the mammal has been diagnosed with a need for treatment of a disorder associated with cellular activity prior to the administering step. In a still further aspect, the disorder associated with cellular proliferation activity is cancer, for example a cancer selected from for example a cancer selected from sarcoma, a carcinoma, a hematological cancer, a solid tumor, breast cancer, cervical cancer, gastrointestinal cancer, colorectal cancer, brain cancer, skin cancer, prostate cancer, ovarian cancer, non-small cell lung carcinoma, thyroid cancer, testicular cancer, pancreatic cancer, liver cancer, endometrial cancer, melanoma, glioma, leukemia, lymphoma, chronic myeloproliferative disorder, myelodysplastic syndrome, myeloproliferative neoplasm, and plasma cell neoplasm (myeloma), and in another example acute lymphoblastic leukemia.

In a further aspect, the mammal has been diagnosed with a need for modulating cellular proliferation activity prior to the administering step.

H. ADDITIONAL METHODS OF USING THE COMPOSITIONS

Provided are methods of using of a disclosed composition or medicament. In one aspect, the method of use is directed to the treatment of a disorder. In a further aspect, the disclosed compounds can be used as single agents or in combination with one or more other drugs in the treatment, prevention, control, amelioration, or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

The pharmaceutical compositions and methods of the present invention can further comprise other therapeutically active compounds as noted herein which are usually applied in the treatment of the above mentioned pathological conditions.

1. Manufacture of a Medicament

In one aspect, the invention relates to a method for the manufacture of a medicament for treating a disorder associated with uncontrolled cellular proliferation in a mammal, the method comprising combining a therapeutically effective amount of a disclosed compound or product of a disclosed method with a pharmaceutically acceptable carrier or diluent.

As regards these applications, the present method includes the administration to an animal, particularly a mammal, and more particularly a human, of a therapeutically effective amount of the compound effective in the inhibition of uncontrolled cellular proliferation, such as cancer, and the cancer's disclosed herein. The dose administered to an animal, particularly a human, in the context of the present invention should be sufficient to affect a therapeutic response in the animal over a reasonable time frame. One skilled in the art will recognize that dosage will depend upon a variety of factors including the condition of the animal, the body weight of the animal, as well as the severity and stage of the disorder.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

2. Use of Compounds and Compositions

Also provided are the uses of the disclosed compounds and compositions. Thus, in one aspect, the invention relates to the uses of modulators of cellular proliferation activity.

In a further aspect, the invention relates to the use of a disclosed compound or product of a disclosed method in the manufacture of a medicament for the treatment of a disorder associated with uncontrolled cellular proliferation, for example, cancer, such as sarcoma, a carcinoma, a hematological cancer, a solid tumor, breast cancer, cervical cancer, gastrointestinal cancer, colorectal cancer, brain cancer, skin cancer, prostate cancer, ovarian cancer, non-small cell lung carcinoma, thyroid cancer, testicular cancer, pancreatic cancer, liver cancer, endometrial cancer, melanoma, glioma, leukemia, lymphoma, chronic myeloproliferative disorder, myelodysplastic syndrome, myeloproliferative neoplasm, and plasma cell neoplasm (myeloma), and in another example acute lymphoblastic leukemia.

In a further aspect, the use relates to a process for preparing a pharmaceutical composition comprising a therapeutically effective amount of a disclosed compound or a product of a disclosed method, and a pharmaceutically acceptable carrier, for use as a medicament.

In a further aspect, the use relates to a process for preparing a pharmaceutical composition comprising a therapeutically effective amount of a disclosed compound or a product of a disclosed method, wherein a pharmaceutically acceptable carrier is intimately mixed with a therapeutically effective amount of the disclosed compound or the product of a disclosed method.

In various aspects, the use relates to the treatment of uncontrolled cellular proliferation in a vertebrate animal. In a further aspect, the use relates to the treatment of uncontrolled cellular proliferation in a human subject.

In a further aspect, the use is the treatment of uncontrolled cellular proliferation, for example cancer, for example a cancer selected from a sarcoma, a carcinoma, a hematological cancer, a solid tumor, breast cancer, cervical cancer, gastrointestinal cancer, colorectal cancer, brain cancer, skin cancer, prostate cancer, ovarian cancer, non-small cell lung carcinoma, thyroid cancer, testicular cancer, pancreatic cancer, liver cancer, endometrial cancer, melanoma, glioma, leukemia, lymphoma, chronic myeloproliferative disorder, myelodysplastic syndrome, myeloproliferative neoplasm, and plasma cell neoplasm (myeloma), and in another example acute lymphoblastic leukemia.

It is understood that the disclosed uses can be employed in connection with the disclosed compounds, methods, compositions, and kits. In a further aspect, the invention relates to the use of a disclosed compound or composition of a medicament for the treatment of a disorder associated with uncontrolled cellular proliferation in a mammal.

In a further aspect, the invention relates to the use of a disclosed compound or composition in the manufacture of a medicament for the treatment of a disorder associated with uncontrolled cellular proliferation, for example cancer, such a cancer selected from a sarcoma, a carcinoma, a hematological cancer, a solid tumor, breast cancer, cervical cancer, gastrointestinal cancer, colorectal cancer, brain cancer, skin cancer, prostate cancer, ovarian cancer, non-small cell lung carcinoma, thyroid cancer, testicular cancer, pancreatic cancer, liver cancer, endometrial cancer, melanoma, glioma, leukemia, lymphoma, chronic myeloproliferative disorder, myelodysplastic syndrome, myeloproliferative neoplasm, and plasma cell neoplasm (myeloma), and in another example acute lymphoblastic leukemia.

3. Kits

In one aspect, disclosed are kits comprising a disclosed compound and one or more of: (a) an agent known to treat a disorder of uncontrolled cellular proliferation; (b) instructions for administering the compound in connection with treating a disorder of uncontrolled cellular proliferation; and (c) instructions for treating a disorder of uncontrolled cellular proliferation.

In various aspects, the agents and pharmaceutical compositions described herein can be provided in a kit. The kit can also include combinations of the agents and pharmaceutical compositions described herein.

In various aspects, the informational material can be descriptive, instructional, marketing or other material that relates to the methods described herein and/or to the use of the agents for the methods described herein. For example, the informational material may relate to the use of the agents herein to treat a subject who has, or who is at risk for developing, a disorder associated with uncontrolled cellular proliferation. The kits can also include paraphernalia for administering the agents of this invention to a cell (in culture or in vivo) and/or for administering a cell to a patient.

In various aspects, the informational material can include instructions for administering the pharmaceutical composition and/or cell(s) in a suitable manner to treat a human, e.g., in a suitable dose, dosage form, or mode of administration (e.g., a dose, dosage form, or mode of administration described herein). In a further aspect, the informational material can include instructions to administer the pharmaceutical composition to a suitable subject, e.g., a human having, or at risk for developing, a disorder associated with uncontrolled cellular proliferation activity.

In various aspects, the composition of the kit can include other ingredients, such as a solvent or buffer, a stabilizer, a preservative, a fragrance or other cosmetic ingredient. In such aspects, the kit can include instructions for admixing the agent and the other ingredients, or for using one or more compounds together with the other ingredients.

In a further aspect, the compound and the at least one agent known to treat a disorder of uncontrolled cellular proliferation are co-formulated. In a still further aspect, the compound and the at least one agent known to treat a disorder of uncontrolled cellular proliferation are co-packaged.

In a further aspect, the at least one agent known to treat uncontrolled cellular proliferation is a chemotherapeutic agent. The chemotherapeutic agent can be selected from an alkylating agent, an antimetabolite agent, an antineoplastic antibiotic agent, a mitotic inhibitor agent, and a mTor inhibitor agent. In one aspect, the at least one agent is an antineoplastic antibiotic agent selected from doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof. In a further aspect, the at least one agent is an antimetabolite agent selected from gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof. In a further aspect, the at least one agent is an alkylating agent selected from carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt thereof. In a further aspect, the at least one agent is a mitotic inhibitor agent selected from irinotecan, topotecan, rubitecan, cabazitaxel, docetaxel, paclitaxel, etopside, vincristine, ixabepilone, vinorelbine, vinblastine, and teniposide, or a pharmaceutically acceptable salt thereof. In a further aspect, the at least one agent is an mTor inhibitor agent selected from everolimus, siroliumus, and temsirolimus, or a pharmaceutically acceptable salt, hydrate, solvate, or polymorph thereof.

In a further aspect, the kit further comprises a plurality of dosage forms, the plurality comprising one or more doses; wherein each dose comprises an effective amount of the compound and the at least one agent known to treat uncontrolled cellular proliferation. In a still further aspect, the effective amount is a therapeutically effective amount. In yet a further aspect, the effective amount is a prophylactically effective amount. In an even further aspect, each dose of the compound and at least one agent known to treat uncontrolled cellular proliferation are co-packaged. In a still further aspect, each dose of the compound and the at least one agent known to treat uncontrolled cellular proliferation are co-formulated.

In a further aspect, the at least one agent known to a disorder associated with uncontrolled cellular proliferation, for example cancer, such a cancer selected from a sarcoma, a carcinoma, a hematological cancer, a solid tumor, breast cancer, cervical cancer, gastrointestinal cancer, colorectal cancer, brain cancer, skin cancer, prostate cancer, ovarian cancer, non-small cell lung carcinoma, thyroid cancer, testicular cancer, pancreatic cancer, liver cancer, endometrial cancer, melanoma, glioma, leukemia, lymphoma, chronic myeloproliferative disorder, myelodysplastic syndrome, myeloproliferative neoplasm, and plasma cell neoplasm (myeloma), and in another example acute lymphoblastic leukemia.

In a further aspect, the kit further comprises a plurality of dosage forms, the plurality comprising one or more doses; wherein each dose comprises an effective amount of the compound and at least one agent known to treat uncontrolled cellular proliferation. In a still further aspect, the effective amount is a therapeutically effective amount. In yet a further aspect, the effective amount is a prophylactically effective amount. In an even further aspect, each dose of the compound and at least one agent known to treat uncontrolled cellular proliferation are co-packaged. In a still further aspect, each dose of the compound and at least one agent known to treat uncontrolled cellular proliferation are co-formulated.

4. Subjects

In various aspects, the subject of the herein disclosed methods is a vertebrate, e.g., a mammal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

In some aspects of the disclosed methods, the subject has been diagnosed with a need for treatment prior to the administering step. In some aspects of the disclosed method, the subject has been diagnosed with a disorder associated with uncontrolled cellular proliferation prior to the administering step. In some aspects of the disclosed methods, the subject has been identified with a need for treatment prior to the administering step. In one aspect, a subject can be treated prophylactically with a compound or composition disclosed herein, as discussed herein elsewhere.

a. Dosage

Toxicity and therapeutic efficacy of the agents and pharmaceutical compositions described herein can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio $LD_{50}/ED_{50}$. Polypeptides or other compounds that exhibit large therapeutic indices are preferred.

Data obtained from cell culture assays and further animal studies can be used in formulating a range of dosage for use in humans. The dosage of such compounds lies preferably within a range of circulating concentrations that include the $ED_{50}$ with little or no toxicity, and with little or no adverse effect on a human's ability to hear. The dosage may vary within this range depending upon the dosage form employed and the route of administration utilized. For any agents used in the methods described herein, the therapeutically effective dose can be estimated initially from cell culture assays. A dose can be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Exemplary dosage amounts of a differentiation agent are at least from about 0.01 to 3000 mg per day, e.g., at least about 0.00001, 0.0001, 0.001, 0.01, 0.1, 1, 2, 5, 10, 25, 50, 100, 200, 500, 1000, 2000, or 3000 mg per kg per day, or more.

The formulations and routes of administration can be tailored to the disease or disorder being treated, and for the specific human being treated. For example, a subject can receive a dose of the agent once or twice or more daily for one week, one month, six months, one year, or more. The treatment can continue indefinitely, such as throughout the lifetime of the human. Treatment can be administered at regular or irregular intervals (once every other day or twice per week), and the dosage and timing of the administration can be adjusted throughout the course of the treatment. The dosage can remain constant over the course of the treatment regimen, or it can be decreased or increased over the course of the treatment.

In various aspects, the dosage facilitates an intended purpose for both prophylaxis and treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., (1990) Chapter 27 in Remington's Pharmaceutical Sciences, 18th Ed., Gennaro, ed., Mack Publishing Co., Easton, PA). In general, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., (1996) Chapter 3, In: Goodman & Gilman's The Pharmacological Basis of Therapeutics, 9th Ed., Hardman et al., eds., McGraw-Hill, New York, NY).

b. Routes of Administration

Also provided are routes of administering the disclosed compounds and compositions. The compounds and compositions of the present invention can be administered by direct therapy using systemic administration and/or local administration. In various aspects, the route of administration can be determined by a patient's health care provider or clinician, for example following an evaluation of the patient. In various aspects, an individual patient's therapy may be customized, e.g., the type of agent used, the routes of administration, and the frequency of administration can be personalized. Alternatively, therapy may be performed using a standard course of treatment, e.g., using pre-selected agents and pre-selected routes of administration and frequency of administration.

Systemic routes of administration can include, but are not limited to, parenteral routes of administration, e.g., intravenous injection, intramuscular injection, and intraperitoneal injection; enteral routes of administration e.g., administration by the oral route, lozenges, compressed tablets, pills, tablets, capsules, drops (e.g., ear drops), syrups, suspensions and emulsions; rectal administration, e.g., a rectal suppository or enema; a vaginal suppository; a urethral suppository; transdermal routes of administration; and inhalation (e.g., nasal sprays).

In various aspects, the modes of administration described above may be combined in any order.

I. REFERENCES

Yao L, Mustafa N, Tan E C, et al. Design and Synthesis of Ligand Efficient Dual Inhibitors of Janus Kinase (JAK) and Histone Deacetylase (HDAC) Based on Ruxolitinib and Vorinostat. *J Med Chem.* 2017; 60(20):8336-8357.

Yao L, Ohlson S, Dymock B W. Design and synthesis of triple inhibitors of janus kinase (JAK), histone deacetylase (HDAC) and Heat Shock Protein 90 (HSP90). *Bioorg Med Chem Lett.* 2018; 28(8):1357-1362.

Yao L, Ramanujulu P M, Poulsen A, Ohlson S, Dymock B W. Merging of ruxolitinib and vorinostat leads to highly potent inhibitors of JAK2 and histone deacetylase 6 (HDAC6). *Bioorg Med Chem Lett.* 2018; 28(15):2636-2640.

Beutner G L, Young I S, Davies M L, et al. TCFH-NMI: Direct Access to N-Acyl Imidazoliums for Challenging Amide Bond Formations. *Org Lett.* 2018; 20(14):4218-4222.

Winter G. xia2: an expert system for macromolecular crystallography data reduction. *Journal of Applied Crystallography.* 2010; 43(1):186-190.

Winn M D, Ballard C C, Cowtan K D, et al. Overview of the CCP4 suite and current developments. *Acta Crystallographica Section D.* 2011; 67(4):235-242.

McCoy A J, Grosse-Kunstleve R W, Adams P D, Winn M D, Storoni L C, Read R J. Phaser crystallographic software. *Journal of Applied Crystallography.* 2007; 40(4):658-674.

Puleo D E, Kucera K, Hammaren H M, et al. Identification and Characterization of JAK2 Pseudokinase Domain Small Molecule Binders. *ACS Med Chem Lett.* 2017; 8(6):618-621.

Emsley P, Lohkamp B, Scott W G, Cowtan K. Features and development of Coot. *Acta Crystallogr D Biol Crystallogr.* 2010; 66(Pt 4):486-501.

Liebschner D, Afonine P V, Baker M L, et al. Macromolecular structure determination using X-rays, neutrons and electrons: recent developments in Phenix. *Acta Crystallogr D Struct Biol.* 2019; 75(Pt 10):861-877.

Liebschner D, Afonine P V, Moriarty N W, et al. Polder maps: improving OMIT maps by excluding bulk solvent. *Acta Crystallographica Section D.* 2017; 73(2):148-157.

Laskowski R A, Swindells M B. LigPlot+: multiple ligand-protein interaction diagrams for drug discovery. *J Chem Inf Model.* 2011; 51(10):2778-2786.

Connelly J P, Pruett-Miller S M. CRIS.py: A Versatile and High-throughput Analysis Program for CRISPR-based Genome Editing. *Sci Rep.* 2019; 9(1):4194.

Uchida M, Fukazawa T, Yamazaki Y, Hashimoto H, Miyamoto Y. A modified fast (4 day) 96-well plate Caco-2 permeability assay. *J Pharmacol Toxicol Methods.* 2009; 59(1):39-43.

Roberts K G. Why and how to treat Ph-like ALL? *Best Pract Res Clin Haematol.* 2018; 31(4):351-356.

Roberts K G, Li Y, Payne-Turner D, et al. Targetable kinase-activating lesions in Ph-like acute lymphoblastic leukemia. N Engl J Med 2014; 371(11):1005-1015.

Roberts K G, Morin R D, Zhang J, et al. Genetic alterations activating kinase and cytokine receptor signaling in high-risk acute lymphoblastic leukemia. *Cancer Cell.* 2012; 22(2):153-166.

Roberts K G, Mullighan C G. The Biology of B-Progenitor Acute Lymphoblastic Leukemia. *Cold Spring Harb Perspect Med.* 2019.

Roberts K G, Yang Y L, Payne-Turner D, et al. Oncogenic role and therapeutic targeting of ABL-class and JAK-STAT activating kinase alterations in Ph-like ALL. *Blood Adv.* 2017; 1(20):1657-1671.

Weston B W, Hayden M A, Roberts K G, et al. Tyrosine kinase inhibitor therapy induces remission in a patient with refractory EBF1-PDGFRB-positive acute lymphoblastic leukemia. *J Clin Oncol.* 2013; 31(25):e413-416.

Tanasi I, Ba I, Sirvent N, et al. Efficacy of tyrosine kinase inhibitors in Ph-like acute lymphoblastic leukemia harboring ABL-class rearrangements. *Blood.* 2019; 134(16): 1351-1355.

Yoda A, Yoda Y, Chiaretti S, et al. Functional screening identifies CRLF2 in precursor B-cell acute lymphoblastic leukemia. *Proc Natl Acad Sci USA.* 2010; 107(1):252-257.

Russell L J, Capasso M, Vater I, et al. Deregulated expression of cytokine receptor gene, CRLF2, is involved in lymphoid transformation in B-cell precursor acute lymphoblastic leukemia. *Blood.* 2009; 114(13):2688-2698.

Mullighan C G, Collins-Underwood J R, Phillips L A, et al. Rearrangement of CRLF2 in B-progenitor- and Down syndrome-associated acute lymphoblastic leukemia. *Nat Genet.* 2009; 41(11):1243-1246.

Tasian S K, Doral M Y, Borowitz M J, et al. Aberrant STAT5 and PI3K/mTOR pathway signaling occurs in human CRLF2-rearranged B-precursor acute lymphoblastic leukemia. *Blood.* 2012; 120(4):833-842.

Jain N, Jabbour E J, McKay P Z, et al. Ruxolitinib or Dasatinib in Combination with Chemotherapy for Patients with Relapsed/Refractory Philadelphia (Ph)-like Acute Lymphoblastic Leukemia: A Phase I-II Trial. *Blood.* 2017; 130(Suppl 1):1322-1322.

Meyer S C, Keller M D, Chiu S, et al. CHZ868, a Type II JAK2 Inhibitor, Reverses Type I JAK Inhibitor Persistence and Demonstrates Efficacy in Myeloproliferative Neoplasms. *Cancer Cell.* 2015; 28(1):15-28.

Wu S C, Li L S, Kopp N, et al. Activity of the Type II JAK2 Inhibitor CHZ868 in B Cell Acute Lymphoblastic Leukemia. *Cancer Cell.* 2015; 28(1):29-41.

Raina K, Crews C M. Targeted protein knockdown using small molecule degraders. *Curr Opin Chem Biol.* 2017; 39:46-53.

Hanzl A, Winter G E. Targeted protein degradation: current and future challenges. *Curr Opin Chem Biol.* 2020; 56:35-41.

Fink E C, Ebert B L. The novel mechanism of lenalidomide activity. *Blood.* 2015; 126(21):2366-2369.

Khan S, Zhang X, Lv D, et al. A selective BCL-XL PROTAC degrader achieves safe and potent antitumor activity. *Nat Med.* 2019; 25(12):1938-1947.

Burslem G M, Schultz A R, Bondeson D P, et al. Targeting BCR-ABL1 in Chronic Myeloid Leukemia by PROTAC-Mediated Targeted Protein Degradation. *Cancer Res.* 2019; 79(18):4744-4753.

Lu J, Qian Y, Altieri M, et al. Hijacking the E3 Ubiquitin Ligase Cereblon to Efficiently Target BRD4. *Chem Biol.* 2015; 22(6):755-763.

Piya S, Mu H, Bhattacharya S, et al. BETP degradation simultaneously targets acute myelogenous leukemia stem cells and the microenvironment. *J Clin Invest.* 2019; 129(5): 1878-1894.

Jaime-Figueroa S, Buhimschi A D, Toure M, Hines J, Crews C M. Design, synthesis and biological evaluation of Proteolysis Targeting Chimeras (PROTACs) as a BTK degraders with improved pharmacokinetic properties. *Bioorg Med Chem Lett.* 2020; 30(3):126877.

Dobrovolsky D, Wang E S, Morrow S, et al. Bruton tyrosine kinase degradation as a therapeutic strategy for cancer. *Blood.* 2019; 133(9):952-961.

Brand M, Jiang B, Bauer S, et al. Homolog-Selective Degradation as a Strategy to Probe the Function of CDK6 in AML. *Cell Chem Biol.* 2019; 26(2):300-306.e309.

Jiang B, Wang E S, Donovan K A, et al. Development of Dual and Selective Degraders of Cyclin-Dependent Kinases 4 and 6. *Angew Chem Int Ed Engl.* 2019; 58(19): 6321-6326.

De Dominici M, Porazzi P, Xiao Y, et al. Selective inhibition of Ph-positive ALL cell growth through kinase-dependent and independent effects by CDK6-specific PROTACs. *Blood.* 2020.

Burslem G M, Song J, Chen X, Hines J, Crews C M. Enhancing Antiproliferative Activity and Selectivity of a FLT-3 Inhibitor by Proteolysis Targeting Chimera Conversion. *J Am Chem Soc.* 2018; 140(48):16428-16432.

Papatzimas J W, Gorobets E, Maity R, et al. From Inhibition to Degradation: Targeting the Antiapoptotic Protein Myeloid Cell Leukemia 1 (MCL1). *J Med Chem.* 2019; 62(11):5522-5540.

Li Y, Yang J, Aguilar A, et al. Discovery of MD-224 as a First-in-Class, Highly Potent, and Efficacious Proteolysis Targeting Chimera Murine Double Minute 2 Degrader Capable of Achieving Complete and Durable Tumor Regression. *J Med Chem.* 2019; 62(2):448-466.

Farnaby W, Koegl M, Roy M J, et al. BAF complex vulnerabilities in cancer demonstrated via structure-based PROTAC design. *Nat Chem Biol.* 2019; 15(7):672-680.

Zhou H, Bai L, Xu R, et al. Structure-Based Discovery of SD-36 as a Potent, Selective, and Efficacious PROTAC Degrader of STAT3 Protein. *J Med Chem.* 2019; 62(24): 11280-11300.

Matyskiela M E, Lu G, Ito T, et al. A novel cereblon modulator recruits GSPT1 to the CRL4(CRBN) ubiquitin ligase. *Nature.* 2016; 535(7611):252-257.

Davis M I, Hunt J P, Herrgard S, et al. Comprehensive analysis of kinase inhibitor selectivity. *Nat Biotechnol.* 2011; 29(11):1046-1051.

Tomeczkowski J, Yakisan E, Wieland B, Reiter A, Welte K, Sykora K W. Absence of G-CSF receptors and absent response to G-CSF in childhood Burkitt's lymphoma and B-ALL cells. *Br J Haematol.* 1995; 89(4):771-779.

Tomoyasu C, Imamura T, Tomii T, et al. Copy number abnormality of acute lymphoblastic leukemia cell lines based on their genetic subtypes. *Int J Hematol.* 2018; 108(3):312-318.

Hurwitz R, Hozier J, LeBien T, et al. Characterization of a leukemic cell line of the pre-B phenotype. *Int J Cancer.* 1979; 23(2):174-180.

Yasuda T, Tsuzuki S, Kawazu M, et al. Recurrent DUX4 fusions in B cell acute lymphoblastic leukemia of adolescents and young adults. *Nat Genet.* 2016; 48(5):569-574.

Findley H W, Jr., Cooper M D, Kim T H, Alvarado C, Ragab A H. Two new acute lymphoblastic leukemia cell lines with early B-cell phenotypes. *Blood.* 1982; 60(6):1305-1309.

Alexander T B, Gu Z, Iacobucci I, et al. The genetic basis and cell of origin of mixed phenotype acute leukaemia. *Nature.* 2018; 562(7727):373-379.

Boitano A E, Wang J, Romeo R, et al. Aryl hydrocarbon receptor antagonists promote the expansion of human hematopoietic stem cells. *Science.* 2010; 329(5997):1345-1348.

Sprowl J A, van Doom L, Hu S, et al. Conjunctive therapy of cisplatin with the OCT2 inhibitor cimetidine: influence on antitumor efficacy and systemic clearance. Clin Pharmacol Ther. 2013; 94(5):585-592.

Bhagwat N, Koppikar P, Keller M, et al. Improved targeting of JAK2 leads to increased therapeutic efficacy in myeloproliferative neoplasms. Blood. 2014; 123(13):2075-2083.

Chen C, Li F, Ma M M, et al. Roles of T875N somatic mutation in the activity, structural stability of JAK2 and the transformation of OCI-AML3 cells. Int J Biol Macromol. 2019; 137:1030-1040.

Mullighan C G, Zhang J, Harvey R C, et al. JAK mutations in high-risk childhood acute lymphoblastic leukemia. Proc Natl Acad Sci USA. 2009; 106(23):9414-9418.

Alicea-Velazquez N L, Boggon T J. The use of structural biology in Janus kinase targeted drug discovery. Curr Drug Targets. 2011; 12(4):546-555.

Novartis. 3-(1-oxoisoindolin-2-yl)-piperidine-2,6-dione derivatives and uses thereof; 2019.

Ishoey M, Chorn S, Singh N, et al. Translation Termination Factor GSPT1 Is a Phenotypically Relevant Off-Target of Heterobifunctional Phthalimide Degraders. ACS Chem Biol. 2018; 13(3):553-560.

Mullighan C G, Miller C B, Radtke I, et al. BCR-ABL1 lymphoblastic leukaemia is characterized by the deletion of Ikaros. Nature. 2008; 453(7191):110-114.

Mullighan C G, Su X, Zhang J, et al. Deletion of IKZF1 and prognosis in acute lymphoblastic leukemia. N Engl J Med. 2009; 360(5):470-480.

Churchman M L, Low J, Qu C, et al. Efficacy of Retinoids in IKZF1-Mutated BCR-ABL1 Acute Lymphoblastic Leukemia. Cancer Cell. 2015; 28(3):343-356.

Virely C, Moulin S, Cobaleda C, et al. Haploinsufficiency of the IKZF1 (IKAROS) tumor suppressor gene cooperates with BCR-ABL in a transgenic model of acute lymphoblastic leukemia. Leukemia. 2010; 24(6):1200-1204.

Joshi I, Yoshida T, Jena N, et al. Loss of Ikaros DNA-binding function confers integrin-dependent survival on pre-B cells and progression to acute lymphoblastic leukemia. Nat Immunol. 2014; 15(3):294-304.

Tasian S K, Loh M L, Hunger S P. Philadelphia chromosome-like acute lymphoblastic leukemia. Blood. 2017; 130(19):2064-2072.

Jain N, Roberts K G, Jabbour E, et al. Ph-like acute lymphoblastic leukemia: a high-risk subtype in adults. Blood. 2017; 129(5):572-581.

Shah R R, Redmond J M, Mihut A, et al. Hi-JAK-ing the ubiquitin system: The design and physicochemical optimisation of JAK PROTACs. Bioorg Med Chem. 2020; 28(5):115326.

Holmfeldt L, Wei L, Diaz-Flores E, et al. The genomic landscape of hypodiploid acute lymphoblastic leukemia. Nat Genet. 2013; 45(3):242-252.

Kim S K, Knight D A, Jones L R, et al. JAK2 is dispensable for maintenance of JAK2 mutant B-cell acute lymphoblastic leukemias. Genes Dev. 2018; 32(11-12):849-864.

Waibel M, Solomon V S, Knight D A, et al. Combined targeting of JAK2 and Bcl-2/Bcl-xL to cure mutant JAK2-driven malignancies and overcome acquired resistance to JAK2 inhibitors. Cell Rep. 2013; 5(4):1047-1059.

Duan Y, Chen L, Chen Y, Fan X G. c-Src binds to the cancer drug Ruxolitinib with an active conformation. PLoS One. 2014; 9(9):e106225.

Sorrell F J, Szklarz M, Abdul Azeez K R, Elkins J M, Knapp S. Family-wide Structural Analysis of Human Numb-Associated Protein Kinases. Structure. 2016; 24(3):401-411.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

J. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Abbreviations

DCM, dichloromethane; DIPEA, N,N-diisopropylethylamine; DMAP, 4-dimethylaminopyridine; DMF, dimethylformamide; DMSO, dimethyl sulfoxide; HATU, 1-[bis(dimethylamino)methylene]-1H-1,2,3-triazolo[4,5-b] pyridinium 3-oxide hexafluorophosphate; EDC, 1-ethyl-3-(3-dimehylaminopropyl)carbodiimide; NMP, N-Methyl-2-pyrrolidone; MeOH, methanol; TCFH, N,N,N',N'-tetramethylchloroformamidinium hexafluorophosphate; XPhos, 2-dicyclohexylphosphino-2',4',6'-triisopropylbiphenyl.

2. Chemistry Methods a. Synthesis of SJ000988497

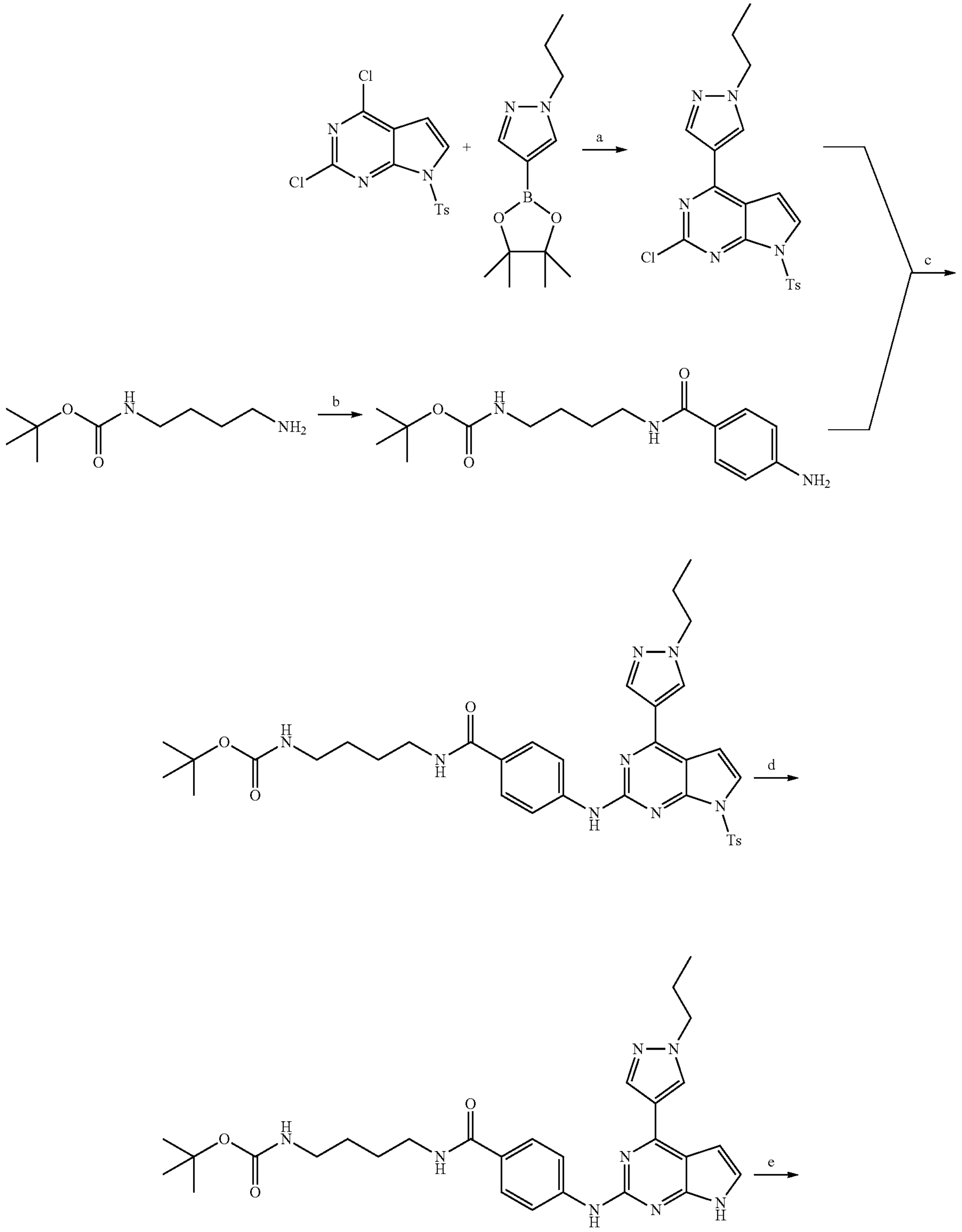

-continued

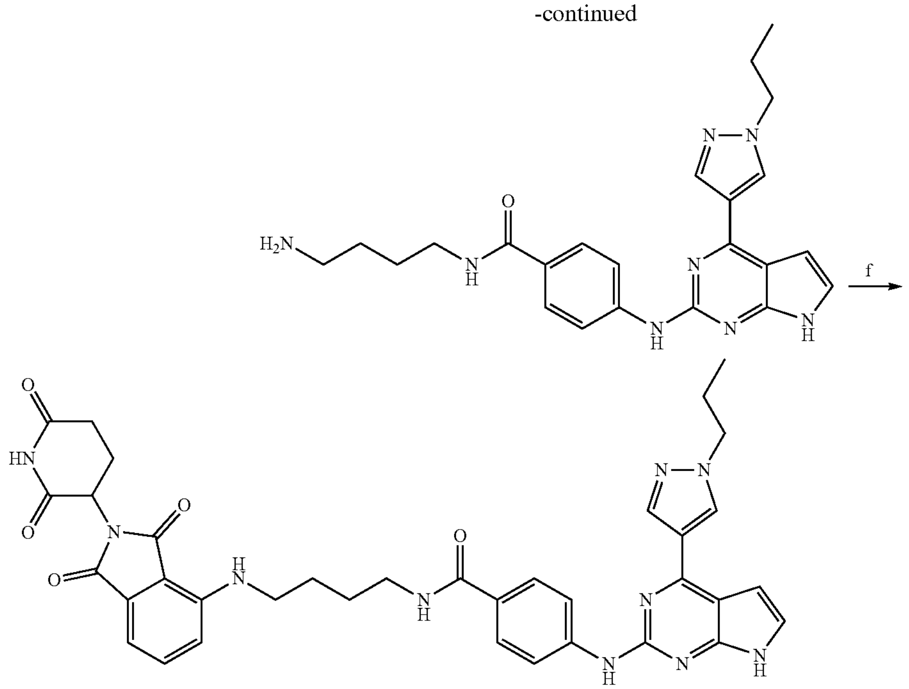

Reagents and conditions: (a) $Pd(Ph_3)_4$, $Na_2CO_3$, dioxane/water (3:1), 100° C., 2 h; (b) 4-aminobenzoic acid, DIPEA, HATU, DMF, rt, 3 h; (c) XPhos, $Pd_2(dba)_3$, $Cs_2CO_3$, dioxane, μwave, 150° C., 10 min.; (d) KOH, MeOH, 80° C., 1 h; (e) TFA, $CH_2Cl_2$, rt, 2 h; (f) 2-(2,6-dioxopiperidin-3-yl)-4-fluoroisoindoline-1,3-dione, DIPEA, DMSO, 90° C., 16 h.

Step a: Preparation of 2-chloro-4-(1-propyl-1H-pyrazol-4-yl)-7-tosyl-7H-pyrrolo[2,3-d]pyrimidine. Based on procedures adapted from Yao, L.; Ohlson, S.; Dymock, B. W. Bioog. Med. Chem. Lett. 2018, 28, 1357-1362 and Yao, L.; Ramanujulu, P. M.; Poulsen, A.; Ohlson, S.; Dymock, B. W. Bioorg. Med. Chem. Lett. 2018, 28, 2636-2640. A mixture of 2,-4-dichloro-7-tosyl-7H-pyrrolo[2,3-d]pyrimidine (0.50 g, 1.5 mmol), 1-propyl-1H-pyrazole-4-boronic acid pinacol ester (0.36 mL, 1.5 mmol), sodium carbonate (0.31 g, 2.9 mmol), and $Pd(Ph_3)_4$ (0.17 g, 0.15 mmol) in 3:1 dioxane/water (8 mL) was degassed then placed under a nitrogen atmosphere and stirred at 100° C. for 2 h. The reaction mixture was cooled to room temperature, then was poured into water (10 mL) and extracted into ethyl acetate (2×20 mL). The combined organics were washed with brine (40 mL), dried over sodium sulfate, filtered, and concentrated in vacuo. Purification using automated silica gel flash column chromatography (ethyl acetate/hexanes) was followed by evaporation giving the title compound as a yellow oil which slowly solidified (0.17 g, 28%). LC-MS (ESI) m/z: 416 $[M+H]^+$. $^1H$ NMR (500 MHz, Chloroform-d) δ 8.17 (s, 1H), 8.11 (d, J=9.2 Hz, 3H), 7.73-7.66 (m, 1H), 7.37-7.30 (m, 2H), 6.84-6.75 (m, 1H), 4.15 (t, J=7.1 Hz, 2H), 2.39 (d, J=3.0 Hz, 3H), 1.94 (hd, J=7.5, 2.2 Hz, 2H), 0.93 (td, J=7.3, 6.7, 3.4 Hz, 3H). $^{13}C$ NMR (126 MHz, Chloroform-d) δ 155.24, 154.17, 152.60, 146.23, 139.28, 134.28, 130.86, 129.89, 128.69, 126.54, 119.74, 114.27, 103.55, 54.43, 23.48, 21.75, 11.09.

Step b: Preparation of tert-butyl (4-(4-aminobenzamido)butyl)carbamate. A mixture of N-Boc-1,4-diaminobutane (0.15 g, 0.80 mmol), 4-aminobenzoic acid (0.12 g, 0.88 mmol), DIPEA (0.42 mL, 2.4 mmol), HATU (0.37 g, 0.96 mmol) was stirred at room temperature in DMF (4 mL) for 3 h. The reaction mixture was diluted with ethyl acetate (5 mL) and washed with brine (2×5 mL) followed by 5% LiCl solution (5 mL). The organic phase was dried over sodium sulfate, filtered, and concentrated in vacuo. The compound was purified using automated silica gel flash column chromatography (ethyl acetate). Additional purification by a second flash column (methanol/dichloromethane) was followed by evaporation giving the title compound as a colorless oil (0.094 g, 38%). LC-MS (ESI) m/z: 308 $[M+H]^+$. $^1H$ NMR (500 MHz, Chloroform-d) δ 7.63 (d, J=8.2 Hz, 2H), 6.66 (d, J=8.5 Hz, 2H), 6.36 (s, 1H), 4.70 (s, 1H), 4.01 (s, 2H), 3.45 (q, J=6.5 Hz, 2H), 3.16 (d, J=6.6 Hz, 2H), 1.67-1.52 (m, 4H), 1.45 (s, 9H). $^{13}C$ NMR (126 MHz, Chloroform-d)) δ 167.37, 156.18, 149.51, 128.68, 124.20, 114.13, 79.21, 40.11, 39.47, 28.43, 27.67, 26.85.

Step c: Preparation of tert-butyl (4-(4-((4-(1-propyl-1H-pyrazol-4-yl)-7-tosyl-7H-pyrrolo[2,3-d]pyrimidin-2-yl)amino)benzamido)butyl)carbamate. To a microwave vial was added 2-chloro-4-(1-propyl-1H-pyrazol-4-yl)-7-tosyl-7H-pyrrolo[2,3-d]pyrimidine (0.050 g, 0.12 mmol), tert-butyl (4-(4-aminobenzamido)butyl)carbamate (0.025 g, 0.13 mmol), XPhos (0.006 g, 0.012 mmol), $Cs_2CO_3$ (0.078 g, 0.24 mmol), $Pd_2(dba)_3$ (0.006 g, 0.006 mmol), and dioxane (2.5 mL). The vial was degassed and backfilled with nitrogen three times, then stirred at 150° C. and 100 W in a microwave reactor for 10 min. The reaction mixture was diluted with ethyl acetate (5 mL) and washed with brine (3×3 mL). The organic phase was dried over sodium sulfate, filtered, and concentrated in vacuo. Purification using automated flash column chromatography (ethyl acetate) was followed by evaporation giving the title compound as a colorless foam (0.048 g, 58%). LC-MS (ESI) m/z: 688 $[M+H]^+$. $^1H$ NMR (500 MHz, Chloroform-d) δ 8.11 (s, 1H), 8.06 (s, 1H), 8.04-7.97 (m, 2H), 7.86 (s, 4H), 7.50 (d, J=4.1 Hz, 1H), 7.45 (t, J=3.6 Hz, 1H), 7.22 (d, J=8.2 Hz, 2H), 6.71 (d, J=4.1 Hz, 1H), 6.50 (d, J=6.0 Hz, 1H), 4.69 (s, 1H), 4.16 (t, J=7.1 Hz, 2H), 3.51 (q, J=6.5 Hz, 2H), 3.18 (t, J=6.6 Hz, 2H), 2.33 (s, 3H), 2.01-1.88 (m, 2H), 1.67 (dd, J=8.9, 5.9 Hz, 2H), 1.60 (t, J=7.5 Hz, 2H), 1.44 (s, 9H), 0.95 (t, J=7.4 Hz, 3H). $^{13}$C NMR (126 MHz, Chloroform-d) δ 167.17, 156.18, 156.01, 153.28, 153.13, 145.63, 142.90, 139.20, 134.99, 132.14, 130.05, 129.85, 128.02, 127.92, 127.53, 123.61, 120.57, 117.79, 109.98, 104.38, 79.23, 54.36, 40.12, 39.65, 28.44, 27.76, 26.81, 23.58, 21.63, 11.11.

Step d: Preparation of tert-butyl (4-(4-((4-(1-propyl-1H-pyrazol-4-yl)-7H-pyrrolo[2,3-d]pyrimidin-2-yl)amino)benzamido)butyl)carbamate. To tert-butyl (4-(4-((4-(1-propyl-1H-pyrazol-4-yl)-7-tosyl-7H-pyrrolo[2,3-d]pyrimidin-2-yl)amino)benzamido)butyl)carbamate (0.045 g, 0.066 mmol) in methanol (2.0 mL) was added 2 M KOH (0.26 mL) and the reaction mixture was stirred at 80° C. for 1 h, then cooled to room temperature. The reaction mixture was concentrated in vacuo, then diluted with dichloromethane (3 mL) and washed with water (3×3 mL). The organic phase was dried over sodium sulfate, filtered, and concentrated in vacuo. Purification using automated silica gel flash column chromatography (methanol/dichloromethane) was followed by evaporation giving the title compound as a colorless foam (0.024 g, 69%). LC-MS (ESI) m/z: 533 $[M+H]^+$. $^1$H NMR (500 MHz, Chloroform-d) δ 9.56 (s, 1H), 8.24 (s, 1H), 8.13 (s, 1H), 7.73 (s, 4H), 7.53 (s, 1H), 7.02 (dd, J=3.7, 2.1 Hz, 1H), 6.63 (dd, J=3.7, 1.9 Hz, 1H), 6.45 (t, J=5.8 Hz, 1H), 4.76 (d, J=6.5 Hz, 1H), 4.17 (t, J=7.1 Hz, 2H), 3.43 (t, J=6.6 Hz, 2H), 3.15 (d, J=6.6 Hz, 2H), 1.96 (q, J=7.2 Hz, 2H), 1.65-1.49 (m, 4H), 1.44 (s, 9H), 0.96 (t, J=7.4 Hz, 3H). $^{13}$C NMR (126 MHz, Chloroform-d) δ 167.42, 156.25, 155.49, 153.80, 152.11, 143.62, 139.34, 129.91, 128.00, 126.85, 122.74, 121.37, 117.54, 108.66, 100.91, 79.26, 54.30, 40.15, 39.60, 28.45, 27.65, 26.83, 23.65, 11.16.

Step e: Preparation of N-(4-aminobutyl)-4-((4-(1-propyl-1H-pyrazol-4-yl)-7H-pyrrolo[2,3-d]pyrimidin-2-yl)amino)benzamide. To tert-butyl (4-(4-((4-(1-propyl-1H-pyrazol-4-yl)-7H-pyrrolo[2,3-d]pyrimidin-2-yl)amino)benzamido)butyl)carbamate (0.024 g, 0.045 mol) in dichloromethane (3 mL) under a nitrogen atmosphere at room temperature was added trifluoroacetic acid (0.17 mL, 2.3 mmol). The reaction mixture was stirred at room temperature under a nitrogen atmosphere for 2 h, then concentrated in vacuo to obtain a yellow solid which was used without purification. LC-MS (ESI) m/z: 433 $[M+H]^+$. $^1$H NMR (500 MHz, Methanol-d4) δ 8.73 (s, 1H), 8.40 (s, 1H), 7.94 (d, J=8.8 Hz, 2H), 7.87 (d, J=8.8 Hz, 2H), 7.40 (d, J=3.8 Hz, 1H), 6.95 (d, J=3.8 Hz, 1H), 4.28 (t, J=7.0 Hz, 2H), 3.52-3.39 (m, 2H), 3.02 (t, J=7.0 Hz, 2H), 2.00 (q, J=7.2 Hz, 2H), 1.75 (dd, J=6.2, 3.1 Hz, 4H), 0.99 (t, J=7.4 Hz, 3H). $^{13}$C NMR (126 MHz, Methanol-d4) δ 168.38, 154.07, 150.54, 145.96, 142.30, 139.25, 132.20, 127.84, 127.81, 126.99, 118.47, 115.14, 107.79, 101.79, 53.91, 39.02, 38.59, 26.25, 24.56, 23.10, 9.84.

Step f: Preparation of SJ000988497. A mixture of 2-(2,6-dioxopiperidin-3-yl)-4-fluoroisoindoline-1,3-dione (0.019 g, 0.068 mmol), N-(4-aminobutyl)-4-((4-(1-propyl-1H-pyrazol-4-yl)-7H-pyrrolo[2,3-d]pyrimidin-2-yl)amino)benzamide (0.019 g, 0.045 mmol), and DIPEA (0.031 mL, 0.18 mmol) in DMSO (1 mL) was stirred at 90° C. under a nitrogen atmosphere for 16 h. The reaction mixture was cooled to room temperature, then was diluted with ethyl acetate (5 mL) and washed sequentially with water (5 mL) and brine (2×5 mL). The organic phase was dried over sodium sulfate, filtered, and concentrated in vacuo. Purification using automated silica gel flash column chromatography (ethyl acetate/hexanes followed by methanol/dichloromethane) was followed by evaporation giving the title compound as a yellow solid (0.014 g, 45%). LC-MS (ESI) m/z: 690 $[M+H]^+$. $^1$H NMR (500 MHz, DMSO-d6) δ 11.60 (s, 1H), 11.09 (s, 1H), 9.46 (s, 1H), 8.60 (s, 1H), 8.25 (d, J=5.3 Hz, 2H), 7.97 (d, J=8.6 Hz, 2H), 7.79 (d, J=8.5 Hz, 2H), 7.58 (dd, J=8.5, 7.1 Hz, 1H), 7.27 (dd, J=3.6, 2.2 Hz, 1H), 7.13 (d, J=8.6 Hz, 1H), 7.02 (d, J=7.0 Hz, 1H), 6.83 (dd, J=3.6, 1.7 Hz, 1H), 6.60 (t, J=6.1 Hz, 1H), 5.05 (dd, J=12.7, 5.4 Hz, 1H), 4.21 (t, J=7.0 Hz, 2H), 3.36 (d, J=6.1 Hz, 2H), 3.31 (d, J=8.1 Hz, 2H), 2.88 (ddd, J=16.7, 13.7, 5.4 Hz, 1H), 2.68-2.53 (m, 2H), 2.03 (ddd, J=13.3, 6.2, 3.9 Hz, 1H), 1.88 (h, J=7.2 Hz, 2H), 1.69-1.55 (m, 4H), 0.88 (t, J=7.4 Hz, 3H). $^{13}$C NMR (126 MHz, DMSO-d6) δ 173.29, 170.59, 169.40, 167.78, 166.42, 155.75, 153.96, 151.35, 146.89, 144.87, 139.07, 136.74, 132.70, 131.34, 128.30, 126.19, 124.28, 121.11, 117.72, 117.10, 110.85, 109.49, 108.20, 100.64, 53.61, 49.00, 42.07, 39.16, 31.45, 27.23, 26.78, 23.64, 22.63, 11.39.

b. Synthesis of SJ000986420

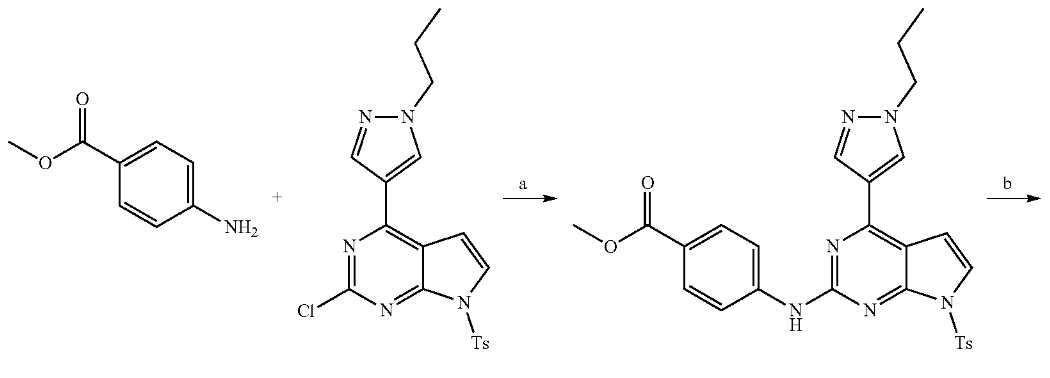

-continued

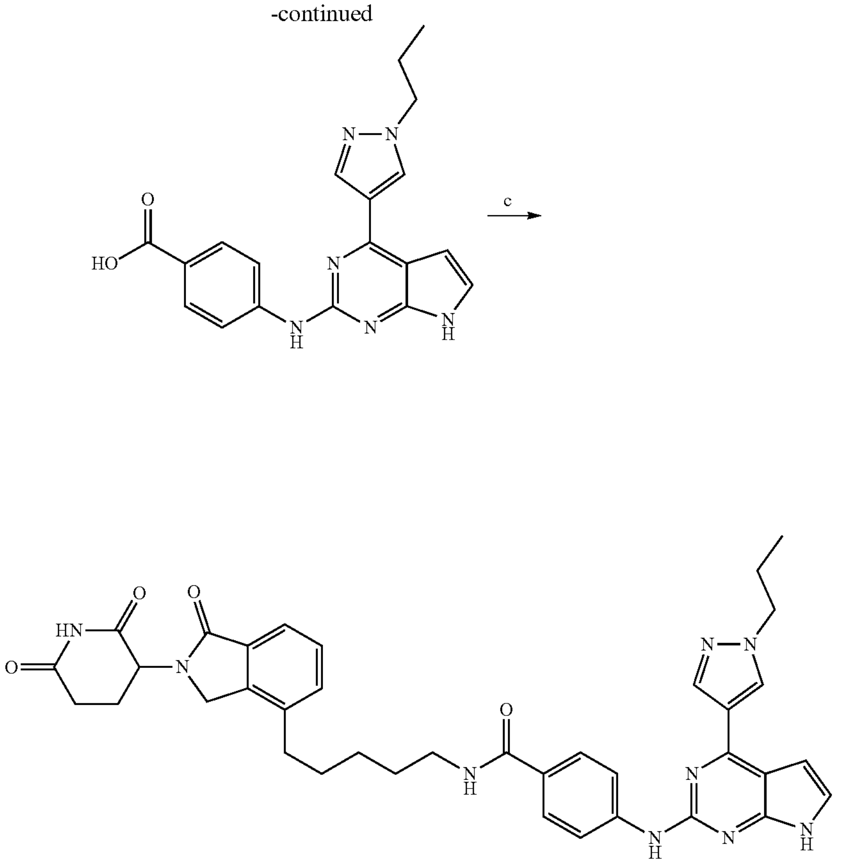

Reagents and conditions: (a) XPhos, $Pd_2(dba)_3$, $Cs_2CO_3$, dioxane, μwave, 150° C., 10 min; (b) KOH, MeOH, 80° C., 2 h; (c) amine HCl salt, DIPEA, HATU, DMF, rt, 4 h.

Step a: Preparation of methyl 4-((4-(1-propyl-1H-pyrazol-4-yl)-7-tosyl-7H-pyrrolo[2,3-d]pyrimidin-2-yl)amino)benzoate. To a microwave vial was added 2-chloro-4-(1-propyl-1H-pyrazol-4-yl)-7-tosyl-7H-pyrrolo[2,3-d]pyrimidine (0.076 g, 0.18 mmol) followed by methyl 4-aminobenzoate (0.030 g, 0.20 mmol) in dioxane (2.5 mL), XPhos (0.009 g, 0.018 mmol), $Cs_2CO_3$ (0.12 g, 0.37 mmol), and $Pd_2(dba)_3$ (0.008 g, 0.009 mmol). The vial was degassed and backfilled with nitrogen three times, then stirred at 150° C. and 100 W in a microwave reactor for 10 min. The reaction mixture was diluted with ethyl acetate (5 mL) and washed with brine (3x3 mL). The organic phase was dried over sodium sulfate, filtered, and concentrated. Purification using automated silica gel flash column chromatography (ethyl acetate/hexanes) was followed by evaporation giving the title compound as a yellow solid (0.058 g, 60%). LC-MS (ESI) m/z: 531 $[M+H]^+$. $^1H$ NMR (500 MHz, Chloroform-d) δ 8.13 (d, J=0.7 Hz, 1H), 8.12-8.08 (m, 2H), 8.07 (s, 1H), 8.02 (d, J=8.3 Hz, 2H), 7.92-7.84 (m, 2H), 7.54 (d, J=4.0 Hz, 1H), 7.37 (s, 1H), 7.24 (d, J=8.3 Hz, 2H), 6.73 (d, J=4.0 Hz, 1H), 4.17 (t, J=7.1 Hz, 2H), 3.93 (s, 3H), 2.35 (s, 3H), 1.96 (q, J=7.3 Hz, 2H), 0.96 (t, J=7.4 Hz, 3H). $^{13}C$ NMR (126 MHz, Chloroform-d) δ 167.00, 155.86, 153.25, 145.64, 144.23, 139.24, 135.04, 130.91, 130.01, 129.86, 127.97, 123.90, 123.17, 120.64, 117.49, 110.20, 104.31, 54.40, 51.90, 23.59, 21.66, 11.12.

Step b: Preparation of 4-((4-(1-propyl-1H-pyrazol-4-yl)-7H-pyrrolo[2,3-d]pyrimidin-2-yl)amino)benzoic acid. To methyl 4-((4-(1-propyl-1H-pyrazol-4-yl)-7-tosyl-7H-pyrrolo[2,3-d]pyrimidin-2-yl)amino)benzoate (0.055 g, 0.10 mmol) in methanol (2 mL) was added 2 M KOH (0.42 mL) and the reaction mixture was stirred at 80° C. under a nitrogen atmosphere for 2 h. The reaction mixture was cooled to room temperature, then water was added (10 mL). The reaction mixture placed on ice bath and acidified with dropwise addition of 1N HCl solution (~1 mL). The precipitate was filtered and washed with water, then ether to obtain a yellow sticky solid. The solid was dried overnight in a dessicator at room temperature giving the title compound as a yellow solid (0.035 g, 93%). LC-MS (ESI) m/z: 364 $[M+H]^+$. $^1H$ NMR (500 MHz, Methanol-d4) δ 8.79 (s, 1H), 8.42 (s, 1H), 8.08 (d, J=8.7 Hz, 2H), 7.89 (d, J=8.7 Hz, 2H), 7.51 (d, J=3.8 Hz, 1H), 7.06 (d, J=3.8 Hz, 1H), 4.32 (t, J=7.0 Hz, 2H), 2.01 (h, J=7.3 Hz, 2H), 1.00 (t, J=7.4 Hz, 3H). $^{13}C$ NMR (126 MHz, Methanol-d4) δ 167.95, 154.19, 142.33, 132.56, 128.45, 128.36, 125.55, 125.30, 107.74, 102.38, 54.05, 23.11, 9.83.

Step c: Preparation of SJ000986420. A mixture of 4-((4-(1-propyl-1H-pyrazol-4-yl)-7H-pyrrolo[2,3-d]pyrimidin-2-yl)amino)benzoic acid (0.010 g, 0.028 mmol), DIPEA (0.019 mL, 0.11 mmol), HATU (0.013 g, 0.033 mmol) and 3-(4-(5-aminopentyl)-1-oxoisoindolin-2-yl)piperidine-2,6-dione hydrochloride (0.011 g, 0.030 mmol) was stirred at room temperature in DMF (1 mL) for 4 h. The reaction mixture was diluted with ethyl acetate (3 mL) and washed with brine (2x3 mL) followed by 5% LiCl solution (3 mL). The precipitate which formed in the organic phase was filtered and washed with additional ethyl acetate then dried under vacuum giving the title compound as a white solid (0.010 g, 54%). LC-MS (ESI) m/z: 675 $[M+H]^+$. $^1H$ NMR (500 MHz, DMSO-d6) δ 11.61 (s, 1H), 10.99 (s, 1H), 9.46 (s, 1H), 8.60 (s, 1H), 8.24 (d, J=6.7 Hz, 2H), 8.04-7.93 (m, 2H), 7.84-7.73 (m, 2H), 7.57 (dd, J=6.8, 1.8 Hz, 1H), 7.53-7.40 (m, 2H), 7.27 (dd, J=3.6, 2.1 Hz, 1H), 6.83 (dd, J=3.6, 1.7 Hz, 1H), 5.14 (dd, J=13.3, 5.2 Hz, 1H), 4.49 (d, J=17.2 Hz, 1H), 4.33 (d, J=17.1 Hz, 1H), 4.21 (t, J=7.0 Hz, 2H), 3.26 (q, J=6.9 Hz, 2H), 2.99-2.87 (m, 1H), 2.70-2.58 (m, 3H), 2.46 (dd, J=13.2, 4.6 Hz, 1H), 2.02 (ddd, J=9.6, 5.4, 2.7 Hz, 1H), 1.88 (h, J=7.3 Hz, 2H), 1.66 (p, J=7.7 Hz, 2H), 1.59 (p, J=7.2 Hz, 2H), 1.39 (p, J=7.5 Hz, 2H), 0.88 (t, J=7.4 Hz, 3H). $^{13}C$ NMR (126 MHz, DMSO-d6) δ 173.39, 171.55, 168.86, 166.35, 155.75, 153.96, 151.35, 144.83, 141.01, 139.07, 137.98, 132.03, 131.96, 131.35, 128.74, 128.28, 126.25, 124.29, 121.12, 121.07, 117.09, 108.20, 100.64, 53.61, 52.01, 46.71, 31.67, 29.55, 29.53, 26.88, 23.64, 22.96, 11.39.
c. Synthesis of SJ000988500
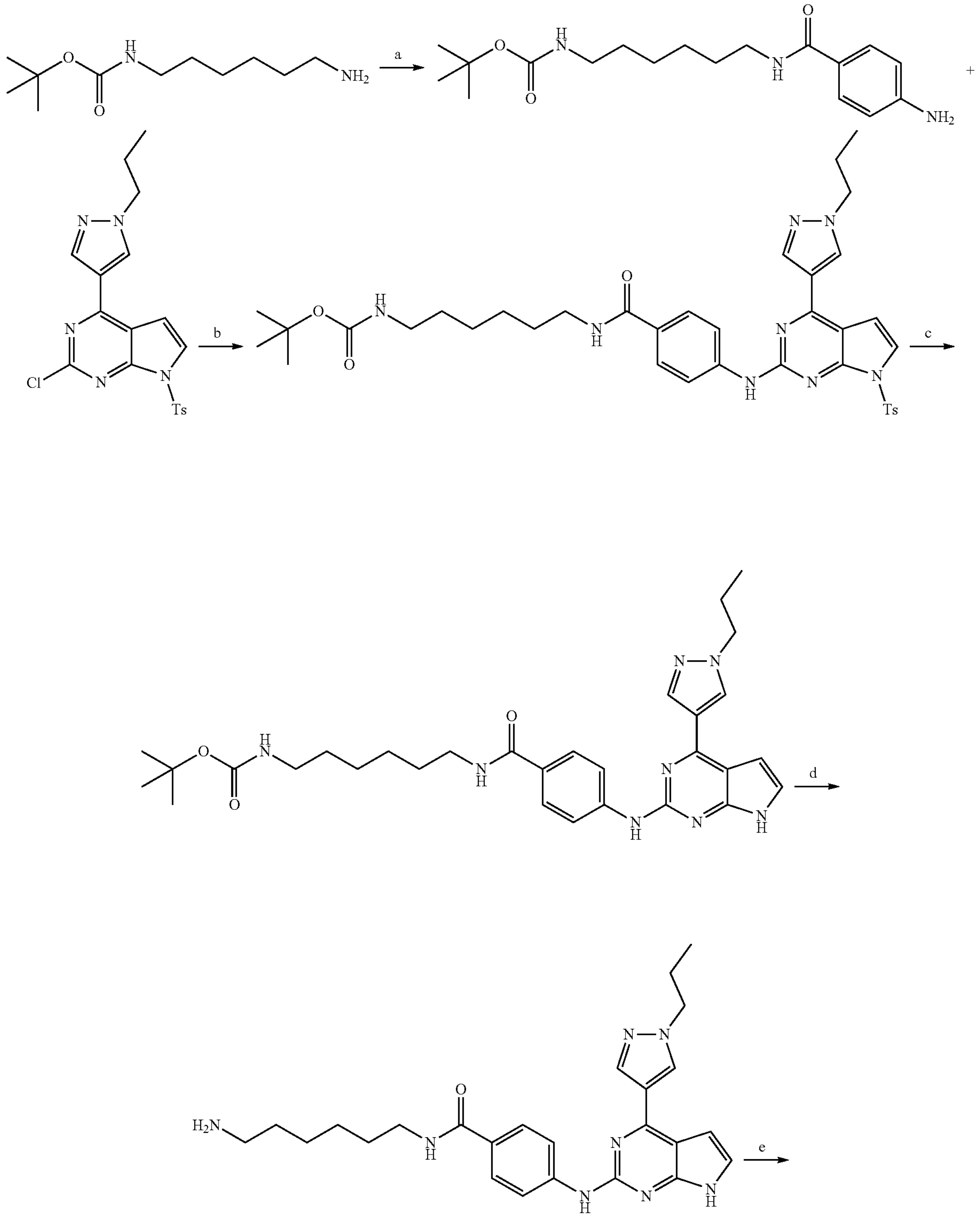

-continued

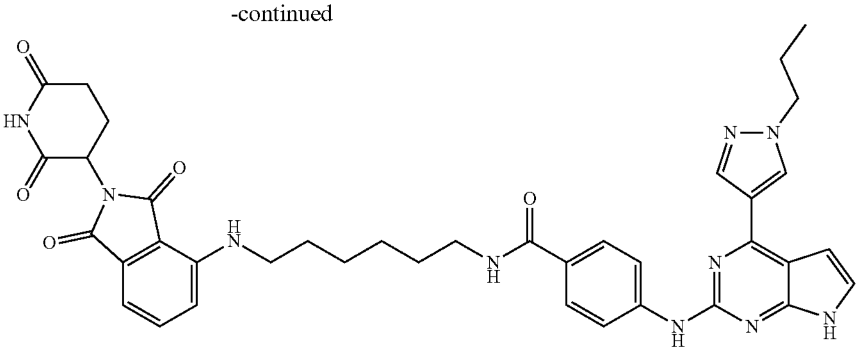

Reagents and conditions: (a) 4-aminobenzoic acid, DIPEA, HATU, DMF, rt, 4 h; (b) XPhos, $Pd_2(dba)_3$, $Cs_2CO_3$, dioxane, µwave, 150° C., 10 min.; (c) KOH, MeOH, 80° C., 1 h; (d) TFA, $CH_2Cl_2$, rt, 4 h; (e) 2-(2,6-dioxopiperidin-3-yl)-4-fluoroisonidoline-1,3-dione, DIPEA, DMSO, 90° C., 16 h.

Step a: Preparation of tert-butyl (6-(4-aminobenzamido)hexyl)carbamate. A mixture of N-Boc-1,6-hexanediamine (0.15 g, 0.74 mmol), 4-aminobenzoic acid (0.10 g, 0.74 mmol), DIPEA (0.35 mL, 2.0 mmol), HATU (0.31 g, 0.80 mmol) was stirred at room temperature in DMF (3 mL) for 4 h. The reaction mixture was diluted with ethyl acetate (5 mL) and washed with brine (2×5 mL) followed by 5% LiCl solution (5 mL). The organic phase was dried over sodium sulfate, filtered, and concentrated in vacuo. The compound was purified using automated silica gel flash column chromatography (ethyl acetate/hexanes). Additional purification by a second flash column (methanol/dichloromethane) was followed by evaporation giving the title compound as a colorless oil (0.10 g, 45%). LC-MS (ESI) m/z: 336 $[M+H]^+$. $^1H$ NMR (500 MHz, Methanol-d4) δ 7.60 (d, J=8.6 Hz, 2H), 6.68 (d, J=8.6 Hz, 2H), 3.35 (d, J=7.2 Hz, 2H), 3.05 (t, J=7.0 Hz, 2H), 1.61 (q, J=7.2 Hz, 2H), 1.54-1.48 (m, 2H), 1.45 (s, 9H), 1.40 (p, J=4.9 Hz, 4H). $^{13}C$ NMR (126 MHz, Methanol-d4) δ 169.03, 157.20, 151.64, 128.44, 122.08, 113.33, 78.38, 39.82, 39.32, 29.50, 29.22, 27.38, 26.32, 26.13.

Step b: Preparation of tert-butyl (6-(4-((4-(1-propyl-1H-pyrazol-4-yl)-7-tosyl-7H-pyrrolo[2,3-d]pyrimidin-2-yl)amino)benzamido)hexyl)carbamate. To a microwave vial was added 2-chloro-4-(1-propyl-1H-pyrazol-4-yl)-7-tosyl-7H-pyrrolo[2,3-d]pyrimidine (0.050 g, 0.12 mmol), tert-butyl (6-(4-aminobenzamido)hexyl)carbamate (0.044 g, 0.132 mmol), XPhos (0.006 g, 0.006 mmol), $Cs_2CO_3$ (0.078 g, 0.24 mmol), $Pd_2(dba)_3$ (0.006 g, 0.012 mmol), and dioxane (2.5 mL). The vial was degassed and backfilled with nitrogen three times, then stirred at 150° C. and 100 W in a microwave reactor for 10 min. The reaction mixture was diluted with ethyl acetate (5 mL) and washed with brine (3×3 mL). The organic phase was dried over sodium sulfate, filtered, and concentrated in vacuo. Purification using automated flash column chromatography (ethyl acetate) was followed by evaporation giving the title compound as a yellow oil (0.062 g, 72%). LC-MS (ESI) m/z: 716 $[M+H]^+$. $^1H$ NMR (500 MHz, Chloroform-d) δ 8.11 (s, 1H), 8.07 (s, 1H), 8.04-7.96 (m, 2H), 7.87 (s, 4H), 7.54 (ddd, J=11.2, 5.6, 2.5 Hz, 1H), 7.50 (d, J=4.0 Hz, 1H), 7.21 (d, J=8.2 Hz, 2H), 6.71 (d, J=4.1 Hz, 1H), 6.47 (t, J=5.8 Hz, 1H), 4.62 (s, 1H), 4.15 (t, J=7.1 Hz, 2H), 3.46 (q, J=6.7 Hz, 2H), 3.13 (d, J=6.7 Hz, 2H), 2.32 (s, 3H), 1.94 (h, J=7.3 Hz, 2H), 1.69-1.59 (m, 2H), 1.55-1.30 (m, 15H), 0.94 (t, J=7.4 Hz, 3H). $^{13}C$ NMR (126 MHz, Chloroform-d) δ 167.11, 156.14, 156.00, 153.28, 145.64, 142.84, 139.20, 134.96, 130.09, 129.84, 127.99, 127.91, 127.69, 123.59, 120.53, 117.82, 109.93, 104.39, 79.05, 54.34, 40.18, 39.65, 30.05, 29.63, 28.44, 26.32, 26.10, 23.57, 21.62, 11.10.

Step c: Preparation of tert-butyl (6-(4-((4-(1-propyl-1H-pyrazol-4-yl)-7H-pyrrolo[2,3-d]pyrimidin-2-yl)amino)benzamido)hexyl)carbamate. To tert-butyl (6-(4-((4-(1-propyl-1H-pyrazol-4-yl)-7-tosyl-7H-pyrrolo[2,3-d]pyrimidin-2-yl)amino)benzamido)hexyl)carbamate (0.062 g, 0.087 mmol) in methanol (2 mL) was added 2 M KOH (0.35 mL) and the reaction mixture was stirred at 80° C. under a nitrogen atmosphere for 1 h. The reaction mixture was cooled to room temperature, then concentrated in vacuo. The crude reaction mixture was diluted with dichloromethane (3 mL) and washed with water (3×3 mL). The organic phase was dried over sodium sulfate, filtered and concentrated in vacuo. Purification using silica gel automated flash column chromatography (methanol/dichloromethane) was followed by evaporation giving the title compound as a yellow foam (0.024 g, 49%). LC-MS (ESI) m/z: 562 $[M+H]^+$. $^1H$ NMR (500 MHz, Chloroform-d) δ 9.28 (s, 1H), 8.23 (s, 1H), 8.14 (s, 1H), 7.76 (s, 4H), 7.43 (s, 1H), 7.03 (dd, J=3.7, 2.2 Hz, 1H), 6.64 (dd, J=3.7, 1.9 Hz, 1H), 6.33 (d, J=6.3 Hz, 1H), 4.63 (d, J=6.2 Hz, 1H), 4.18 (t, J=7.1 Hz, 2H), 3.42 (q, J=6.7 Hz, 2H), 3.11 (q, J=6.8 Hz, 2H), 1.97 (q, J=7.2 Hz, 2H), 1.63-1.54 (m, 2H), 1.44 (s, 11H), 1.35 (s, 4H), 0.97 (t, J=7.4 Hz, 3H). $^{13}C$ NMR (126 MHz, Chloroform-d) δ 167.27, 156.17, 155.52, 153.79, 152.14, 143.55, 139.33, 129.90, 127.98, 127.04, 122.60, 121.37, 117.55, 108.61, 100.98, 79.11, 54.31, 40.19, 39.60, 30.02, 29.61, 28.45, 26.27, 26.08, 23.66, 11.16.

Step d: Preparation N-(6-aminohexyl)-4-((4-(1-propyl-1H-pyrazol-4-yl)-7H-pyrrolo[2,3-d]pyrimidin-2-yl)amino)benzamide. To tert-butyl (6-(4-((4-(1-propyl-1H-pyrazol-4-yl)-7H-pyrrolo[2,3-d]pyrimidin-2-yl)amino)benzamido)hexyl)carbamate (0.024 g, 0.043 mmol) in dichloromethane (3 mL) under a nitrogen atmosphere at room temperature was added trifluoroacetic acid (0.16 mL, 2.1 mmol). The reaction mixture was stirred at room temperature under a nitrogen atmosphere for 4 h, then concentrated in vacuo to obtain a yellow solid which was used without purification. LC-MS (ESI) m/z: 462 $[M+H]^+$. $^1H$ NMR (500 MHz, Methanol-d4) δ 8.77 (s, 1H), 8.42 (s, 1H), 7.93 (d, J=8.9 Hz, 2H), 7.87 (d, J=8.9 Hz, 2H), 7.43 (d, J=3.8 Hz, 1H), 6.98 (d, J=3.8 Hz, 1H), 4.28 (t, J=7.0 Hz, 2H), 3.42 (t, J=7.2 Hz, 2H), 2.95 (t, J=7.6 Hz, 2H), 2.00 (q, J=7.2 Hz, 2H), 1.75-1.65 (m, 4H), 1.49 (t, J=3.7 Hz, 4H), 0.99 (t, J=7.4 Hz, 3H). $^{13}C$ NMR (126 MHz, Methanol-d4) δ 168.19, 154.13, 149.98, 145.34, 141.86, 139.28, 132.37, 128.40, 127.80, 127.43, 118.68, 114.41, 107.73, 102.01, 53.96, 39.26, 39.24, 28.98, 27.11, 26.03, 25.63, 23.08, 9.84.

Step e: Preparation of SJ000988500. A mixture of 2-(2,6-dioxopiperidin-3-yl)-4-fluoroisoindoline-1,3-dione (0.018 g, 0.065 mmol), N-(6-aminohexyl)-4-((4-(1-propyl-1H-pyrazol-4-yl)-7H-pyrrolo[2,3-d]pyrimidin-2-yl)amino)benzamide (0.020 g, 0.043 mmol), and DIPEA (0.030 mL, 0.17 mmol) in DMSO (1 mL) was stirred at 90° C. under a nitrogen atmosphere for 16 h. The reaction mixture was cooled to room temperature, then was diluted with ethyl acetate (5 mL) and washed sequentially with water (5 mL) and brine (2×5 mL). The organic phase was dried over sodium sulfate, filtered, and concentrated in vacuo. Purification using automated silica gel flash column chromatography (ethyl acetate/hexanes, then methanol/dichloromethane) was followed by evaporation giving the title compound as a yellow solid (0.006 g, 19%). LC-MS (ESI) m/z: 718 $[M+H]^+$. $^1$H NMR (500 MHz, Methanol-d4) δ 8.36 (s, 1H), 8.18 (s, 1H), 7.82 (d, J=8.8 Hz, 2H), 7.69 (d, J=8.9 Hz, 2H), 7.42 (dd, J=8.6, 7.1 Hz, 1H), 7.08 (d, J=3.7 Hz, 1H), 6.92 (dd, J=7.8, 5.1 Hz, 2H), 6.65 (d, J=3.6 Hz, 1H), 4.94 (dd, J=12.5, 5.5 Hz, 1H), 4.14 (t, J=7.0 Hz, 2H), 3.29 (t, J=7.0 Hz, 2H), 3.24 (d, J=7.0 Hz, 2H), 2.74 (ddd, J=17.9, 14.3, 5.1 Hz, 1H), 2.68-2.50 (m, 2H), 2.05-1.94 (m, 1H), 1.86 (q, J=7.2 Hz, 2H), 1.58 (dq, J=20.6, 6.9 Hz, 4H), 1.39 (d, J=5.0 Hz, 4H), 0.87 (t, J=7.4 Hz, 3H). $^{13}$C NMR (126 MHz, Methanol-d4) δ 173.27, 170.29, 169.40, 168.72, 167.94, 155.56, 153.79, 151.20, 146.91, 144.79, 138.82, 135.84, 132.52, 130.75, 127.69, 125.65, 123.28, 121.43, 116.87, 116.57, 110.31, 109.58, 108.31, 99.85, 53.50, 48.76, 41.92, 39.43, 30.79, 29.11, 28.80, 26.37, 26.28, 23.35, 22.39, 9.90.

d. Synthesis of SJ000988498

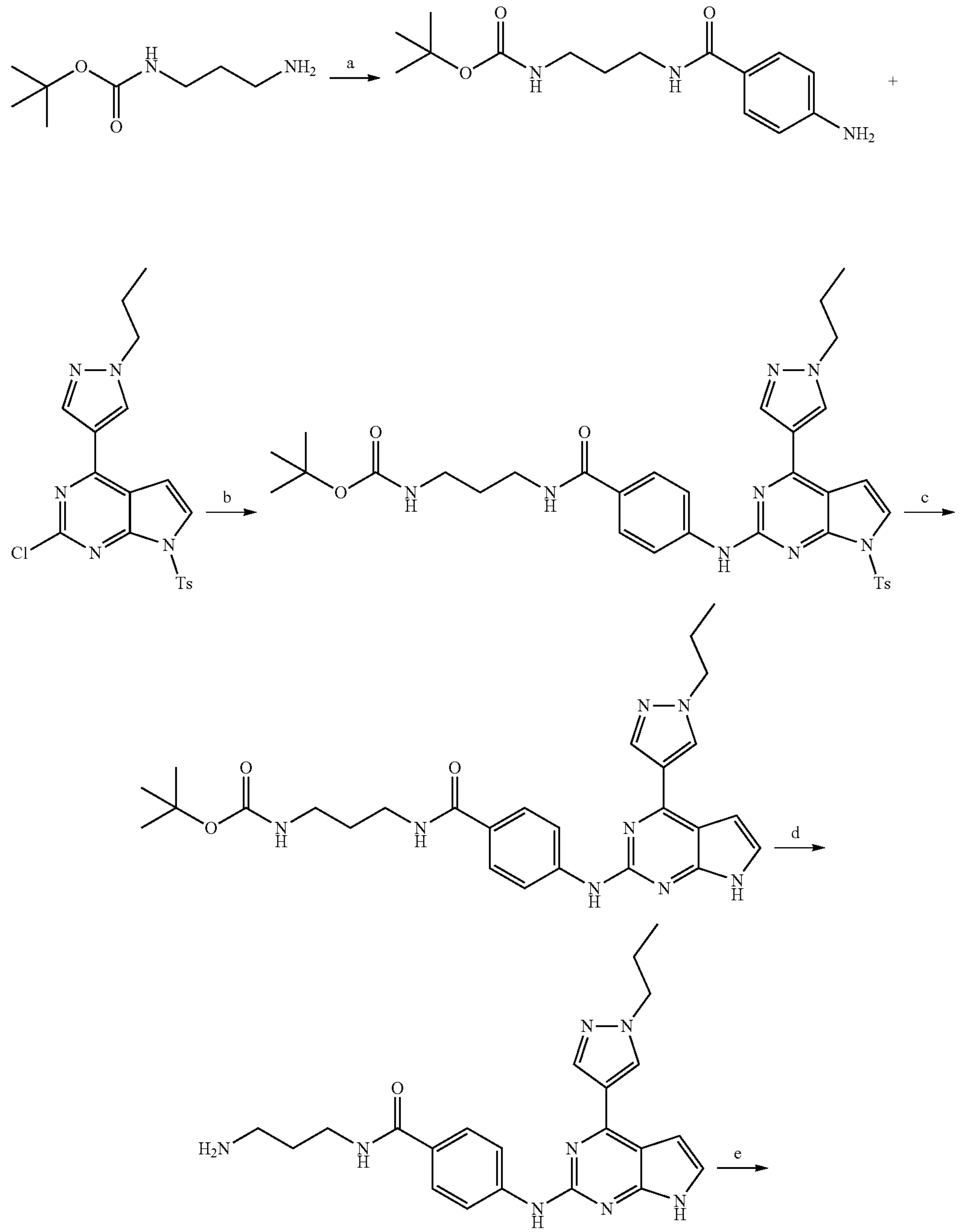

-continued

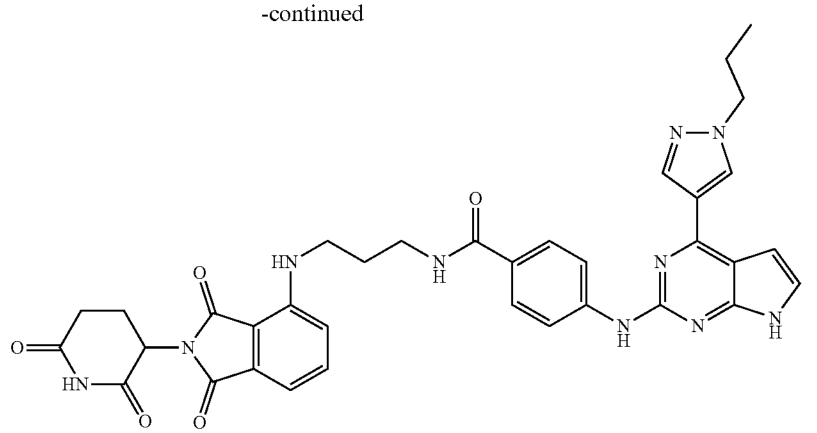

Reagents and conditions: (a) 4-aminobenzoic acid, DIPEA, HATU, DMF, rt, 3 h; (b) XPhos, $Pd_2(dba)_3$, $Cs_2CO_3$, dioxane, µwave, 150° C., 10 min; (c) KOH, MeOH, 80° C., 1 h; (d) TFA, $CH_2Cl_2$, rt, 3 h; (e) 2-(2,6-dioxopiperidin-3-yl)-4-fluoroisoindoline-1,3-dione, DIPEA, DMSO, 90° C., 20 h.

Step a: Preparation of tert-butyl (3-(4-aminobenzamido)propyl)carbamate. A mixture of N-Boc-1,3-diaminopropane (0.14 g, 0.82 mmol), 4-aminobenzoic acid (0.12 g, 0.90 mmol), DIPEA (0.43 mL, 2.5 mmol), HATU (0.37 g, 0.96 mmol) was stirred at room temperature in DMF (4 mL) for 3 h. The reaction mixture was diluted with ethyl acetate (5 mL) and washed with brine (2×5 mL), followed by 5% LiCl solution (5 mL). The organic phase was dried over sodium sulfate, filtered, and concentrated in vacuo. The compound was purified using automated silica gel flash column chromatography (ethyl acetate/hexanes). Additional purification by a second flash column (methanol/dichloromethane) was followed by evaporation giving the title compound as a colorless oil (0.098 g, 41%). LC-MS (ESI) m/z: 294 [M+H]+. $^1$H NMR (500 MHz, Methanol-d4) δ 7.61 (d, J=8.6 Hz, 2H), 6.68 (d, J=8.6 Hz, 2H), 3.39 (t, J=6.7 Hz, 2H), 3.13 (t, J=6.6 Hz, 2H), 1.81-1.68 (m, 2H), 1.46 (s, 9H). $^{13}$C NMR (126 MHz, Methanol-d4) δ 169.10, 157.27, 151.75, 128.46, 121.84, 113.32, 78.61, 37.38, 36.66, 29.58, 27.36.

Step b: Preparation of tert-butyl (3-(4-((4-(1-propyl-1H-pyrazol-4-yl)-7-tosyl-7H-pyrrolo[2,3-d]pyrimidin-2-yl)amino)benzamido)propyl)carbamate. To a microwave vial was added 2-chloro-4-(1-propyl-1H-pyrazol-4-yl)-7-tosyl-7H-pyrrolo[2,3-d]pyrimidine (0.050 g, 0.12 mmol), tert-butyl (3-(4-aminobenzamido)propyl)carbamate (0.039 g, 0.13 mmol), XPhos (0.006 g, 0.012 mmol), $Cs_2CO_3$ (0.078 g, 0.24 mmol), $Pd_2(dba)_3$ (0.006 g, 0.006 mmol), and dioxane (2.5 mL). The vial was degassed and backfilled with nitrogen three time, then stirred at 150° C. and 100 W in a microwave reactor for 10 min. The reaction mixture was diluted with ethyl acetate (5 mL) and washed with brine (3×3 mL). The organic phase was dried over sodium sulfate, filtered, and concentrated in vacuo. Purification using automated flash column chromatography (ethyl acetate) was followed by evaporation giving the title compound as a colorless foam (0.049 g, 61%). LC-MS (ESI) m/z: 674 [M+H]+. $^1$H NMR (500 MHz, Chloroform-d) δ 8.12 (s, 1H), 8.08 (s, 1H), 7.91 (d, J=8.5 Hz, 2H), 7.86 (d, J=8.7 Hz, 2H), 7.53 (d, J=4.1 Hz, 1H), 7.24 (s, 2H), 7.15 (s, 1H), 6.72 (d, J=4.1 Hz, 1H), 4.99 (d, J=6.8 Hz, 1H), 4.16 (t, J=7.1 Hz, 2H), 3.54 (q, J=6.2 Hz, 2H), 3.28 (q, J=6.3 Hz, 2H), 2.34 (s, 3H), 1.95 (q, J=7.2 Hz, 2H), 1.75 (t, J=6.2 Hz, 2H), 1.46 (s, 9H), 0.95 (t, J=7.4 Hz, 3H). $^{13}$C NMR (126 MHz, Chloroform-d) δ 167.20, 156.93, 155.99, 153.31, 145.63, 142.78, 139.21, 134.99, 132.14, 130.10, 129.87, 128.08, 127.97, 127.58, 123.71, 120.63, 117.88, 109.98, 104.32, 79.50, 54.38, 37.10, 36.06, 30.40, 28.43, 23.58, 21.65, 11.11.

Step c: Preparation of tert-butyl (3-(4-((4-(1-propyl-1H-pyrazol-4-yl)-7H-pyrrolo[2,3-d]pyrimidin-2-yl)amino)benzamido)propyl)carbamate. To tert-butyl (3-(4-((4-(1-propyl-1H-pyrazol-4-yl)-7-tosyl-7H-pyrrolo[2,3-d]pyrimidin-2-yl)amino)benzamido)propyl)carbamate (0.047 g, 0.070 mmol) in methanol (2 mL) was added 2 M KOH (0.28 mL). The reaction mixture was stirred at 80° C. under a nitrogen atmosphere for 1 h, then cooled to room temperature. The reaction mixture was concentrated in vacuo, then diluted with dichloromethane (3 mL) and washed with water (3×3 mL). The organic phase was dried over sodium sulfate, filtered, and concentrated in vacuo. Purification using silica gel automated flash column chromatography (methanol/dichloromethane) was followed by evaporation giving the title compound as a yellow foam (0.023 g, 64%). LC-MS (ESI) m/z: 520 [M+H]+. $^1$H NMR (500 MHz, Chloroform-d) δ 9.35 (s, 1H), 8.23 (s, 1H), 8.14 (s, 1H), 7.80 (d, J=8.4 Hz, 2H), 7.75 (d, J=8.7 Hz, 2H), 7.44 (s, 1H), 7.11-7.05 (m, 1H), 7.02 (dd, J=3.7, 2.1 Hz, 1H), 6.63 (dd, J=3.7, 1.9 Hz, 1H), 5.07 (t, J=6.6 Hz, 1H), 4.18 (t, J=7.1 Hz, 2H), 3.50 (q, J=6.3 Hz, 2H), 3.24 (d, J=6.3 Hz, 2H), 1.97 (q, J=7.3 Hz, 2H), 1.71 (q, J=6.0 Hz, 2H), 1.46 (s, 9H), 0.97 (t, J=7.4 Hz, 3H). $^{13}$C NMR (126 MHz, Chloroform-d) δ 167.45, 156.92, 155.52, 153.80, 152.13, 143.59, 139.32, 129.91, 128.07, 126.82, 122.62, 121.39, 117.57, 108.63, 100.97, 79.47, 54.30, 37.11, 36.08, 30.34, 28.44, 23.65, 11.16.

Step d: Preparation of N-(3-aminopropyl)-4-((4-(1-propyl-1H-pyrazol-4-yl)-7H-pyrrolo[2,3-d]pyrimidin-2-yl)amino)benzamide. To tert-butyl (3-(4-((4-(1-propyl-1H-pyrazol-4-yl)-7H-pyrrolo[2,3-d]pyrimidin-2-yl)amino)benzamido)propyl)carbamate (0.023 g, 0.044 mol) in dichloromethane (3 mL) under a nitrogen atmosphere at room temperature was added trifluoroacetic acid (0.17 mL, 2.2 mmol). The reaction mixture was stirred at room temperature under a nitrogen atmosphere for 3 h, then concentrated in vacuo giving the title compound as a yellow foam which was used without purification. LC-MS (ESI) m/z: 419 [M+H]+. $^1$H NMR (500 MHz, Methanol-d4) δ 8.80 (s, 1H), 8.43 (s, 1H), 7.94 (d, J=8.8 Hz, 2H), 7.89 (d, J=8.8 Hz, 2H), 7.44 (d, J=3.8 Hz, 1H), 6.99 (d, J=3.8 Hz, 1H), 4.27 (t, J=7.0 Hz, 2H), 3.53 (t, J=6.6 Hz, 2H), 3.03 (t, J=7.3 Hz, 2H), 2.09-1.89 (m, 4H), 0.99 (t, J=7.4 Hz, 3H). $^{13}$C NMR (126 MHz, Methanol-d4) δ 168.81, 154.09, 149.18, 144.57, 141.80, 139.42, 132.60, 127.95, 127.91, 118.88, 113.45, 107.63, 102.31, 54.02, 36.91, 35.99, 27.62, 23.02, 9.83.

Step e: Preparation of SJ000988498. A mixture of 2-(2,6-dioxopiperidin-3-yl)-4-fluoroisoindoline-1,3-dione (0.018 g, 0.066 mmol), N-(3-aminopropyl)-4-((4-(1-propyl-1H-pyrazol-4-yl)-7H-pyrrolo[2,3-d]pyrimidin-2-yl)amino)benzamide (0.018 g, 0.044 mmol), and DIPEA (0.031 mL, 0.176 mmol) in DMSO (1 mL) was stirred at 90° C. under a nitrogen atmosphere for 20 h. The reaction mixture was cooled to room temperature, then was diluted with ethyl acetate (5 mL) and washed sequentially with water (5 mL) and brine (2×5 mL). The organic phase was dried over sodium sulfate, filtered, and concentrated in vacuo. Purification using automated silica gel flash column chromatography (methanol/dichloromethane) was followed by evaporation giving the title compound as a yellow solid (0.003 g, 10%). LC-MS (ESI) m/z: 676 [M+H]+. $^1$H NMR (500 MHz, Methanol-d4) δ 8.48 (s, 1H), 8.30 (s, 1H), 7.94 (d, J=8.8 Hz, 2H), 7.80 (d, J=8.8 Hz, 2H), 7.61-7.53 (m, 1H), 7.20 (d, J=3.6 Hz, 1H), 7.10 (d, J=8.5 Hz, 1H), 7.06 (d, J=7.1 Hz, 1H), 6.77 (d, J=3.6 Hz, 1H), 5.04 (dd, J=12.6, 5.5 Hz, 1H), 4.26 (t, J=7.0 Hz, 2H), 3.55 (t, J=6.6 Hz, 2H), 3.49 (t, J=6.6 Hz, 2H), 2.88-2.77 (m, 1H), 2.77-2.62 (m, 2H), 2.14-2.04 (m, 1H), 2.05-1.93 (m, 4H), 0.99 (t, J=7.4 Hz, 3H). $^{13}$C NMR (126 MHz, Methanol-d4) δ 173.27, 170.24, 169.18, 168.89, 167.93, 155.54, 153.78, 151.21, 146.67, 144.87, 138.82, 135.82, 132.59, 130.76, 127.76, 125.44, 123.30, 121.42, 116.81, 116.57, 110.37, 109.83, 108.32, 99.86, 53.51, 48.74, 39.91, 37.27, 30.76, 28.79, 23.35, 22.39, 9.90.

e. Synthesis of SJ000988499

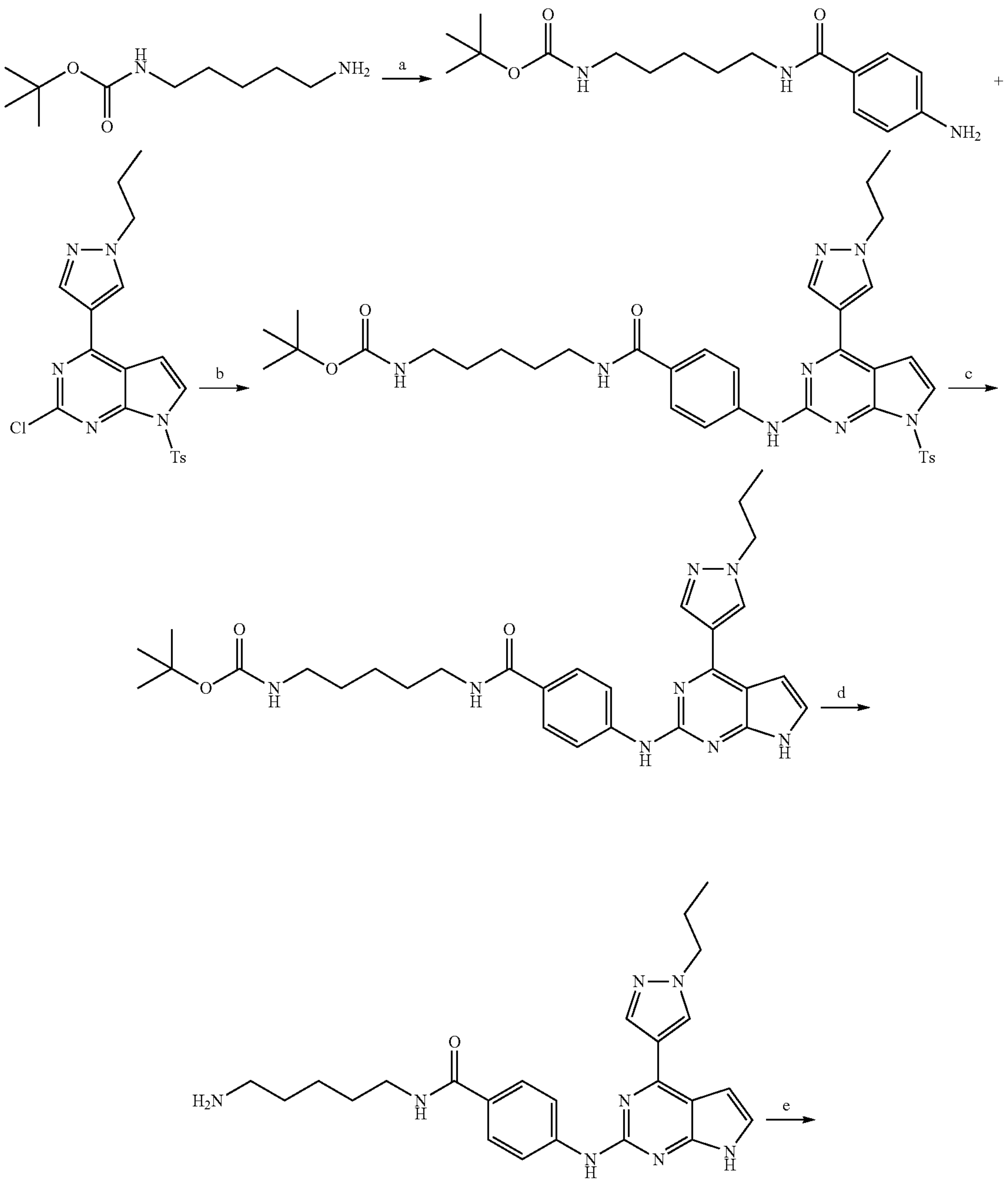

-continued

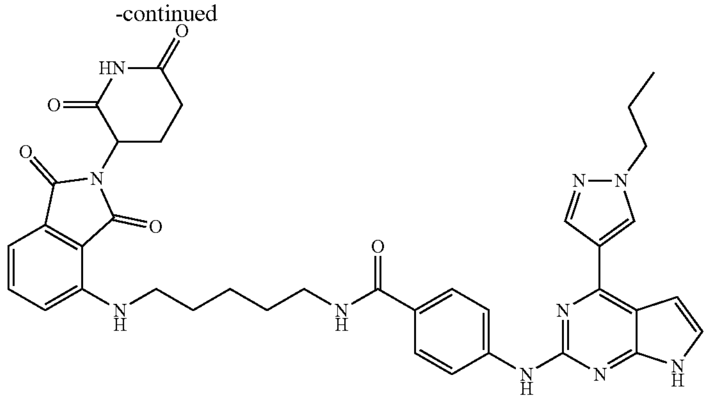

Step a: Preparation of tert-butyl (5-(4-aminobenzamido)pentyl)carbamate. A mixture of N-Boc-1,5-diaminopentane (0.13 g, 0.62 mmol), 4-aminobenzoic acid (0.093 g, 0.68 mmol), DIPEA (0.32 mL, 1.85 mmol), and HATU (0.28 g, 0.74 mmol) was stirred at room temperature in DMF (3 mL) for 4 h. The reaction mixture was diluted with ethyl acetate (5 mL) and washed with brine (2×5 mL), followed by 5% LiCl solution (5 mL). The organic phase was dried over sodium sulfate, filtered, and concentrated in vacuo. The compound was purified using automated silica gel flash column chromatography (ethyl acetate/hexanes). Additional purification by a second flash column (methanol/dichloromethane) was followed by evaporation giving the title compound as a white foam (0.063 g, 32%). LC-MS (ESI) m/z: 322 [M+H]+. $^1$H NMR (500 MHz, Methanol-d4) δ 7.61 (d, J=8.6 Hz, 2H), 6.68 (d, J=8.6 Hz, 2H), 3.35 (td, J=7.1, 5.2 Hz, 2H), 3.06 (td, J=6.8, 5.4 Hz, 2H), 1.62 (p, J=7.3 Hz, 2H), 1.53 (p, J=7.1 Hz, 2H), 1.44 (s, 9H), 1.42-1.36 (m, 2H). $^{13}$C NMR (126 MHz, Methanol-d4) δ 169.05, 157.25, 157.20, 151.65, 128.46, 122.05, 113.34, 78.40, 39.84, 39.30, 29.27, 28.97, 27.39, 23.84.

Step b: Preparation of tert-butyl (5-(4-((4-(1-propyl-1H-pyrazol-4-yl)-7-tosyl-7H-pyrrolo[2,3-d]pyrimidin-2-yl)amino)benzamido)pentyl)carbamate. To a microwave vial was added 2-chloro-4-(1-propyl-1H-pyrazol-4-yl)-7-tosyl-7H-pyrrolo[2,3-d]pyrimidine (0.053 g, 0.13 mmol), tert-butyl (5-(4-aminobenzamido)pentyl)carbamate (0.045 g, 0.14 mmol) in dioxane (2.5 mL), XPhos (0.006 g, 0.013 mmol), $Cs_2CO_3$ (0.083 g, 0.26 mmol), and $Pd_2(dba)_3$ (0.006 g, 0.006 mmol). The vial was degassed and backfilled with nitrogen three times, then stirred at 150° C. at 100 W in a microwave reactor for 10 min. The reaction mixture was diluted with ethyl acetate (5 mL) and washed with brine (3×3 mL). The organic phase was dried over sodium sulfate, filtered, and concentrated in vacuo. Purification using automated flash column chromatography (ethyl acetate) was followed by evaporation giving the title compound as a yellow oil (0.064 g, 72%). LC-MS (ESI) m/z: 702 [M+H]+. $^1$H NMR (500 MHz, Chloroform-d) δ 8.11 (s, 1H), 8.08 (s, 1H), 8.01 (d, J=8.3 Hz, 2H), 7.86 (q, J=8.9 Hz, 4H), 7.50 (d, J=4.0 Hz, 1H), 7.22 (d, J=8.2 Hz, 2H), 6.71 (d, J=4.1 Hz, 1H), 6.35 (s, 1H), 4.65 (t, J=6.1 Hz, 1H), 4.15 (t, J=7.1 Hz, 2H), 3.47 (q, J=6.7 Hz, 2H), 3.14 (q, J=6.7 Hz, 2H), 2.33 (s, 3H), 1.94 (q, J=7.2 Hz, 2H), 1.68 (d, J=7.2 Hz, 2H), 1.54 (p, J=7.1 Hz, 2H), 1.43 (s, 11H), 0.94 (t, J=7.4 Hz, 3H). $^{13}$C NMR (126 MHz, Chloroform-d) δ 167.20, 156.12, 155.94, 153.28, 153.05, 145.66, 142.85, 139.21, 134.96, 132.05, 130.11, 129.85, 128.56, 127.98, 127.91, 127.64, 123.64, 120.49, 117.82, 109.94, 104.40, 79.06, 54.36, 40.34, 39.83, 29.78, 29.44, 28.43, 24.11, 23.57, 21.63, 11.10.

Step c: Preparation of tert-butyl (5-(4-((4-(1-propyl-1H-pyrazol-4-yl)-7H-pyrrolo[2,3-d]pyrimidin-2-yl)amino)benzamido)pentyl)carbamate. To tert-butyl (5-(4-((4-(1-propyl-1H-pyrazol-4-yl)-7-tosyl-7H-pyrrolo[2,3-d]pyrimidin-2-yl)amino)benzamido)pentyl)carbamate (0.064 g, 0.091 mmol) in methanol (2 mL) was added 2 M KOH (0.37 mL) and the reaction mixture was stirred at 80° C. under a nitrogen atmosphere for 1 h. The reaction mixture was cooled to room temperature, then concentrated in vacuo. The reaction mixture was then diluted with dichloromethane (3 mL) and washed with water (3×3 mL). The organic phase was dried over sodium sulfate, filtered, and concentrated in vacuo. Purification using automated silica gel flash column chromatography (methanol/dichloromethane) was followed by evaporation giving the title compound as a colorless foam (0.024 g, 48%). LC-MS (ESI) m/z: 548 [M+H]+. $^1$H NMR (500 MHz, Chloroform-d) δ 9.54 (s, 1H), 8.24 (s, 1H), 8.13 (s, 1H), 7.81-7.68 (m, 4H), 7.52 (s, 1H), 7.02 (dd, J=3.6, 2.1 Hz, 1H), 6.63 (dd, J=3.7, 1.9 Hz, 1H), 6.30 (d, J=5.6 Hz, 1H), 4.68 (t, J=6.1 Hz, 1H), 4.17 (t, J=7.1 Hz, 2H), 3.40 (t, J=6.7 Hz, 2H), 3.11 (d, J=6.7 Hz, 2H), 1.96 (q, J=7.3 Hz, 2H), 1.59 (dd, J=10.9, 4.4 Hz, 2H), 1.49 (q, J=7.5, 7.0 Hz, 2H), 1.43 (s, 9H), 1.35 (d, J=9.4 Hz, 2H), 0.96 (t, J=7.4 Hz, 3H). $^{13}$C NMR (126 MHz, Chloroform-d) δ 167.44, 156.19, 155.50, 153.80, 152.12, 143.61, 139.33, 129.90, 127.98, 126.94, 122.72, 121.37, 117.55, 108.65, 100.91, 79.14, 54.30, 40.34, 39.79, 29.73, 29.38, 28.44, 24.06, 23.65, 11.16.

Step d: Preparation of N-(5-aminopentyl)-4-((4-(1-propyl-1H-pyrazol-4-yl)-7H-pyrrolo[2,3-d]pyrimidin-2-yl)amino)benzamide. To tert-butyl (5-(4-((4-(1-propyl-1H-pyrazol-4-yl)-7H-pyrrolo[2,3-d]pyrimidin-2-yl)amino)benzamido)pentyl)carbamate (0.024 g, 0.044 mmol) in dichloromethane (3 mL) under a nitrogen atmosphere at room temperature was added trifluoroacetic acid (0.17 mL, 2.2 mmol). The reaction mixture was stirred at room temperature for 3 h, then concentrated giving the title compound as a yellow solid which was used without purification. LC-MS (ESI) m/z: 448 [M+H]+. $^1$H NMR (500 MHz, Methanol-d4) δ 8.60 (s, 1H), 8.28 (s, 1H), 7.82 (d, J=8.9 Hz, 2H), 7.75 (d, J=8.8 Hz, 2H), 7.28 (d, J=3.7 Hz, 1H), 6.83 (d, J=3.8 Hz, 1H), 4.17 (t, J=7.0 Hz, 2H), 3.32 (t, J=7.1 Hz, 2H), 2.85 (t, J=7.6 Hz, 2H), 1.88 (h, J=7.3 Hz, 2H), 1.68-1.54 (m, 4H), 1.39 (qd, J=9.2, 8.7, 6.0 Hz, 2H), 0.87 (t, J=7.4 Hz, 3H). $^{13}$C NMR (126 MHz, Methanol-d4) δ 168.35, 154.07, 150.96, 146.38, 142.43, 139.17, 132.08, 127.82, 127.80, 126.72, 118.36, 115.66, 107.86, 101.63, 53.88, 39.24, 39.06, 28.74, 26.82, 23.38, 23.13, 9.84.

Step e: Preparation of SJ000988499. A mixture of 2-(2,6-dioxopiperidin-3-yl)-4-fluoroisoindoline-1,3-dione (0.018 g, 0.066 mmol), N-(5-aminopentyl)-4-((4-(1-propyl-1H-pyrazol-4-yl)-7H-pyrrolo[2,3-d]pyrimidin-2-yl)amino)benzamide (0.020 g, 0.044 mmol), and DIPEA (0.031 mL, 0.176 mmol) in DMSO (1 mL) was stirred at 90° C. under a nitrogen atmosphere for 22 h. The reaction mixture was cooled to room temperature, then was diluted with ethyl acetate (5 mL) and washed sequentially with water (5 mL) and brine (2×5 mL). The organic phase was dried over sodium sulfate, filtered, and concentrated in vacuo. The compound was purified using automated silica gel flash column chromatography (methanol/dichloromethane). Additional purification by a second flash column (methanol/ethyl acetate) was followed by evaporation giving the title compound as a yellow solid (0.003 g, 10%). LC-MS (ESI) m/z: 704 [M+H]+. $^{1}$H NMR (500 MHz, DMSO-d6) δ 11.60 (s, 1H), 11.10 (s, 1H), 9.45 (s, 1H), 8.60 (s, 1H), 8.25 (s, 1H), 7.97 (dd, J=8.9, 1.9 Hz, 2H), 7.88-7.72 (m, 2H), 7.59 (dd, J=8.6, 7.1 Hz, 1H), 7.27 (dd, J=3.6, 1.9 Hz, 1H), 7.12 (d, J=8.6 Hz, 1H), 7.03 (d, J=7.0 Hz, 1H), 6.89-6.79 (m, 1H), 5.05 (dd, J=12.7, 5.4 Hz, 1H), 4.21 (t, J=6.9 Hz, 2H), 3.27 (t, J=7.0 Hz, 2H), 2.94-2.81 (m, 1H), 2.67-2.55 (m, 2H), 2.07-1.98 (m, 1H), 1.88 (h, J=7.2 Hz, 2H), 1.61 (dp, J=22.6, 7.3 Hz, 4H), 1.41 (q, J=8.0 Hz, 2H), 0.88 (t, J=7.4 Hz, 3H). $^{13}$C NMR (126 MHz, DMSO-d6) δ 173.30, 170.59, 169.42, 167.79, 166.38, 155.75, 153.96, 151.35, 146.81, 144.83, 139.07, 136.78, 132.67, 131.34, 128.29, 126.26, 124.28, 121.12, 117.71, 117.09, 110.86, 109.49, 108.20, 100.65, 53.61, 49.00, 42.31, 42.19, 31.44, 29.53, 28.95, 24.34, 23.64, 22.62, 11.39.

f. Synthesis of SJ000986340

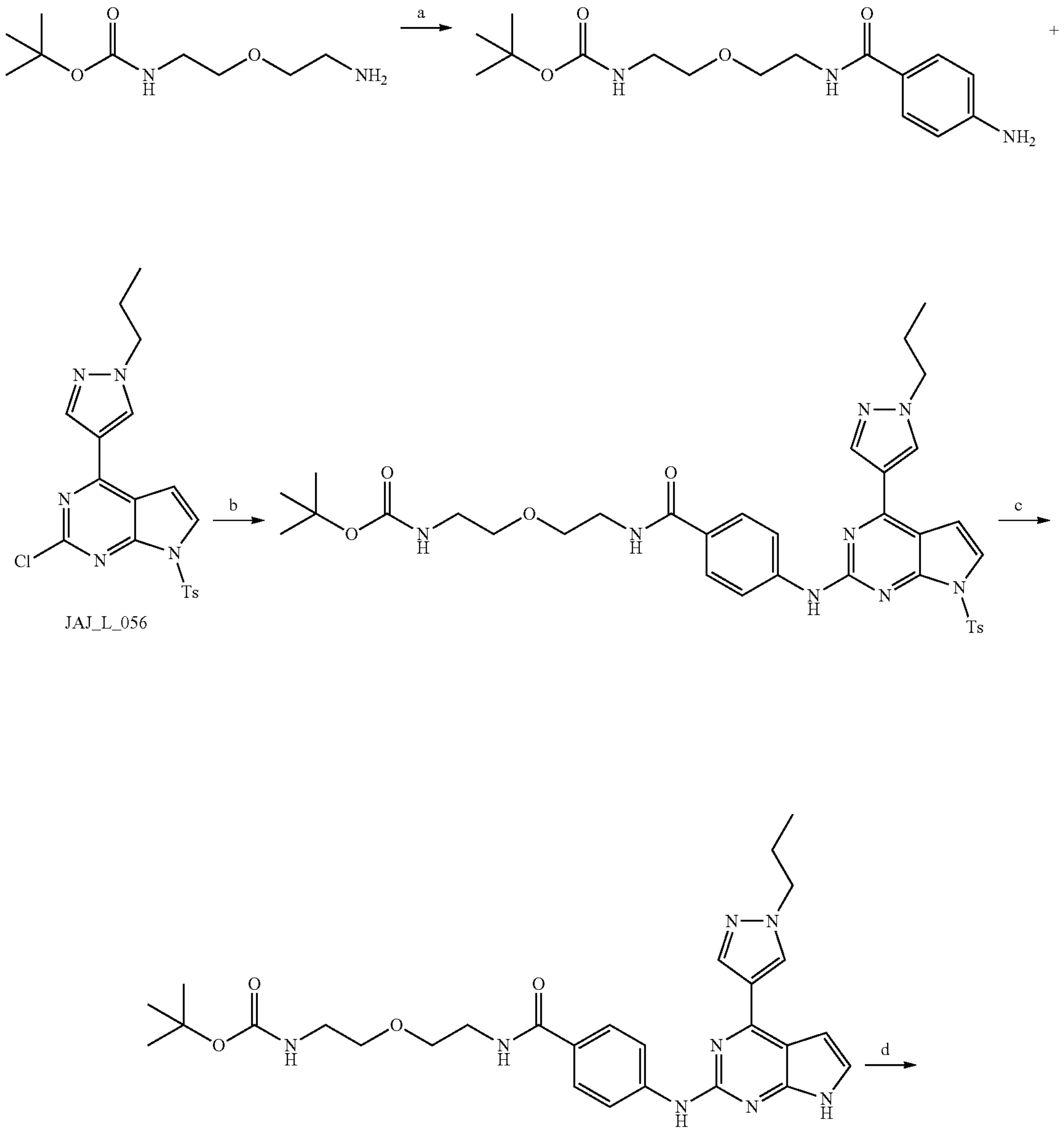

JAJ_L_056

-continued

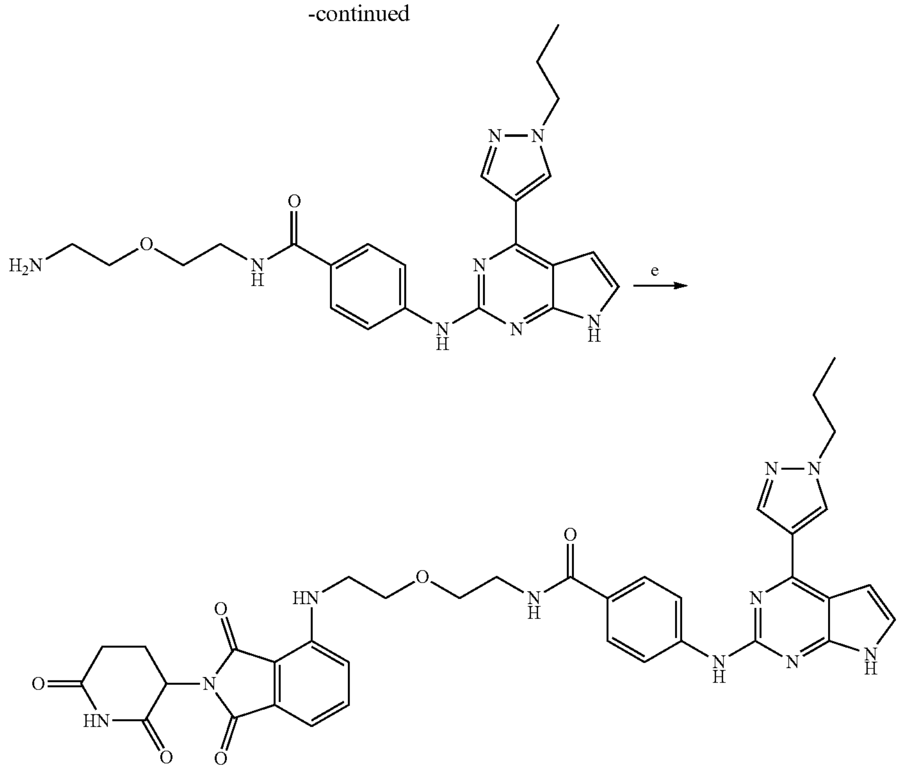

Reagents and conditions: (a) 4-aminobenzoic acid, DIPEA, HATU, DMF, rt, 2 h; (b) XPhos, $Pd_2(dba)_3$, $Cs_2CO_3$, dioxane, μwave, 150° C., 10 min.; (c) KOH, MeOH, 80° C., 1 h; (d) TFA, $CH_2Cl_2$, rt, 3 h; (e) 2-(2,6-dioxopiperidin-3-yl)-4-fluoroisoindoline-1,3-dione, DIPEA, DMSO, 90° C., 18 h.

Step a: Preparation of tert-butyl (2-(2-(4-aminobenzamido)ethoxy)ethyl)carbamate. A mixture of N-Boc-2-(2-aminoethoxy)ethylamine (0.12 g, 0.56 mmol), 4-aminobenzoic acid (0.085 g, 0.62 mmol), DIPEA (0.29 mL, 1.7 mmol), and HATU (0.26 g, 0.68 mmol) was stirred at room temperature in DMF (2 mL) for 4 h. The reaction mixture was diluted with ethyl acetate (3 mL) and washed with brine (2×3 mL), followed by 5% LiCl solution (3 mL). The organic phase was dried over sodium sulfate, filtered, and concentrated in vacuo. Purification using automated silica gel flash column chromatography (ethyl acetate/hexanes) was followed by evaporation giving the title compound as a colorless oil (0.099 g, 54%). LC-MS (ESI) m/z: 324 [M+H]+. $^1$H NMR (500 MHz, Chloroform-d) δ 7.56 (d, J=8.6 Hz, 2H), 6.61 (d, J=8.6 Hz, 2H), 6.33 (s, 1H), 4.79 (s, 1H), 3.55 (d, J=3.4 Hz, 4H), 3.47 (t, J=5.2 Hz, 2H), 3.26 (d, J=5.9 Hz, 2H), 1.37 (s, 9H). $^{13}$C NMR (126 MHz, Chloroform-d) δ 167.29, 156.03, 149.28, 128.77, 124.25, 114.31, 79.42, 69.93, 40.41, 39.59, 28.40.

Step b: Preparation of tert-butyl (2-(2-(4-((4-(1-propyl-1H-pyrazol-4-yl)-7-tosyl-7H-pyrrolo[2,3-d]pyrimidin-2-yl)amino)benzamido)ethoxy)ethyl)carbamate. To a microwave vial was added 2-chloro-4-(1-propyl-1H-pyrazol-4-yl)-7-tosyl-7H-pyrrolo[2,3-d]pyrimidine (0.070 g, 0.17 mmol) followed by tert-butyl (2-(2-(2-(4-aminobenzamido)ethoxy)ethoxy)ethyl)carbamate (0.06 g, 0.19 mmol) in dioxane (2.5 mL), XPhos (0.008 g, 0.017 mmol), $Cs_2CO_3$ (0.11 g, 0.34 mmol), and $Pd_2(dba)_3$ (0.008 g, 0.008 mmol). The vial was degassed and backfilled with nitrogen three times, then stirred at 150° C. and 100 W in a microwave reactor for 10 min. The reaction mixture was diluted with ethyl acetate (5 mL) and washed with brine (3×3 mL). The organic phase was dried over sodium sulfate, filtered, and concentrated in vacuo. The compound was purified using automated flash column chromatography (ethyl acetate) followed by evaporation, giving the title compound as a yellow foam (0.074 g, 63%). LC-MS (ESI) m/z: 704 [M+H]+. $^1$H NMR (500 MHz, Chloroform-d) δ 8.14 (s, 1H), 8.09 (s, 1H), 8.07-8.01 (m, 2H), 7.96-7.85 (m, 4H), 7.54 (d, J=4.0 Hz, 1H), 7.38 (s, 1H), 7.26 (d, J=8.3 Hz, 2H), 6.74 (d, J=4.1 Hz, 1H), 6.58 (s, 1H), 4.92 (s, 1H), 4.19 (t, J=7.1 Hz, 2H), 3.70 (dq, J=8.6, 4.8 Hz, 4H), 3.60 (t, J=5.2 Hz, 2H), 3.37 (q, J=5.5 Hz, 2H), 2.37 (s, 3H), 1.98 (q, J=7.2 Hz, 2H), 1.46 (s, 9H), 0.98 (t, J=7.4 Hz, 3H). $^{13}$C NMR (126 MHz, Chloroform-d) δ 167.16, 156.02, 153.32, 153.19, 145.64, 143.03, 139.22, 135.05, 130.02, 129.87, 128.15, 127.94, 127.37, 123.69, 120.63, 117.81, 110.08, 104.38, 79.42, 70.18, 69.88, 54.39, 40.41, 39.74, 28.41, 23.60, 21.66, 11.13.

Step c: Preparation of tert-butyl (2-(2-(4-((4-(1-propyl-1H-pyrazol-4-yl)-7H-pyrrolo[2,3-d]pyrimidin-2-yl)amino)benzamido)ethoxy)ethyl)carbamate. To tert-butyl (2-(2-(4-((4-(1-propyl-1H-pyrazol-4-yl)-7-tosyl-7H-pyrrolo[2,3-d]pyrimidin-2-yl)amino)benzamido)ethoxy)ethyl)carbamate (0.070 g, 0.10 mmol) in methanol (2 mL) was added 2 M KOH (0.4 mL) and the reaction mixture was stirred at 80° C. under a nitrogen atmosphere for 1 h, then cooled to room temperature and concentrated in vacuo. The crude mixture was diluted in dichloromethane (3 mL) and washed with water (3×3 mL). The organic phase was dried over sodium sulfate, filtered, and concentrated in vacuo. The compound was purified using automated silica gel flash column chromatography (methanol/dichloromethane) followed by evaporation giving the title compound as a white solid (0.041 g, 75%). LC-MS (ESI) m/z: 550 [M+H]+. $^1$H NMR (500 MHz, Chloroform-d) δ 8.25 (s, 1H), 7.77 (s, 4H), 7.11 (s, 1H), 6.66 (dd, J=3.8, 1.9 Hz, 1H), 5.08 (s, 1H), 4.19 (t, J=7.1 Hz, 2H), 3.67 (d, J=3.1 Hz, 4H), 3.59 (t, J=5.2 Hz, 2H), 3.37 (d, J=5.4 Hz, 2H), 1.99 (h, J=7.3 Hz, 2H), 1.45 (s, 9H), 0.99 (t, J=7.4 Hz, 3H). $^{13}C$ NMR (126 MHz, Chloroform-d) δ 167.34, 156.11, 155.50, 153.81, 152.16, 143.72, 139.36, 129.92, 128.09, 126.70, 122.54, 121.39, 79.45, 70.16, 69.92, 54.33, 40.42, 39.67, 28.43, 23.66, 11.17.

Step d: Preparation of N-(2-(2-aminoethoxy)ethyl)-4-((4-(1-propyl-1H-pyrazol-4-yl)-7H-pyrrolo[2,3-d]pyrimidin-2-yl)amino)benzamide. To tert-butyl (2-(2-(4-((4-(1-propyl-1H-pyrazol-4-yl)-7H-pyrrolo[2,3-d]pyrimidin-2-yl)amino)benzamido)ethoxy)ethyl)carbamate (0.040 g, 0.073 mol) in dichloromethane (4 mL) under a nitrogen atmosphere at room temperature was added trifluoroacetic acid (0.28 mL, 3.7 mmol). The reaction mixture was stirred at room temperature for 3 h, then concentrated in vacuo giving a yellow oil, which slowly solidified and was used without purification. LC-MS (ESI) m/z: 450 [M+H]+. $^1H$ NMR (500 MHz, Methanol-d4) δ 8.68 (s, 1H), 8.38 (s, 1H), 7.95 (d, J=8.8 Hz, 2H), 7.88 (d, J=8.9 Hz, 2H), 7.38 (d, J=3.7 Hz, 1H), 6.94 (d, J=3.8 Hz, 1H), 4.29 (t, J=7.0 Hz, 2H), 3.80-3.69 (m, 4H), 3.65 (t, J=5.5 Hz, 2H), 3.16 (t, J=5.0 Hz, 2H), 2.00 (h, J=7.3 Hz, 2H), 0.99 (t, J=7.4 Hz, 3H). $^{13}C$ NMR (126 MHz, MeOD) δ 168.64, 154.04, 151.40, 146.82, 142.81, 139.11, 131.94, 127.92, 127.36, 126.41, 118.14, 107.91, 101.47, 69.78, 66.22, 53.85, 47.08, 39.24, 39.08, 23.17, 9.85.

Step e: Preparation of SJ000986340. A mixture of 2-(2,6-dioxopiperidin-3-yl)-4-fluoroisoindoline-1,3-dione (0.028 g, 0.10 mmol), N-(2-(2-aminoethoxy)ethyl)-4-((4-(1-propyl-1H-pyrazol-4-yl)-7H-pyrrolo[2,3-d]pyrimidin-2-yl)amino)benzamide (0.030 g, 0.067 mmol), and DIPEA (0.047 mL, 0.27 mmol) in DMSO (2 mL) was stirred at 90° C. under a nitrogen atmosphere for 18 h. The reaction mixture was cooled to room temperature, then the reaction mixture was diluted with ethyl acetate (10 mL) and washed sequentially with water (10 mL) and brine (2×10 mL). The organic phase was dried over sodium sulfate, filtered, and concentrated in vacuo. Purification using automated silica gel flash column chromatography (methanol/dichloromethane) was followed by a second flash column (methanol/ethyl acetate) and evaporation giving the title compound as a yellow solid (0.012 g, 26%). LC-MS (ESI) m/z: 706 [M+H]+. $^1H$ NMR (500 MHz, DMSO-d6) δ 11.61 (s, 1H), 11.09 (s, 1H), 9.47 (s, 1H), 8.60 (s, 1H), 8.28 (t, J=5.7 Hz, 1H), 8.25 (s, 1H), 8.03-7.92 (m, 2H), 7.79 (d, J=8.9 Hz, 2H), 7.58 (dd, J=8.6, 7.1 Hz, 1H), 7.27 (dd, J=3.7, 2.1 Hz, 1H), 7.17 (d, J=8.6 Hz, 1H), 7.04 (d, J=7.0 Hz, 1H), 6.83 (dd, J=3.6, 1.6 Hz, 1H), 6.64 (t, J=5.8 Hz, 1H), 5.05 (dd, J=12.7, 5.4 Hz, 1H), 4.20 (t, J=6.9 Hz, 2H), 3.66 (t, J=5.5 Hz, 2H), 3.59 (t, J=6.1 Hz, 2H), 3.50 (q, J=5.5 Hz, 2H), 3.44 (q, J=6.0 Hz, 2H), 2.87 (ddd, J=17.0, 13.9, 5.5 Hz, 1H), 2.69-2.53 (m, 2H), 2.07-1.96 (m, 1H), 1.88 (h, J=7.3 Hz, 2H), 0.88 (t, J=7.3 Hz, 3H). $^{13}C$ NMR (126 MHz, DMSO-d6) δ 173.27, 170.56, 169.42, 167.76, 166.60, 155.73, 153.94, 151.36, 146.89, 144.96, 139.08, 136.73, 132.57, 131.34, 128.36, 125.90, 124.30, 121.11, 117.94, 117.08, 111.16, 109.72, 108.21, 100.65, 69.48, 69.20, 53.61, 49.02, 42.16, 31.43, 23.63, 22.60, 11.39.

g. Synthesis of SJ000986050

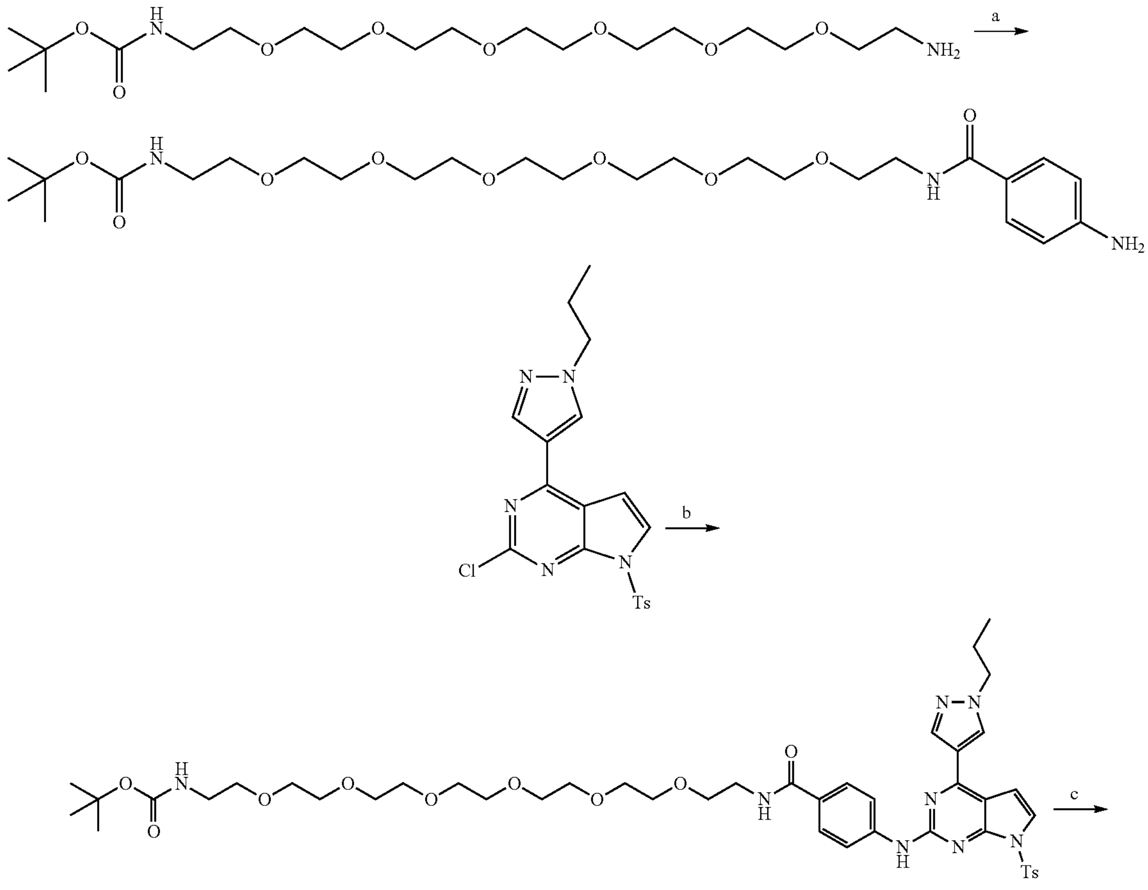

-continued

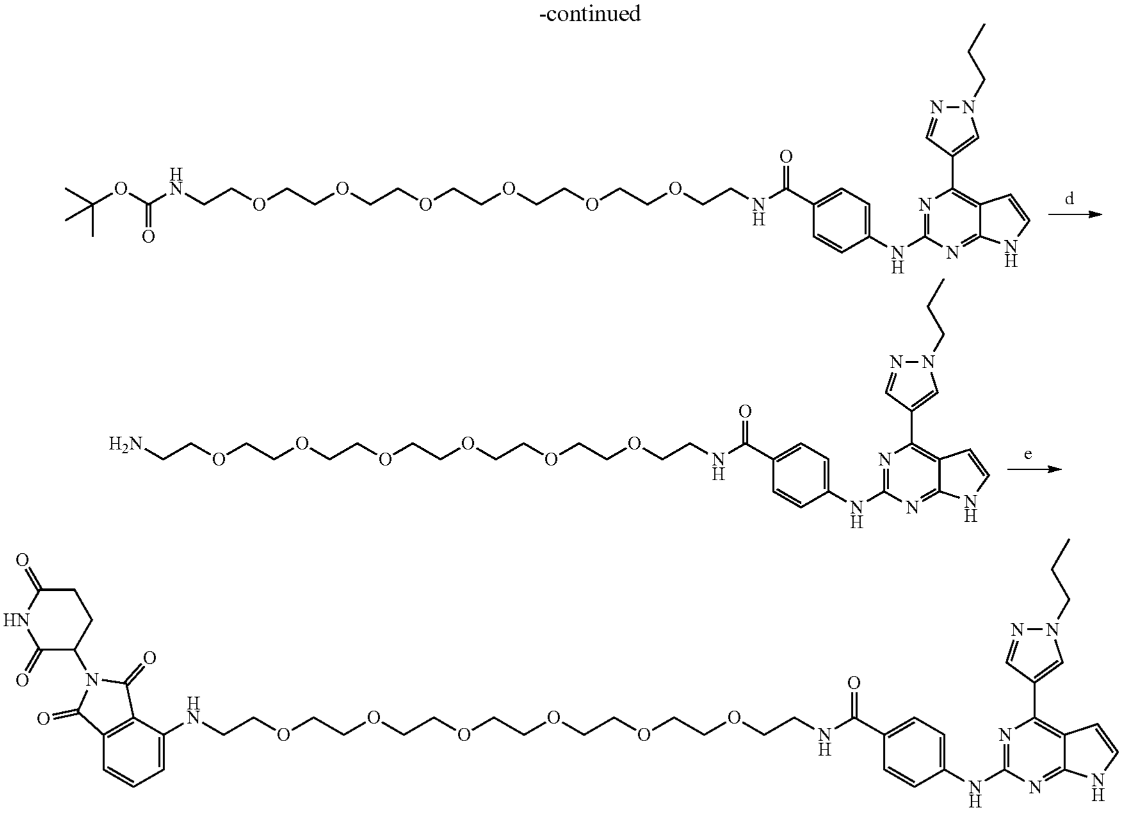

Reagents and conditions: (a) 4-aminobenzoic acid, DIPEA, HATU, DMF, rt, 3 h; (b) XPhos, $Pd_2(dba)_3$, $Cs_2CO_3$, dioxane, μwave, 150° C., 10 min.; (c) KOH, MeOH, 80° C., 1 h; (d) TFA, $CH_2Cl_2$, rt, 3 h; (e) 2-(2,6-dioxopiperidin-3-yl)-4-fluoroisoindoline-1,3-dione, DIPEA, DMSO, 90° C., 20 h.

Step a: Preparation of tert-butyl (1-(4-aminophenyl)-1-oxo-5,8,11,14,17,20-hexaoxa-2-azadocosan-22-yl)carbamate. A mixture of t-Boc-N-amido-PEG6-amine (0.15 g, 0.35 mmol), 4-aminobenzoic acid (0.053 g, 0.38 mmol), DIPEA (0.18 mL, 1.1 mmol), HATU (0.16 g, 0.42 mmol) was stirred at room temperature in DMF (2 mL) for 3 h. The reaction mixture was diluted with ethyl acetate (3 mL) and washed with brine (2×3 mL), followed by 5% LiCl solution (3 mL). The organic phase was dried over sodium sulfate, filtered, and concentrated in vacuo. Purification using automated silica gel flash column chromatography (methanol/ethyl acetate) and a second flash column (methanol/dichloromethane) was followed by evaporation giving the title compound as a colorless oil (0.020 g, 11%). LC-MS (ESI) m/z: 544 [M+H]+. $^1$H NMR (500 MHz, Chloroform-d) δ 7.65 (d, J=8.5 Hz, 2H), 6.77 (s, 1H), 6.70-6.62 (m, 2H), 5.12 (s, 1H), 4.03 (s, 2H), 3.69-3.57 (m, 24H), 3.52 (t, J=5.2 Hz, 2H), 3.30 (d, J=5.4 Hz, 2H), 1.44 (s, 9H). $^{13}$C NMR (126 MHz, Chloroform-d) δ 167.27, 156.06, 149.57, 128.85, 124.13, 114.08, 79.18, 70.53, 70.49, 70.26, 70.20, 70.09, 40.36, 39.60, 28.44.

Step b: Preparation of tert-butyl (1-oxo-1-(4-((4-(1-propyl-1H-pyrazol-4-yl)-7-tosyl-7H-pyrrolo[2,3-d]pyrimidin-2-yl)amino)phenyl)-5,8,11,14,17,20-hexaoxa-2-azadocosan-22-yl)carbamate. To a microwave vial was added 2-chloro-4-(1-propyl-1H-pyrazol-4-yl)-7-tosyl-7H-pyrrolo[2,3-d]pyrimidine (0.025 g, 0.060 mmol) followed by tert-butyl (1-(4-aminophenyl)-1-oxo-5,8,11,14,17,20-hexaoxa-2-azadocosan-22-yl)carbamate (0.036 g, 0.066 mmol) in dioxane (2.5 mL), XPhos (0.003 g, 0.006 mmol), $Cs_2CO_3$ (0.039 g, 0.12 mmol), and $Pd_2(dba)_3$ (0.003 g, 0.003 mmol). The vial was degassed and backfilled with nitrogen three times, then stirred at 150° C. and 100 W in a microwave reactor for 10 min. The reaction mixture was diluted with ethyl acetate (5 mL) and washed with brine (3×3 mL). The organic phase was dried over sodium sulfate, filtered, and concentrated in vacuo. Purification using automated flash column chromatography (ethyl acetate) was followed by evaporation giving the title compound as a yellow foam (0.033 g, 60%). LC-MS (ESI) m/z: 924 [M+H]+. $^1$H NMR (500 MHz, Chloroform-d) δ 8.14 (d, J=0.6 Hz, 1H), 8.09 (d, J=0.7 Hz, 1H), 8.07-8.01 (m, 2H), 7.92 (d, J=1.2 Hz, 4H), 7.54 (d, J=4.1 Hz, 1H), 7.49 (d, J=3.3 Hz, 1H), 7.28-7.24 (m, 2H), 7.00 (s, 1H), 6.74 (d, J=4.1 Hz, 1H), 5.14 (s, 1H), 4.19 (t, J=7.1 Hz, 2H), 3.74-3.65 (m, 12H), 3.65-3.58 (m, 12H), 3.54 (t, J=5.2 Hz, 2H), 3.31 (d, J=5.5 Hz, 2H), 2.37 (s, 3H), 1.98 (q, J=7.3 Hz, 2H), 1.44 (s, 9H), 0.98 (t, J=7.4 Hz, 3H). $^{13}$C NMR (126 MHz, Chloroform-d)) δ 167.14, 156.10, 156.04, 153.34, 153.17, 145.63, 142.94, 139.20, 135.06, 130.01, 129.88, 128.25, 127.94, 127.55, 123.62, 120.66, 117.79, 110.00, 104.36, 79.13, 70.59, 70.57, 70.55, 70.52, 70.49, 70.27, 70.25, 70.23, 70.05, 54.38, 40.37, 39.78, 28.43, 23.60, 21.66, 11.13.

Step c: Preparation of tert-butyl (1-oxo-1-(4-((4-(1-propyl-1H-pyrazol-4-yl)-7H-pyrrolo[2,3-d]pyrimidin-2-yl)amino)phenyl)-5,8,11,14,17,20-hexaoxa-2-azadocosan-22-yl)carbamate. To tert-butyl (1-oxo-1-(4-((4-(1-propyl-1H-pyrazol-4-yl)-7-tosyl-7H-pyrrolo[2,3-d]pyrimidin-2-yl)amino)phenyl)-5,8,11,14,17,20-hexaoxa-2-azadocosan-22-yl)carbamate (0.053 g, 0.057 mmol) in methanol (3 mL) was added 2 M KOH (0.23 mL) and the reaction mixture was stirred at 80° C. under a nitrogen atmosphere for 1 h. The reaction mixture was cooled to room temperature and concentrated in vacuo. The crude reaction mixture was diluted in dichloromethane (3 mL) and washed with water (3×3 mL). The organic phase was dried over sodium sulfate, filtered, and concentrated in vacuo. Purification using automated silica gel flash column chromatography (methanol/dichloromethane) was followed by evaporation giving the title compound as a colorless oil (0.030 g, 68%). LC-MS (ESI) m/z: 770 [M+H]+. $^1$H NMR (500 MHz, Chloroform-d) δ 9.36 (s, 1H), 8.25 (s, 1H), 8.17 (s, 1H), 7.83 (s, 4H), 7.44 (s, 1H), 7.12 (t, J=2.9 Hz, 1H), 6.91 (s, 1H), 6.66 (dd, J=3.7, 1.9 Hz, 1H), 5.23 (s, 1H), 4.21 (t, J=7.1 Hz, 2H), 3.73-3.49 (m, 26H), 3.32 (t, J=5.5 Hz, 2H), 2.02-1.97 (m, 2H), 1.45 (s, 9H), 1.00 (t, J=7.3 Hz, 3H). $^{13}$C NMR (126 MHz, Chloroform-d) δ 167.20, 156.13, 155.51, 153.81, 152.03, 143.67, 139.33, 129.89, 128.14, 126.76, 122.78, 121.51, 117.45, 108.56, 100.87, 79.26, 70.61, 70.58, 70.54, 70.53, 70.51, 70.46, 70.28, 70.21, 69.94, 54.32, 40.39, 39.71, 28.46, 23.67, 11.18.

Step d: Preparation of N-(20-amino-3,6,9,12,15,18-hexaoxaicosyl)-4-((4-(1-propyl-1H-pyrazol-4-yl)-7H-pyrrolo[2,3-d]pyrimidin-2-yl)amino)benzamide. To tert-butyl (1-oxo-1-(4-((4-(1-propyl-1H-pyrazol-4-yl)-7H-pyrrolo[2,3-d]pyrimidin-2-yl)amino)phenyl)-5,8,11,14,17,20-hexaoxa-2-azadocosan-22-yl)carbamate (0.030 g, 0.039 mmol) in dichloromethane (3 mL) at room temperature under a nitrogen atmosphere was added trifluoroacetic acid (0.15 mL, 1.95 mmol). The reaction mixture was stirred at room temperature for 3 h, then concentrated in vacuo giving the title compound as a yellow oil, which was used without purification. LC-MS (ESI) m/z: 670 [M+H]+. $^1$H NMR (500 MHz, Methanol-d4) δ 8.77 (d, J=0.7 Hz, 1H), 8.42 (d, J=0.7 Hz, 1H), 7.95 (d, J=8.9 Hz, 2H), 7.90 (d, J=8.8 Hz, 2H), 7.44 (d, J=3.8 Hz, 1H), 6.99 (d, J=3.8 Hz, 1H), 4.29 (t, J=7.0 Hz, 2H), 3.79-3.73 (m, 2H), 3.73-3.59 (m, 24H), 3.15 (t, J=5.1 Hz, 2H), 2.00 (h, J=7.3 Hz, 2H), 0.99 (t, J=7.4 Hz, 3H). $^{13}$C NMR (126 MHz, Methanol-d4) δ 168.25, 154.14, 150.05, 145.45, 142.02, 139.27, 132.37, 128.21, 127.94, 127.44, 118.69, 114.48, 107.78, 102.02, 70.04, 69.98, 69.96, 69.88, 69.85, 69.83, 69.80, 69.75, 69.62, 69.43, 69.33, 66.50, 53.96, 39.31, 39.09, 23.09, 9.83.

Step e: Preparation of SJ000986050. A mixture of 2-(2,6-dioxopiperidin-3-yl)-4-fluoroisoindoline-1,3-dione (0.016 g, 0.058 mmol), N-(20-amino-3,6,9,12,15,18-hexaoxaicosyl)-4-((4-(1-propyl-1H-pyrazol-4-yl)-7H-pyrrolo[2,3-d]pyrimidin-2-yl)amino)benzamide (0.026 g, 0.039 mmol), and DIPEA (0.027 mL, 0.16 mmol) in DMSO (1 mL) was stirred at 90° C. under a nitrogen atmosphere for 20 h. The reaction mixture was cooled to room temperature. The reaction mixture was diluted with ethyl acetate (5 mL), then washed sequentially with water (3 mL) and brine (3 mL). The organic phase was dried over sodium sulfate, filtered, and concentrated in vacuo. Purification using automated silica gel flash column chromatography (methanol/dichloromethane), then by a second flash column (methanol/ethyl acetate) was followed by evaporation giving the title compound as a yellow solid (0.010 g, 28%). LC-MS (ESI) m/z: 926 [M+H]+. $^1$H NMR (500 MHz, Methanol-d4) δ 8.46 (s, 1H), 8.28 (s, 1H), 7.96 (d, J=8.8 Hz, 2H), 7.83 (d, J=8.8 Hz, 2H), 7.47 (dd, J=8.6, 7.1 Hz, 1H), 7.19 (d, J=3.6 Hz, 1H), 6.98 (dd, J=10.6, 7.8 Hz, 2H), 6.75 (d, J=3.6 Hz, 1H), 5.04 (dd, J=12.7, 5.4 Hz, 1H), 4.25 (t, J=6.9 Hz, 2H), 3.71-3.62 (m, 10H), 3.63-3.50 (m, 16H), 3.41 (t, J=5.2 Hz, 2H), 2.85 (ddd, J=17.4, 13.9, 5.2 Hz, 1H), 2.78-2.60 (m, 2H), 2.16-2.05 (m, 1H), 1.97 (dt, J=14.9, 7.5 Hz, 2H), 0.98 (t, J=7.4 Hz, 3H). $^{13}$C NMR (126 MHz, Methanol-d4) δ 173.29, 170.26, 169.20, 168.68, 167.87, 155.50, 153.74, 151.16, 146.70, 144.91, 138.83, 135.69, 132.39, 130.76, 127.86, 125.37, 123.29, 121.42, 116.87, 116.73, 110.55, 109.81, 108.31, 99.86, 70.18, 70.15, 70.13, 70.11, 70.07, 69.95, 69.28, 69.12, 53.51, 48.77, 41.78, 39.56, 30.80, 23.35, 22.41, 9.93.

h. Synthesis of SJ000986049

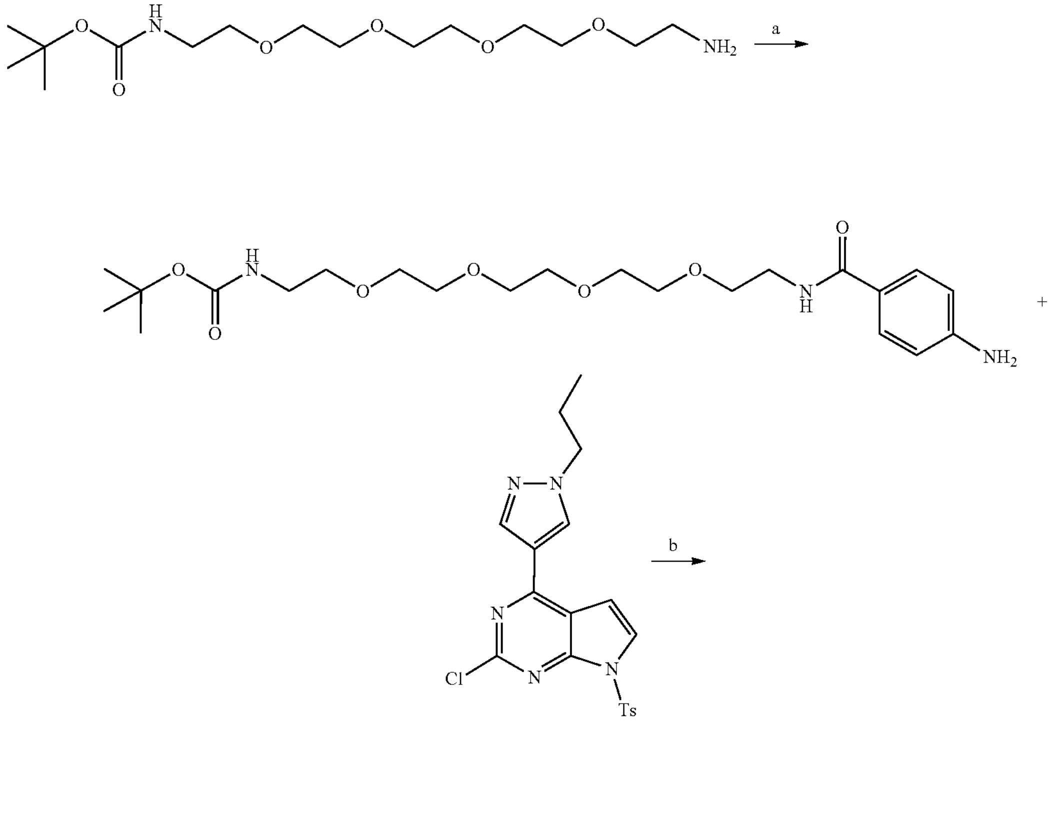

-continued

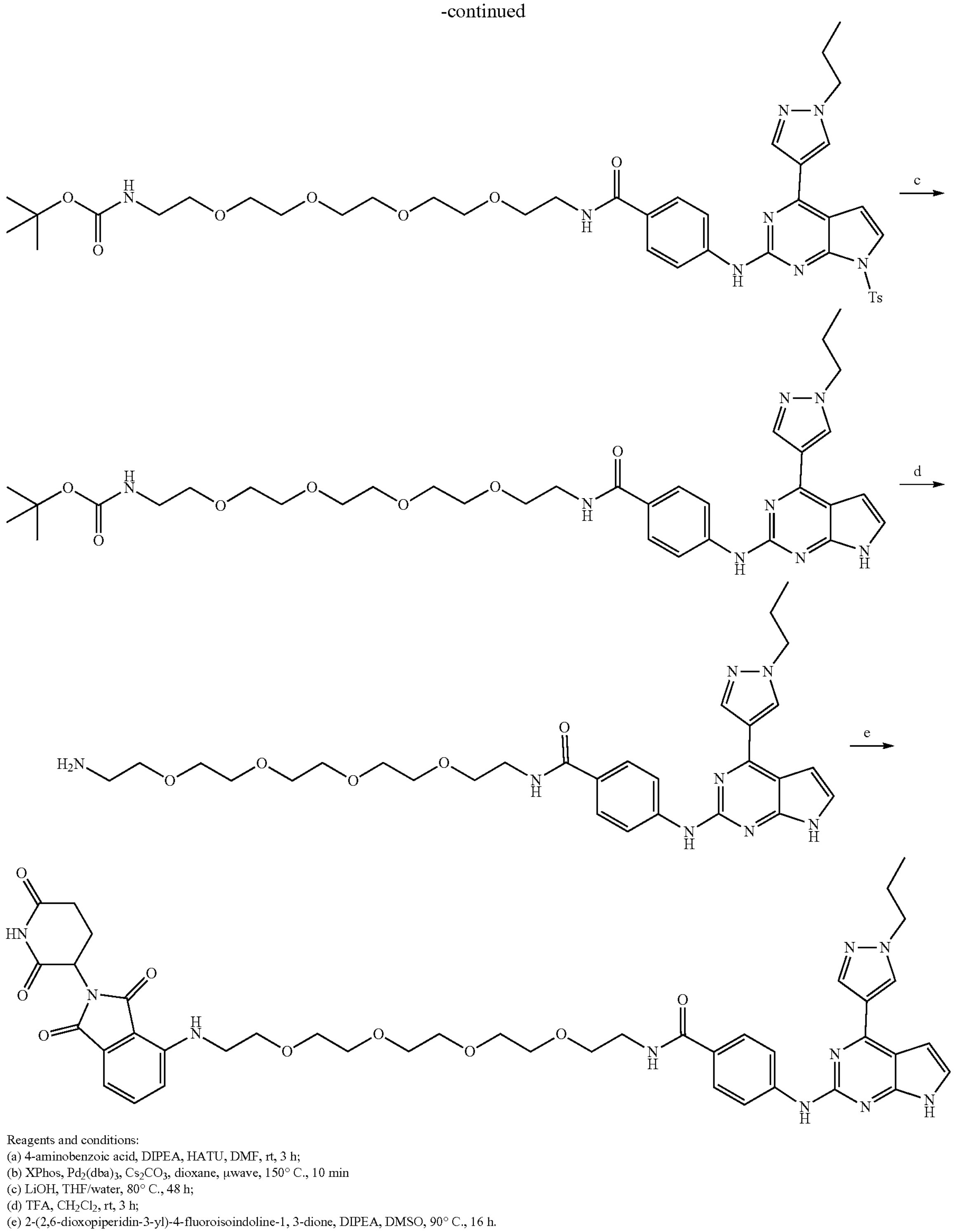

Step a: Preparation of tert-butyl (1-(4-aminophenyl)-1-oxo-5,8,11,14-tetraoxa-2-azahexadecan-16-yl)carbamate. A mixture of t-Boc-N-amido-PEG4-amine (0.10 g, 0.30 mmol), 4-aminobenzoic acid (0.045 g, 0.33 mmol), DIPEA (0.16 mL, 0.89 mmol), HATU (0.14 g, 0.36 mmol) was stirred at room temperature in DMF (2 mL) for 3 h. The reaction mixture was diluted with ethyl acetate (3 mL) and washed with brine (2×3 mL), followed by 5% LiCl solution (3 mL). The organic phase was dried over sodium sulfate, filtered, and concentrated in vacuo. Purification using automated silica gel flash column chromatography (methanol/ethyl acetate) was followed by evaporation giving the title compound as a colorless oil (0.056 g, 41%). LC-MS (ESI) m/z: 457 [M+H]+. $^1$H NMR (500 MHz, Chloroform-d) δ 7.68 (d, J=8.2 Hz, 2H), 6.78 (s, 1H), 6.71-6.65 (m, 2H), 5.09 (s, 1H), 4.04-3.93 (m, 2H), 3.73-3.59 (m, 16H), 3.54 (t, J=5.0 Hz, 2H), 3.33 (d, J=5.6 Hz, 2H), 1.46 (s, 9H). $^{13}$C NMR (126 MHz, Chloroform-d) δ 167.56, 156.49, 149.60, 128.87, 124.02, 114.08, 79.33, 70.43, 70.41, 70.37, 70.31, 70.07, 40.30, 39.59, 38.62, 28.42.

Step b: Preparation of tert-butyl (1-oxo-1-(4-((4-(1-propyl-1H-pyrazol-4-yl)-7-tosyl-7H-pyrrolo[2,3-d]pyrimidin-2-yl)amino)phenyl)-5,8,11,14-tetraoxa-2-azahexadecan-16-yl)carbamate. To a microwave vial was added 2-chloro-4-(1-propyl-1H-pyrazol-4-yl)-7-tosyl-7H-pyrrolo[2,3-d] pyrimidine (0.044 g, 0.11 mmol) followed by tert-butyl (1-(4-aminophenyl)-1-oxo-5,8,11,14-tetraoxa-2-azahexadecan-16-yl)carbamate (0.053 g, 0.116 mmol) in dioxane (2.5 mL), XPhos (0.005 g, 0.011 mmol), $Cs_2CO_3$ (0.069 g, 0.212 mmol), and $Pd_2(dba)_3$ (0.005 g, 0.005 mmol). The vial was degassed and backfilled with nitrogen three times, then stirred at 150° C. and 100 W in a microwave reactor for 10 min. The reaction mixture was diluted with ethyl acetate (5 mL) and washed with brine (3×3 mL). The organic phase was dried over sodium sulfate, filtered, and concentrated in vacuo. Purification using automated flash column chromatography (ethyl acetate) was followed by evaporation giving the title compound as a yellow foam (0.048 g, 54%). LC-MS (ESI) m/z: 836 [M+H]+. $^{1}$H NMR (500 MHz, Chloroform-d) δ 8.14 (s, 1H), 8.09 (s, 1H), 8.06-8.02 (m, 2H), 7.96-7.87 (m, 4H), 7.53 (d, J=4.0 Hz, 1H), 7.46 (s, 1H), 7.26 (d, J=8.2 Hz, 2H), 7.02 (s, 1H), 6.74 (d, J=4.1 Hz, 1H), 5.20 (s, 1H), 4.18 (t, J=7.1 Hz, 2H), 3.74-3.68 (m, 10H), 3.68-3.64 (m, 2H), 3.60 (tt, J=5.8, 3.4 Hz, 4H), 3.52 (t, J=5.1 Hz, 2H), 3.30 (d, J=5.7 Hz, 2H), 2.36 (s, 3H), 2.02-1.91 (m, 2H), 1.44 (s, 9H), 0.97 (t, J=7.4 Hz, 3H). $^{13}$C NMR (126 MHz, Chloroform-d) δ 167.16, 156.08, 153.32, 153.18, 145.64, 142.91, 139.20, 135.04, 130.03, 129.87, 128.25, 127.94, 127.57, 123.61, 120.64, 117.76, 110.01, 104.38, 79.15, 70.57, 70.55, 70.53, 70.48, 70.31, 70.25, 70.17, 70.10, 54.37, 40.35, 39.78, 28.44, 23.60, 21.65, 11.12.

Step c: Preparation of tert-butyl (1-oxo-1-(4-((4-(1-propyl-1H-pyrazol-4-yl)-7H-pyrrolo[2,3-d]pyrimidin-2-yl) amino)phenyl)-5,8,11,14-tetraoxa-2-azahexadecan-16-yl) carbamate. To tert-butyl (1-oxo-1-(4-((4-(1-propyl-1H-pyrazol-4-yl)-7-tosyl-7H-pyrrolo[2,3-d]pyrimidin-2-yl) amino)phenyl)-5,8,11,14-tetraoxa-2-azahexadecan-16-yl) carbamate (0.048 g, 0.057 mmol) in THF (4 mL) and water (1 mL) was added LiOH monohydrate (0.12 g, 2.9 mmol). The reaction mixture was stirred at 80° C. under a nitrogen atmosphere for 48 h. The reaction mixture was cooled to room temperature, then diluted with dichloromethane (5 mL) and washed with water (3×5 mL). The organic phase was dried over sodium sulfate, filtered, and concentrated in vacuo. Purification using automated silica gel flash column chromatography (methanol/dichloromethane) was followed by evaporation giving the title compound as an amber solid (0.027 g, 69%). LC-MS (ESI) m/z: 682 [M+H]+. $^{1}$H NMR (500 MHz, Chloroform-d) δ 9.39 (s, 1H), 8.25 (s, 1H), 8.16 (s, 1H), 7.91-7.77 (m, 4H), 7.37 (s, 1H), 7.12 (dd, J=3.7, 2.2 Hz, 1H), 7.06 (d, J=8.6 Hz, 1H), 6.66 (dd, J=3.7, 1.9 Hz, 1H), 5.45 (s, 1H), 4.21 (t, J=7.1 Hz, 2H), 3.73-3.67 (m, 10H), 3.64 (d, J=5.2 Hz, 2H), 3.59 (d, J=4.3 Hz, 4H), 3.54 (dd, J=5.5, 4.7 Hz, 2H), 3.37 (d, J=5.3 Hz, 1H), 2.00 (h, J=7.3 Hz, 2H), 1.46 (s, 9H), 1.00 (t, J=7.4 Hz, 3H). $^{13}$C NMR (126 MHz, Chloroform-d) δ 167.33, 156.38, 155.53, 153.81, 152.10, 143.65, 139.31, 129.86, 128.22, 126.86, 122.62, 121.45, 117.39, 108.55, 100.89, 79.44, 70.54, 70.52, 70.48, 70.39, 70.32, 70.15, 70.11, 54.32, 40.46, 39.70, 28.47, 23.67, 11.18.

Step d: Preparation of N-(14-amino-3,6,9,12-tetraoxatetradecyl)-4-((4-(1-propyl-1H-pyrazol-4-yl)-7H-pyrrolo[2,3-d]pyrimidin-2-yl)amino)benzamide. To tert-butyl (1-oxo-1-(4-((4-(1-propyl-1H-pyrazol-4-yl)-7H-pyrrolo[2,3-d] pyrimidin-2-yl)amino)phenyl)-5,8,11,14-tetraoxa-2-azahexadecan-16-yl)carbamate (0.027 g, 0.040 mmol) in dichloromethane (2 mL) at room temperature under a nitrogen atmosphere was added trifluoroacetic acid (0.15 mL, 2.0 mmol). The reaction mixture was stirred at room temperature for 3 h under a nitrogen atmosphere, then concentrated in vacuo giving the title compound as a yellow foam, which was used without purification. LC-MS (ESI) m/z: 582 [M+H]+. $^{1}$H NMR (500 MHz, Methanol-d4) δ 8.75 (s, 1H), 8.41 (s, 1H), 7.98-7.91 (m, 2H), 7.91-7.83 (m, 2H), 7.41 (d, J=3.7 Hz, 1H), 6.96 (d, J=3.8 Hz, 1H), 4.27 (t, J=7.0 Hz, 2H), 3.74-3.63 (m, 16H), 3.61 (t, J=5.5 Hz, 2H), 3.14 (t, J=5.1 Hz, 2H), 1.99 (q, J=7.2 Hz, 2H), 0.99 (t, J=7.4 Hz, 3H). $^{13}$C NMR (126 MHz, Methanol-d4) δ 168.33, 154.07, 150.23, 145.63, 142.15, 139.32, 132.31, 128.00, 127.90, 127.23, 118.57, 114.74, 107.75, 101.92, 70.03, 70.00, 69.94, 69.90, 69.89, 69.59, 69.44, 66.41, 53.94, 39.43, 39.17, 23.08, 9.85.

Step e: Preparation of SJ000986049. A mixture of 2-(2,6-dioxopiperidin-3-yl)-4-fluoroisoindoline-1,3-dione (0.019 g, 0.070 mmol), N-(14-amino-3,6,9,12-tetraoxatetradecyl)-4-((4-(1-propyl-1H-pyrazol-4-yl)-7H-pyrrolo[2,3-d]pyrimidin-2-yl)amino)benzamide (0.027 g, 0.046 mmol), and DIPEA (0.032 mL, 0.19 mmol) in DMSO (1 mL) was stirred at 90° C. under a nitrogen atmosphere for 16 h, then the reaction mixture was cooled to room temperature. The reaction mixture was diluted with ethyl acetate (5 mL), then washed sequentially with water (3 mL) and brine (3 mL). The organic phase was dried over sodium sulfate, filtered, and concentrated in vacuo. Purification using automated silica gel flash column chromatography (methanol/ethyl acetate) and a second flash column (methanol/dichloromethane) was followed by evaporation giving the title compound as a yellow solid (0.005 g, 13%). LC-MS (ESI) m/z: 838 [M+H]+. $^{1}$H NMR (500 MHz, Chloroform-d) δ 13.23 (s, 1H), 10.28 (s, 1H), 8.62 (s, 1H), 8.16 (d, J=0.7 Hz, 1H), 8.09 (s, 1H), 7.85-7.77 (m, 2H), 7.69 (d, J=8.5 Hz, 2H), 7.40 (dd, J=8.5, 7.1 Hz, 1H), 7.05 (d, J=7.1 Hz, 1H), 7.02-6.96 (m, 1H), 6.87 (d, J=8.6 Hz, 1H), 6.79 (s, 1H), 6.41 (t, J=5.8 Hz, 1H), 4.93 (dd, J=12.1, 5.4 Hz, 1H), 4.13 (t, J=7.1 Hz, 2H), 3.64 (q, J=4.8 Hz, 2H), 3.60-3.50 (m, 10H), 3.51-3.46 (m, 4H), 3.47-3.42 (m, 2H), 3.39 (d, J=5.6 Hz, 2H), 2.91-2.67 (m, 3H), 2.16-2.04 (m, 1H), 1.92 (h, J=7.4 Hz, 2H), 0.92 (t, J=7.4 Hz, 3H). $^{13}$C NMR (126 MHz, Chloroform-d) δ 174.45, 171.16, 169.33, 167.69, 167.43, 155.01, 153.84, 151.83, 147.01, 144.26, 139.41, 135.94, 132.44, 130.17, 127.97, 126.45, 123.13, 121.83, 117.66, 117.07, 111.72, 110.25, 108.75, 100.56, 70.74, 70.72, 70.59, 70.50, 70.34, 69.97, 69.79, 54.33, 48.72, 42.61, 39.65, 31.60, 23.72, 22.94, 11.17.

i. Synthesis of SJ000986419

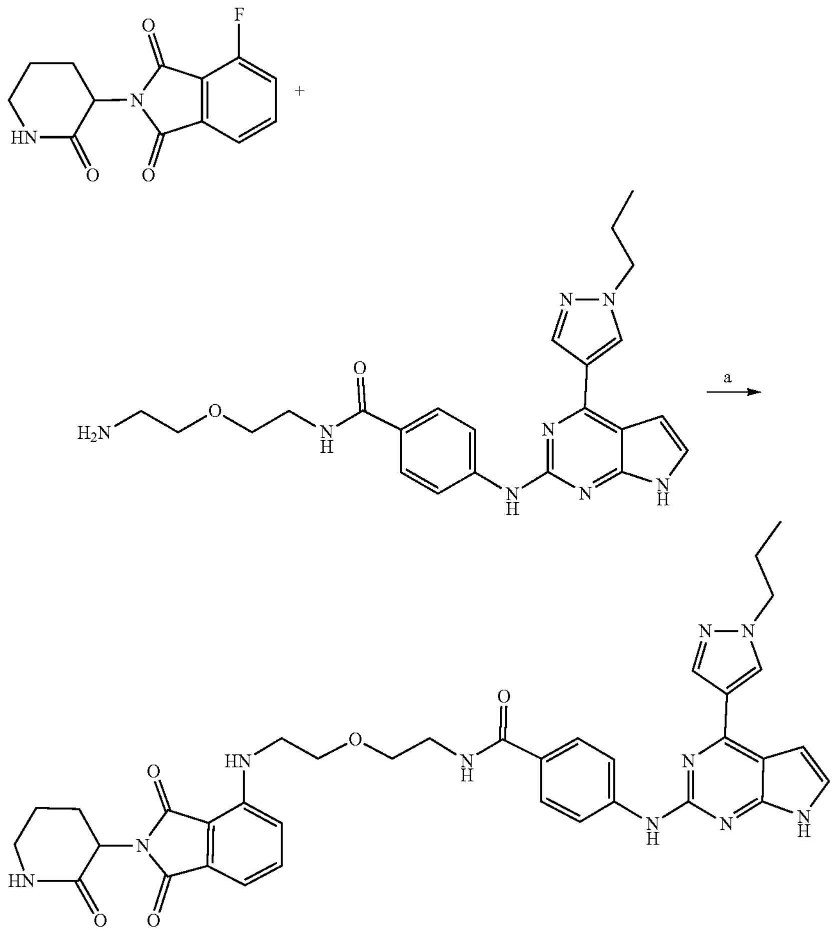

Reagents and conditions: (a) DIPEA, DMSO, 90° C., 20 h.

Step a: Preparation of SJ000986419. A mixture of 4-fluoro-2-(2-oxopiperidin-3-yl)isoindoline-1,3-dione (0.022 g, 0.084 mmol), N-(2-(2-aminoethoxy)ethyl)-4-((4-(1-propyl-1H-pyrazol-4-yl)-7H-pyrrolo[2,3-d]pyrimidin-2-yl)amino)benzamide (0.025 g, 0.056 mmol), and DIPEA (0.039 mL, 0.22 mmol) in DMSO (1 mL) was stirred at 90° C. under a nitrogen atmosphere for 20 h. The reaction mixture was cooled to room temperature, then was diluted with ethyl acetate (5 mL) and washed sequentially with water (5 mL) and brine (2×5 mL). The organic phase was dried over sodium sulfate, filtered, and concentrated in vacuo. Purification using automated silica gel flash column chromatography (ethyl acetate/hexanes, then methanol/dichloromethane) was followed by evaporation giving the title compound as a yellow solid (0.005 g, 13%). LC-MS (ESI) m/z: 692 [M+H]+. $^{1}$H NMR (500 MHz, Methanol-d4) δ 8.48 (s, 1H), 8.30 (s, 1H), 7.92 (d, J=8.8 Hz, 2H), 7.79 (d, J=8.8 Hz, 2H), 7.51 (dd, J=8.5, 7.1 Hz, 1H), 7.21 (d, J=3.6 Hz, 1H), 7.08 (d, J=8.5 Hz, 1H), 7.02 (d, J=7.0 Hz, 1H), 6.78 (d, J=3.7 Hz, 1H), 4.59 (dd, J=11.8, 6.4 Hz, 1H), 4.25 (t, J=7.0 Hz, 2H), 3.77 (t, J=5.1 Hz, 2H), 3.73 (t, J=5.4 Hz, 2H), 3.63 (t, J=5.4 Hz, 2H), 3.53 (t, J=5.1 Hz, 2H), 3.27 (td, J=11.8, 4.5 Hz, 1H), 3.19 (ddd, J=10.3, 4.7, 2.7 Hz, 1H), 2.22 (dd, J=12.2, 3.6 Hz, 1H), 1.97 (dt, J=14.4, 7.2 Hz, 3H), 1.84 (dddt, J=19.0, 15.6, 11.6, 3.7 Hz, 2H), 0.98 (t, J=7.4 Hz, 3H). $^{13}$C NMR (126 MHz, Methanol-d4) δ 169.54, 169.09, 168.87, 168.14, 155.55, 153.77, 151.24, 146.76, 144.81, 138.83, 135.60, 132.62, 130.77, 127.89, 125.42, 123.30, 121.42, 116.82, 116.69, 110.54, 110.22, 108.30, 99.86, 69.18, 69.12, 53.51, 48.43, 41.87, 41.57, 39.57, 25.91, 23.35, 21.54, 9.91.

j. Synthesis SJ000986051

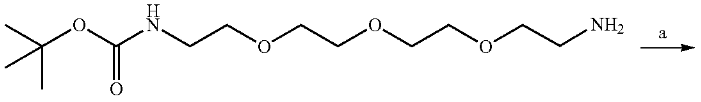

-continued
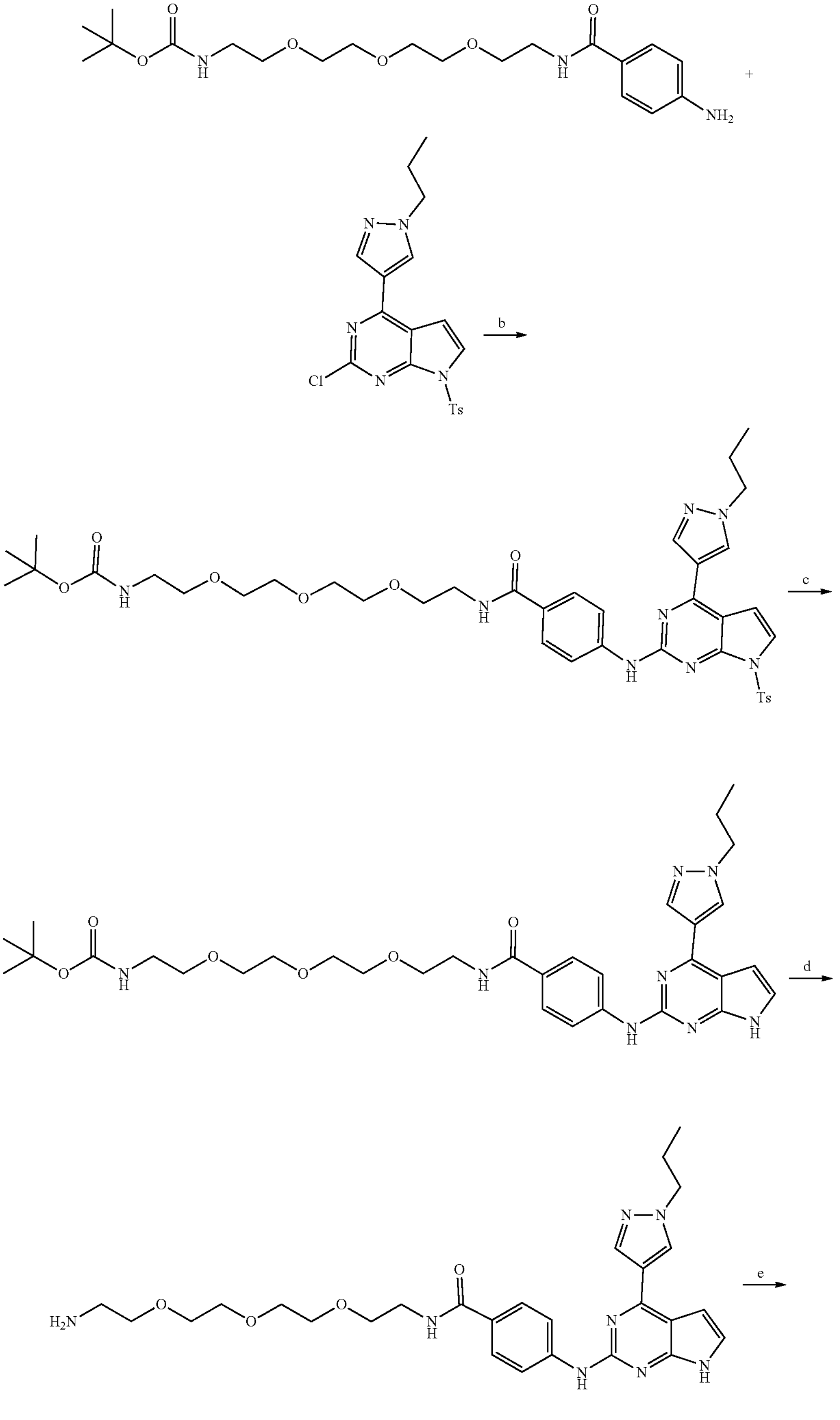

-continued

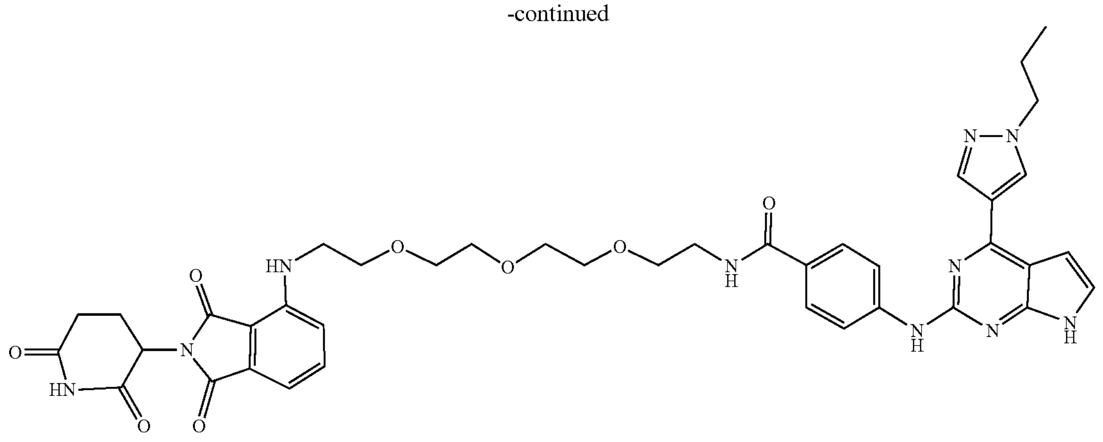

Reagents and conditions:
(a) 4-aminobenzoic acid, DIPEA, HATU, DMF, rt, 3 h;
(b) XPhos, $Pd_2(dba)_3$, $Cs_2CO_3$, dioxane, μwave, 150° C., 10 min.;
(c) LiOH, THF/water, 80° C., 48 h;
(d) TFA, $CH_2Cl_2$, rt, 3 h;
(e) 2-(2,6-dioxopiperidin-3-yl)-4-fluoroisoindoline-1,3-dione, DIPEA, DMSO, 90° C., 20 h.

Step a: Preparation of tert-butyl (1-(4-aminophenyl)-1-oxo-5,8,11-trioxa-2-azatridecan-13-yl)carbamate. A mixture of t-Boc-N-amido-PEG3-amine (0.095 g, 0.33 mmol), 4-aminobenzoic acid (0.049 g, 0.36 mmol), DIPEA (0.17 mL, 0.98 mmol), HATU (0.15 g, 0.39 mmol) was stirred at room temperature in DMF (2 mL) for 3 h. The reaction mixture was diluted with ethyl acetate (3 mL) and washed with brine (2×3 mL) followed by 5% LiCl solution (3 mL). The organic phase was dried over sodium sulfate, filtered, and concentrated in vacuo. Purification using automated silica gel flash column chromatography (methanol/ethyl acetate) was followed by evaporation, giving the title compound as a colorless oil (0.039 g, 29%). LC-MS (ESI) m/z: 413 [M+H]+. $^1H$ NMR (500 MHz, Chloroform-d) δ 7.56 (d, J=8.1 Hz, 2H), 6.58 (d, J=8.6 Hz, 2H), 4.99 (d, J=6.1 Hz, 1H), 3.93 (s, 2H), 3.63-3.54 (m, 10H), 3.52 (dt, J=6.0, 1.9 Hz, 2H), 3.44 (t, J=5.2 Hz, 2H), 3.22 (d, J=5.4 Hz, 2H), 1.37 (s, 9H). $^{13}C$ NMR (126 MHz, Chloroform-d) δ 167.33, 156.09, 149.57, 128.82, 124.11, 114.09, 79.31, 70.46, 70.43, 70.20, 70.17, 28.43.

Step b: Preparation of tert-butyl (1-oxo-1-(4-((4-(1-propyl-1H-pyrazol-4-yl)-7-tosyl-7H-pyrrolo[2,3-d]pyrimidin-2-yl)amino)phenyl)-5,8,11-trioxa-2-azatridecan-13-yl)carbamate. To a microwave vial was added 2-chloro-4-(1-propyl-1H-pyrazol-4-yl)-7-tosyl-7H-pyrrolo[2,3-d]pyrimidine (0.048 g, 0.12 mmol) followed by tert-butyl (1-(4-aminophenyl)-1-oxo-5,8,11-trioxa-2-azatridecan-13-yl)carbamate (0.052 g, 0.13 mmol) in dioxane (2.5 mL), XPhos (0.006 g, 0.012 mmol), $Cs_2CO_3$ (0.075 g, 0.23 mmol), and $Pd_2(dba)_3$ (0.005 g, 0.006 mmol). The vial was degassed and backfilled with nitrogen three times, then stirred at 150° C. and 100 W in a microwave reactor for 10 min. The reaction mixture was diluted with ethyl acetate (5 mL) and washed with brine (3×3 mL). The organic phase was dried over sodium sulfate, filtered, and concentrated in vacuo. Purification using automated flash column chromatography (ethyl acetate) was followed by evaporation, giving the title compound as a yellow foam (0.029 g, 32%). LC-MS (ESI) m/z: 792 [M+H]+. $^1H$ NMR (500 MHz, Chloroform-d) δ 8.14 (s, 1H), 8.09 (s, 1H), 8.07-8.00 (m, 2H), 7.90 (s, 4H), 7.53 (d, J=4.0 Hz, 1H), 7.44 (s, 1H), 7.25 (d, J=8.3 Hz, 2H), 6.82 (s, 1H), 6.74 (d, J=4.0 Hz, 1H), 5.07 (d, J=7.3 Hz, 1H), 4.18 (t, J=7.1 Hz, 2H), 3.76-3.65 (m, 10H), 3.65-3.61 (m, 2H), 3.53 (t, J=5.2 Hz, 2H), 3.29 (t, J=5.5 Hz, 2H), 2.36 (s, 3H), 1.97 (q, J=7.2 Hz, 2H), 1.44 (s, 9H), 0.97 (t, J=7.4 Hz, 3H). $^{13}C$ NMR (126 MHz, Chloroform-d) δ 167.12, 156.06, 156.03, 153.32, 153.18, 145.63, 142.96, 139.20, 135.04, 130.03, 129.87, 128.19, 127.94, 127.49, 123.62, 120.64, 117.77, 110.03, 104.38, 79.22, 70.53, 70.50, 70.29, 70.22, 70.20, 70.03, 54.37, 40.34, 39.75, 28.43, 23.60, 21.65, 11.12.

Step c: Preparation of tert-butyl (1-oxo-1-(4-((4-(1-propyl-1H-pyrazol-4-yl)-7H-pyrrolo[2,3-d]pyrimidin-2-yl)amino)phenyl)-5,8,11-trioxa-2-azatridecan-13-yl)carbamate. To tert-butyl (1-oxo-1-(4-((4-(1-propyl-1H-pyrazol-4-yl)-7-tosyl-7H-pyrrolo[2,3-d]pyrimidin-2-yl)amino)phenyl)-5,8,11-trioxa-2-azatridecan-13-yl)carbamate (0.029 g, 0.037 mmol) in THF (2 mL) and water (0.5 mL) was added LiOH monohydrate (0.077 g, 1.8 mmol). The reaction mixture was stirred at 80° C. under a nitrogen atmosphere for 48 h, then was cooled to room temperature. The reaction mixture was diluted with dichloromethane (5 mL) and washed with water (3×5 mL). The organic phase was dried over sodium sulfate, filtered, and concentrated. Purification using automated silica gel flash column chromatography (methanol/dichloromethane) was followed by evaporation, giving the title compound as a colorless oil (0.014 g, 60%). LC-MS (ESI) m/z: 638 [M+H]+. $^1H$ NMR (500 MHz, Chloroform-d) δ 9.61 (s, 1H), 8.24 (s, 1H), 8.16 (s, 1H), 7.83 (d, J=3.3 Hz, 4H), 7.37 (s, 1H), 7.12 (dd, J=3.7, 2.2 Hz, 1H), 6.95 (s, 1H), 6.66 (dd, J=3.6, 1.9 Hz, 1H), 5.36 (s, 1H), 4.21 (t, J=7.1 Hz, 2H), 3.73-3.66 (m, 8H), 3.64 (dt, J=3.9, 2.7 Hz, 2H), 3.61-3.57 (m, 2H), 3.54 (t, J=5.0 Hz, 2H), 3.41 (d, J=5.6 Hz, 2H), 2.00 (q, J=7.3 Hz, 2H), 1.47 (s, 9H), 1.00 (t, J=7.4 Hz, 3H). $^{13}C$ NMR (126 MHz, Chloroform-d) δ 167.23, 156.48, 155.50, 153.79, 152.07, 143.73, 139.31, 129.84, 128.13, 126.66, 122.74, 121.44, 117.30, 108.60, 100.79, 79.62, 70.42, 70.26, 70.16, 70.04, 54.31, 40.51, 39.64, 28.48, 23.67, 11.17.

Step d: Preparation of N-(2-(2-(2-(2-aminoethoxy)ethoxy)ethoxy)ethyl)-4-((4-(1-propyl-1H-pyrazol-4-yl)-7H-pyrrolo[2,3-d]pyrimidin-2-yl)amino)benzamide. To tert-butyl (1-oxo-1-(4-((4-(1-propyl-1H-pyrazol-4-yl)-7H-pyrrolo[2,3-d]pyrimidin-2-yl)amino)phenyl)-5,8,11-trioxa-2-azatridecan-13-yl)carbamate (0.014 g, 0.022 mol) in dichloromethane (2 mL) under a nitrogen atmosphere at room temperature was added trifluoroacetic acid (0.084 mL, 1.1 mmol). The reaction mixture was stirred at room temperature for 3 h, then was concentrated in vacuo giving the title compound as a yellow solid, which was used without purification. LC-MS (ESI) m/z: 538 [M+H]+. $^1$H NMR (500 MHz, Methanol-d4) δ 8.78 (s, 1H), 8.43 (s, 1H), 7.94 (d, J=8.8 Hz, 2H), 7.88 (d, J=8.9 Hz, 2H), 7.44 (d, J=3.8 Hz, 1H), 6.99 (d, J=3.7 Hz, 1H), 4.28 (t, J=7.0 Hz, 2H), 3.74-3.65 (m, 12H), 3.62 (t, J=5.7 Hz, 2H), 3.13 (t, J=5.0 Hz, 2H), 2.00 (q, J=7.2 Hz, 2H), 0.99 (t, J=7.4 Hz, 3H). $^{13}$C NMR (126 MHz, Methanol-d4) δ 168.28, 154.12, 149.75, 145.12, 141.87, 139.35, 132.45, 128.31, 127.89, 127.61, 118.76, 114.10, 107.71, 102.12, 70.13, 70.08, 69.82, 69.80, 69.28, 66.44, 53.98, 39.39, 39.24, 23.06, 9.83.

Step e: Preparation of SJ000986051. A mixture of 2-(2,6-dioxopiperidin-3-yl)-4-fluoroisoindoline-1,3-dione (0.010 g, 0.036 mmol), N-(2-(2-(2-(2-aminoethoxy)ethoxy)ethoxy)ethyl)-4-((4-(1-propyl-1H-pyrazol-4-yl)-7H-pyrrolo[2,3-d]pyrimidin-2-yl)amino)benzamide (0.013 g, 0.024 mmol), and DIPEA (0.017 mL, 0.097 mmol) in DMSO (1 mL) was stirred at 90° C. under a nitrogen atmosphere for 20 h. The reaction mixture was then cooled to room temperature. The reaction mixture was diluted with ethyl acetate (5 mL), then washed sequentially with water (3 mL) and brine (3 mL). The organic phase was dried over sodium sulfate, filtered, and concentrated in vacuo. Purification using automated silica gel flash column chromatography (methanol/ethyl acetate) was followed by evaporation, giving the title compound as a yellow solid (0.004 g, 21%). LC-MS (ESI) m/z: 794 [M+H]+. $^1$H NMR (500 MHz, Chloroform-d) δ 13.15 (s, 1H), 10.17 (s, 1H), 8.65 (s, 1H), 8.13 (s, 1H), 8.06 (s, 1H), 7.81 (d, J=8.5 Hz, 2H), 7.68 (d, J=8.4 Hz, 2H), 7.45-7.36 (m, 1H), 7.04 (d, J=6.9 Hz, 1H), 6.93 (s, 1H), 6.89 (d, J=8.5 Hz, 1H), 6.75 (s, 1H), 6.48 (s, 1H), 6.39 (t, J=5.9 Hz, 1H), 4.89 (dd, J=12.1, 5.4 Hz, 1H), 4.12 (t, J=7.1 Hz, 2H), 3.69-3.50 (m, 14H), 3.49-3.34 (m, 2H), 2.88-2.64 (m, 3H), 2.06 (d, J=8.8 Hz, 1H), 1.90 (p, J=7.2 Hz, 2H), 0.92 (t, J=7.4 Hz, 3H). $^{13}$C NMR (126 MHz, Chloroform-d) δ 174.36, 171.25, 169.46, 167.76, 167.32, 154.92, 153.74, 151.74, 147.01, 144.45, 139.41, 135.96, 132.50, 130.15, 127.90, 126.20, 123.11, 121.82, 117.55, 117.11, 111.80, 110.28, 108.71, 100.53, 70.69, 70.58, 70.39, 70.01, 69.87, 54.31, 48.82, 42.66, 39.56, 31.57, 23.71, 22.85, 11.16.

k. Synthesis of SJ000986052

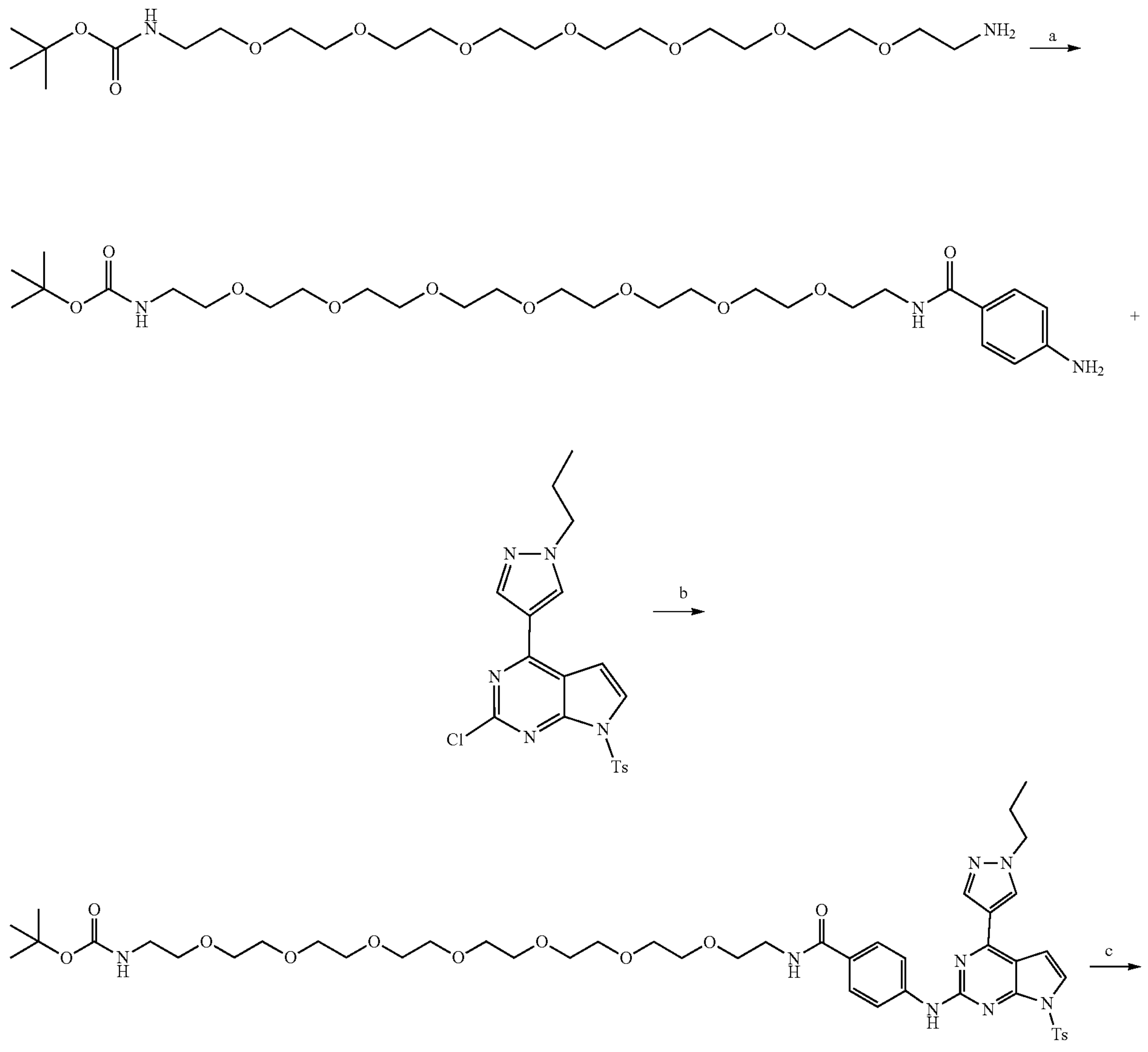

-continued

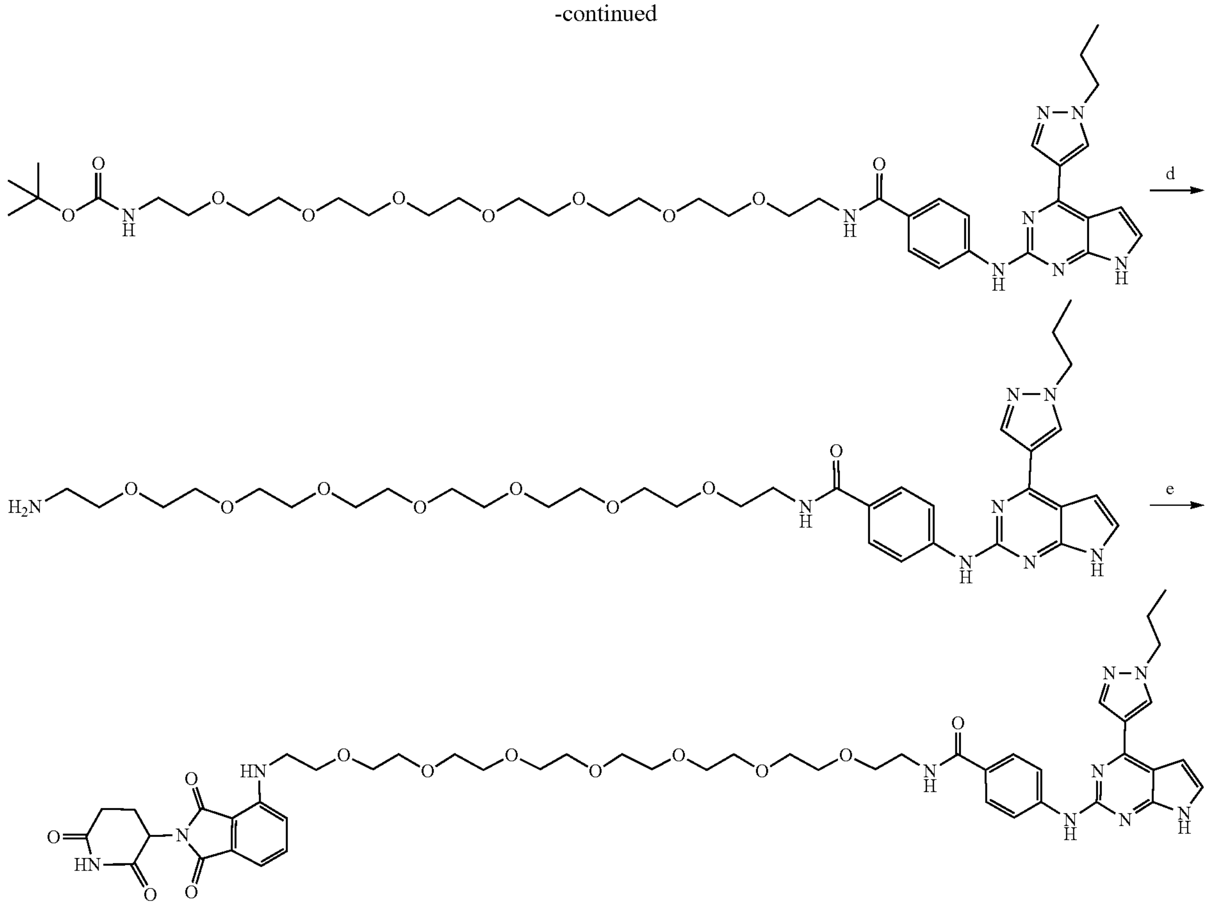

Reagents and conditions:
(a) 4-aminobenzoic acid, DIPEA, HATU, DMF, rt, 16 h;
(b) XPhos, $Pd_2(dba)_3$, $Cs_2CO_3$, dioxane, μwave, 150° C., 10 min.;
(c) LiOH, THF/, 80° C., 48 h.;
(d) TFA, $CH_2Cl_2$, rt, 5 h;
(e) 2-(2,6-dioxopiperidin-3-yl)-4-fluoroisoindoline-1, 3-dione, DIPEA, DMSO 90° C., 20 h.

Step a: Preparation of tert-butyl (1-(4-aminophenyl)-1-oxo-5,8,11,14,17,20,23-heptaoxa-2-azapentacosan-25-yl) carbamate. A mixture of t-Boc-N-amido-PEG7-amine (0.15 g, 0.32 mmol), 4-aminobenzoic acid (0.048 g, 0.35 mmol), DIPEA (0.17 mL, 0.96 mmol), HATU (0.15 g, 0.38 mmol) was stirred at room temperature in DMF (2 mL) for 16 h. The reaction mixture was diluted with ethyl acetate (3 mL) and washed with brine (2x3 mL), followed by 5% LiCl solution (3 mL). The organic phase was dried over sodium sulfate, filtered, and concentrated in vacuo. Purification using automated silica gel flash column chromatography (methanol/ethyl acetate) was followed by evaporation, giving the title compound as a colorless oil (0.065 g, 35%). LC-MS (ESI) m/z: 589 [M+H]+. $^1$H NMR (500 MHz, Methanol-d4) δ 7.74-7.43 (m, 2H), 6.79-6.48 (m, 2H), 3.69-3.59 (m, 26H), 3.55 (t, J=5.5 Hz, 2H), 3.51 (t, J=5.6 Hz, 2H), 3.23 (t, J=5.6 Hz, 2H), 1.45 (s, 9H). $^{13}$C NMR (126 MHz, Methanol-d4) δ 169.04, 157.06, 151.82, 128.60, 121.74, 113.29, 78.66, 70.15, 70.12, 70.11, 70.09, 69.92, 69.85, 69.67, 69.38, 39.89, 39.39, 27.37.

Step b: tert-butyl (1-oxo-1-(4-((4-(1-propyl-1H-pyrazol-4-yl)-7-tosyl-7H-pyrrolo[2,3-d]pyrimidin-2-yl)amino)phenyl)-5,8,11,14,17,20,23-heptaoxa-2-azapentacosan-25-yl) carbamate. To a microwave vial was added 2-chloro-4-(1-propyl-1H-pyrazol-4-yl)-7-tosyl-7H-pyrrolo[2,3-d]pyrimidine (0.042 g, 0.10 mmol) followed by tert-butyl (1-(4-aminophenyl)-1-oxo-5,8,11,14,17,20,23-heptaoxa-2-azapentacosan-25-yl)carbamate (0.065 g, 0.11 mmol) in dioxane (2.5 mL), XPhos (0.005 g, 0.010 mmol), $Cs_2CO_3$ (0.066 g, 0.20 mmol), and $Pd_2(dba)_3$ (0.005 g, 0.005 mmol). The vial was degassed and backfilled with nitrogen three times, then stirred at 150° C. and 100 W in a microwave reactor for 10 min. The reaction mixture was diluted with ethyl acetate (5 mL) and washed with brine (3x3 mL). The organic phase was dried over sodium sulfate, filtered, and concentrated in vacuo. Purification using automated flash column chromatography (ethyl acetate) was followed by evaporation, giving the title compound as an amber oil (0.045 g, 46%). LC-MS (ESI) m/z: 968 [M+H]+. $^1$H NMR (500 MHz, Chloroform-d) δ 8.14 (s, 1H), 8.09 (s, 1H), 8.04 (d, J=8.4 Hz, 2H), 7.92 (s, 4H), 7.55-7.52 (m, 1H), 7.51 (s, 1H), 7.26 (d, J=8.2 Hz, 2H), 6.96 (s, 1H), 6.74 (d, J=4.1 Hz, 1H), 5.11 (s, 1H), 4.19 (t, J=7.0 Hz, 2H), 3.74-3.58 (m, 28H), 3.53 (t, J=5.2 Hz, 2H), 3.31 (d, J=5.3 Hz, 2H), 2.37 (s, 3H), 1.98 (h, J=7.3 Hz, 2H), 1.44 (s, 9H), 0.98 (t, J=7.4 Hz, 3H). $^{13}$C NMR (126 MHz, Chloroform-d) δ 167.13, 156.10, 153.34, 153.16, 145.62, 142.95, 139.20, 135.06, 130.01, 129.87, 128.22, 127.94, 127.53, 123.61, 120.66, 117.79, 109.99, 104.36, 79.13, 70.59, 70.57, 70.54, 70.50, 70.28, 70.24, 70.02, 54.38, 40.37, 39.78, 28.43, 23.60, 21.66, 11.13.

Step c: Preparation of tert-butyl (1-oxo-1-(444-(1-propyl-1H-pyrazol-4-yl)-7H-pyrrolo[2,3-d]pyrimidin-2-yl)amino) phenyl)-5,8,11,14,17,20,23-heptaoxa-2-azapentacosan-25-yl)carbamate. To tert-butyl (1-oxo-1-(4-((4-(1-propyl-1H-pyrazol-4-yl)-7-tosyl-7H-pyrrolo[2,3-d]pyrimidin-2-yl) amino)phenyl)-5,8,11,14,17,20,23-heptaoxa-2-azapentacosan-25-yl)carbamate (0.039 g, 0.040 mmol) in THF (2 mL) and water (0.5 mL) was added LiOH monohydrate (0.085 g, 2.0 mmol). The reaction mixture was stirred at 80° C. under a nitrogen atmosphere for (s—3:15) 48 h, then was cooled to room temperature. The reaction mixture was diluted with dichloromethane (5 mL) and washed with water (3×5 mL). The organic phase was dried over sodium sulfate, filtered, and concentrated in vacuo. Purification using automated silica gel flash column chromatography (methanol/dichloromethane) was followed by evaporation, giving the title compound as a colorless oil (0.017 g, 52%). LC-MS (ESI) m/z: 814 [M+H]+. $^{1}$H NMR (500 MHz, Chloroform-d) δ 9.41 (s, 1H), 8.25 (s, 1H), 8.17 (s, 1H), 7.84 (q, J=8.4 Hz, 4H), 7.44 (s, 1H), 7.12 (dd, J=3.7, 2.2 Hz, 1H), 7.06 (d, J=8.7 Hz, 1H), 6.66 (dd, J=3.7, 1.9 Hz, 1H), 5.23 (s, 1H), 4.21 (t, J=7.1 Hz, 2H), 3.74-3.50 (m, 30H), 3.32 (d, J=5.5 Hz, 2H), 2.00 (d, J=7.2 Hz, 2H), 1.45 (s, 9H), 1.00 (t, J=7.4 Hz, 3H). $^{13}$C NMR (126 MHz, Chloroform-d) δ 167.24, 156.13, 155.53, 153.79, 152.03, 143.70, 139.31, 129.86, 128.19, 126.76, 122.81, 121.48, 117.40, 108.57, 100.79, 79.23, 70.57, 70.55, 70.52, 70.49, 70.44, 70.27, 70.23, 70.20, 70.01, 54.31, 40.38, 39.71, 28.45, 23.68, 11.18.

Step d: Preparation of N-(23-amino-3,6,9,12,15,18,21-heptaoxatricosyl)-4-((4-(1-propyl-1H-pyrazol-4-yl)-7H-pyrrolo[2,3-d]pyrimidin-2-yl)amino)benzamide. To tert-butyl (1-oxo-1-(4-((4-(1-propyl-1H-pyrazol-4-yl)-7H-pyrrolo[2,3-d]pyrimidin-2-yl)amino)phenyl)-5,8,11,14,17,20,23-heptaoxa-2-azapentacosan-25-yl)carbamate (0.017 g, 0.021 mol) in dichloromethane (2 mL) under a nitrogen atmosphere at room temperature was added trifluoroacetic acid (0.080 mL, 1.1 mmol). The reaction mixture was stirred at room temperature for 5 h, then was concentrated in vacuo giving the title compound as a yellow solid, which was used without purification. LC-MS (ESI) m/z: 714 [M+H]+. $^{1}$H NMR (500 MHz, Methanol-d4) δ 8.74 (s, 1H), 8.41 (s, 1H), 7.95 (d, J=8.8 Hz, 2H), 7.90 (d, J=8.8 Hz, 2H), 7.42 (d, J=3.8 Hz, 1H), 6.98 (d, J=3.8 Hz, 1H), 4.30 (t, J=7.0 Hz, 2H), 3.80-3.73 (m, 2H), 3.74-3.58 (m, 28H), 3.15 (t, J=5.1 Hz, 2H), 2.06-1.96 (m, 2H), 0.99 (t, J=7.4 Hz, 3H). $^{13}$C NMR (126 MHz, Methanol-d4) δ 168.24, 154.11, 150.69, 146.13, 142.35, 139.17, 132.17, 127.95, 127.91, 126.97, 118.47, 115.31, 107.87, 101.76, 70.02, 69.95, 69.93, 69.89, 69.81, 69.79, 69.75, 69.68, 69.66, 69.56, 69.21, 69.17, 66.43, 53.91, 39.31, 39.04, 23.13, 9.84.

Step e: Preparation of SJ000986052. A mixture of 2-(2,6-dioxopiperidin-3-yl)-4-fluoroisoindoline-1,3-dione (0.010 g, 0.036 mmol), N-(23-amino-3,6,9,12,15,18,21-heptaoxatricosyl)-4-((4-(1-propyl-1H-pyrazol-4-yl)-7H-pyrrolo[2,3-d]pyrimidin-2-yl)amino)benzamide (0.017 g, 0.024 mmol), and DIPEA (0.017 mL, 0.095 mmol) in DMSO (1 mL) was stirred at 90° C. under a nitrogen atmosphere for 20 h. The reaction mixture was cooled to room temperature. The reaction mixture was diluted with ethyl acetate (5 mL), then washed sequentially with water (3 mL) and brine (3 mL). The organic phase was dried over sodium sulfate, filtered, and concentrated in vacuo. Purification using automated silica gel flash column chromatography (methanol/ethyl acetate) was followed by evaporation, giving the title compound as a yellow oil (0.002 g, 9%). LC-MS (ESI) m/z: 970 [M+H]+. $^{1}$H NMR (500 MHz, Chloroform-d) δ 13.27 (s, 1H), 10.34 (s, 1H), 8.72 (s, 1H), 8.24 (s, 1H), 8.17 (s, 1H), 7.90 (d, J=8.5 Hz, 2H), 7.82 (d, J=8.7 Hz, 2H), 7.57-7.47 (m, 1H), 7.14 (d, J=7.1 Hz, 1H), 7.08 (dd, J=3.7, 2.1 Hz, 1H), 6.92 (d, J=8.6 Hz, 1H), 6.62 (dd, J=3.7, 1.9 Hz, 1H), 6.55 (s, 1H), 5.01 (dd, J=11.9, 5.5 Hz, 1H), 4.21 (t, J=7.1 Hz, 2H), 3.74-3.57 (m, 18H), 3.55-3.38 (m, 14H), 2.97 (d, J=21.6 Hz, 1H), 2.91-2.76 (m, 2H), 2.25-2.14 (m, 1H), 1.99 (q, J=7.2 Hz, 2H), 1.00 (t, J=7.4 Hz, 3H). $^{13}$C NMR (126 MHz, Chloroform-d) δ 174.29, 171.30, 169.24, 167.65, 167.53, 155.11, 153.86, 151.97, 146.89, 144.17, 139.43, 136.13, 132.56, 130.19, 128.14, 126.62, 123.18, 121.80, 117.59, 116.93, 111.73, 110.27, 108.77, 100.57, 70.78, 70.40, 70.28, 70.24, 70.13, 70.07, 70.05, 70.00, 69.22, 54.33, 48.74, 42.37, 39.62, 31.55, 23.73, 23.02, 11.17.

1. Synthesis of SJ000986341

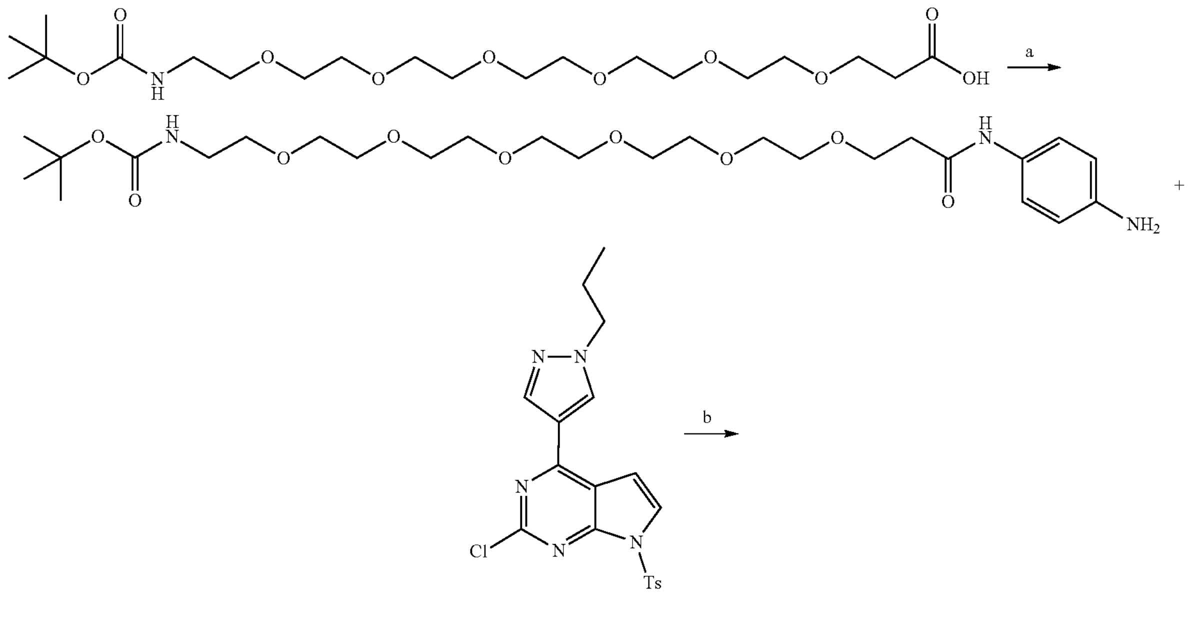

-continued

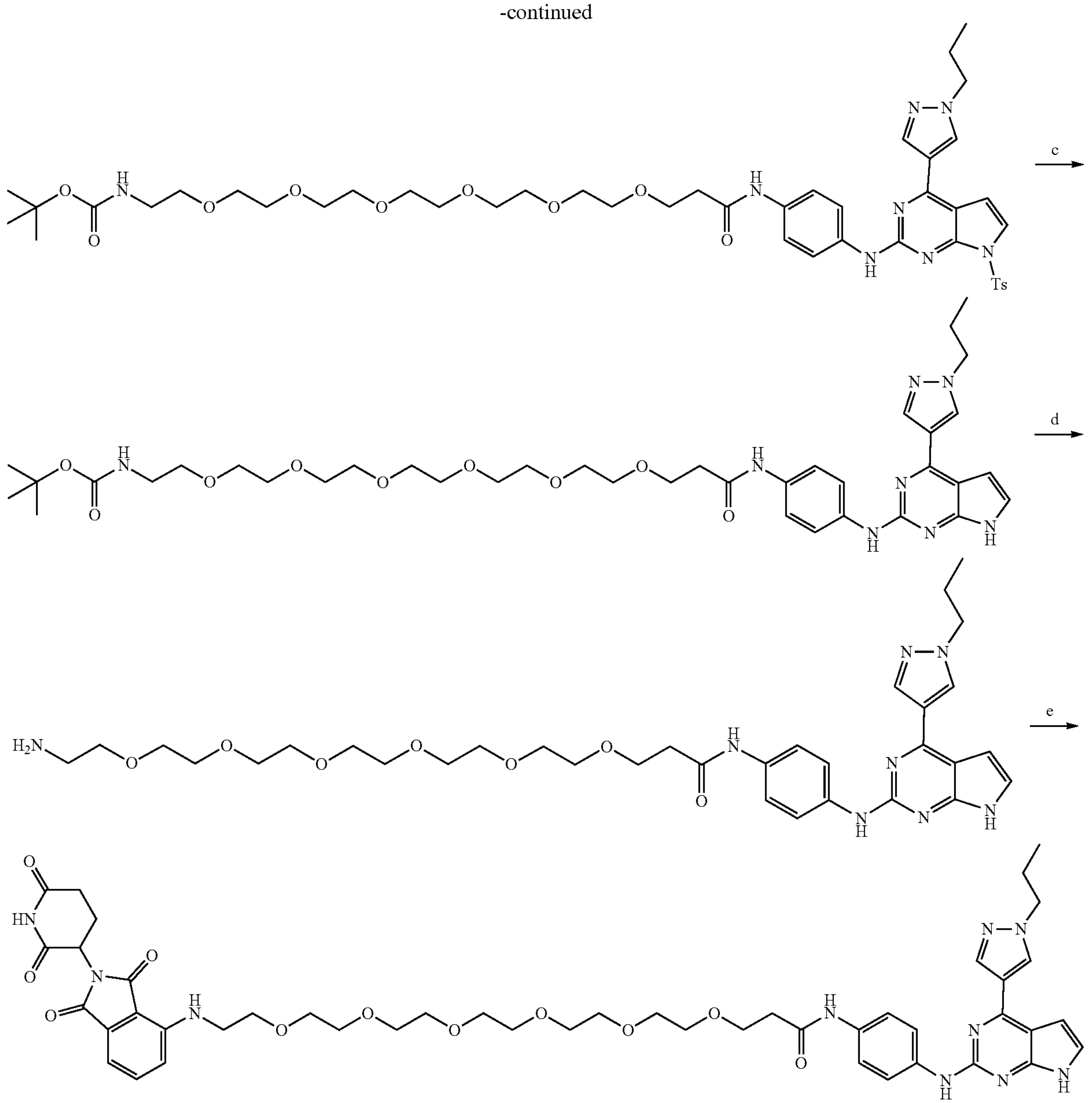

Reagents and conditions:
(a) p-phenylenediamine, DIPEA, HATU, DMF, rt, 3 h;
(b) XPhos, $Pd_2(dba)_3$, $CsCO_3$, dioxane, μwave, 150° C., 10 min.;
(c) KOH, MeOH, 80° C., 1 h;
(d) TFA, $CH_2Cl_2$, rt, 3 h;
(e) 2-(2,6-dioxopiperidin-3-yl)-4-fluoroisoindoline-1,3-dione, DIPEA, DMSO, 90° C., 16 h.

Step a: Preparation of tert-butyl (21-((4-aminophenyl)amino)-21-oxo-3,6,9,12,15,18-hexaoxahenicosyl)carbamate. A mixture of t-Boc-N-amido-PEG6-acid (0.070 g, 0.15 mmol), DIPEA (0.081 mL, 0.46 mmol), HATU (0.070 g, 0.19 mmol), and p-phenylenediamine (0.033 g, 0.31 mmol) was stirred at room temperature in DMF (2 mL) for 3 h. The reaction mixture was diluted with ethyl acetate (5 mL) and washed sequentially with brine (2×4 mL) and 5% LiCl solution (4 mL). The organic phase was dried over sodium sulfate, filtered, and concentrated in vacuo. Purification using automated silica gel flash column chromatography (methanol/dichloromethane) was followed by evaporation, giving the title compound as an orange oil (0.048 g, 57%). LC-MS (ESI) m/z: 545 [M+H]+. $^1$H NMR (500 MHz, Chloroform-d) δ 8.44 (s, 1H), 7.41-7.31 (m, 2H), 6.72-6.60 (m, 2H), 5.11 (s, 1H), 3.83 (t, J=5.6 Hz, 2H), 3.70 (s, 4H), 3.68-3.65 (m, 6H), 3.63 (tq, J=7.0, 4.2, 3.7 Hz, 10H), 3.54 (t, J=5.2 Hz, 2H), 3.32 (d, J=5.4 Hz, 2H), 2.64 (t, J=5.6 Hz, 2H), 1.46 (s, 9H). $^{13}$C NMR (126 MHz, Chloroform-d) δ 169.65, 156.05, 142.95, 129.99, 121.89, 115.44, 79.18, 70.60, 70.57, 70.55, 70.53, 70.51, 70.33, 70.31, 70.25, 67.29, 40.38, 37.77, 28.45.

Step b: Preparation of tert-butyl (21-oxo-21-((4-((4-(1-propyl-1H-pyrazol-4-yl)-7-tosyl-7H-pyrrolo[2,3-d]pyrimidin-2-yl)amino)phenyl)amino)-3,6,9,12,15,18-hexaoxahenicosyl)carbamate. To a microwave vial was added 2-chloro-4-(1-propyl-1H-pyrazol-4-yl)-7-tosyl-7H-pyrrolo[2,3-d]pyrimidine (0.045 g, 0.11 mmol) followed by tert-butyl (21-((4-aminophenyl)amino)-21-oxo-3,6,9,12,15,18-hexaoxahenicosyl)carbamate (0.065 g, 0.12 mmol) in dioxane (2.5 mL), XPhos (0.005 g, 0.011 mmol), $Cs_2CO_3$ (0.071 g, 0.22 mmol), and $Pd_2(dba)_3$ (0.005 g, 0.005 mmol). The vial was degassed and backfilled with nitrogen three times, then stirred at 150° C. and 100 W in a microwave reactor for 10 min. The reaction mixture was diluted with ethyl acetate (5 mL) and washed with brine (3×3 mL). The organic phase was dried over sodium sulfate, filtered, and concentrated in vacuo. Purification using automated flash column chromatography (ethyl acetate) was followed by evaporationg, giving the title compound as a tan foam (0.049 g, 49%). LC-MS (ESI) m/z: 924 [M+H]+. $^1$H NMR (500 MHz, Chloroform-d) δ 8.70 (s, 1H), 8.12 (s, 1H), 8.07 (s, 1H), 8.02 (d, J=8.1 Hz, 2H), 7.79-7.70 (m, 2H), 7.64 (d, J=8.8 Hz, 2H), 7.49 (d, J=4.1 Hz, 1H), 7.25 (d, J=8.2 Hz, 2H), 6.71 (d, J=4.1 Hz, 1H), 5.09 (s, 1H), 4.18 (t, J=7.1 Hz, 2H), 3.88 (t, J=5.6 Hz, 2H), 3.75 (s, 4H), 3.71 (dd, J=5.8, 3.2 Hz, 2H), 3.66 (dd, J=5.1, 2.5 Hz, 2H), 3.63 (t, J=3.9 Hz, 12H), 3.53 (t, J=5.1 Hz, 2H), 3.31 (d, J=5.5 Hz, 2H), 2.70 (t, J=5.5 Hz, 2H), 2.37 (s, 3H), 1.98 (h, J=7.3 Hz, 2H), 1.45 (s, 9H), 0.98 (t, J=7.4 Hz, 3H). $^{13}$C NMR (126 MHz, Chloroform-d) δ 169.89, 156.74, 156.03, 153.63, 153.07, 145.51, 139.18, 136.10, 135.02, 133.05, 129.96, 129.79, 128.08, 123.03, 120.76, 119.46, 109.43, 104.35, 79.15, 70.62, 70.58, 70.56, 70.54, 70.50, 70.40, 70.38, 70.23, 67.24, 54.36, 40.37, 37.92, 28.44, 23.61, 21.66, 11.12.

Step c: Preparation of tert-butyl (21-oxo-21-((4-((4-(1-propyl-1H-pyrazol-4-yl)-7H-pyrrolo[2,3-d]pyrimidin-2-yl)amino)phenyl)amino)-3,6,9,12,15,18-hexaoxahenicosyl)carbamate. To tert-butyl (21-oxo-21-((4-((4-(1-propyl-1H-pyrazol-4-yl)-7-tosyl-7H-pyrrolo[2,3-d]pyrimidin-2-yl)amino)phenyl)amino)-3,6,9,12,15,18-hexaoxahenicosyl)carbamate (0.044 g, 0.048 mmol) in methanol (2 mL) was added 2 M KOH (0.19 mL) and the reaction mixture was stirred at 80° C. for under a nitrogen atmosphere for 1 h. The reaction mixture was then cooled to room temperature and concentrated in vacuo. The reaction mixture was diluted with dichloromethane (3 mL) and washed with water (3×3 mL). The organic phase was dried over sodium sulfate, filtered, and concentrated in vacuo. Purification using automated silica gel flash column chromatography (methanol/dichloromethane) was followed by evaporation, giving the title compound as a colorless oil (0.020 g, 55%). LC-MS (ESI) m/z: 770 [M+H]+. $^1$H NMR (500 MHz, Methanol-d4) δ 8.45 (s, 1H), 8.27 (d, J=0.7 Hz, 1H), 7.85-7.72 (m, 2H), 7.56-7.46 (m, 2H), 7.15 (d, J=3.7 Hz, 1H), 6.73 (d, J=3.7 Hz, 1H), 4.25 (t, J=7.0 Hz, 2H), 3.85 (t, J=6.0 Hz, 2H), 3.68-3.63 (m, 6H), 3.60-3.53 (m, 14H), 3.47 (t, J=5.6 Hz, 2H), 3.20 (t, J=5.6 Hz, 2H), 2.64 (t, J=6.0 Hz, 2H), 1.98 (q, J=7.3 Hz, 2H), 1.43 (s, 9H), 0.98 (t, J=7.4 Hz, 3H). $^{13}$C NMR (126 MHz, Methanol-d4) δ 170.66, 157.04, 156.19, 153.97, 151.25, 138.79, 137.91, 131.79, 130.70, 122.76, 121.46, 120.56, 118.44, 107.85, 99.84, 78.66, 70.20, 70.17, 70.16, 70.09, 70.06, 70.04, 69.80, 69.62, 66.92, 53.49, 39.87, 37.18, 27.36, 23.35, 9.92.

Step d: Preparation of 1-amino-N-(4-((4-(1-propyl-1H-pyrazol-4-yl)-7H-pyrrolo[2,3-d]pyrimidin-2-yl)amino)phenyl)-3,6,9,12,15,18-hexaoxahenicosan-21-amide. To tert-butyl (21-oxo-21-((4-((4-(1-propyl-1H-pyrazol-4-yl)-7H-pyrrolo[2,3-d]pyrimidin-2-yl)amino)phenyl)amino)-3,6,9,12,15,18-hexaoxahenicosyl)carbamate (0.020 g, 0.026 mol) in dichloromethane (2 mL) under a nitrogen atmosphere at room temperature was added trifluoroacetic acid (0.10 mL, 1.3 mmol). The reaction mixture was stirred at room temperature for 3 h, then was concentrated in vacuo, giving the title compound as an orange oil, which was used without purification. LC-MS (ESI) m/z: 670 [M+H]+. $^1$H NMR (500 MHz, Methanol-d4) δ 8.80 (s, 1H), 8.42 (d, J=0.7 Hz, 1H), 7.73 (d, J=9.0 Hz, 2H), 7.64 (d, J=9.0 Hz, 2H), 7.43 (d, J=3.8 Hz, 1H), 6.99 (d, J=3.8 Hz, 1H), 4.30 (t, J=7.0 Hz, 2H), 3.87 (t, J=5.9 Hz, 2H), 3.79-3.73 (m, 2H), 3.71-3.66 (m, 9H), 3.66-3.61 (m, 11H), 3.14 (t, J=5.1 Hz, 2H), 2.70 (t, J=5.8 Hz, 2H), 2.01 (h, J=7.3 Hz, 2H), 0.99 (t, J=7.4 Hz, 3H). $^{13}$C NMR (126 MHz, Methanol-d4) δ 170.84, 154.62, 149.78, 144.25, 139.21, 134.63, 134.15, 132.49, 127.78, 120.78, 120.36, 113.40, 107.34, 102.19, 70.00, 69.97, 69.89, 69.82, 69.80, 69.76, 69.54, 69.29, 66.73, 66.53, 54.02, 39.12, 36.75, 23.06, 9.82.

Step e: Preparation of SJ000986341. A mixture of 2-(2,6-dioxopiperidin-3-yl)-4-fluoroisoindoline-1,3-dione (0.011 g, 0.040 mmol), 1-amino-N-(4-((4-(1-propyl-1H-pyrazol-4-yl)-7H-pyrrolo[2,3-d]pyrimidin-2-yl)amino)phenyl)-3,6,9,12,15,18-hexaoxahenicosan-21-amide (0.018 g, 0.027 mmol), and DIPEA (0.019 mL, 0.11 mmol) in DMSO (2 mL) was stirred at 90° C. under a nitrogen atmosphere for 16 h. The reaction mixture was then cooled to room temperature. The reaction mixture was diluted with ethyl acetate (5 mL), then washed sequentially with water (3 mL), brine (3 mL), and 5% LiCl solution (2 mL). The organic phase was dried over sodium sulfate, filtered, and concentrated in vacuo. Purification using automated silica gel flash column chromatography (methanol/ethyl acetate) was followed by evaporation, giving the title compound as a yellow solid (0.003 g, 12%). LC-MS (ESI) m/z: 926 [M+H]+. $^1$H NMR (500 MHz, Methanol-d4) δ 8.43 (s, 1H), 8.25 (d, J=0.7 Hz, 1H), 7.78 (d, J=9.0 Hz, 2H), 7.54-7.44 (m, 3H), 7.13 (d, J=3.6 Hz, 1H), 7.00 (t, J=7.7 Hz, 2H), 6.71 (d, J=3.7 Hz, 1H), 5.04 (dd, J=12.7, 5.5 Hz, 1H), 4.24 (t, J=7.0 Hz, 2H), 3.84 (t, J=5.9 Hz, 2H), 3.68-3.62 (m, 9H), 3.60 (s, 4H), 3.58-3.54 (m, 10H), 3.43 (d, J=5.3 Hz, 2H), 2.85 (ddd, J=17.5, 13.9, 5.3 Hz, 1H), 2.79-2.66 (m, 2H), 2.63 (t, J=5.9 Hz, 2H), 2.16-2.06 (m, 1H), 1.97 (q, J=7.3 Hz, 2H), 0.98 (t, J=7.4 Hz, 3H). $^{13}$C NMR (126 MHz, Methanol-d4) δ 173.31, 170.68, 170.25, 169.21, 167.89, 156.14, 153.93, 151.20, 146.72, 138.79, 137.88, 135.70, 132.41, 131.78, 130.70, 122.75, 121.46, 120.54, 118.44, 116.76, 110.54, 109.83, 107.85, 99.84, 70.19, 70.17, 70.13, 70.11, 70.07, 70.04, 70.02, 69.13, 66.91, 60.13, 53.49, 48.77, 41.78, 37.20, 30.01, 23.35, 22.41, 9.92.

m. Synthesis of SJ000986342

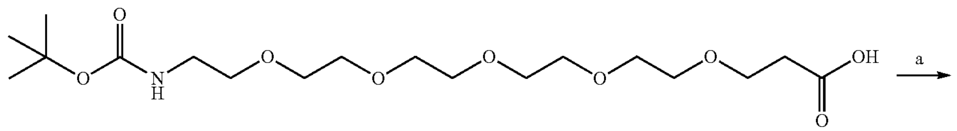

-continued
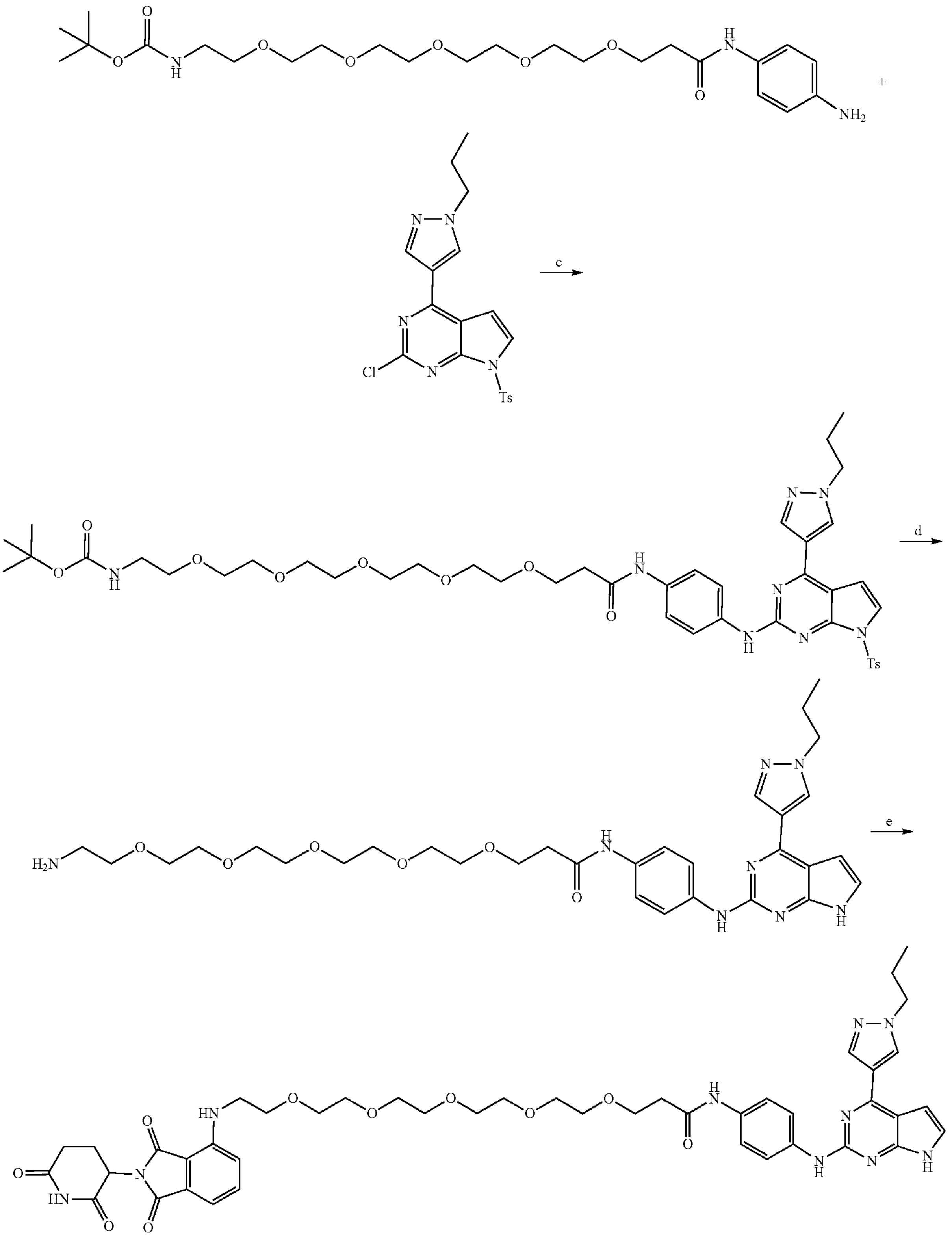
Reagents and conditions:
(a) p-phenylenediamine, DIPEA, HATU, DMF, rt, 16 h;
(b) XPhos, $Pd_2(dba)_3$, $Cs_2CO_3$, dioxane, μwave, 150° C., 10 min.;
(c) KOH, MeOH, 80° C., 1 h;
(d) TFA, $CH_2Cl_2$, rt, 3 h;
(e) 2-(2,6-dioxopiperidin-3-yl)-4-fluoroisoindoline-1,3-dione, DIPEA, DMSO, 90° C., 18 h.

Step a: Preparation of tert-butyl (18-((4-aminophenyl) amino)-18-oxo-3,6,9,12,15-pentaoxaoctadecyl)carbamate. A mixture of t-Boc-N-amido-PEG5-acid (0.075 g, 0.18 mmol), DIPEA (0.096 mL, 0.55 mmol), HATU (0.084 g, 0.22 mmol), and p-phenylenediamine (0.040 g, 0.37 mmol) was stirred at room temperature in DMF (2 mL) for 16 h. The reaction mixture was diluted with ethyl acetate (5 mL) and washed sequentially with brine (2×4 mL) and 5% LiCl solution (4 mL). The organic phase was dried over sodium sulfate, filtered, and concentrated in vacuo. Purification using automated silica gel flash column chromatography (methanol/dichloromethane), was followed by a second flash column (ethyl acetate/hexanes with 1% methanol additive) and evaporation, giving the title compound as a colorless oil (0.041 g, 45%). LC-MS (ESI) m/z: 501 [M+H]+. $^{1}$H NMR (500 MHz, Chloroform-d) δ 8.43 (s, 1H), 7.34 (d, J=8.6 Hz, 2H), 6.66 (d, J=8.7 Hz, 2H), 5.10 (s, 1H), 3.82 (t, J=5.6 Hz, 2H), 3.70 (s, 4H), 3.68-3.65 (m, 2H), 3.64-3.58 (m, 10H), 3.53 (t, J=5.1 Hz, 2H), 3.31 (q, J=5.4 Hz, 2H), 2.63 (t, J=5.6 Hz, 2H), 1.46 (s, 9H). $^{13}$C NMR (126 MHz, Chloroform-d) δ 169.64, 156.04, 142.89, 129.94, 121.90, 115.38, 79.19, 70.56, 70.52, 70.34, 70.30, 70.24, 70.22, 67.28, 40.37, 37.76, 28.45.

Step b: Preparation of tert-butyl (18-oxo-18-((4-((4-(1-propyl-1H-pyrazol-4-yl)-7-tosyl-7H-pyrrolo[2,3-d]pyrimidin-2-yl)amino)phenyl)amino)-3,6,9,12,15-pentaoxaoctadecyl)carbamate. To a microwave vial was added 2-chloro-4-(1-propyl-1H-pyrazol-4-yl)-7-tosyl-7H-pyrrolo[2,3-d] pyrimidine (0.030 g, 0.072 mmol) followed by tert-butyl (18-((4-aminophenyl)amino)-18-oxo-3,6,9,12,15-pentaoxaoctadecyl)carbamate (0.040 g, 0.079 mmol) in dioxane (2.5 mL), XPhos (0.003 g, 0.007 mmol), $Cs_2CO_3$ (0.047 g, 0.14 mmol), and $Pd_2(dba)_3$ (0.003 g, 0.004 mmol). The vial was degassed and backfilled with nitrogen three times, then stirred at 150° C. and 100 W for 10 min. The reaction mixture was diluted with ethyl acetate (5 mL) and washed with brine (3×3 mL). The organic phase was dried over sodium sulfate, filtered, and concentrated in vacuo. Purification using automated flash column chromatography (ethyl acetate) was followed by evaporation, giving the title compound as a tan oil (0.030 g, 47%). LC-MS (ESI) m/z: 880 [M+H]+. $^{1}$H NMR (500 MHz, Chloroform-d) δ 8.73 (s, 1H), 8.13 (s, 1H), 8.07 (s, 1H), 8.01 (d, J=7.5 Hz, 2H), 7.75 (d, J=8.7 Hz, 2H), 7.65 (d, J=8.5 Hz, 2H), 7.49 (s, 1H), 7.25 (d, J=8.2 Hz, 2H), 6.72 (s, 1H), 5.14 (s, 1H), 4.19 (t, J=7.1 Hz, 2H), 3.88 (t, J=5.5 Hz, 2H), 3.76-3.73 (m, 4H), 3.72 (dd, J=5.8, 3.2 Hz, 2H), 3.66 (dd, J=5.9, 3.3 Hz, 2H), 3.63 (s, 4H), 3.61 (s, 4H), 3.54 (t, J=5.1 Hz, 2H), 3.32 (d, J=5.6 Hz, 2H), 2.71 (t, J=5.5 Hz, 2H), 2.37 (s, 3H), 1.98 (h, J=7.3 Hz, 2H), 1.44 (s, 9H), 0.98 (t, J=7.4 Hz, 3H). $^{13}$C NMR (126 MHz, Chloroform-d) δ 169.89, 156.74, 156.04, 153.62, 153.07, 145.50, 139.18, 135.02, 133.05, 129.96, 129.79, 128.08, 123.03, 121.91, 120.77, 119.44, 115.38, 109.45, 104.36, 79.16, 70.62, 70.58, 70.55, 70.48, 70.38, 70.24, 67.24, 54.36, 40.38, 37.91, 28.43, 23.60, 21.67, 11.12.

Step c: Preparation of tert-butyl (18-oxo-18-((4-((4-(1-propyl-1H-pyrazol-4-yl)-7H-pyrrolo[2,3-d]pyrimidin-2-yl) amino)phenyl)amino)-3,6,9,12,15-pentaoxaoctadecyl)carbamate. To tert-butyl (18-oxo-18-((4-((4-(1-propyl-1H-pyrazol-4-yl)-7-tosyl-7H-pyrrolo[2,3-d]pyrimidin-2-yl) amino)phenyl)amino)-3,6,9,12,15-pentaoxaoctadecyl) carbamate (0.027 g, 0.031 mmol) in methanol (1 mL) was added 2 M KOH (0.12 mL) and the reaction mixture was stirred at 80° C. under a nitrogen atmosphere for 1 h. The reaction mixture was then cooled to room temperature and concentrated in vacuo. The crude reaction mixture was diluted with dichloromethane (3 mL) and washed with water (3×3 mL). The organic phase was dried over sodium sulfate, filtered, and concentrated in vacuo. Purification using automated silica gel flash column chromatography (methanol/dichloromethane) was followed by a second flash column (methanol/ethyl acetate) and evaporation giving the title compound as a tan oil (0.017 g, 76%). LC-MS (ESI) m/z: 726 [M+H]+. $^{1}$H NMR (500 MHz, Chloroform-d) δ 9.22 (s, 1H), 8.68 (s, 1H), 8.21 (s, 1H), 8.14 (s, 1H), 7.67 (d, J=8.3 Hz, 2H), 7.56 (d, J=8.6 Hz, 2H), 7.18 (s, 1H), 7.01 (s, 1H), 6.61 (dd, J=3.8, 1.9 Hz, 1H), 5.31 (s, 1H), 4.19 (t, J=7.1 Hz, 2H), 3.83 (t, J=5.5 Hz, 2H), 3.73-3.69 (m, 4H), 3.68 (dt, J=5.9, 2.8 Hz, 5H), 3.65-3.61 (m, 7H), 3.56-3.51 (m, 2H), 3.30 (q, J=6.2 Hz, 2H), 2.66 (t, J=5.5 Hz, 2H), 1.98 (q, J=7.3 Hz, 2H), 1.44 (d, J=6.6 Hz, 9H), 0.98 (t, J=7.4 Hz, 3H). $^{13}$C NMR (126 MHz, Chloroform-d) δ 169.80, 156.16, 154.05, 152.06, 139.29, 136.80, 132.52, 129.84, 122.06, 121.57, 120.78, 119.21, 115.35, 108.07, 100.84, 79.32, 72.57, 70.58, 70.53, 70.51, 70.48, 70.30, 70.25, 70.23, 70.18, 67.24, 61.64, 54.27, 40.38, 37.87, 28.45, 23.68, 11.17.

Step d: Preparation of 1-amino-N-(4-((4-(1-propyl-1H-pyrazol-4-yl)-7H-pyrrolo[2,3-d]pyrimidin-2-yl)amino)phenyl)-3,6,9,12,15-pentaoxaoctadecan-18-amide. To tert-butyl (18-oxo-18-((4-((4-(1-propyl-1H-pyrazol-4-yl)-7H-pyrrolo [2,3-d]pyrimidin-2-yl)amino)phenyl)amino)-3,6,9,12,15-pentaoxaoctadecyl)carbamate (0.013 g, 0.018 mol) in dichloromethane (1.5 mL) under a nitrogen atmosphere at room temperature was added trifluoroacetic acid (0.069 mL, 0.9 mmol). The reaction mixture was stirred at room temperature for 3 h, then was concentrated in vacuo giving the title compound as an orange oil, which was used without purification. LC-MS (ESI) m/z: 626 [M+H]+.

Step e: Preparation of SJ000986342. A mixture of 2-(2,6-dioxopiperidin-3-yl)-4-fluoroisoindoline-1,3-dione (0.0080 g, 0.030 mmol), 1-amino-N-(4-((4-(1-propyl-1H-pyrazol-4-yl)-7H-pyrrolo[2,3-d]pyrimidin-2-yl)amino)phenyl)-3,6,9,12,15-pentaoxaoctadecan-18-amide (0.011 g, 0.018 mmol), and DIPEA (0.013 mL, 0.072 mmol) in DMSO (1 mL) was stirred at 90° C. under a nitrogen atmosphere for 18 h. The reaction mixture was then cooled to room temperature. The reaction mixture was diluted with ethyl acetate (5 mL), then washed sequentially with water (3 mL), brine (3 mL), and 5% LiCl solution (2 mL). The organic phase was dried over sodium sulfate, filtered, and concentrated in vacuo. Purification using automated silica gel flash column chromatography (ethyl acetate/hexanes, then methanol/dichloromethane) was followed by evaporation, giving the title compound as a yellow solid (0.004 g, 25%). LC-MS (ESI) m/z: 882 [M+H]+. $^{1}$H NMR (500 MHz, Methanol-d4) δ 8.42 (s, 1H), 8.25 (d, J=0.7 Hz, 1H), 7.77 (d, J=9.0 Hz, 2H), 7.56-7.49 (m, 2H), 7.46 (dd, J=8.6, 7.1 Hz, 1H), 7.13 (d, J=3.7 Hz, 1H), 6.99 (d, J=7.0 Hz, 1H), 6.96 (d, J=8.6 Hz, 1H), 6.71 (d, J=3.7 Hz, 1H), 5.04 (dd, J=12.7, 5.5 Hz, 1H), 4.24 (t, J=7.0 Hz, 2H), 3.84 (t, J=5.9 Hz, 2H), 3.69-3.61 (m, 10H), 3.57 (t, J=7.0 Hz, 8H), 3.39 (q, J=5.4 Hz, 1H), 2.90-2.80 (m, 1H), 2.85-2.70 (m, 2H), 2.63 (t, J=5.9 Hz, 3H), 2.09 (ddt, J=13.1, 5.5, 2.7 Hz, 1H), 2.03-1.93 (m, 2H), 0.98 (t, J=7.4 Hz, 3H). $^{13}$C NMR (126 MHz, Methanol-d4) δ 173.31, 170.69, 170.27, 169.20, 167.89, 156.12, 153.92, 151.19, 146.69, 138.78, 137.89, 135.67, 132.38, 131.77, 130.70, 122.75, 121.45, 120.56, 118.43, 116.72, 110.52, 109.81, 107.86, 99.85, 72.24, 70.18, 70.14, 70.11, 70.10, 70.06, 70.01, 69.10, 66.90, 60.81, 53.49, 48.77, 41.75, 37.19, 30.80, 23.35, 22.41, 9.92.

n. Synthesis of SJ000986343

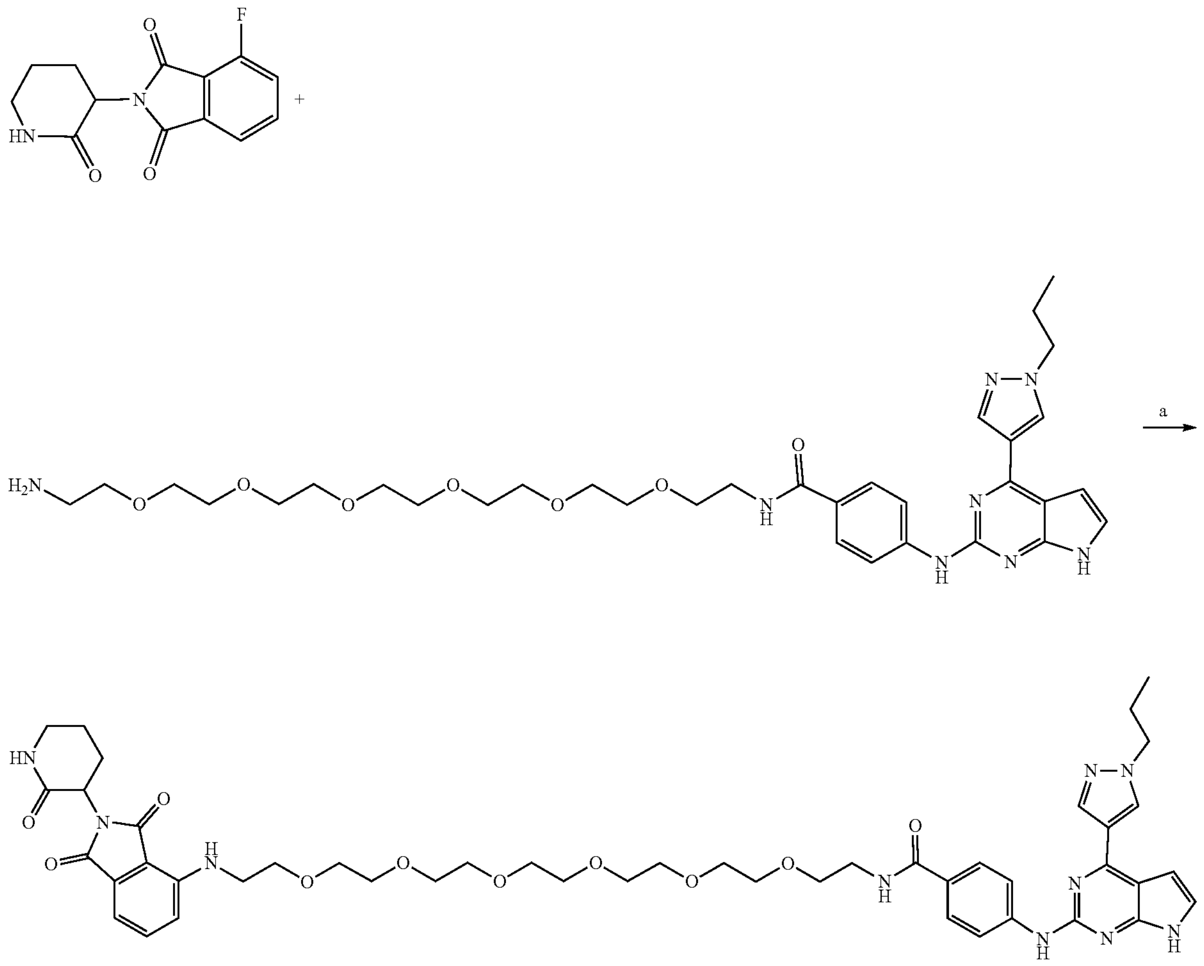

Reagents and conditions: (a) DIPEA, DMSO, 90° C., 18 h.

Step a: Preparation of SJ000986343. A mixture of 4-fluoro-2-(2-oxopiperidin-3-yl)isoindoline-1,3-dione (0.013 g, 0.049 mmol), N-(20-amino-3,6,9,12,15,18-hexaoxaicosyl)-4-((4-(1-propyl-1H-pyrazol-4-yl)-7H-pyrrolo[2,3-d]pyrimidin-2-yl)amino)benzamide (0.022 g, 0.033 mmol), and DIPEA (0.023 mL, 0.132 mmol) in DMSO (1 mL) was stirred at 90° C. under a nitrogen atmosphere for 18 h. The reaction mixture was cooled to room temperature and was diluted with ethyl acetate (5 mL), then washed sequentially with water (3 mL), brine (3 mL), and 5% LiCl solution (2 mL). The organic phase was dried over sodium sulfate, filtered, and concentrated in vacuo. Purification using automated silica gel flash column chromatography (methanol/dichloromethane) was followed by evaporation, giving the title compound as a yellow solid (0.005 g, 17%). LC-MS (ESI) m/z: 912 [M+H]+. $^{1}$H NMR (500 MHz, Methanol-d4) δ 8.34 (d, J=0.7 Hz, 1H), 8.16 (d, J=0.7 Hz, 1H), 7.84 (d, J=8.9 Hz, 2H), 7.71 (d, J=8.9 Hz, 2H), 7.33 (dd, J=8.4, 7.0 Hz, 1H), 7.06 (d, J=3.6 Hz, 1H), 6.86 (d, J=7.0 Hz, 1H), 6.83 (d, J=8.5 Hz, 1H), 6.63 (d, J=3.6 Hz, 1H), 4.56 (dd, J=11.8, 6.2 Hz, 1H), 4.13 (t, J=7.0 Hz, 2H), 3.56 (d, J=9.6 Hz, 6H), 3.52 (ddd, J=5.1, 3.4, 2.3 Hz, 4H), 3.51-3.41 (m, 16H), 3.29 (t, J=5.4 Hz, 3H), 3.23 (dt, J=5.2, 1.8 Hz, 1H), 2.25-2.13 (m, 1H), 1.97-1.77 (m, 5H), 0.86 (t, J=7.4 Hz, 3H). $^{13}$C NMR (126 MHz, Methanol-d4) δ 169.51, 169.48, 168.68, 168.15, 155.53, 153.75, 151.16, 146.57, 144.93, 138.82, 135.50, 132.61, 130.76, 127.86, 125.35, 123.28, 121.43, 116.87, 116.52, 110.40, 110.09, 108.30, 99.85, 70.18, 70.17, 70.15, 70.12, 70.08, 69.96, 69.29, 69.15, 53.51, 48.48, 41.78, 41.69, 39.56, 26.03, 23.36, 21.69, 9.93.

o. Synthesis of SJ000986339

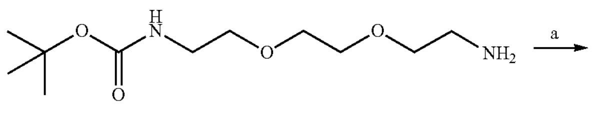

-continued
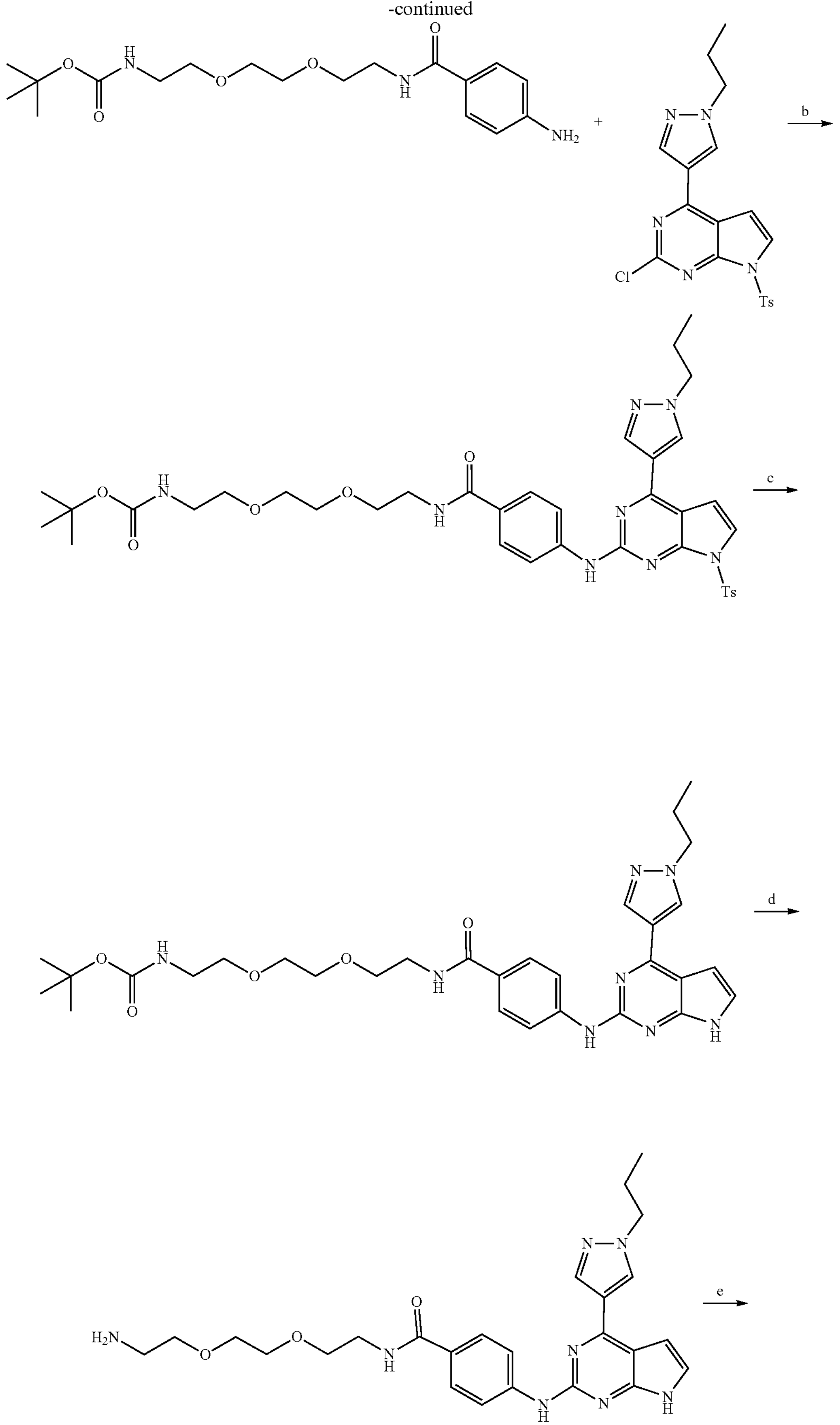

-continued

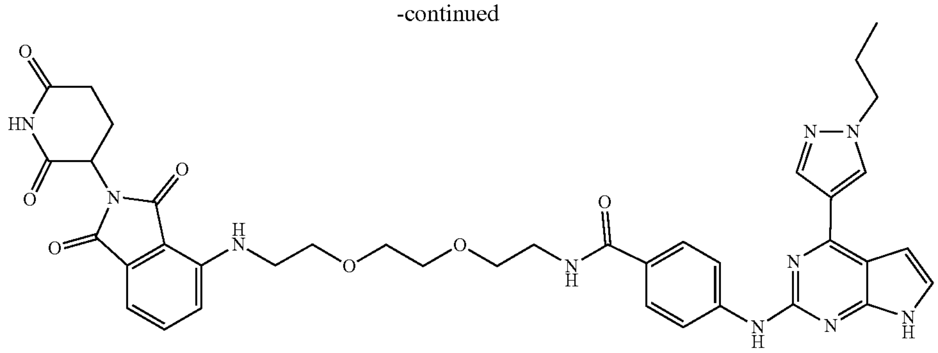

Reagents and conditions:
(a) 4-aminobenzoic acid, DIPEA, HATU, DMF, rt, 2 h;
(b) XPhos, $Pd_2(dba)_3$, $Cs_2CO_3$, dioxane, μwave, 150° C., 10 min.;
(c) KOH, MeOH, 80° C., 1 h;
(d) TFA, $CH_2Cl_2$, rt, 4 h;
(e) 2-(2,6-dioxopiperidin-3-yl)-4-fluoroisoindoline-1, 3-dione, DIPEA, DMSO, 90° C., 20 h.

Step a: Preparation of tert-butyl (2-(2-(2-(4-aminobenzamido)ethoxy)ethoxy)ethyl)carbamate. A mixture of t-Boc-N-amido-PEG2-amine (0.10 g, 0.45 mmol), 4-aminobenzoic acid (0.061 g, 0.45 mmol), DIPEA (0.21 mL, 1.2 mmol), HATU (0.19 g, 0.49 mmol) was stirred at room temperature in DMF (2 mL) for 2 h. The reaction mixture was then diluted with ethyl acetate (3 mL) and washed with brine (2×3 mL), followed by 5% LiCl solution (3 mL). The organic phase was dried over sodium sulfate, filtered, and concentrated in vacuo. Purification using automated silica gel flash column chromatography (methanol/ethyl acetate) was followed by evaporation, giving the title compound as a colorless oil (0.062 g, 42%). LC-MS (ESI) m/z: 368 [M+H]+. $^1$H NMR (500 MHz, Chloroform-d) δ 7.65 (d, J=8.1 Hz, 2H), 6.68 (d, J=8.2 Hz, 2H), 6.56 (s, 1H), 5.04 (s, 1H), 3.97 (s, 2H), 3.66 (d, J=11.6 Hz, 8H), 3.57 (t, J=5.2 Hz, 2H), 3.33 (t, J=5.5 Hz, 2H), 1.46 (s, 9H). $^{13}$C NMR (126 MHz, Chloroform-d) δ 167.37, 156.15, 149.57, 129.05, 125.31, 114.13, 79.49, 70.38, 70.27, 70.20, 39.59, 38.63, 28.42.

Step b: Preparation of tert-butyl (2-(2-(2-(4-((4-(1-propyl-1H-pyrazol-4-yl)-7-tosyl-7H-pyrrolo[2,3-d]pyrimidin-2-yl)amino)benzamido)ethoxy)ethoxy)ethyl)carbamate. To a microwave vial was added 2-chloro-4-(1-propyl-1H-pyrazol-4-yl)-7-tosyl-7H-pyrrolo[2,3-d]pyrimidine (0.060 g, 0.14 mmol) followed by tert-butyl (2-(2-(2-(4-aminobenzamido)ethoxy)ethoxy)ethyl)carbamate (0.058 g, 0.16 mmol) in dioxane (2.5 mL), XPhos (0.007 g, 0.014 mmol), $Cs_2CO_3$ (0.094 g, 0.29 mmol), and $Pd_2(dba)_3$ (0.007 g, 0.007 mmol). The vial was degassed and backfilled with nitrogen three times, then stirred at 150° C. and 100 W in a microwave reactor for 10 min. The reaction mixture was then diluted with ethyl acetate (5 mL) and washed with brine (3×3 mL). The organic phase was dried over sodium sulfate, filtered, and concentrated in vacuo. Purification using automated flash column chromatography (ethyl acetate) was followed by evaporation, giving the title compound as a yellow solid (0.059 g, 55%). LC-MS (ESI) m/z: 748 [M+H]+. $^1$H NMR (500 MHz, Chloroform-d) δ 8.14 (s, 1H), 8.09 (s, 1H), 8.07-8.01 (m, 2H), 7.98-7.81 (m, 3H), 7.54 (d, J=4.0 Hz, 1H), 7.36 (s, 1H), 7.26 (d, J=8.2 Hz, 2H), 6.74 (d, J=4.1 Hz, 1H), 6.71 (s, 1H), 5.04 (s, 1H), 4.19 (t, J=7.1 Hz, 2H), 3.73 (d, J=2.8 Hz, 4H), 3.71-3.65 (m, 4H), 3.59 (t, J=5.3 Hz, 2H), 3.42-3.24 (m, 2H), 2.37 (s, 3H), 1.98 (q, J=7.2 Hz, 2H), 1.45 (s, 9H), 0.98 (t, J=7.4 Hz, 3H). $^{13}$C NMR (126 MHz, Chloroform-d)) δ 167.10, 156.03, 153.33, 153.18, 145.63, 142.99, 139.21, 135.05, 130.01, 129.87, 128.14, 127.94, 127.45, 123.67, 120.65, 117.78, 110.07, 104.37, 79.36, 70.28, 70.16, 70.03, 54.39, 40.29, 39.71, 28.42, 23.61, 21.66, 11.13.

Step c: Preparation of tert-butyl (2-(2-(2-(4-((4-(1-propyl-1H-pyrazol-4-yl)-7H-pyrrolo[2,3-d]pyrimidin-2-yl)amino)benzamido)ethoxy)ethoxy)ethyl)carbamate. To tert-butyl (2-(2-(2-(4-((4-(1-propyl-1H-pyrazol-4-yl)-7-tosyl-7H-pyrrolo[2,3-d]pyrimidin-2-yl)amino)benzamido)ethoxy)ethoxy)ethyl)carbamate (0.038 g, 0.051 mmol) in methanol (1 mL) was added 2 M KOH (0.2 mL) and the reaction mixture was stirred at 80° C. for under a nitrogen atmosphere for 1 h, then was cooled to room temperature. The reaction mixture was diluted with dichloromethane (3 mL) and washed with water (3×3 mL). The organic phase was dried over sodium sulfate, filtered, and concentrated in vacuo. Purification using automated silica gel flash column chromatography (methanol/dichloromethane) was followed by evaporation, giving the title compound as a colorless oil (0.019 g, 63%). LC-MS (ESI) m/z: 594 [M+H]+. $^1$H NMR (500 MHz, Chloroform-d) δ 9.81 (s, 1H), 8.24 (s, 1H), 8.15 (s, 1H), 7.89-7.68 (m, 4H), 7.54 (s, 1H), 7.08 (dd, J=3.7, 2.1 Hz, 1H), 6.77 (s, 1H), 6.65 (dd, J=3.7, 1.8 Hz, 1H), 5.24 (d, J=6.4 Hz, 1H), 4.19 (t, J=7.1 Hz, 2H), 3.73-3.62 (m, 8H), 3.59 (t, J=5.2 Hz, 2H), 3.44 (d, J=5.1 Hz, 2H), 1.99 (dt, J=14.4, 7.2 Hz, 2H), 1.45 (s, 9H), 0.98 (t, J=7.4 Hz, 3H). $^{13}$C NMR (126 MHz, Chloroform-d) δ 167.20, 156.27, 155.45, 153.77, 152.03, 143.85, 139.32, 129.88, 127.97, 126.56, 122.80, 121.43, 117.45, 108.64, 100.79, 79.63, 70.29, 70.27, 70.11, 69.77, 54.29, 40.48, 39.53, 28.46, 23.66, 11.16.

Step d: Preparation of N-(2-(2-(2-aminoethoxy)ethoxy)ethyl)-4-((4-(1-propyl-1H-pyrazol-4-yl)-7H-pyrrolo[2,3-d]pyrimidin-2-yl)amino)benzamide. To tert-butyl (2-(2-(2-(4-((4-(1-propyl-1H-pyrazol-4-yl)-7H-pyrrolo[2,3-d]pyrimidin-2-yl)amino)benzamido)ethoxy)ethoxy)ethyl)carbamate (0.019 g, 0.032 mol) in dichloromethane (2 mL) at room temperature under a nitrogen atmosphere was added trifluoroacetic acid (0.12 mL, 1.6 mmol). The reaction mixture was stirred at room temperature under a nitrogen atmosphere for 4 h, then was concentrated in vacuo to obtain a yellow solid which was used without purification. LC-MS (ESI) m/z: 494 [M+H]+. $^1$H NMR (500 MHz, Methanol-d4) δ 8.75 (s, 1H), 8.41 (s, 1H), 7.94 (d, J=8.9 Hz, 2H), 7.88 (d, J=8.8 Hz, 2H), 7.42 (d, J=3.8 Hz, 1H), 6.97 (d, J=3.8 Hz, 1H), 4.29 (t, J=7.0 Hz, 2H), 3.72 (dtd, J=7.8, 3.9, 2.3 Hz, 8H), 3.62 (t, J=5.8 Hz, 2H), 3.11 (t, J=5.0 Hz, 2H), 2.00 (q, J=7.2 Hz, 2H), 0.99 (t, J=7.4 Hz, 3H). $^{13}C$ NMR (126 MHz, Methanol-d4) δ 168.39, 154.10, 150.34, 145.75, 142.20, 139.27, 132.27, 128.00, 127.86, 127.19, 118.58, 114.86, 107.80, 101.89, 70.02, 69.96, 69.33, 66.50, 53.93, 39.26, 23.09, 9.84.

Step e: Preparation of SJ000986339. A mixture of 2-(2,6-dioxopiperidin-3-yl)-4-fluoroisoindoline-1,3-dione (0.016 g, 0.058 mmol), N-(2-(2-(2-aminoethoxy)ethoxy)ethyl)-4-((4-(1-propyl-1H-pyrazol-4-yl)-7H-pyrrolo[2,3-d]pyrimidin-2-yl)amino)benzamide (0.019 g, 0.039 mmol), and DIPEA (0.027 mL, 0.15 mmol) in DMSO (1 mL) was stirred at 90° C. under a nitrogen atmosphere for 20 h. The reaction mixture was then cooled too room temperature, was diluted with ethyl acetate (5 mL), then washed sequentially with water (3 mL), brine (3 mL), and 5% LiCl solution (2 mL). The organic phase was dried over sodium sulfate, filtered, and concentrated in vacuo. Purification using automated silica gel flash column chromatography (methanol/ethyl acetate) was followed by a second flash column (methanol/dichloromethane) and evaporation, giving the title compound as a yellow solid (0.010, 33%). LC-MS (ESI) m/z: 750 [M+H]+. $^1H$ NMR (500 MHz, Methanol-d4) δ 8.36 (s, 1H), 8.17 (s, 1H), 7.74 (d, J=8.9 Hz, 2H), 7.66 (d, J=8.8 Hz, 2H), 7.31-7.23 (m, 1H), 7.09 (d, J=3.7 Hz, 1H), 6.85 (d, J=8.5 Hz, 1H), 6.80 (d, J=7.0 Hz, 1H), 6.65 (d, J=3.7 Hz, 1H), 4.88 (dd, J=12.8, 5.5 Hz, 1H), 4.14 (t, J=7.0 Hz, 2H), 3.65 (t, J=5.2 Hz, 2H), 3.60 (d, J=2.4 Hz, 6H), 3.49 (dd, J=6.6, 4.3 Hz, 2H), 3.37-3.30 (m, 2H), 2.76-2.63 (m, 1H), 2.73-2.47 (m, 2H), 1.94 (d, J=7.2 Hz, 1H), 1.87 (q, J=7.3 Hz, 2H), 0.87 (t, J=7.4 Hz, 3H). $^{13}C$ NMR (126 MHz, Methanol-d4) δ 173.23, 170.27, 169.31, 168.66, 167.84, 155.47, 153.76, 151.15, 146.66, 144.84, 138.84, 135.69, 132.33, 130.79, 127.70, 125.33, 123.31, 121.43, 116.77, 116.70, 110.61, 109.85, 108.34, 99.84, 70.13, 70.06, 69.28, 69.15, 53.51, 48.75, 41.81, 39.47, 30.77, 23.35, 22.38, 9.91.

p. Synthesis of SJ000986078

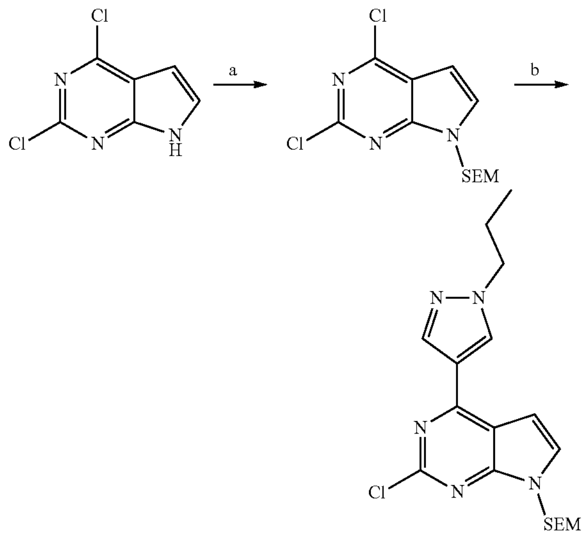

Reagents and conditions:
a) (2-(chloromethoxy)ethyl)trimethylsilane, NaH, DMF, 0° C., 2 h, 88%;
b) 1-propyl-4-(4,4,5,5-tetramethyl-1,3,2-dioxaborolan-2-yl)-1H-pyrazole, $Pd(PPh_3)_4$, $Na_2CO_3$, dioxane/water (3:1), 100° C., 2 h, 98%.

Step a: Preparation of 2,4-dichloro-7-((2-(trimethylsilyl)ethoxy)methyl)-7H-pyrrolo[2,3-d]pyrimidine. NaH (60% in oil, 0.213 g, 5.32 mmol) was added to a solution of 2,4-dichloro-7H-pyrrolo[2,3-d]pyrimidine (1 g, 5.32 mmol) in DMF (25 mL) stirring under N2 at 0° C. After 15 min (2-(chloromethoxy)ethyl)trimethylsilane (0.988 mL, 5.58 mmol) was added dropwise. After 2 h the reaction mixture was added to water (200 mL) and extracted with EtOAc (2×200 mL). The combined organic layers were washed with saturated brine, dried over anhydrous $Na_2SO_4$, filtered, and concentrated. The crude product was purified by flash column chromatography (Biotage Isolera, 50 g KP-Sil column, eluting with hexanes:EtOAc, 0-25% gradient) to give 2,4-dichloro-7-((2-(trimethylsilyl)ethoxy)methyl)-7H-pyrrolo[2,3-d]pyrimidine (1.46 g, 86% yield). $^1H$ NMR (500 MHz, Chloroform-d) δ 7.37 (d, J=3.7 Hz, 1H), 6.66 (d, J=3.7 Hz, 1H), 5.60 (s, 2H), 3.59-3.45 (m, 2H), 0.98-0.86 (m, 2H), −0.04 (s, 9H).

Step b: Preparation of 2-chloro-4-(1-propyl-1H-pyrazol-4-yl)-7-((2-(trimethylsilyl)ethoxy)methyl)-7H-pyrrolo[2,3-d]pyrimidine. To a 100 mL round-bottom flask was added 2,4-dichloro-7-((2-(trimethylsilyl)ethoxy)methyl)-7H-pyrrolo[2,3-d]pyrimidine (1 g, 3.14 mmol), 1-propyl-4-(4,4,5,5-tetramethyl-1,3,2-dioxaborolan-2-yl)-1H-pyrazole (0.779 g, 3.30 mmol), $Na_2CO_3$ (0.666 g, 6.28 mmol), dioxane (15 mL), and water (5 mL). The solution was degassed by sonication and then $Pd(PPh_3)_4$ (0.363 g, 0.314 mmol) was added. The reaction mixture was stirred under N2 and heated to 100° C. for 2 h, then added to water (100 mL) and extracted with EtOAc (2×100 mL). The combined organic layers were washed with saturated brine, dried over anhydrous $Na_2SO_4$, filtered, and concentrated. The crude product was purified by flash column chromatography (Biotage Isolera, 50 g KP-Sil column, eluting with hexanes: EtOAc, 0-60% gradient) to give 2-chloro-4-(1-propyl-1H-pyrazol-4-yl)-7-((2-(trimethylsilyl)ethoxy)methyl)-7H-pyrrolo[2,3-d]pyrimidine (1.21 g, 98% yield).

q. Synthesis of (2-(2,6-dioxopiperidin-3-yl)-1-oxoisoindolin-4-yl)glycine

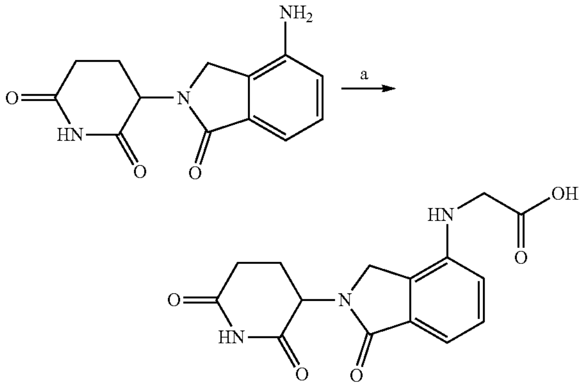

Reagents and conditions:
a) glyoxylic acid (40% in water), $NaCNBH_3$, $MeOH:H_2O$ (5:1), rt, O/N, 65%

Sodium cyanoborohydride (72.7 mg, 1.157 mmol) was added portionwise to a solution of lenalidomide (100 mg, 0.386 mmol), and glyoxylic acid (0.107 mL, 0.771 mmol), in MeOH (3 mL) and water (0.600 mL). The reaction mixture was stirred under N2 overnight and the precipitate was collected by filtration, which was used without further purification.

r. Synthesis of SJ000986078

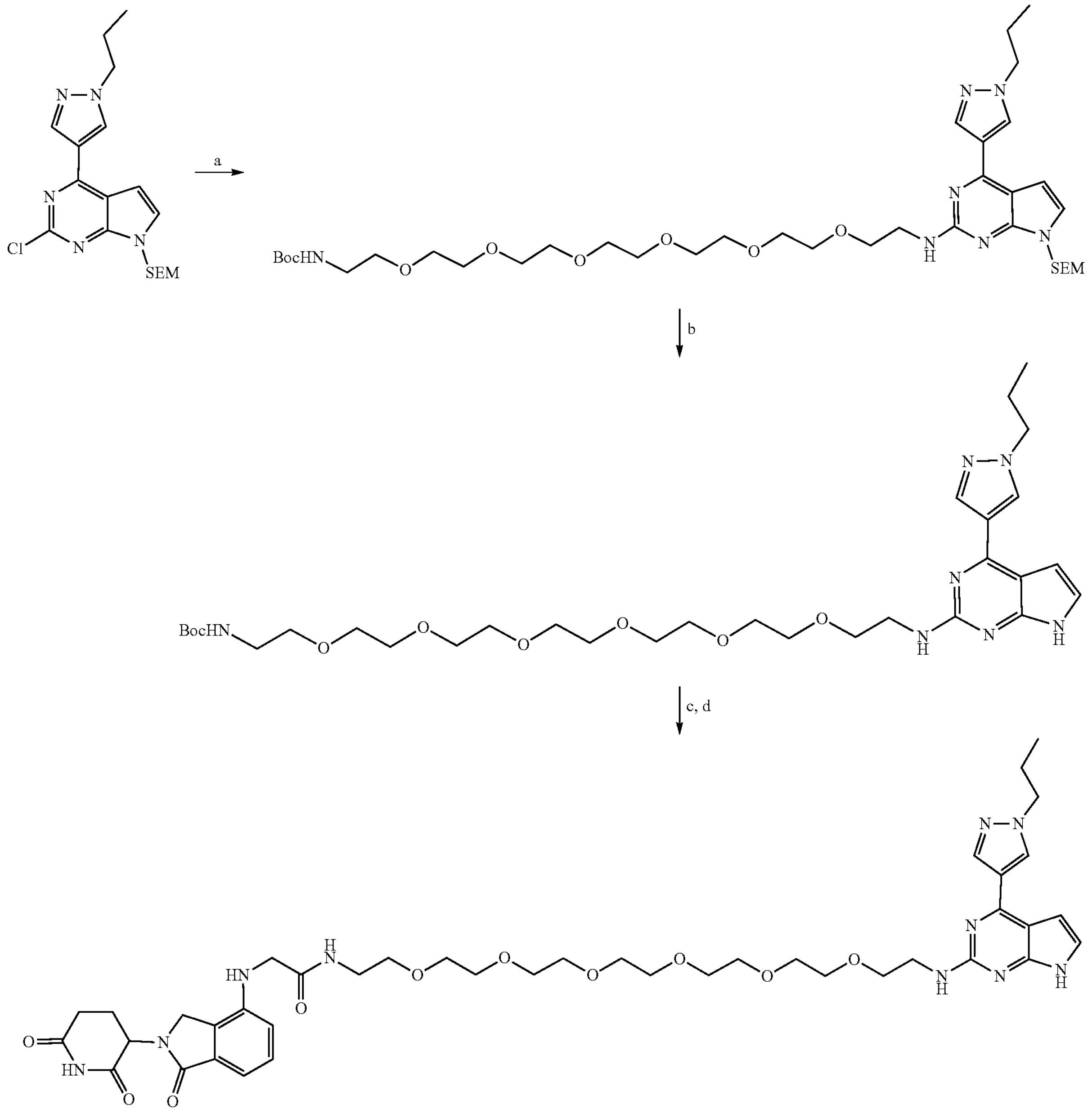

SJ000986078

Reagents and conditions:
a) tert-butyl (20-amino-3,6,9,12,15,18-hexaoxaicosyl)carbamate, Pd2(dba)3, XPhos,NaOtBu, tBuOH, 85° C., O/N, 51%;
b) TBAF, THF, 55° C., O/N, 40%;
c) DCM/TFA (1:1), rt, 1 h;
d) (2-(2,6-dioxopiperidin-3-yl)-1-oxoisoindolin-4-yl)glycine, HATU, DIPEA, DMF, rt, O/N, 30%.

Step a: Preparation of tert-butyl (20-((4-(1-propyl-1H-pyrazol-4-yl)-7-((2-(trimethylsilyl)ethoxy)methyl)-7H-pyrrolo[2,3-d]pyrimidin-2-yl)amino)-3,6,9,12,15,18-hexaoxaicosyl)carbamate. A solution of 2-chloro-4-(1-propyl-1H-pyrazol-4-yl)-7-((2-(trimethylsilyl)ethoxy)methyl)-7H-pyrrolo[2,3-d]pyrimidine (50 mg, 0.128 mmol), NaOtBu (42.9 mg, 0.446 mmol), tert-butyl (20-amino-3,6,9,12,15,18-hexaoxaicosyl)carbamate (81 mg, 0.191 mmol), and tBuOH (1.5 mL) was degassed by sonication and stirred under $N_2$. XPhos (12.2 mg, 0.026 mmol) and $Pd_2(dba)_3$ (11.7 mg, 0.013 mmol) were added to the reaction mixture and stirred overnight at 85° C. The reaction mixture was added to water (5 mL) and extracted with ethyl acetate (3×5 mL). The combined organic layers were washed with saturated brine, dried over anhydrous $Na_2SO_4$, filtered, and concentrated. The crude product was purified by flash column chromatography (Biotage Isolera, 28 g KP-NH amine column, eluting with hexanes: EtOAc, 0-85% gradient) to give tert-butyl (20-((4-(1-propyl-1H-pyrazol-4-yl)-7-((2-(trimethylsilypethoxy)methyl)-7H-pyrrolo[2,3-d]pyrimidin-2-yl)amino)-3,6,9,12,15,18-hexaoxaicosyl)carbamate (51 mg, 51% yield). $^1$H NMR (500 MHz, Chloroform-d) δ 8.15 (s, 1H), 8.09 (s, 1H), 6.98 (d, J=3.7 Hz, 1H), 6.57 (d, J=3.7 Hz, 1H), 5.48 (s, 2H), 5.33 (s, 1H), 5.09 (s, 1H), 4.15 (t, J=7.1 Hz, 2H), 3.75-3.57 (m, 24H), 3.57-3.47 (m, 4H), 3.30 (q, J=5.5 Hz, 2H), 1.95 (h, J=7.3 Hz, 2H), 1.43 (s, 9H), 0.96 (t, J=7.5 Hz, 3H), 0.94-0.88 (m, 2H), −0.06 (s, 9H).

Step b: Preparation of tert-butyl (20-((4-(1-propyl-1H-pyrazol-4-yl)-7H-pyrrolo[2,3-d]pyrimidin-2-yl)amino)-3,6,9,12,15,18-hexaoxaicosyl)carbamate. A solution of tert-butyl (20-((4-(1-propyl-1H-pyrazol-4-yl)-7-((2-(trimethylsilyl)ethoxy)methyl)-7H-pyrrolo[2,3-d]pyrimidin-2-yl)amino)-3,6,9,12,15,18-hexaoxaicosyl) carbamate (46 mg, 0.059 mmol) in TBAF (1 M in THF, 2 mL, 2.00 mmol) was stirred at 55° C. for 6 h under $N_2$. The reaction mixture was added to water (5 mL) and extracted with ethyl acetate (2×5 mL). The combined organic layers were washed with saturated brine, dried over anhydrous $Na_2SO_4$, filtered, and concentrated. The crude product was purified by flash column chromatography (Biotage Isolera, 11 g KP-NH amine column, eluting with DCM:MeOH, 0-5% gradient) to give tert-butyl (20-((4-(1-propyl-1H-pyrazol-4-yl)-7H-pyrrolo[2,3-d]pyrimidin-2-yl)amino)-3,6,9,12,15,18-hexaoxaicosyl)carbamate (15 mg, 39% yield). NMR MLAV-016-2 $^1$H NMR (500 MHz, Chloroform-d) δ 9.34 (s, 1H), 8.18 (s, 1H), 8.10 (s, 1H), 6.96 (dd, J=3.6, 2.0 Hz, 1H), 6.55 (dd, J=3.8, 1.7 Hz, 1H), 5.57 (s, 1H), 5.21 (s, 1H), 4.16 (t, J=7.1 Hz, 2H), 3.74-3.69 (m, 4H), 3.69-3.59 (m, 20H), 3.53 (t, J=5.1 Hz, 2H), 3.30 (t, J=5.4 Hz, 2H), 2.01-1.92 (m, 2H), 1.44 (s, 9H), 0.97 (t, J=7.3 Hz, 3H).

Step c: Preparation of 2-((2-(2,6-dioxopiperidin-3-yl)-1-oxoisoindolin-4-yl)amino)-N-(20-((4-(1-propyl-1H-pyrazol-4-yl)-7H-pyrrolo[2,3-d]pyrimidin-2-yl)amino)-3,6,9,12,15,18-hexaoxaicosyl)acetamide (SJ000986078). TFA (200 μL) was added to a solution of tert-butyl (20-((4-(1-propyl-1H-pyrazol-4-yl)-7H-pyrrolo[2,3-d]pyrimidin-2-yl)amino)-3,6,9,12,15,18-hexaoxaicosyl)carbamate (12.3 mg, 0.019 mmol) in DCM (200 μL) and stirred for 1 h at rt. The reaction mixture was concentrated and dried under high vacuum. A solution of 2-((2-(2,6-dioxopiperidin-3-yl)-1-oxoisoindolin-4-yl)amino)acetic acid (5 mg, 0.016 mmol), HATU (15 mg, 0.039 mmol), and DIPEA (13.8 μL, 0.079 mmol), in DMF (500 μL) and stir for 15 min. The reaction mixture was added to the residue from the TFA deprotection above and the solution stirred overnight. The reaction mixture was diluted with DMSO and purified by reverse phase preparative HPLC to give 2-((2-(2,6-dioxopiperidin-3-yl)-1-oxoisoindolin-4-yl)amino)-N-(20-((4-(1-propyl-1H-pyrazol-4-yl)-7H-pyrrolo[2,3-d]pyrimidin-2-yl)amino)-3,6,9,12,15,18-hexaoxaicosyl)acetamide (4.1 mg, 30.6% yield). $^1$H NMR (500 MHz, Chloroform-d) δ 10.19 (s, 1H), 8.17 (s, 1H), 8.13 (s, 1H), 7.47-7.38 (m, 1H), 7.31 (t, J=7.7 Hz, 1H), 6.96 (dd, J=3.6, 1.8 Hz, 1H), 6.67 (d, J=7.8 Hz, 1H), 6.56 (s, 1H), 6.51 (dd, J=3.7, 1.7 Hz, 1H), 5.26-5.12 (m, 2H), 4.45-4.34 (m, 2H), 4.16 (t, J=7.1 Hz, 2H), 3.93 (s, 2H), 3.77-3.68 (m, 2H), 3.67-3.30 (m, 16H), 2.98-2.80 (m, 2H), 2.50-2.38 (m, 1H), 2.24-2.16 (m, 1H), 1.96 (q, J=7.3 Hz, 2H), 0.97 (t, J=7.4 Hz, 3H). $^{13}$C NMR (126 MHz, Chloroform-d) δ 171.94, 171.32, 170.26, 154.76, 142.57, 139.48, 132.30, 130.11, 129.67, 127.43, 113.24, 112.99, 107.30, 100.56, 70.46, 70.44, 70.21, 70.14, 70.08, 70.04, 70.01, 69.99, 69.94, 69.93, 69.84, 69.82, 54.41, 53.57, 51.96, 47.68, 45.44, 41.66, 41.64, 39.44, 31.96, 29.84, 23.80, 23.50, 14.35, 11.29.

s. Synthesis of SJ000986079

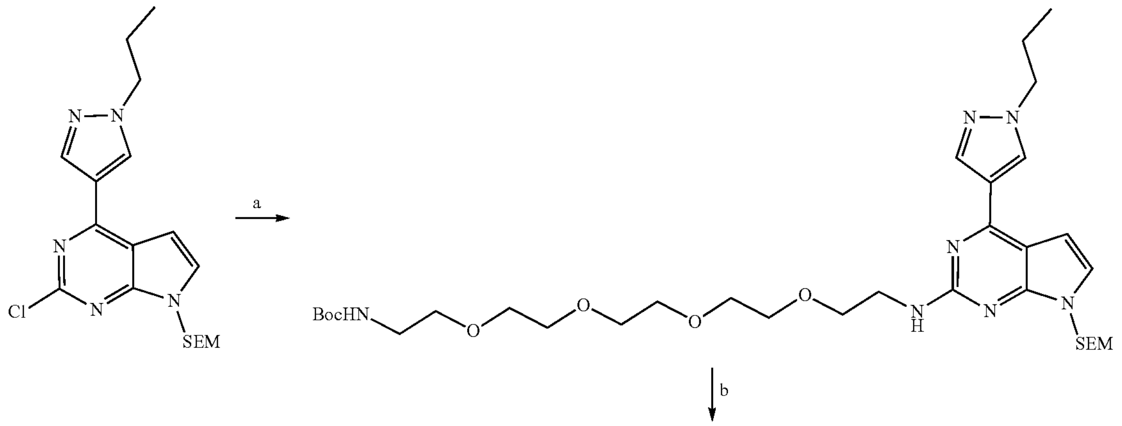

-continued

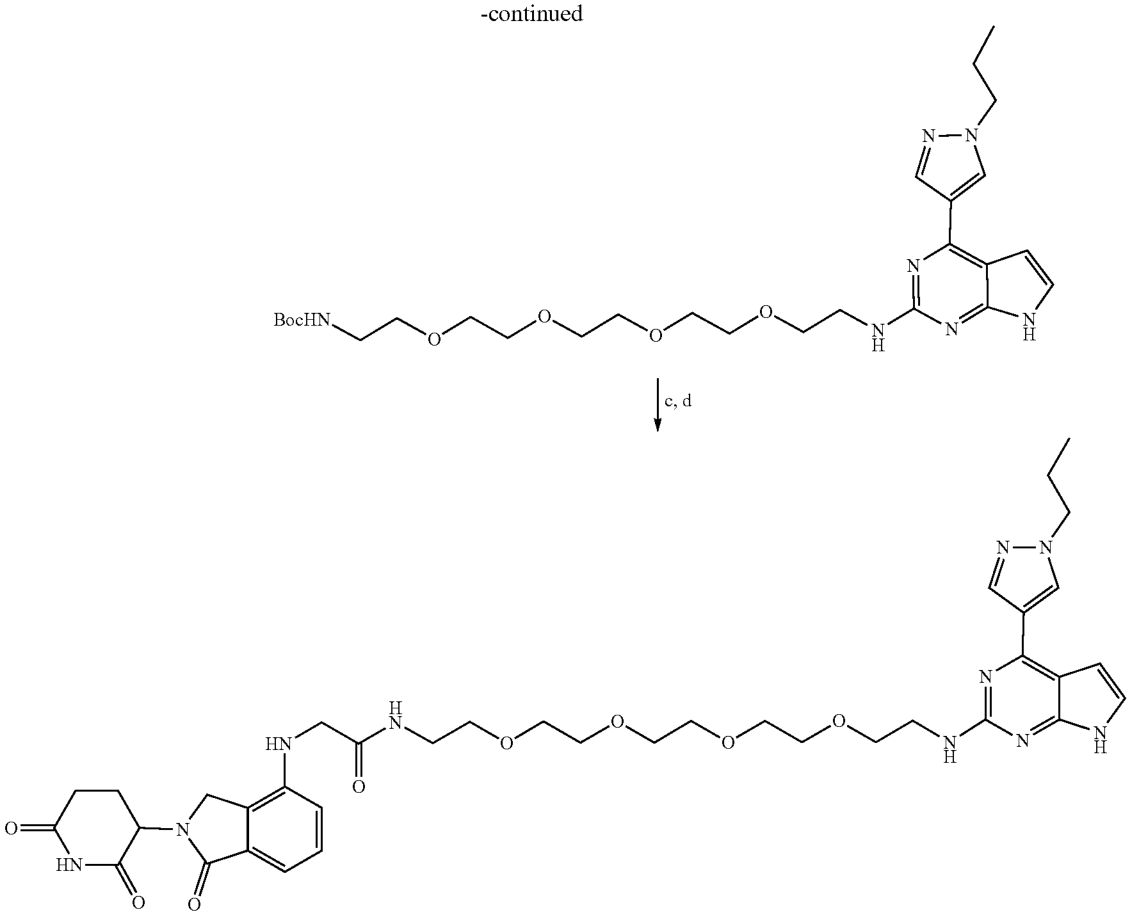

SJ000986079

Reagents and conditions:
a) tert-butyl (14-amino-3,6,9,12-tetraoxatetradecyl)carbamate, $Pd_2(dba)_3$, XPhos, NaOtBu, tBuOH, 85° C., O/N, 56%;
b) TBAF, THF, 55° C., O/N, 37%;
c) DCM/TFA (1:1), rt, 1 h;
d) (2-(2,6-dioxopiperidin-3-yl)-1-oxoisoindolin-4-yl)glycine, HATU, DIPEA, DMF, rt, O/N, 48%.

Step a: Preparation of tert-butyl (14-((4-(1-propyl-1H-pyrazol-4-yl)-7-((2-(trimethylsilyl)ethoxy)methyl)-7H-pyrrolo[2,3-d]pyrimidin-2-yl)amino)-3,6,9,12-tetraoxatetradecyl)carbamate. A solution of 2-chloro-4-(1-propyl-1H-pyrazol-4-yl)-7-((2-(trimethylsilyl)ethoxy)methyl)-7H-pyrrolo[2,3-d]pyrimidine (50 mg, 0.128 mmol), NaOtBu (42.9 mg, 0.446 mmol), tert-butyl (14-amino-3,6,9,12-tetraoxatetradecyl)carbamate (81 mg, 0.241 mmol), and tBuOH (1.5 mL) was degassed by sonication and stirred under N2. XPhos (12.2 mg, 0.026 mmol) and $Pd_2(dba)_3$ (11.7 mg, 0.013 mmol) were added to the reaction mixture and stirred overnight at 85° C. The reaction mixture was added to water (5 mL) and extracted with EtOAc (3x5 mL). The combined organic layers were washed with saturated brine, dried over anhydrous $Na_2SO_4$, filtered, and concentrated. The crude product was purified by flash column chromatography (Biotage Isolera, 28 g KP-NH amine column, eluting with hexanes:EtOAc, 0-65% gradient) to give tert-butyl (14-((4-(1-propyl-1H-pyrazol-4-yl)-7-((2-(trimethylsilyl)ethoxy)methyl)-7H-pyrrolo[2,3-d]pyrimidin-2-yl)amino)-3,6,9,12-tetraoxatetradecyl)carbamate (49 mg, 56% yield). $^1$H NMR (500 MHz, Chloroform-d) δ 8.16 (s, 1H), 8.08 (s, 1H), 6.98 (d, J=3.7 Hz, 1H), 6.57 (d, J=3.7 Hz, 1H), 5.49 (s, 2H), 5.36 (s, 1H), 5.12 (s, 1H), 4.15 (t, J=7.1 Hz, 2H), 3.74-3.58 (m, 16H), 3.57-3.49 (m, 4H), 3.30 (q, J=5.4 Hz, 2H), 1.95 (h, J=7.3 Hz, 2H), 1.43 (s, 9H), 0.96 (t, J=7.4 Hz, 3H), 0.92 (dd, J=8.8, 7.6 Hz, 2H), −0.06 (s, 9H).

Step b: Preparation of tert-butyl (14-((4-(1-propyl-1H-pyrazol-4-yl)-7H-pyrrolo[2,3-d]pyrimidin-2-yl)amino)-3,6,9,12-tetraoxatetradecyl)carbamate. A solution of tert-butyl (14-((4-(1-propyl-1H-pyrazol-4-yl)-7-((2-(trimethylsilyl)ethoxy)methyl)-7H-pyrrolo[2,3-d]pyrimidin-2-yl)amino)-3,6,9,12-tetraoxatetradecyl)carbamate (43 mg, 0.062 mmol) in TBAF (1 M in THF, 2.00 mL, 2.00 mmol) was stirred at 55° C. overnight. The reaction mixture was added to water (5 mL) and extracted with ethyl acetate (2x5 mL). The combined organic layers were washed with saturated brine, dried over anhydrous $Na_2SO_4$, filtered, and concentrated. The crude product was purified by flash column chromatography (Biotage Isolera, 11 g KP-NH amine column, eluting with DCM:MeOH, 0-5% gradient) to give tert-butyl (14-((4-(1-propyl-1H-pyrazol-4-yl)-7H-pyrrolo[2,3-d]pyrimidin-2-yl)amino)-3,6,9,12-tetraoxatetradecyl)carbamate (13 mg, 37% yield). $^1$H NMR (500 MHz, Chloroform-d) δ 9.33 (s, 1H), 8.18 (s, 1H), 8.10 (s, 1H), 6.96 (dd, J=3.7, 2.1 Hz, 1H), 6.55 (dd, J=3.7, 1.8 Hz, 1H), 5.61 (s, 1H), 5.30 (s, 1H), 4.16 (t, J=7.1 Hz, 2H), 3.72 (t, J=5.0 Hz, 4H), 3.69-3.58 (m, 12H), 3.54 (t, J=5.1 Hz, 2H), 3.32 (q, J=5.6 Hz, 2H), 1.96 (h, J=7.3 Hz, 2H), 1.43 (s, 9H), 0.97 (t, J=7.4 Hz, 3H).

Step c: Preparation of 2-((2-(2,6-dioxopiperidin-3-yl)-1-oxoisoindolin-4-yl)amino)-N-(14-((4-(1-propyl-1H-pyrazol-4-yl)-7H-pyrrolo[2,3-d]pyrimidin-2-yl)amino)-3,6,9,12-tetraoxatetradecyl)acetamide (SJ000986079). TFA (250 μL) was added to a solution of tert-butyl (14-((4-(1-propyl-1H-pyrazol-4-yl)-7H-pyrrolo[2,3-d]pyrimidin-2-yl)amino)-3,6,9,12-tetraoxatetradecyl)carbamate (13 mg, 0.023 mmol) in DCM (250 μL) and stirred for 1 h. The reaction mixture was concentrated and dried under high vacuum. A solution of 2-((2-(2,6-dioxopiperidin-3-yl)-1-oxoisoindolin-4-yl) amino)acetic acid (8.8 mg, 0.028 mmol), HATU (17.6 mg, 0.046 mmol), and DIPEA (20.2 μL, 0.116 mmol), in DMF (500 μL) was stirred for 15 min. The reaction mixture was added to the residue from the TFA deprotection above and the solution stirred overnight. The reaction mixture was purified by reverse phase preparative HPLC to give 2-((2-(2,6-dioxopiperidin-3-yl)-1-oxoisoindolin-4-yl)amino)-N-(14-((4-(1-propyl-1H-pyrazol-4-yl)-7H-pyrrolo[2,3-d]pyrimidin-2-yl)amino)-3,6,9,12-tetraoxatetradecyl)acetamide (8.5 mg, 48% yield). $^1$H NMR (500 MHz, Methanol-d4) δ 8.38 (s, 1H), 8.18 (s, 1H), 7.30 (t, J=7.7 Hz, 1H), 7.12 (d, J=7.5 Hz, 1H), 7.05 (d, J=3.8 Hz, 1H), 6.64 (dd, J=8.5, 5.9 Hz, 2H), 5.12 (dd, J=13.4, 5.2 Hz, 1H), 4.31 (s, 2H), 4.19 (t, J=7.0 Hz, 2H), 3.88 (s, 2H), 3.78-3.43 (m, 18H), 3.38 (t, J=5.4 Hz, 2H), 2.93-2.82 (m, 1H), 2.81-2.70 (m, 1H), 2.46-2.34 (m, 1H), 2.15-2.09 (m, 1H), 1.93 (h, J=7.2 Hz, 2H), 0.93 (t, J=7.4 Hz, 3H). $^{13}$C NMR (126 MHz, Methanol-d4) δ 174.72, 173.41, 172.19, 172.12, 159.42, 155.99, 151.56, 144.13, 140.07, 133.17, 132.30, 130.67, 128.70, 124.20, 113.95, 113.31, 108.30, 101.56, 71.57, 71.49, 71.43, 71.35, 71.17, 71.02, 70.59, 54.93, 53.59, 53.54, 48.05, 47.20, 42.41, 40.41, 40.30, 32.35, 24.69, 24.23, 11.30.

t. Synthesis of SJ001005328 (5)

Synthesis of the ester intermediate 15 was carried out by adapting a previously reported Suzuki-Miyaura coupling procedure followed by a modified Buchwald-Hartwig coupling reaction to install the pyrazole and amino benzoate moieties (Yao, et al. (2017) *J Med Chem.* 60(20): 8336-8357; Yao, et al. (2018) *Bioorg Med Chem Lett.* 28(8): 1357-1362; Yao, et al. (2018) *Bioorg Med Chem Lett.* 28(15): 2636-2640). Base hydrolysis of 15 provided 16, which was then coupled to 11 using an adapted amide coupling procedure[4] to provide 5.

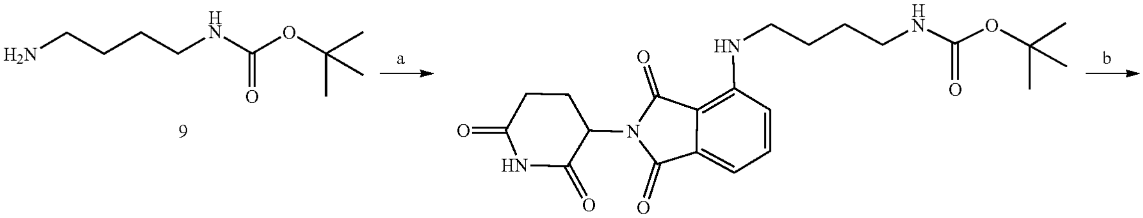

9

10

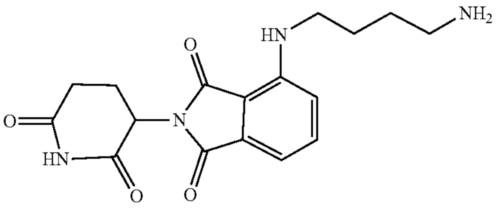

11

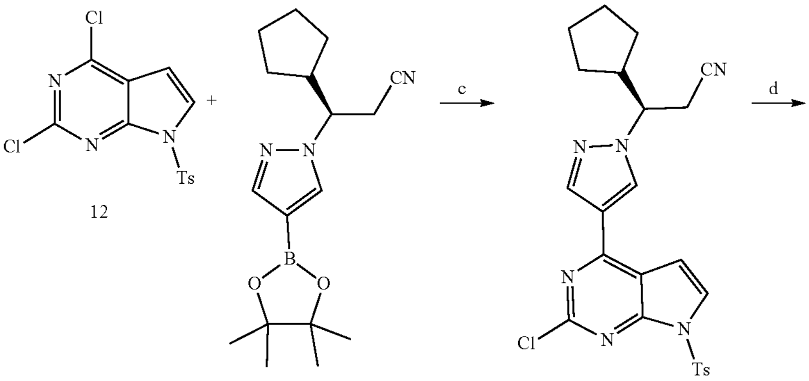

12

13

14

-continued

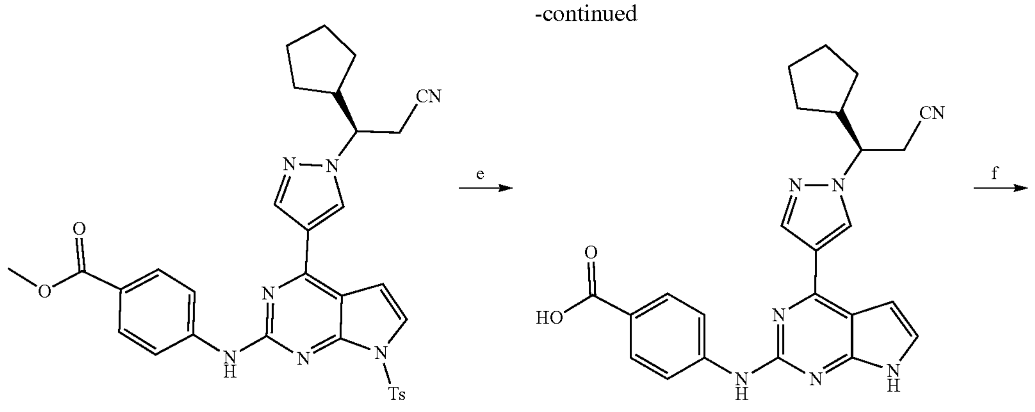

15

16

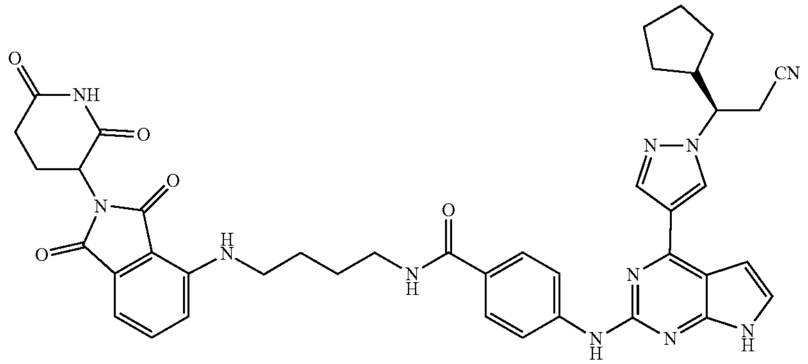

5

Synthesis of compound 5. Reagents and conditions: (a) 2-(2,6-dioxopiperidin-3-yl)-4-fluoroisoindoline-1,3-dione, N,N-diisopropylethylamine, dimethyl sulfoxide, 90° C., 16 h; (b) trifluoracetic acid, $CH_2Cl_2$, room temperature, 3 h; (c) $Pd(PPh_3)_4$, $Na_2CO_3$, dioxane:water (3:1), 100° C., 1 h, 78%; (d) methyl 4-aminobenzoate, $Pd_2(dba)_3$, XPhos, $K_2CO_3$, tBuOH, 100° C., 90 min, 90%; (e) KOH, MeOH:water (2.5:1), 75° C., 1 h, 88%; (f) 11, TCFH, 1-methylimidazole, MeCN, rt, 1 h, 35%.

u. Synthesis of SJ001005354 (6)

Synthesis of the ester intermediate 19 was carried out by adapting a previously reported Suzuki-Miyaura coupling procedure followed by a modified Buchwald-Hartwig coupling reaction to install the pyrazole and amino benzoate moieties (Yao, et al. (2017) *J Med Chem.* 60(20): 8336-8357; Yao, et al. (2018) *Bioorg Med Chem Lett.* 28(8): 1357-1362; Yao, et al. (2018) *Bioorg Med Chem Lett.*

28(15): 2636-2640). Treating 19 briefly with base provided 3, which was then treated with acid to provide carboxylic acid 20. Typical amide coupling conditions between 11 and 20 provided target compound 6.
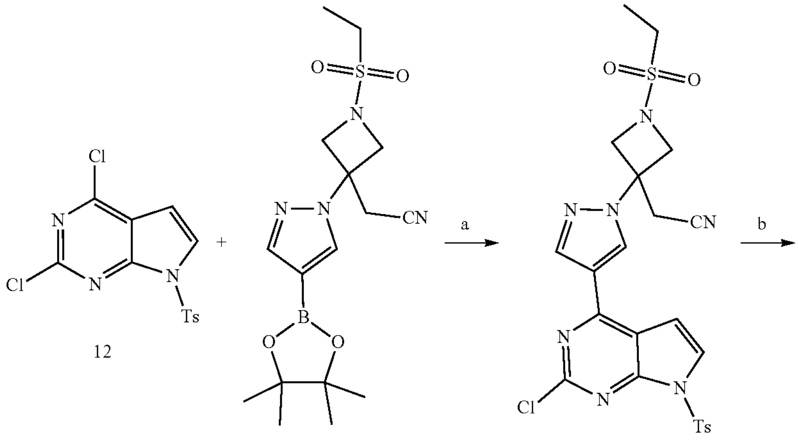
12 17 18
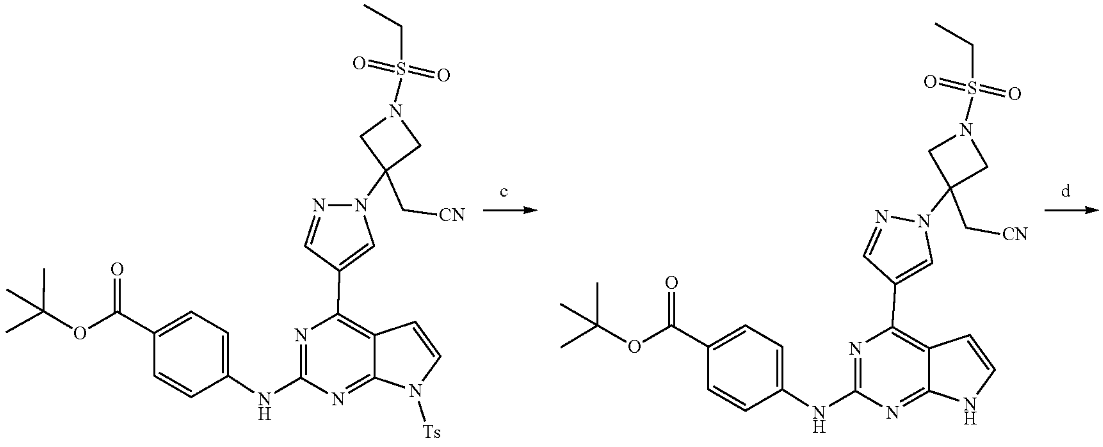
19 3
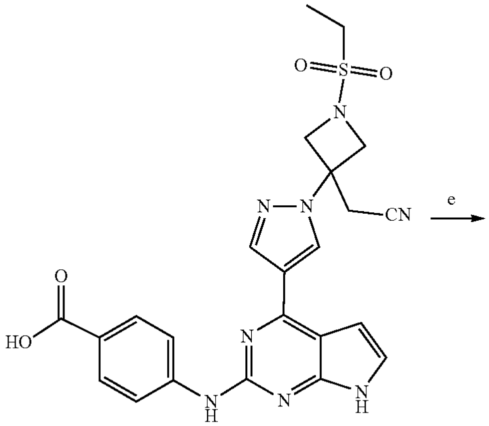
20

-continued

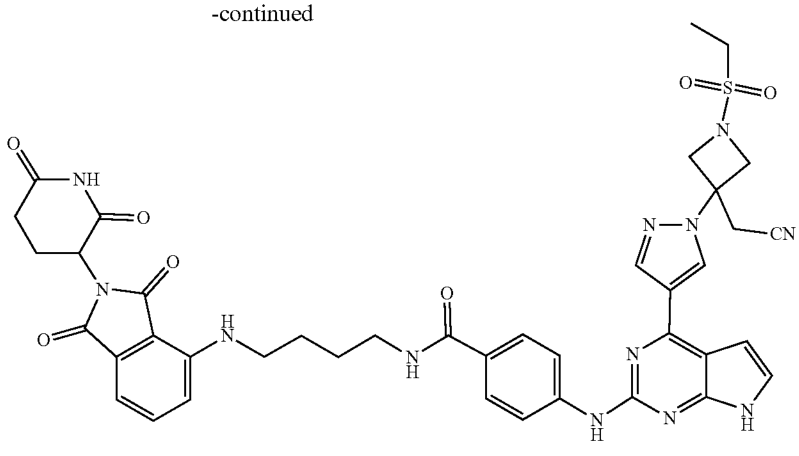

6

Synthesis of compound 6. Reagents and conditions: (a) $Pd(PPh_3)_4$, $Na_2CO_3$, dioxane:water (3:1), 100° C., 1 h, 83%; (b) tert-butyl 4-aminobenzoate, $Pd_2(dba)_3$, XPhos, $K_2CO_3$, tBuOH, 100° C., 2 h, 84%; (c) KOH, MeOH:water (2.5:1), 60° C., 5 min, 66%; (d) DCM:TFA (1:1), rt, 1 h; (e) 11, HATU, DIPEA, DMF, rt, 16 h, 20%.

v. Synthesis of SJ001008030 (8)

Intermediate 27 was prepared by nucleophilic aromatic substitution of 25 with 26. Subsequent amine deprotection was followed by amide coupling of 28 with carboxylic acid 20 to provide 8.

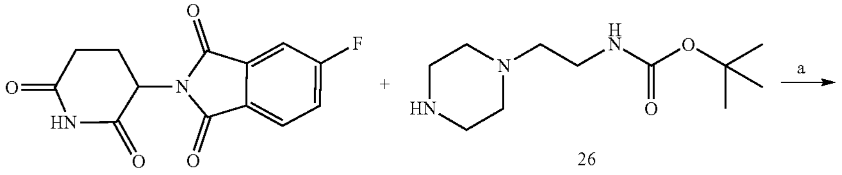

25

26

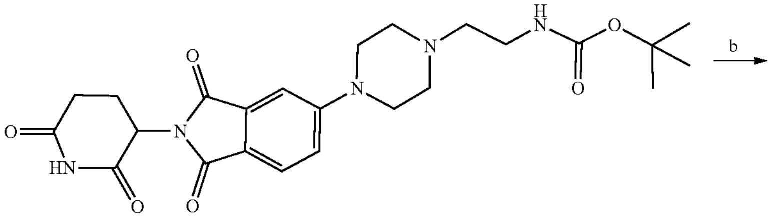

27

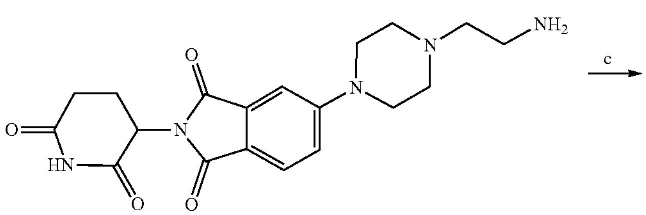

28

-continued

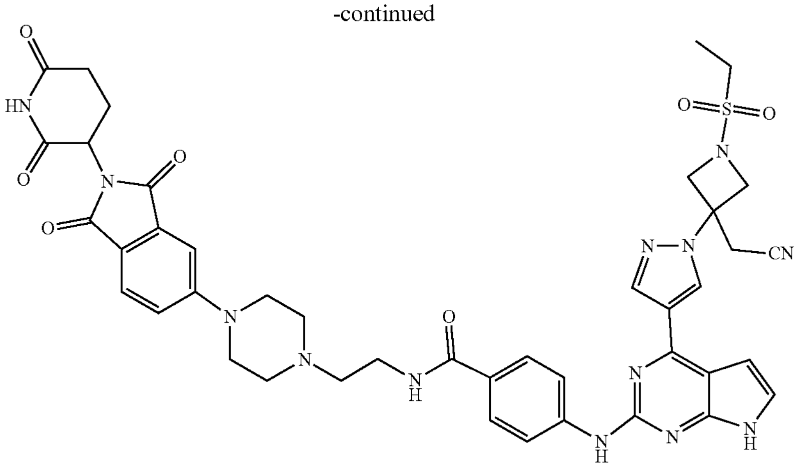

8

Synthesis of compound 8. Reagents and conditions: (a) N,N-diisopropylethylamine, NMP, 90° C., 16 h, 36%; (b) trifluoracetic acid, $CH_2Cl_2$, room temperature, 3 h; (c) carboxylic acid 20, EDC HCl, DMAP, N,N-diisopropylethylamine, DMF, room temperature, 16 h, 17%.

3. Protein Purification and Crystallization

Human JAK2 kinase JH1 domain (residues 835-1132, Uniprot ID 060674) was cloned into pFastBac, fused to a C-terminal His 10× tag cleavable by tobacco etch virus (TEV) protease. Recombinant bacmid DNA containing the JAK2 insert was isolated and transfected to Spodoptera frugiperda (Sf9) insect cells to generate Baculovirus incorporated with the kinase insert. Baculovirus were amplified for two to three rounds to achieve a high titer ($2\times10^8$ pfu/ml) before being used to infect BTI-Tn-5B1-4 (High Five) insect cells for protein expression. High Five insect cells were cultured in suspension to a density of $2\times10^6$ cells per milliliter and infected at a multiplicity of infection (MOI) greater than 10 to obtain a maximum protein yield. Infected High Five cells were incubated at 27° C. for 24 hours and then at 20° C. for 48 hours before harvest.

Harvested insect cell pellets were resuspended into a buffer consisting of 20 mM Tris-Cl pH 8.5, 250 mM NaCl, 0.5% Thesit, 5% glycerol, and 1 mM TECP supplemented with complete protease inhibitors cocktail (Roche), lysed by sonication, and centrifuged at 45,000g for 1 hour. The supernatant was filtered and loaded onto a Ni sepharose column (HisTrap HP, GE healthcare life sciences), and purified through nickel affinity chromatography. After extensive washes with 20 mM Imidazole supplemented suspension buffer, the His tagged protein was eluted with a linear gradient of Imidazole to 500 mM. Fractions containing JAK2 fusion protein were pooled and concentrated to 5-10 mg/ml.

The concentrated Ni column elutions were incubated with TEV protease overnight at 4° C. while being dialyzed into a buffer of 20 mM Tris-Cl pH8.5, 0.25 M NaCl, 20% Glycerol, 1 mM TCEP, using 10,000 MWCO Slide-A-Lyzer dialysis cassettes (Thermo Scientific). The dialyzed sample was then diluted 10-fold in a buffer of 20 mM Tris-Cl pH 8.5, 20% Glycerol, 1 mM TCEP, before being applied to a Mono Q HR 16/60 column pre-equilibrated in 20 mM Tris-Cl pH 8.5, 25 mM NaCl, 20% Glycerol, 1 mM TCEP. Protein was eluted in a linear gradient to 500 mM NaCl. For size exclusion chromatography, Mono Q elution pool was concentrated and loaded onto Superdex 75 HiLoad 16/60 column (GE healthcare life sciences) equilibrated in 20 mM Tris-Cl pH 8, 250 mM NaCl, and 1 mM TCEP.

Crystals were grown at 18° C. using the hanging drop vapor-diffusion method. The purified JAK2 kinase domain was mixed with 2 mM of the respective ligand at a concentration of 10 mg/ml and incubated at room temperature for 30 minutes, before being mixed with an equal volume of a reservoir solution. Protein-ligand complexes were co-crystalized in the three following crystallization conditions: a) 1.6-2.4 M sodium malonate, pH 5; b) 0.1 M Sodium Citrate pH 5-6.5, 21-33% polyethylene glycol 4000, 0.2 M ammonium sulfate; c) 0.1 M Sodium Citrate pH 5-6.5, 18-27% polyethylene glycol 8000, 0.2 M ammonium acetate. Crystals of all three conditions formed after 3 to 7 days.

4. X-Ray Data Collection, Structure Determination, and Refinement

Crystals were flash frozen prior to data collection using 35% glycerol or 35% ethylene glycol as cryoprotectants, supplemented in the crystallization mother liquid. Datasets of 1.5-2.5 Å resolution collected at SER-CAT beamline 22-ID (Advanced Photon Source) were merged and processed with xia2 (Winter, G. (2010) *Journal of Applied Crystallography* 43(1): 186-190) in the CCP4 suite (Winn, et al. (2011) *Acta Crystallographica Section D* 67(4): 235-242). Structures were determined by the molecular replacement method using the program Phaser MR (McCoy, et al. (2007) *Journal of Applied Crystallography* 40(4): 658-674), using JAK2 kinase JH1 domain structure 5USY (Puleo, et al. (2017) *ACS Med Chem Lett.* 8(6): 618-621) as the search model. Subsequent runs of manual fitting and crystallographic refinement were performed in Coot (Emsley, et al. (2010) *Acta Crystallogr D Biol Crystallogr.* 66(Pt 4): 486-501), and Phenix (Liebschner, et al. (2019) *Acta Crystallogr D Struct Biol.* 75(Pt 10): 861-877). RMSDs were calculated via SSM superposition in Coot (Emsley, et al. (2010) *Acta Crystallogr D Biol Crystallogr.* 66(Pt 4): 486-501); Polder OMIT maps were calculated within Phenix (Liebschner, et al. (2017) *Acta Crystallographica Section D* 73(2): 148-157). Images were made with PyMOL [The PyMOL Molecular Graphics System, Version 2.0 Schrödinger, LLC.]. Interaction analysis is represented as a LigPlot+ diagram (Laskowski, et al. (2011) *J Chem Inf Model.* 51(10): 2778-2786). Complexes were deposited to the Protein Data Bank as 6WTN (Ruxolitinib), 6WTO (Baricitinib), 6WTP (compound 3), and 6WTQ (compound 4).

5. CRISPR-Cas9 Editing for CRBN Knockdown Cells

CRBN-deficient MHH-CALL-4 cell pools were generated using CRISPR-Cas9 technology. Briefly, 400,000 MHH-CALL-4 cells were transiently co-transfected with precomplexed ribonuclear proteins (RNPs) consisting of 100 pmol of chemically modified sgRNA (5'-UGUAUGUGAUGUCGGCAGAC-3' (SEQ ID NO:1), Synthego) and 35 pmol of Cas9 protein (St. Jude Protein Production Core) via nucleofection (Lonza, 4D-Nucleofector™ X-unit) using solution P3 and program DS-150 in small (20 μl) cuvettes according to the manufacturer's recommended protocol. Five days post nucleofection, a portion of cells were harvested and verified for the desired modification via targeted deep sequencing using gene specific primers with partial Illumina adapter overhangs (hCRBN.F-5'-gcagagagtgaggaagaagatga-3' (SEQ ID NO:2) and hCRBN.R-5'-gcccatgtcctcatccacaa-3', (SEQ ID NO:3) overhangs not shown) and analyzed using CRIS.py (Connelly, et al. (2019) Sci Rep. 9(1): 4194). Sequencing analysis indicated 86% total indels and 60% out-of-frame indels for the MHH-CALL-4 edited cell pool.

6. Caco-2 Cell Permeability

Compound Caco-2 cell permeability was determined using the Transwell® 0.4 μm polycarbonate membrane 96-well as described before (Uchida, et al. (2009) *J Pharmacol Toxicol Methods* 59(1): 39-43). Briefly, Caco-2 cells monolayers were incubated over 2 hours at 37° C. Fractions were collected from receivers (basal side, B), and concentrations were assessed by UPLC/MS (Waters; Milford, MA). All compounds were tested in triplicates. The A→B (or B→A) apparent permeability coefficients (Papp) of each compound were calculated using the equation, Papp=dQ/dt×1/AC0, where dQ/dt equals the flux of a drug across the monolayer, A equals the total insert well surface area, and C0 is the initial concentration of substrate in the donor compartment.

7. In Vivo Pharmacokinetic (PK) Studies

Nontumor bearing female NSG mice (n=6), aged 8-12 weeks were dosed i.p. with single dose of compound 7 at 30 mg/kg and 100 mg/kg, respectively. Compound 7 was suspended in 60% PEG400+10% DMSO+10% DPBS and the dosing volume is 5 ml/kg to get the target dose. For each dose, three mice were injected with a single dose and blood samples were collected at 0.5, 1, 2, 4, 8 and 24 hours by retro-orbital eye bleed technique. Blood samples (~0 μL) were collected and compound 7 concentration levels determined by LC-MS.

8. KINOMEscan™ Profiling and Kd Measurement

The relative selectivity of compound 7 for Janus kinases was evaluated by KINOMEscan screening of 468 kinases at an assay concentration of 0.1 μM (Eurofins DiscoveRx, San Diego, CA) (Davis, et al. (2011) *Nat Biotechnol.* 29(11): 1046-1051). TREEspot™ Kinase Dendrogram Images generated using TREEspot™ Software Tool and reprinted with permission from KINOMEscan®, a division of DiscoveRx Corporation©. KdELECT experiments utilize the same platform that is employed for the scanMAX service with 11 dose concentration points in duplicate up to 3.0 μM.

9. Cell Lines and Xenografts

The CRLF2r cell lines MHH-CALL-4 (Russell, et al. (2009) *Blood.* 114(13): 2688-2698; Mullighan, et al. (2009) *Nat Genet.* 41(11): 1243-1246; Tomeczkowski, et al. (1995) *Br J Haematol.* 89(4): 771-779) (JAK2 I682F) and KOPN49 (Tomoyasu, et al. (2018) *Int J Hematol.* 108(3): 312-318) (JAK2 R683G), the DUX4-rearranged cell line NALM-6 (Hurwitz, et al. (1979) *Int J Cancer.* 23(2): 174-180; Yasuda, et al. (2016) *Nat Genet.* 48(5): 569-574), the hypodiploid cell line MHH-CALL-2 (34), the PAX5-ETV6 cell line KOPN75 (Tomoyasu, et al. (2018) *Int J Hematol.* 108(3): 312-318), and the TCF3-PBX1 cell line 697 (Findley, et al. (1982) *Blood.* 60(6): 1305-1309) were confirmed as *Mycoplasma* spp. free using the Universal Mycoplasma Detection Kit (American Type Culture Collection, Manassas, VA). Cell lines were maintained in RPMI1640 medium supplemented with 10% FBS (Hyclone), Penicillin/Streptomycin (100 units/mL) and Glutamine (100 μM), Cell identity was checked by STR profiling using PowerPlex® Fusion System (Promega) and confirmed using the ATCC or DSMZ STR databases. Cell lines were subject to whole genome and transcriptome sequencing as previously described (Alexander, et al. (2018) *Nature* 562(7727): 373-379). Human CD34+ cells were purified from cord blood using CD34 MicroBeads (Miltenyi Biotech) and expanded (Boitano, et al. (2010) *Science* 329(5997): 1345-1348). The IGH-CRLF2, JAK2 wild type xenograft SJBALL047370 was used for in vivo preclinical studies and overexpression of CRLF2 was confirmed by flow cytometry using CRLF2-PE antibodies (#1205499-42, eBioscience).

10. Immunoblot Analysis

Cells were washed twice with ice-cold PBS and lysed in RIPA lysis buffer (Sigma) freshly supplemented with Halt™ Protease Inhibitor Cocktail (ThermoFisher) for 15 minutes on ice. The cell pellet was removed by centrifugation at 13,000 g at 4° C. for 15 minutes. Protein concentration was measured by BCA assay (Thermo Fisher Scientific). Proteins were denatured in NuPAGE LDS 4× sample buffer supplemented with reducing agents (Invitrogen). Typically, 10-20 μg of total protein was loaded per lane on a 4%-12% NuPAGE Bis-Tris gradient gel (Invitrogen) and analyzed by standard immunoblotting and imaged using Li-COR Odyssey CLx (LI-COR Biotechnology, Lincoln, NE). Primary antibodies used were: JAK1 (Cell Signaling #3332S), JAK2 (#3230S), JAK3 (#8827S), TYK2 (#9312S), GSPT1 (#14980S), CRBN (#71810S), IKZF1 (Santa Cruz Biotechnology, SC-398265) and ACBT (Santa Cruz Biotechnology, SC-47778).

11. Cytotoxicity Assay

2×105 cells were seeded in 100 μl/well in 96 well assay plates (Corning). Assays were performed in triplicate; compounds to be screened were added to assay plates from DMSO stock solutions by pin transfer using 50SS pins (V&P Scientific). The assay plates incubated at 37° C. in 5% CO2 for 72 hours. Cells were then incubated for four hours with resazurin (Sigma) solution and read on a Synergy HT plate reader (Biotek, Winooski, VT). High-throughput assay data was analyzed using our in-house Robust Interpretation of Screening Experiments (RISE) application written in Pipeline Pilot (Biovia, v. 17.2.0) and the R program (R Core Team, 2013). Selected data were plotted and analyzed by GraphPad Prism software v7 using non-linear regression curve fitting.

12. Xenograft and In Vivo Preclinical Studies

Female NOD.Cg-Prkdcscid Il2rgtm1Wjl/SzJ (NSG) mice aged 8-12 weeks were used for xenotransplantation. All experimental work was carried out according to Office of Laboratory Animal Welfare guidelines and was approved by Institutional Animal Care and Use Committee of St. Jude Children's Research Hospital. Mice aged 8-12 weeks were inoculated by tail vein injection with 1×106 leukemic cells transduced with a lentiviral vector containing the firefly luciferase and yellow fluorescent protein genes (CL20SF2-Luc2aYFP) (Sprowl, et al. (2013) *Clin Pharmacol Ther.* 94(5): 585-592). Leukemia burden was determined by weekly bioluminescence imaging using the Xenogen IVIS-200 system and Living Image software (Caliper Life Sciences). Treatment was commenced when luminescence averaged approximately 1×108 photons/second. Mice were dosed with compound 7 at 30 mg/kg i.p. daily. Ruxolitinib was delivered by oral gavage at 50 mg/kg twice daily (Bhagwat, et al. (2014) *Blood.* 123(13): 2075-2083). At the end of the study, cells from spleen, bone marrow and blood were harvested and stained with mouse CD45-APC-Cy7, human CD45-BV405, human CD19-PE antibodies and analyzed by flow cytometry to determine the percentage of human CD45 positive cells. For western blot, spleen leukemia cells were obtained by purification with hCD19 MicroBeads (Miltenyi biotech, Cat #130-050-301) per manufacturer's protocol. Efficacy was determined by linear regression and two-way ANOVA analysis in Prism (GraphPad Software, version 8.4.2).

For pharmacodynamic studies, after engraftment, mice with >50% hCD45 cells in peripheral blood were dosed with 10, 30 or 100 mg/kg i.p. of compound 7 for 2 daily doses. One hour after the second dose, mice were euthanized, and cells collected from bone marrow and spleen. For phosphoflow cytometry analysis, 0.75×106 bone marrow cells in 3 ml of medium were fixed by adding 1 ml of 10% formaldehyde and incubated at room temperature for 10 minutes. The cells then were spun down at 450 g for 5 minutes and resuspended in cold 95% methanol and stored at −20° C. For immunoblotting, splenic leukemia cells were purified by hCD19 MicroBeads (Miltenyi). Cells were pelleted and total protein extracted using RIPA buffer supplemented with Halt™ Protease Inhibitor Cocktail (ThermoFisher).

13. Ex Vivo Cytotoxicity

Human CD45+ leukemic cells were purified from patient derived xenografts (PDX) by magnetic-activated cell sorting (MACS), and cytotoxicity determined by the MTT assay was then used to determine ex vivo cytotoxicity. Leukemia cells were resuspended in RPMI 1640 without L-glutamine or phenol red (Gibco) supplemented by 10% Heat-inactivated FBS (Gibco), 2 mM L-Glutamine (Lonza), 1% Antibiotic-Antimycotic (Gibco), and 1% Insulin-Transferrin-Selenium (ITS) (Gibco) at a density of 2×106 cells/mL, and 80 μL (160,000 cells) of cell suspension was then plated in round-bottom 96-well plates. Drug stocks were made by serial dilution in the cell culture medium. Duplicates were included for each of the six drug concentrations (100, 20, 4, 0.8, 0.16 and 0.032 nM for the three PROTACs tested; 10000, 1000, 100, 10, 1 and 0.1 nM for CHZ868 and ruxolitinib). After 4 days incubation at 37° C./5% CO2, 10 μL of MTT solution (ThermoFisher, dissolved in sterile 0.9% NaCl, 15 mM) was added to each well. Cells were then incubated at 37° C./5% CO2 for 4-6 hours. 100 μL of isopropanol (Sigma, supplemented with 0.04 N hydrochloric acid) was added to each well and mixed thoroughly to dissolve the Formazan crystals. The mixture was kept at room temperature for 5 minutes before measuring the absorbance at 562 nm.

14. Phosphoflow Analysis

Cells (7.5×105) were treated with compounds in 3 ml of IMDM containing 1% BSA for one hour followed by treatment with or without 25 ng/mL TSLP (R&D systems) for 30 minutes. Cells were fixed for 10 minutes at room temperature by adding 1 ml of 10% UltraPure Formaldehyde (Polysciences), centrifuged for 5 minutes at 450 g, resuspended in 95% methanol (Electron Microscopy Sciences) and store at −20° C. Cells were stained with phosphorylated (p)STAT5-Ax647(#612599, BD), pJAK2 Y1007/1008 (#3776, Cell Signaling Technologies), Anti-Rabbit-BV-421 (#406410, Biolegend), hCD45-BV605 (#564047, BD) and hCD19-PE (t #349209, BD). Mouse IgG2α-Ax647 (Cat #558053, BD) was used as isotype control. Cells were analyzed on BD Biosciences LSR/Fortessa (BD Biosciences, Franklin Lakes, NJ) with BD FACSDiva 7.0 software followed by FlowJo v10 (Tree Star, Inc., Ashland, OR).

15. Data Sharing Statement

Protein structure data have been deposited in the Protein Data Bank as 6WTN (JAK2+ruxolitinib), 6WTO (JAK2+baricitinib), 6WTP (JAK2+compound 3), 6WTQ (JAK2+compound 4). Cell line RNA and genome sequencing data have been deposited at the Sequence Read Archive, accession SUB7347082. The CRLF2r xenograft is available at the Public Resource of Patient-Derived and Expanded Leukemias, www.stjude.org/propel; propel@stjude.org.

16. Evaluation of Proteolysis-Targeting Chimeras (PROTACS)

$EC_{50}$ values (in μM) for exemplary compounds tested in MHH-CALL-4 is provided in Table 1.

TABLE 1
| Sample | Compound | $EC_{50}$ (μM) |
|---|---|---|
| SJ000988497 (cmpd no. 7) | 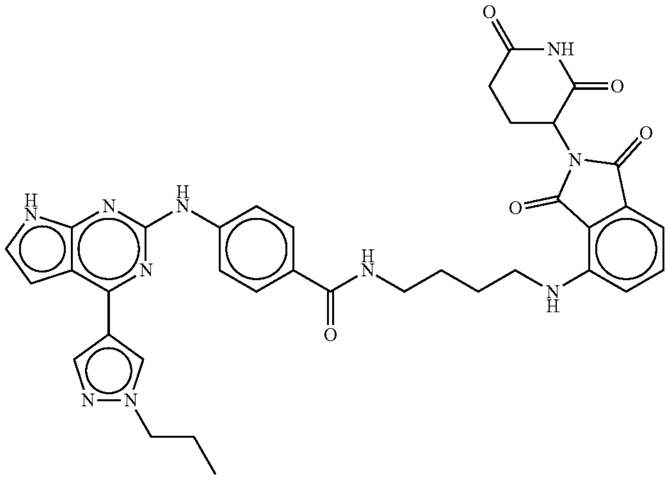 | 0.0002 |
| SJ000986420 | 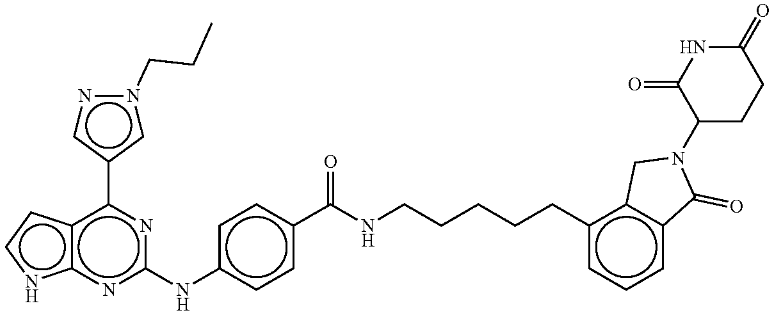 | 0.0005 |
| SJ000988500 | 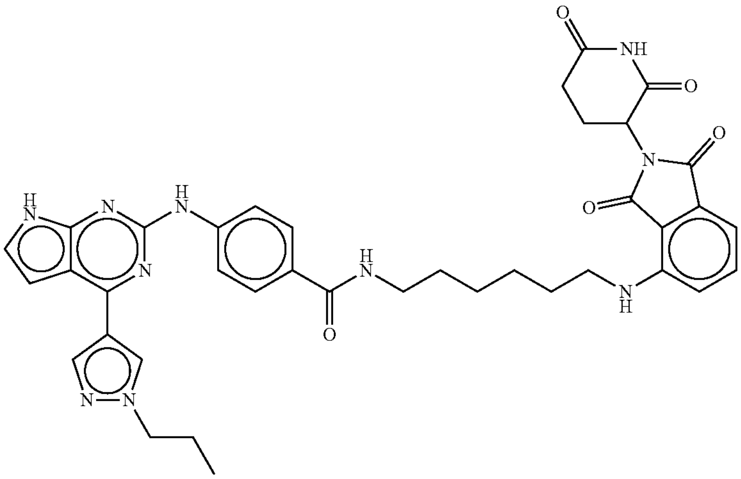 | 0.0027 |

TABLE 1-continued
| Sample | Compound | EC50 (μM) |
| --- | --- | --- |
| SJ000988498 | 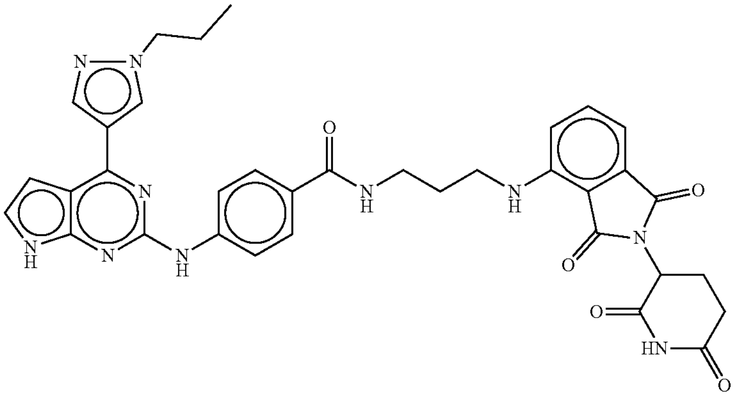 | 0.0005 |
| SJ000988499 | 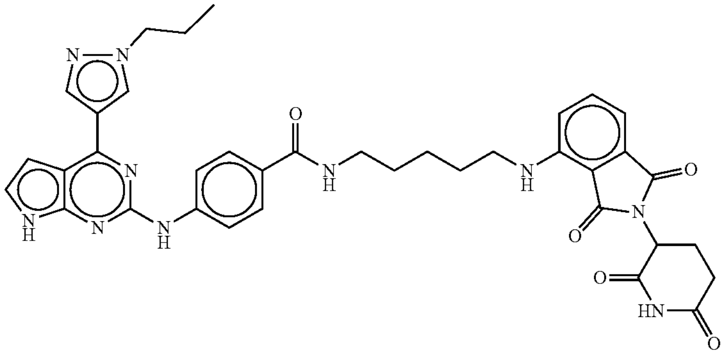 | 0.0009 |
| SJ000986340 | 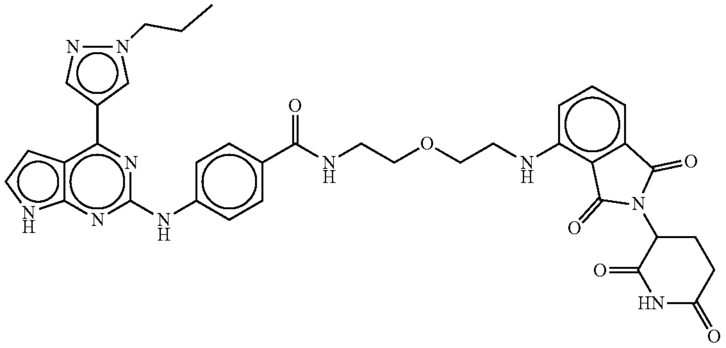 | 0.0150 |
| SJ000986050 | 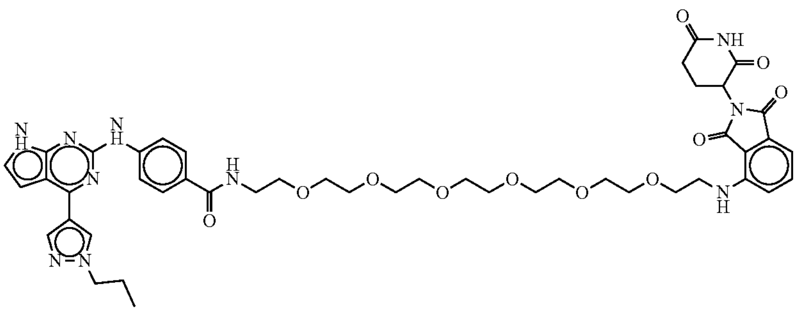 | 0.7200 |

TABLE 1-continued
| Sample | Compound | EC50 (μM) |
|---|---|---|
| SJ000986048 | 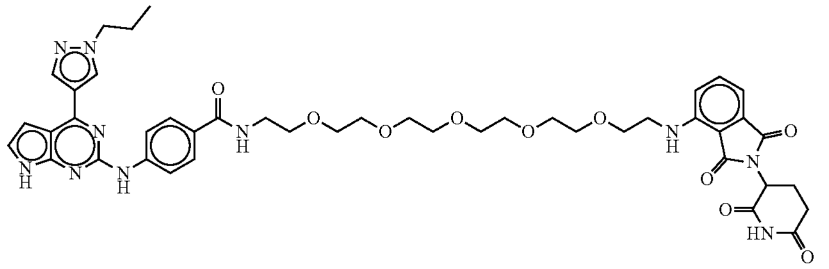 | 1.1000 |
| SJ000986049 | 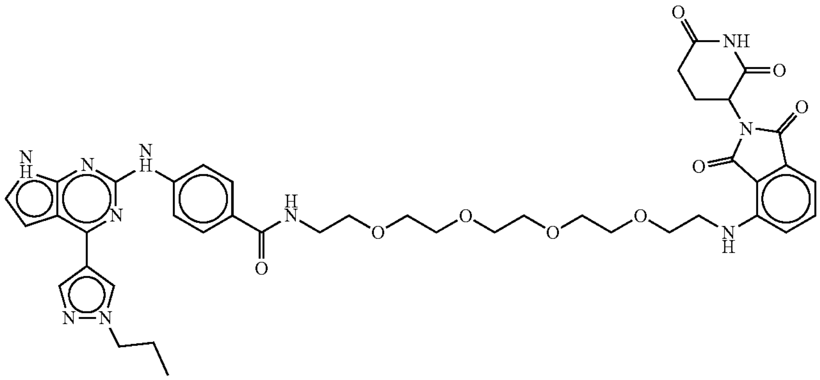 | 2.3000 |
| SJ000986419 | 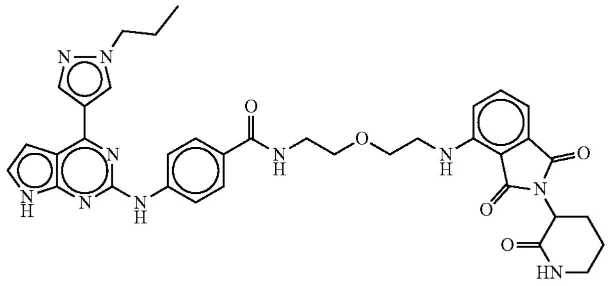 | 2.7500 |
| SJ000986051 | 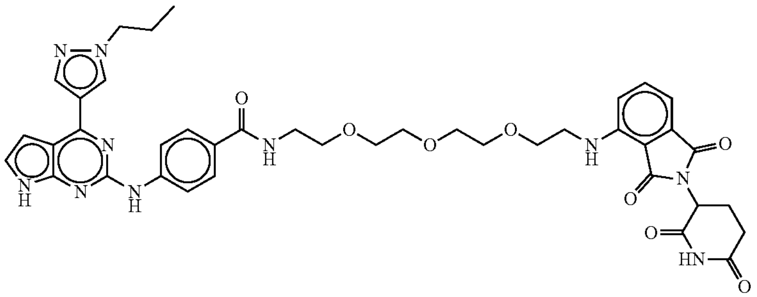 | 2.9000 |
| SJ000986052 | 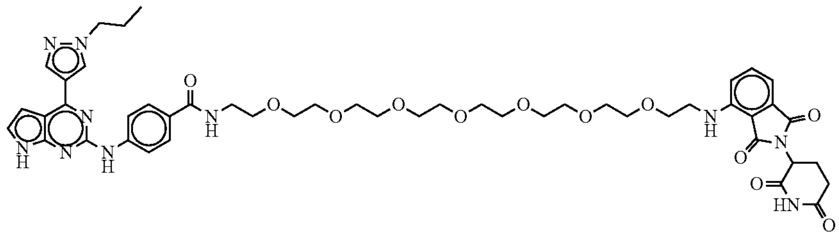 | 3.8500 |

TABLE 1-continued
| Sample | Compound | EC50 (μM) |
| --- | --- | --- |
| SJ000986341 | 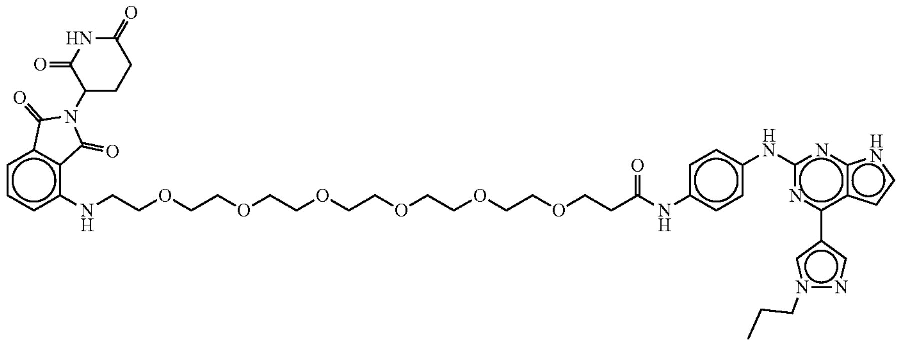 | 5.8300 |
| SJ000986342 | 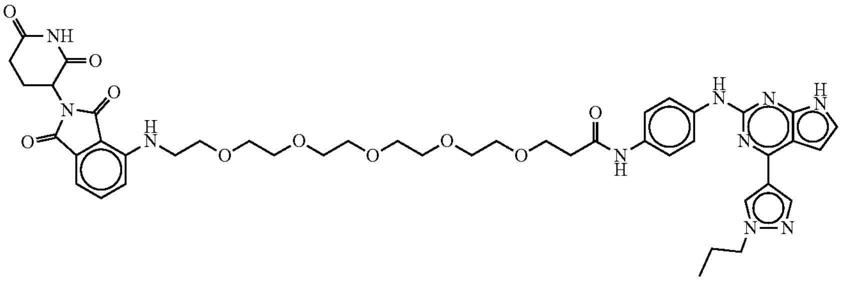 | 6.8900 |
| SJ000986343 | 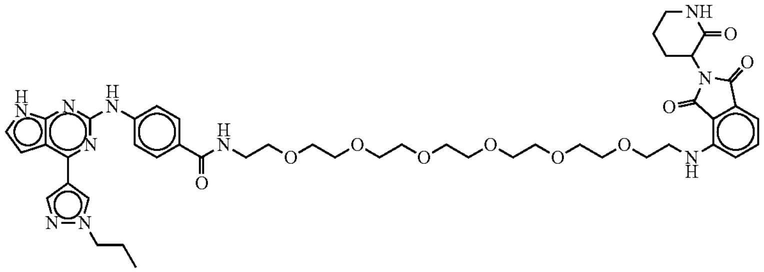 | 12.7900 |
| SJ000986078 | 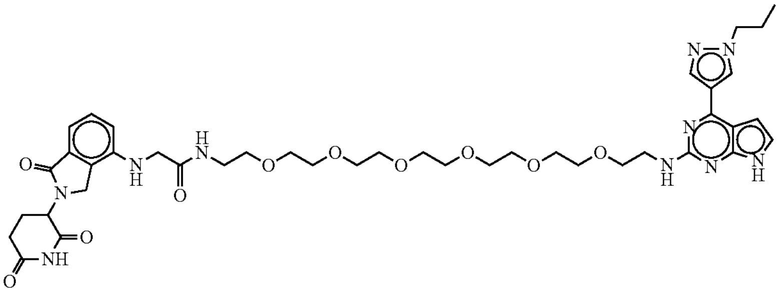 | >100 |
| SJ000986079 | 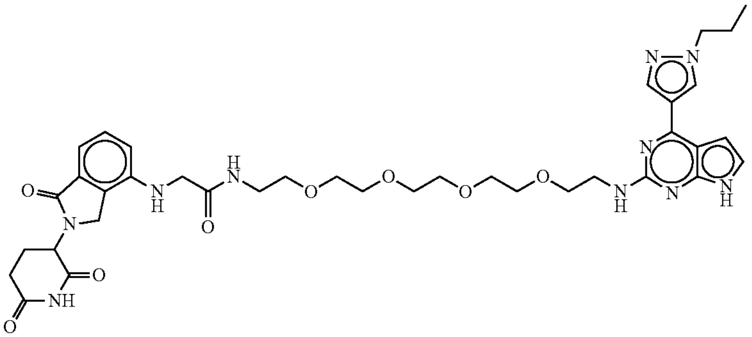 | >100 |

TABLE 1-continued
| Sample | Compound | $EC_{50}$ (μM) |
|---|---|---|
| SJ000986339 | 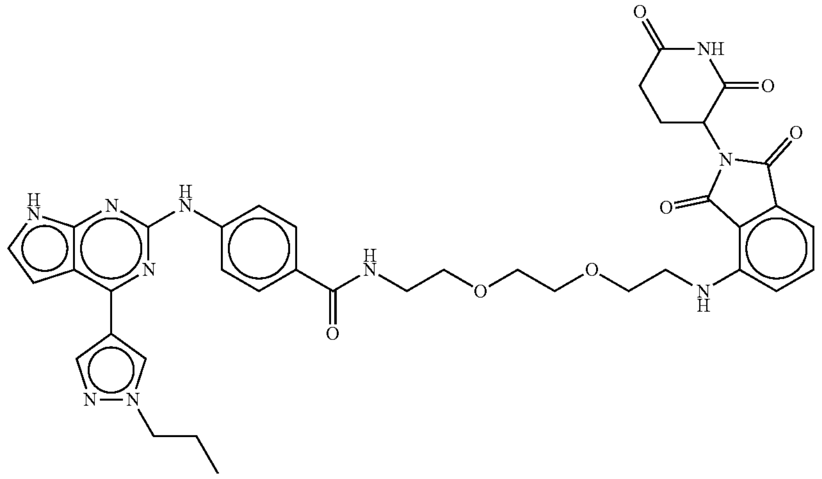 | >100 |
| SJ001005328 (Cmpd no. 5) | 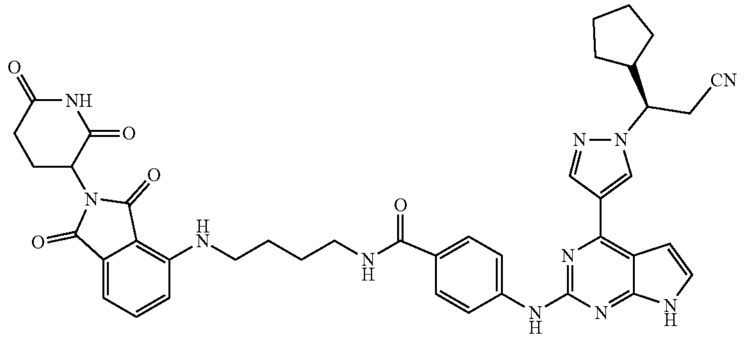 [SMILES: N#CC[C@H](C1CCCC1)n1cc(-c2nc(Nc3ccc(C(=O)NCCCCNc4cccc5c4C(=O)N(C4CCC(=O)NC4=O)C5=O)cc3)nc3[nH]ccc23)cn1] | 0.0039 |
| SJ001005350 (Cmpd no. 6) | 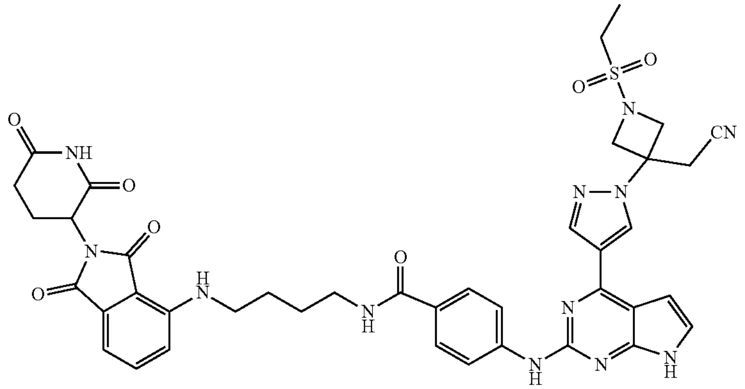 [SMILES: CCS(=O)(=O)N1CC(CC#N)(n2cc(-c3nc(Nc4ccc(C(=O)NCCCCNc5cccc6c5C(=O)N(C5CCC(=O)NC5=O)C6=O)cc4)nc4[nH]ccc34)cn2)C1] | 0.00054 |
| SJ001008030 (Cmpd no. 8) | 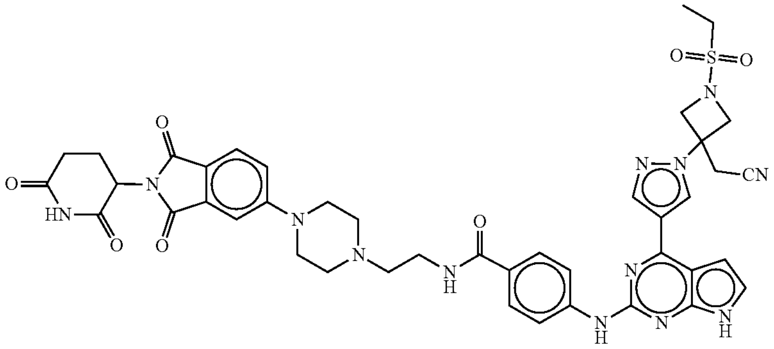 | 0.122 |

TABLE 1-continued
| Sample | Compound | EC50 (μM) |
| --- | --- | --- |
| Cmpd. no. 53 | 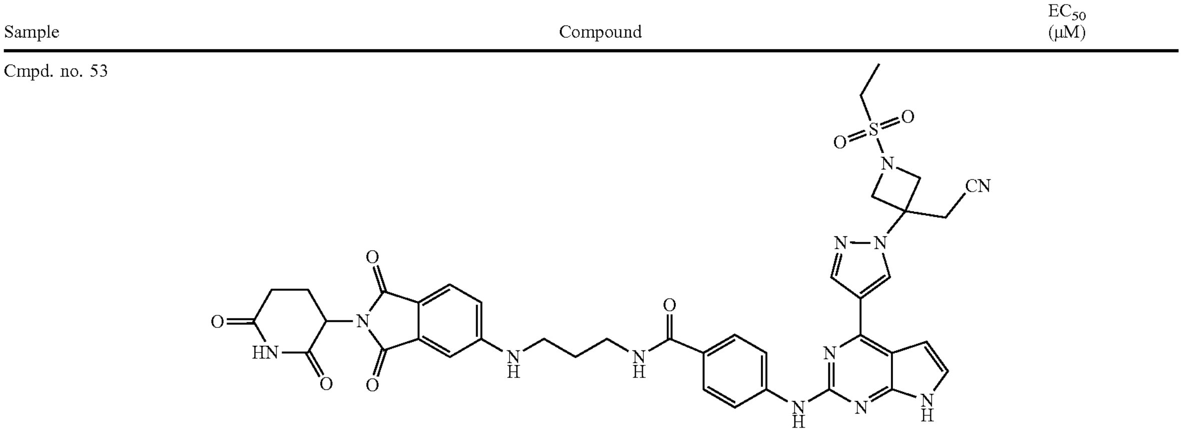 | |
| Cmpd. no. 56 | 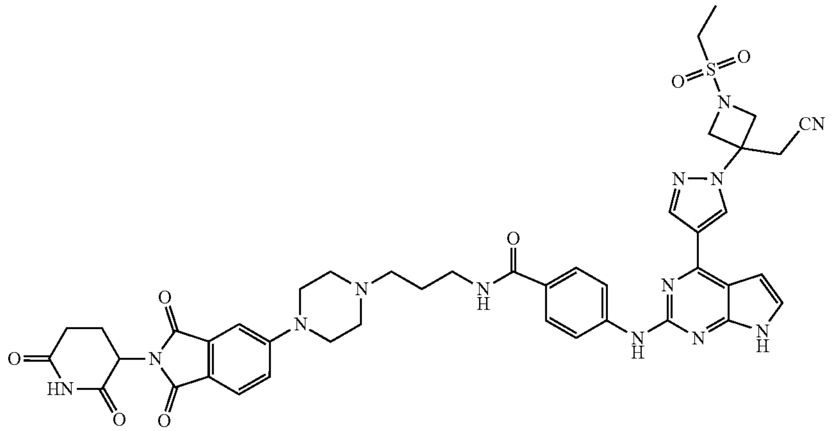 [SMILES: CCS(=O)(=O)N1CC(CC#N)(n2cc(-c3nc(Nc4ccc(C(=O)NCCCN5CCN(c6ccc7c(c6)C(=O)N(C6CCC(=O)NC6=O)C7=O)CC5)cc4)nc4[nH]ccc34)cn2)C1] | |
| Cmpd. no. 59 | 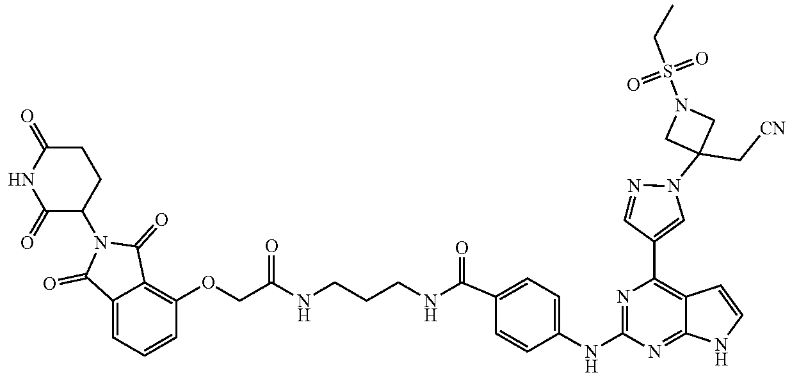 [SMILES: CCS(=O)(=O)N1CC(CC#N)(n2cc(-c3nc(Nc4ccc(C(=O)NCCCNC(=O)COc5cccc6c5C(=O)N(C5CCC(=O)NC5=O)C6=O)cc4)nc4[nH]ccc34)cn2)C1] | |
| Cmpd. no. 61 | 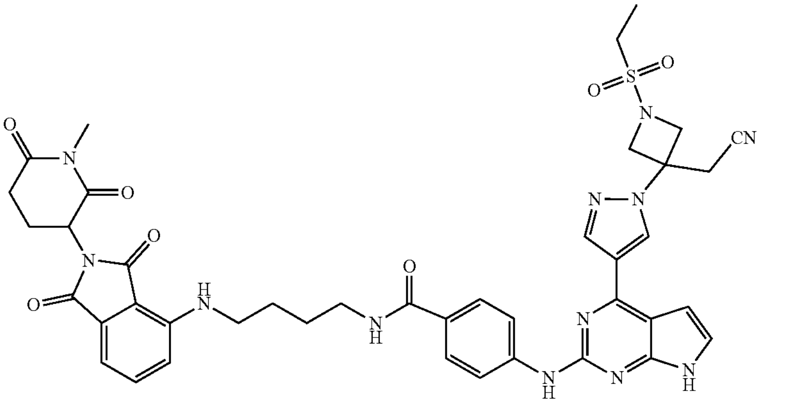 [SMILES: CCS(=O)(=O)N1CC(CC#N)(n2cc(-c3nc(Nc4ccc(C(=O)NCCCCNc5cccc6c5C(=O)N(C5CCC(=O)N(C)C5=O)C6=O)cc4)nc4[nH]ccc34)cn2)C1] | |

TABLE 1-continued

| Sample | Compound | $EC_{50}$ (μM) |
|---|---|---|
| Cmpd. no. 80 | 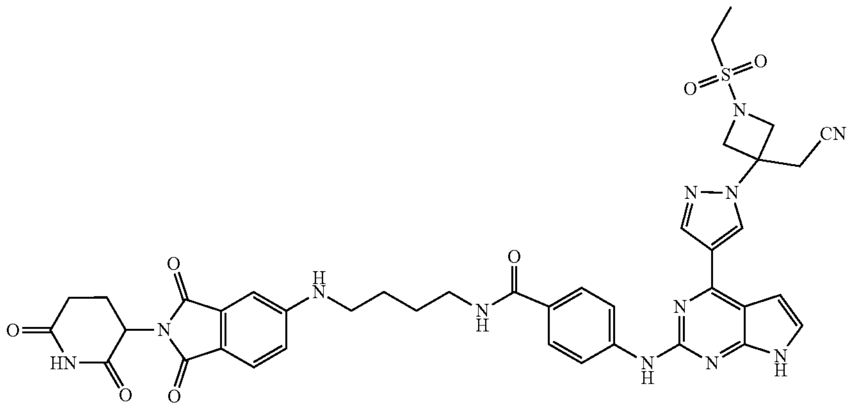 [SMILES: CCS(=O)(=O)N1CC(CC#N)(n2cc(-c3nc(Nc4ccc(C(=O)NCCCCNc5ccc6c(c5)C(=O)N(C5CCC(=O)NC5=O)C6=O)cc4)nc4[nH]ccc34)cn2)C1] | |

17. Results a. Structure-Based Design of JAK- and CRBN-Directed PROTACs

Figure 1C:
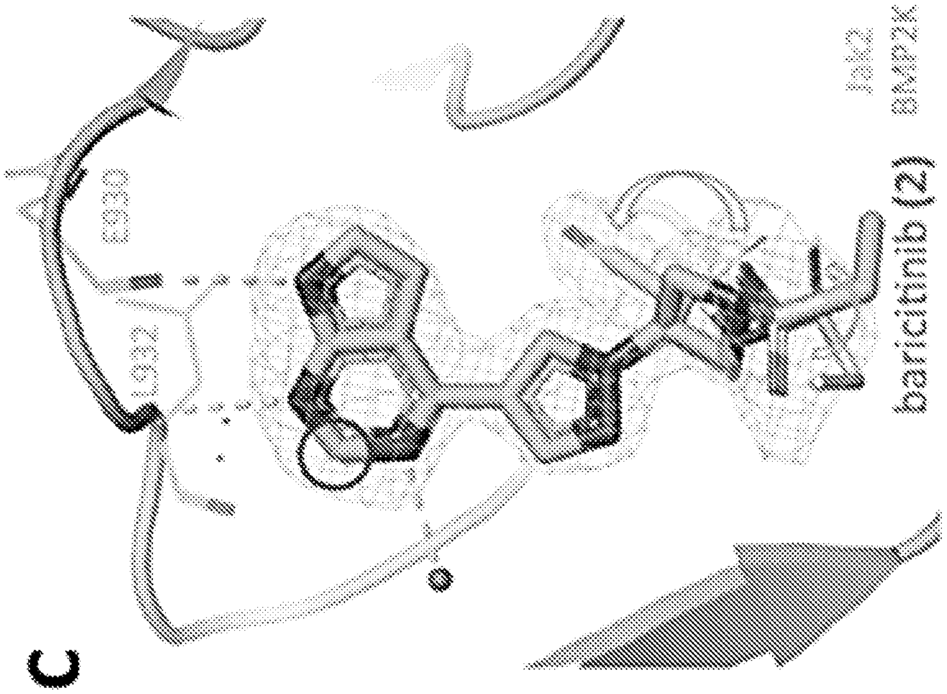
Figure 1B:
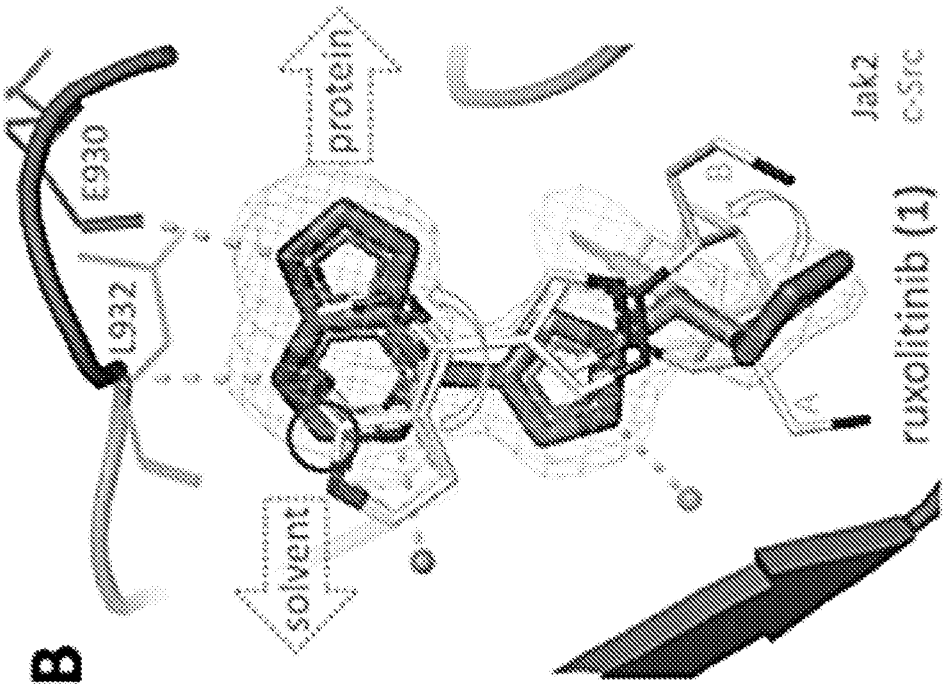
Figure 3:
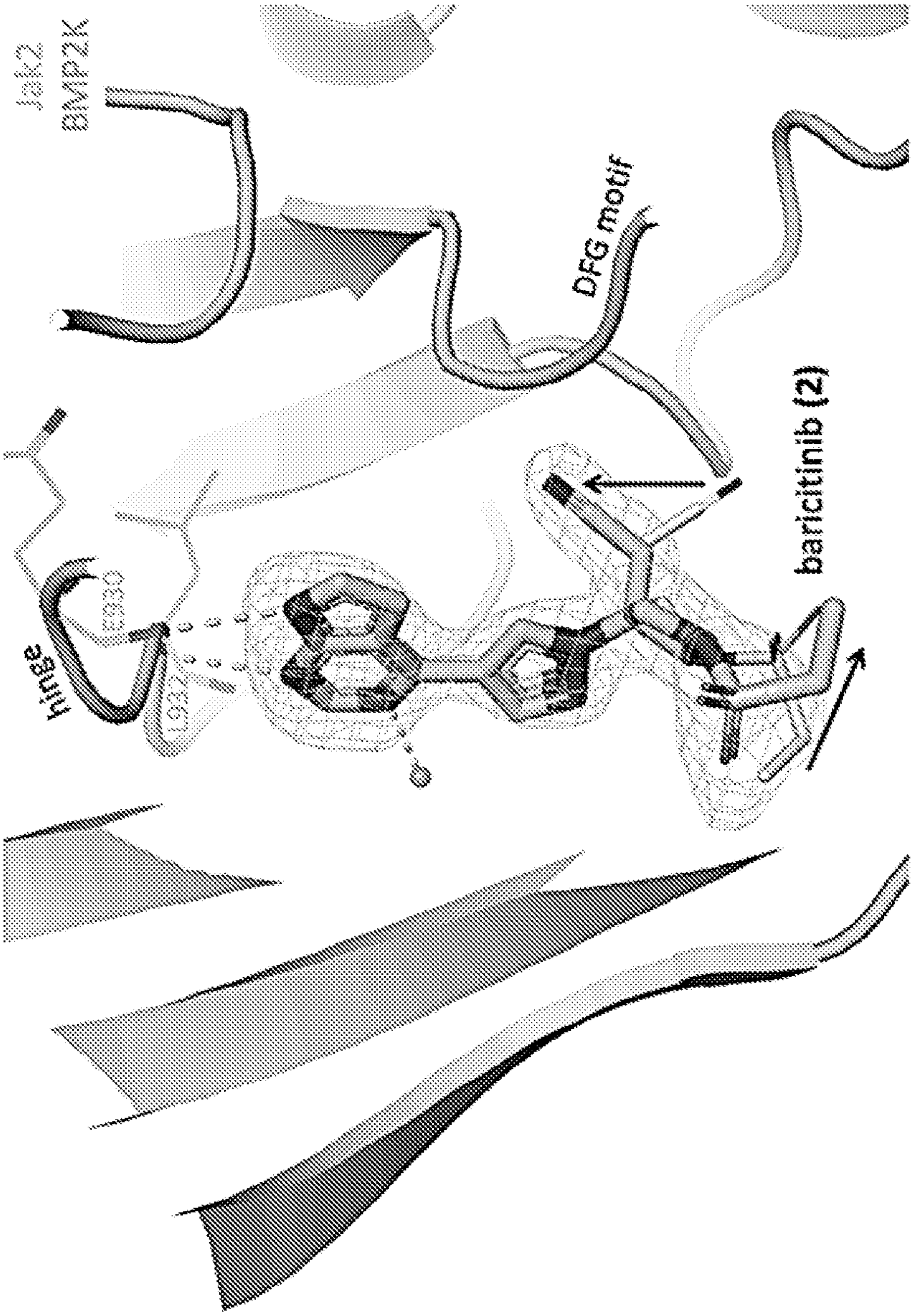
FIG. 3 shows a representative close-up image of baricitinib binding to JAK2 JH1 (cyan) as displayed in FIG. 1C, rotated to show detail of ligand changes compared to baricitinib bound to BMP2K (grey).
Figure 4:
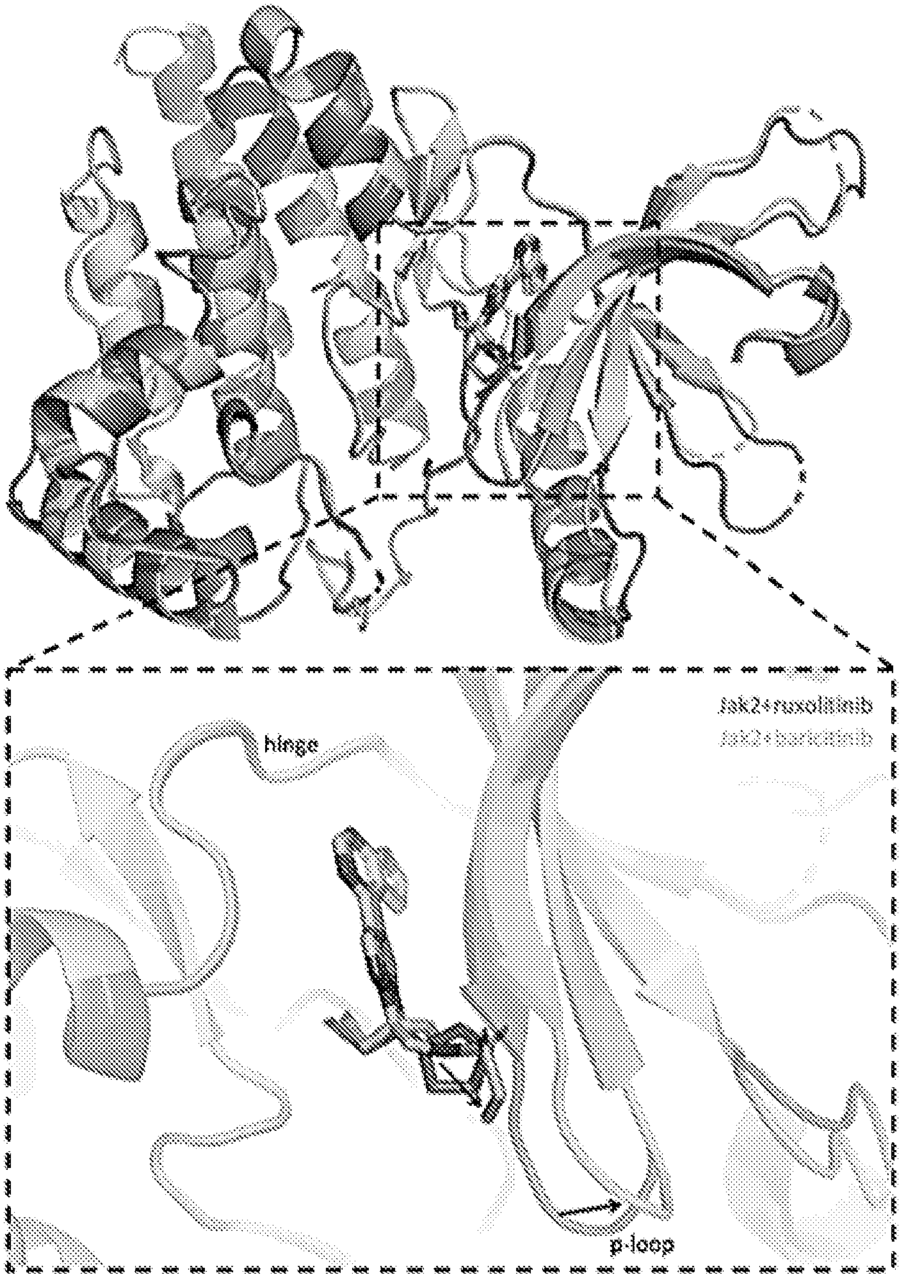
FIG. 4 shows a representative image illustrating that the overall structure of the JAK2 JH1 domain bound to ruxolitinib and baricitinib is very similar, both for the protein and the ligand.

In view of the suboptimal efficacy of existing type I (e.g., ruxolitinib) (compound 1) and baricitinib (compound 2) and type II (e.g., CHZ-868) Janus kinase inhibitors in CRLF2 ALL (Table 2 and Table 3), the ability to directly degrade Janus kinases using JAK-directed PROTACs based on derivatives of ruxolitinib or baricitinib conjugated via a linker to CRBN-binding molecules including derivatives of lenalidomide and pomalidomide was evaluated. To inform the design of JAK-directed PROTACs, the crystal structures of human JAK2 JH1 (kinase) domain were determined in the presence of ruxolitinib and baricitinib to 1.8 Å and 1.7 Å resolution, respectively, providing the first such structures of these drugs bound to their primary target (FIG. 1A-E, FIG. 2A, and FIG. 2B). The previously reported structures of ruxolitinib (bound to chicken SRC (c-Src) (Boitano, et al. (2010) *Science* 329(5997): 1345-1348), PDB code 4U5J) and one of baricitinib (bound to human BMP2K41, PDB code 4W9X) were used for comparison. As is common for type I JAK inhibitors, both compounds bind to JAK2-JH1 ATP-binding site in the active "DFG-in" conformation, within a cleft between the N- and C-terminal lobes of the protein (FIG. 1A). This structure also shows the location of the JAK2 kinase domain mutations observed in CRLF2r B-ALL, which are likely to disrupt the compact conformation of the kinase domain leading to constitutive activation and enhanced STAT5 phosphorylation (Chen, et al. (2019) *Int J Biol Macromol.* 137: 1030-1040), consistent with their known transforming effect (Mullighan, et al. (2009) *Nat Genet.* 41(11): 1243-1246; Mullighan, et al. (2009) *Proc Natl Acad Sci USA.* 106(23): 9414-9418). Each compound forms two direct hydrogen bonding interactions between the pyrimidine ring and the protein backbone atoms of Glu930 and Leu932 in the hinge domain that connects the N- to the C-terminal lobe (FIG. 1B and FIG. 1C). In addition, compound binding is accommodated by numerous hydrophobic interactions with various residues lining its binding pocket and a hydrogen bonding interaction with up to two nearby water molecules (FIG. 3). The overall conformation of ruxolitinib is flipped by ~180° compared to its position in the SRC protein, where two pyrimidine nitrogens interact only with the backbone of the SRC residue that is equivalent to Leu932 in JAK2 (FIG. 1B). The pyrimidine and pyrazole groups of baricitinib bind similarly to JAK2 and BMP2K41, while the azetidine substituents are displaced; its nitrile group is rotated by ~100° aligning parallel to the DFG motif rather than pointing towards it as seen in JAK2 for both ruxolitinib and baricitinib (FIG. 1C and FIG. 4). Structurally, the overlap of the common core shared by ruxolitinib and baricitinib is high (FIG. 4 and FIG. 6A), and both JAK2 structures align with an overall root mean square deviation (RMSD) of <0.5 Å. Yet, the differences in the substitution at position 1 manifest in baricitinib's bulkier substituent displacing the tip of the glycine-rich p-loop by up to 3.1 Å (FIG. 4). With its ability to accommodate ligands of various sizes, the flexibility of the p-loop is one of the structural elements that could be exploited for PROTAC design. Differences in flexibility may also help distinguish the four JAK family members (JAK1-3 and TYK2) (Alicea-Velazquez and Boggon) (2011) *Curr Drug Targets.* 12(4): 546-555). However, the key insight for rational PROTAC design was the conformation of the pyrimidine ring.

TABLE 2

| Compound | $EC_{50}$ (nM) in ALL cells and normal cells | | | | |
|---|---|---|---|---|---|
| | MHH-CALL-4 | MHH-CALL-4-CRBN-KD | MHH-CALL-4 + baricitinib (0.6 μM) | MHH-CALL-4 + lenalidomide (30 μM) | KOPN49 |
| Cmpd 5 | 1.20 | >102 | 2.7 | | 1.76 |
| Cmpd 6 | 1.86 | >102 | 3.4 | | 3.28 |
| Cmpd 7 | 0.16 | >102 | 0.4 | >57 | 0.25 |
| Cmpd 8 | 122.18 | | | | |
| Ruxolitinib | 25800 | | | | |
| Baricitinib | 1482 | | | | |
| CHZ868 | 180 | | | | |
| Thalidomide | 60,013 | | | | |
| Lenalidomide | 34,480 | | | | |
| Pomalidomide | 63,662 | | | | |

TABLE 3

| | EC$_{50}$ (nM) in ALL cells and normal cells | | | | |
|---|---|---|---|---|---|
| Compound | MHH-CALL-2 | KOPN75 | NALM-6 | 697 | hCD34+ cells |
| Cmpd 5 | 4.19 | 2.35 | 34.35 | 8.40 | 8.36 |
| Cmpd 6 | 7.48 | 6.64 | 217.58 | 37.82 | 19.22 |
| Cmpd 7 | 0.46 | 0.28 | 5.13 | 0.98 | 0.94 |

Figure 1D:
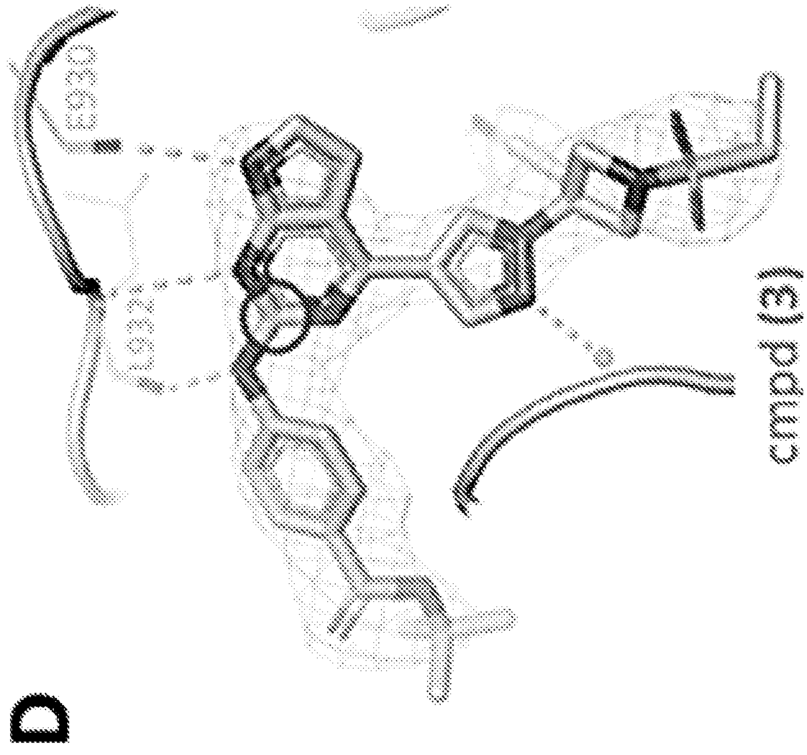
Figure 1E:
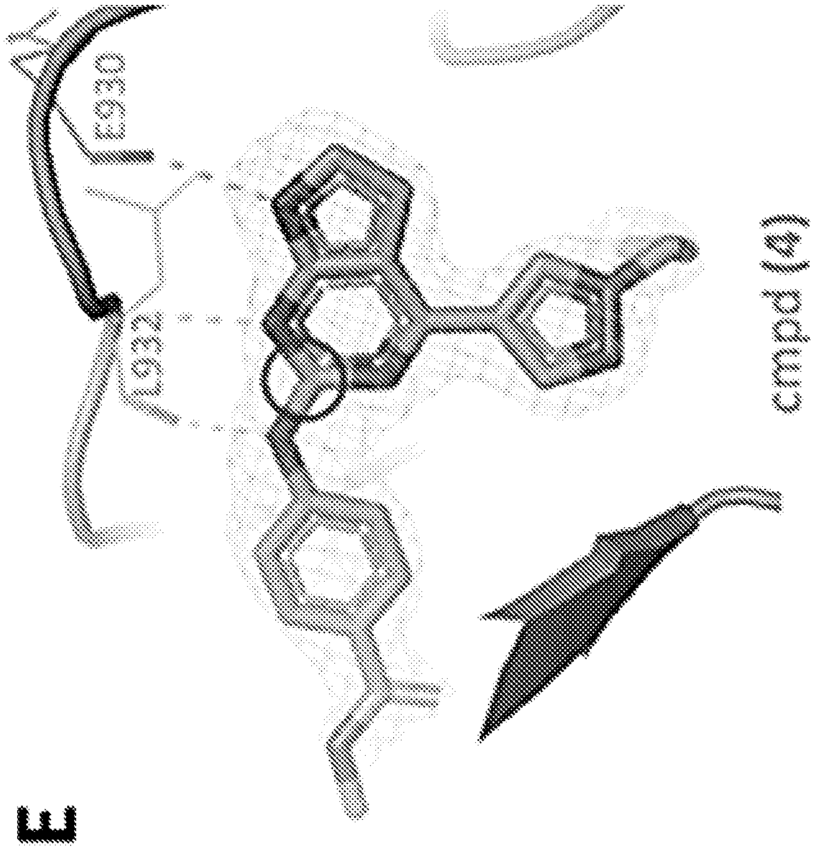

Referring to FIG. 1A, the JAK2 JH1 (kinase) domain assumes a "DFG-in" conformation upon binding ruxolitinib (pink sticks). Protein color is graded from blue at the N-terminus to red at the C-terminus, with acute lymphoblastic leukemia (ALL) mutations shown as red dots, the mobile p-loop in dark blue, and the ruxolitinib binding site shown as a pink surface close to the activation loop containing the DFG motif (green dots); two phosphorylated tyrosines (p-Tyr) shown as yellow dots. The black arrow near ruxolitinib indicates the direction of linker extension for the design of PROTACs as shown in FIG. 1B. Referring to FIG. 1B, the orientation of ruxolitinib bound to human JAK2 (pink) is flipped with respect to its position in complex with SRC (4U5J, from chicken) (Duan, et al. (2014) *PLoS One* 9(9): e106225) shown in grey as conformation A and B for both molecules in the asymmetric unit, guiding the linker attachment point (red circle) for the PROTAC design towards solvent. Polder OMIT electron density maps are shown as green mesh at 3sigma and hydrogen bonds are shown as yellow dotted lines for all structures in FIG. 1B-E. Referring to FIG. 1C, baricitinib bound to JAK2 shows a different placement of ligand moieties such as the nitrile group compared to BMP2-inducible kinase (4W9X) (Sorrell, et al. (2016) *Structure* 24(3): 401-411). Referring to FIG. 1D and FIG. 1E, PROTAC precursor compounds 3 (FIG. 1D) and 4 (FIG. 1E) engage in an additional H-bond interaction between the linker and the backbone of the hinge region and extend into solvent.

Figure 2A:
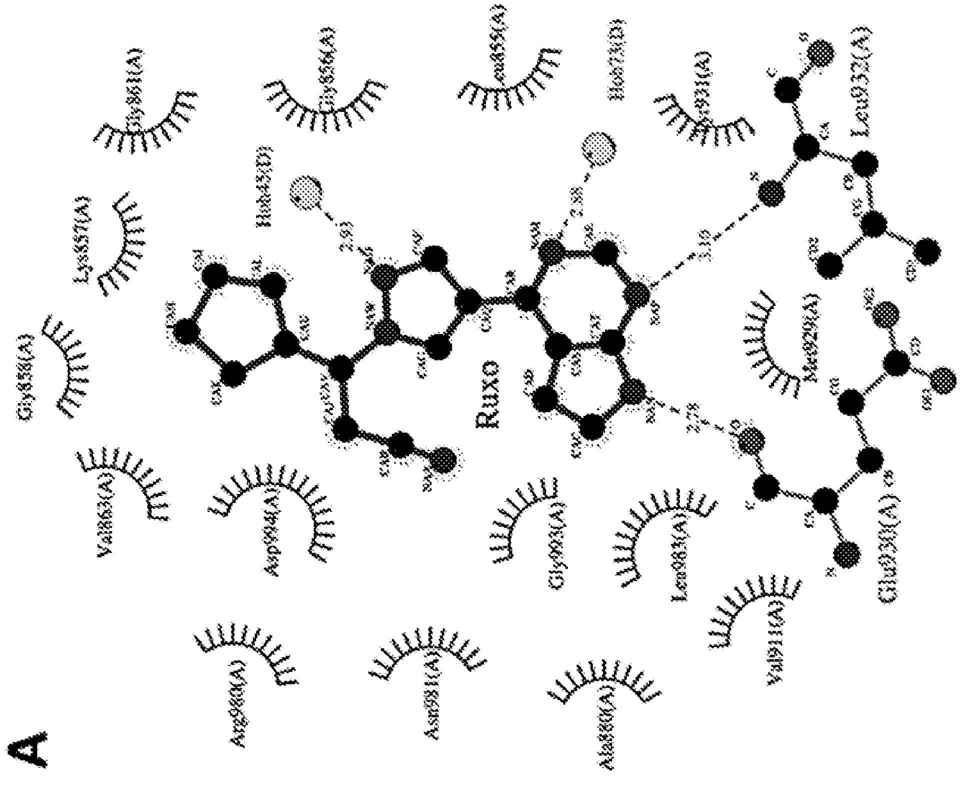
FIG. 2A and FIG. 2B show a representative LigPlot (Laskowski and Swindells (2011) *J Chem Inf Model.* 51(10): 2778-2786) interaction analysis of ruxolitinib (FIG. 2A) and baricitinib (FIG. 2B) binding to human JAK2 JH1.
Figure 2B:
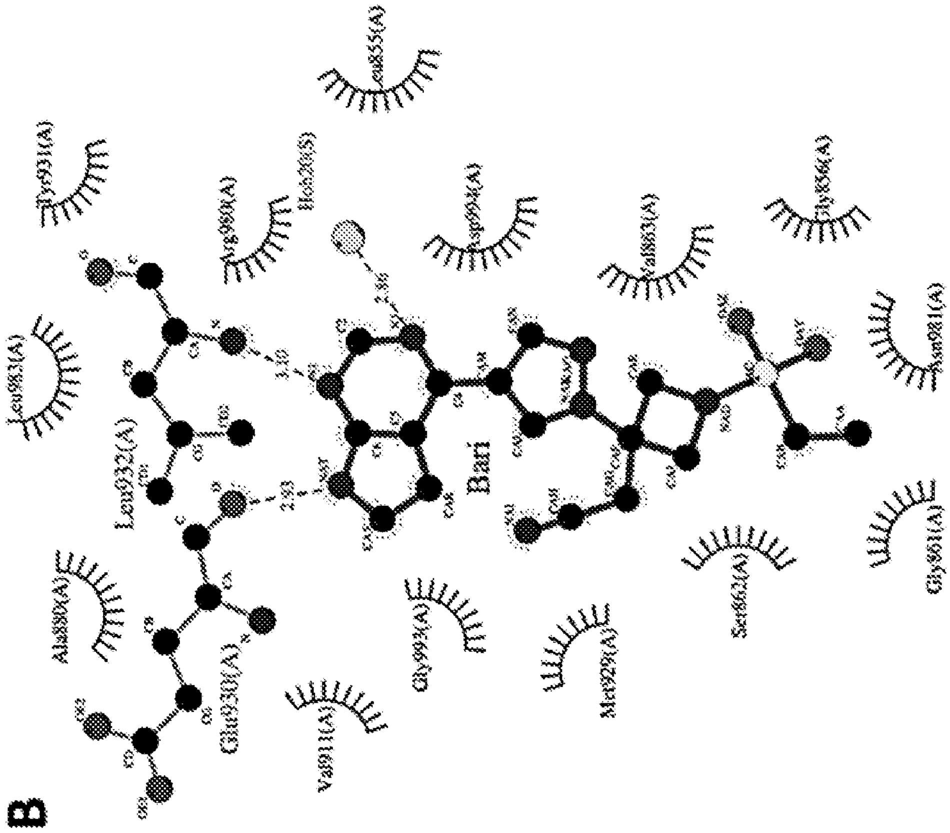

Referring to FIG. 2A and FIG. 2B, LigPlot (Laskowski, et al. (2011) *J Chem Inf Model.* 51(10): 2778-2786) interaction analysis of ruxolitinib (FIG. 2A) and baricitinib (FIG. 2B) binding to human JAK2 JH1 is shown. Hydrogen bonds are indicated by dashed lines between the atoms involved, hydrophobic contacts are represented by an arc with spokes radiating towards the ligand atoms they contact.

Referring to FIG. 3, a close-up of baricitinib binding to JAK2 JH1 (cyan) displayed in FIG. 1C is shown, rotated to show detail of ligand changes compared to baricitinib bound to BMP2K (grey).

Referring to FIG. 4, as shown, the overall structure of the JAK2 JH1 domain bound to ruxolitinib and baricitinib is very similar, both for the protein and the ligand. Ligand differences manifest in adjusted placements of the proximal p-loop to accommodate each ligand.

Thus, the solvent orientated C2-carbon of the pyrimidine core present in both ruxolitinib and baricitinib was identified as the most promising linker attachment point for PROTAC design (FIG. 5A), as the exit vector points into solvent and is amenable to chemical modification. In contrast, reliance on the SRC bound ruxolitinib crystal structure would have misled PROTAC design, as the C2-carbon in the flipped pyrimidine points towards the protein rather than solvent (FIG. 1B). Lacking a suitable functional group in this position, a 4-amino-benzamide moiety was introduced as a synthetically amenable handle for linker incorporation via amide bond formation (FIG. 5B and FIG. 5C). This proved to be a well-tolerated structural modification, and structures of the related intermediate compounds 3 and 4 co-crystallized with JAK2 were generated. The electron density maps of both structures show the handle moiety unambiguously pointing toward solvent (FIG. 1D and FIG. 1E) while the linker nitrogen forms another H-bond interaction with the backbone carbonyl of Leu932, forming an alternating H-bond donor and acceptor pattern with the backbone in the hinge region. While this interaction stabilizes the linker within the binding pocket, the electron density map is less defined for the tert-butyl group of compound 3 compared to the carboxamide moiety in compound 4. The enhanced flexibility is evident across the protein in complex with compound 4, most notably at the tip of the p-loop.

Figure 5A:
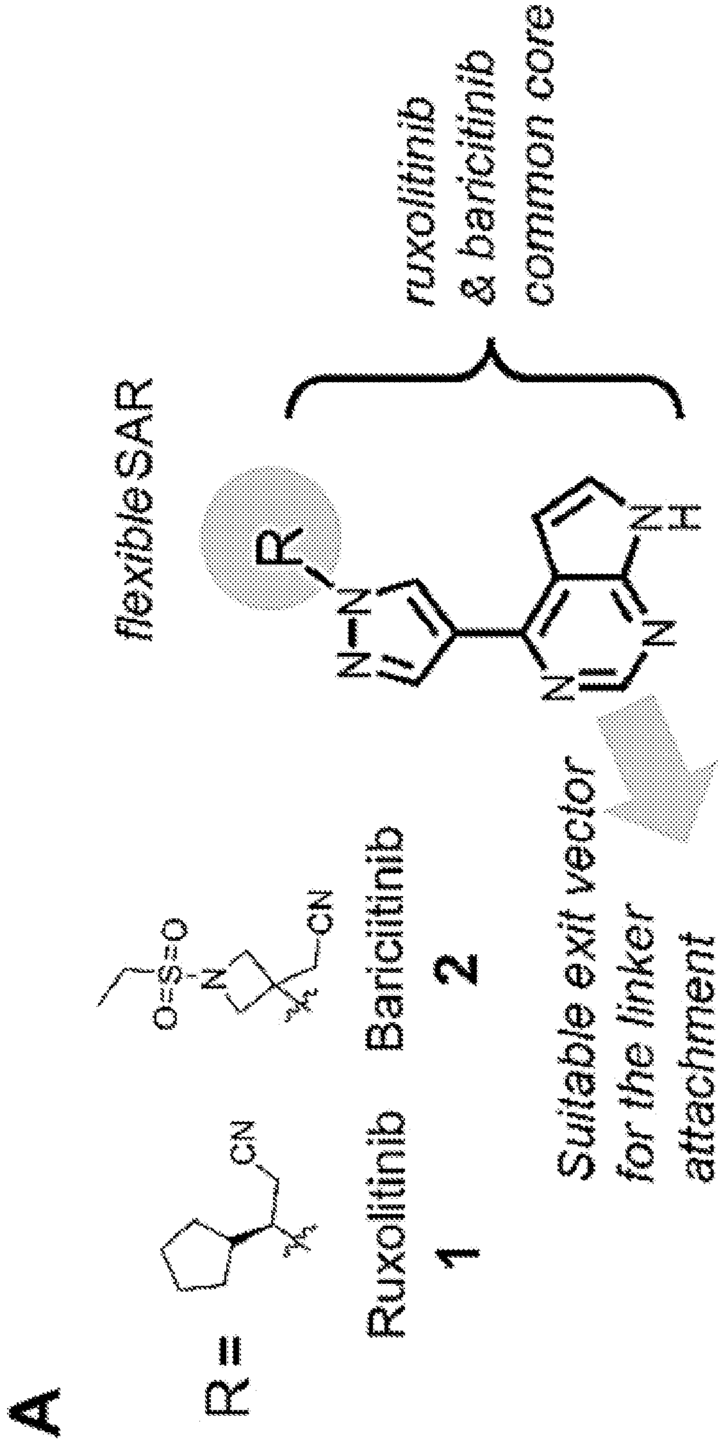
FIG. 5A-D show representative design principles, molecular structure, and properties of JAK PROTACs.
Figure 5B:
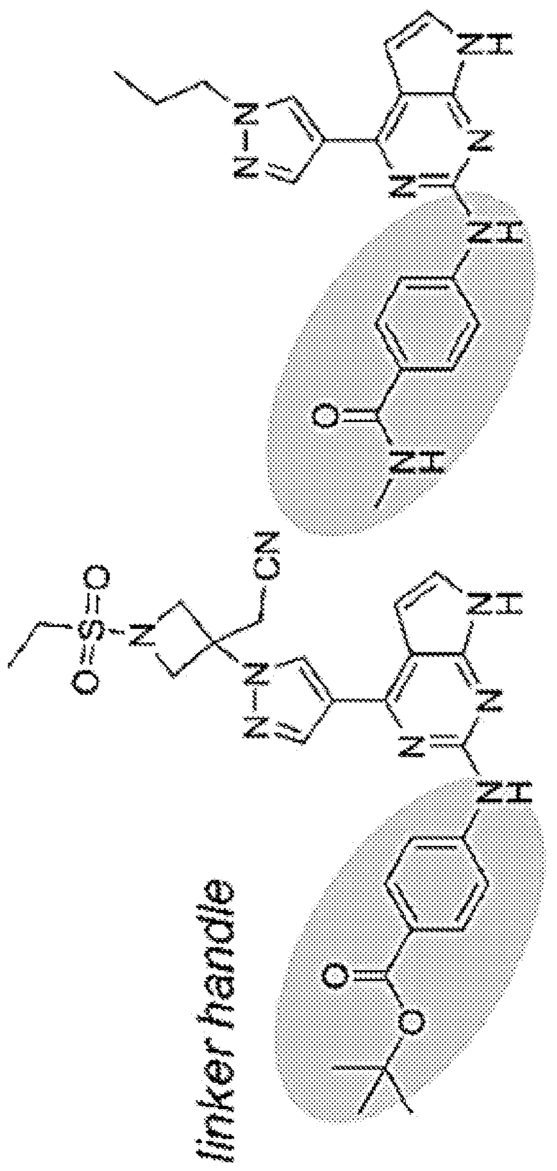
Figure 5C:
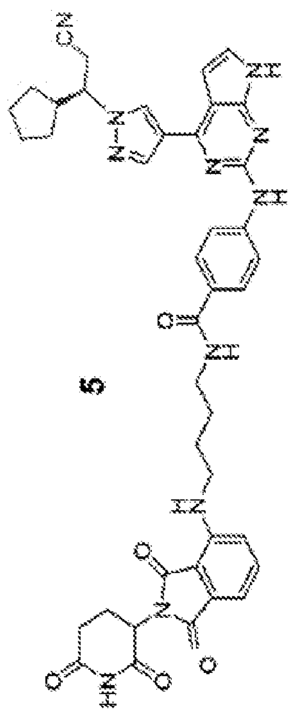
Figure 5C:
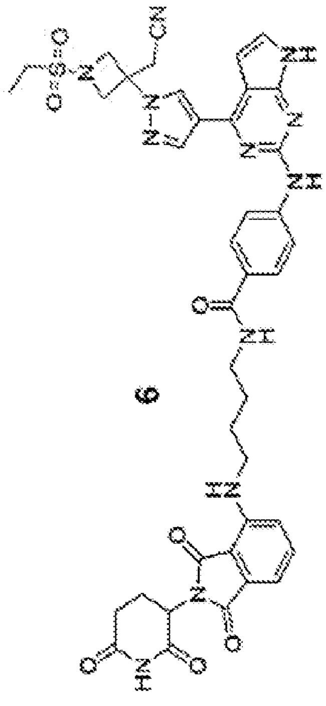
Figure 5C:
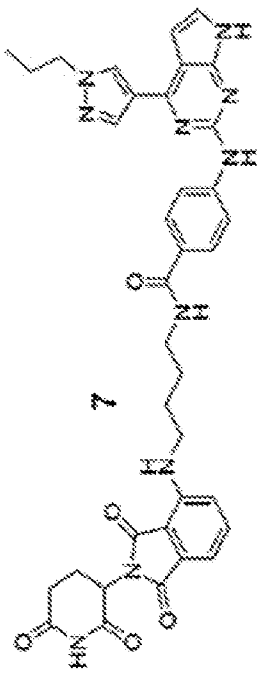
Figure 5C:
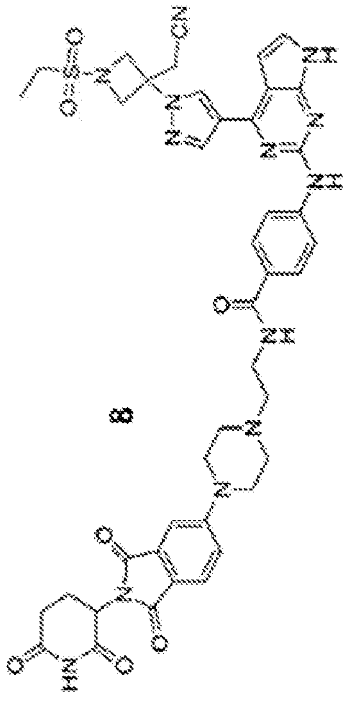

Referring to FIG. 5A, the PROTAC design strategy is shown. Referring to FIG. 5B, structures of key intermediates 3 and 4, containing the linker handle, are shown. Referring to FIG. 5C, structures of PROTACs 5-8 are shown.

Figure 5D:
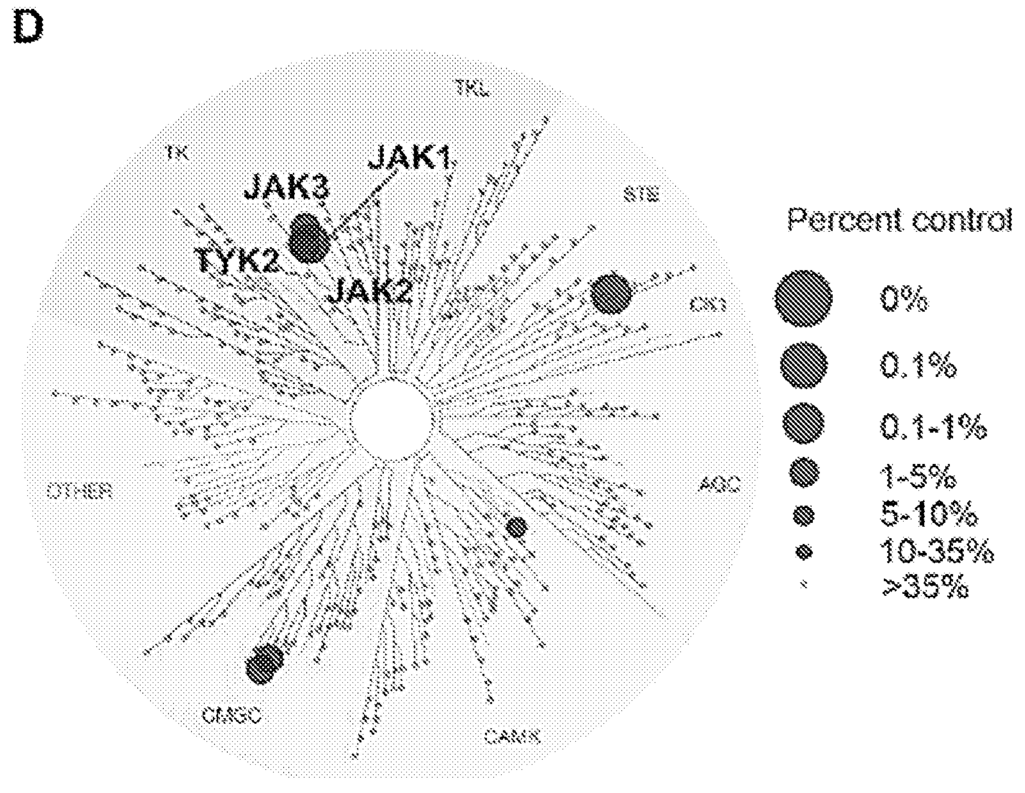

In light of these findings, corresponding ruxolitinib- and baricitinib-based PROTAC compounds 5 and 6 were synthesized, respectively, containing the 4-amino-benzamide handle attached to a four-carbon chain-linked pomalidomide as the E3 ligase recruiting element (FIG. 5C). Based on the reportedly flexible structure-activity relationship (SAR) around the pyrazole region, N-propyl analogue compound 7 was also synthesized. This structural adjustment was made to minimize the PROTAC molecular size and polar surface area, and thus improve its cellular permeability. Indeed, the lower molecular weight (MW=688.29 Da) and topological polar surface area (TPSA=189.06 Å2) of PROTAC 7 resulted in a considerably higher cell permeability in the Caco-2 assay (Papp=19.12 nm/s, data not shown). See also Table 4 below. Importantly, compounds 5, 6, and 7 retained the high affinity for JAK2 (Kds=0.63, 0.11, and 0.3 nM respectively) and the kinome-wide selectivity of compound 7 similar to the parent inhibitors (FIG. 5D). See also Table 5 and Table 6 below. Utilizing previously reported SAR data (Novartis (2019) 3-(1-oxoisoindolin-2-yl)-piperidine-2,6-dione derivatives and uses thereof), baricitinib-based compound 8 was designed containing a piperazine-linked thalidomide moiety with the aim to reduce the risk of GSPT1 off-target degradation.

Referring to FIG. 5D, TREEspot visualization of the kinome selectivity profile of compound 7 at 100 nM concentration (Kinome Scan) is shown.

TABLE 4

| Cmpd. No. | Cac2 Papp A/B (nm/S) | TP SA (A2) | MW | cLogP |
|---|---|---|---|---|
| 5 | 0.24 | 212.9 | 767.33 | 4.5 |
| 6 | 0.19 | 250.2 | 832.29 | 2.7 |
| 7 | 19.12 | 189.1 | 688.29 | 4.2 |
| 8 | 0.02 | 244.7 | 873.3 | 2.9 |

TABLE 5

| Cmpd. | Kd (nM) to JAK family kinases | | | |
|---|---|---|---|---|
| No. | JAK1 | JAK2 | JAK3 | TYK2 |
| Ruxolitinib | 12 | 0.091 | 2.9 | 0.52 |
| Baricitinib | 1.3 | 0.092 | 3.3 | 1.3 |
| 7 | 9.3 | 0.34 | 1.4 | 0.54 |
| 5 | 5.4 | 0.63 | 2.9 | 1.7 |
| 6 | 2.4 | 0.11 | 0.35 | 0.25 |

TABLE 6

| SAR Point | Cmpd. No. | MHHCALL4 (nM) | Target Degradation (Western Blot) JAK1 | JAK2 | JAK3 | TYK2 | GSPT1 | IKZF1 |
|---|---|---|---|---|---|---|---|---|
| | Ruxolitinib | 25800 | | | | | | |
| | Baricitinib | 1482 | | | | | | |
| Varied | 7 | 0.15 | 3 | 2 | 3 | 2 | 3 | 3 |
| JAK ligand | 5 | 1.2 | 3 | 3 | 2 | 2 | 3 | 3 |
| | 6 | 1.86 | 3 | 3 | 2 | 2 | 3 | 3 |
| Varied | 6 | 1.86 | 3 | 3 | 2 | 2 | 3 | 3 |
| CRBN ligand | 32 | 66.64 | 2* | 3* | 2* | 1 | 3 | 3 |
| (Bari series) | 76 | 21.52* | | 1 | | 1 | | |
| Varied | 34 | 0.6 | 3 | 2 | 3 | 2 | 3 | 3 |
| CRBN ligand (propyl series) | 7 | 0.15 | 3 | 2 | 3 | 2 | 3 | 3 |
| Varied CRBN | 7 | 0.15 | 3 | 2 | 3 | 2 | 3 | 3 |
| ligand & linker | 40 | 2.45 | 2 | 1 | 2 | 1 | 3 | |
| (propyl series) | 43 | 83.57 | | | | | 3 | |
| | 49 | 7350 | | | | | 2* | |
| | 88 | >3200 | 1 | 1 | 1 | 1 | 1 | 2* |
| Varied CRBN | 53 | 34.58* | | 1 | | | 3 | |
| ligand & linker | 6 | 1.86 | 3 | 3 | 2 | 2 | 3 | 3 |
| (Bari series) | 69 | >3000 | | 2 | | | | 1 |
| | 80 | >5500 | | 1 | | | | 1 |
| | 8 | 122.18* | | 3 | | | | 1 |
| | 56 | 562.39* | | 2 | | | | 1 |
| | 59 | 4191.00* | | 1 | | | | 1 |
| | 61 | 51.55* | | 1 | | | | 2 |
| | 76 | 21.52* | | 1 | | | | 1 |
| Varied lnker | 72 | >5061.59 | 1 | 2* | 2* | 1 | 1 | 1 |
| (PG/Bari series) | 65 | >783.88 | 1 | 2* | 2* | 1 | 2* | 1 |
| | 67 | >811.87 | 1 | 3* | 2 | 1 | 1 | 1 |
| | 76 | 21.52 | | 1 | | | 1 | |

MHHCALL4 EC50: *EC50 from partial dose response curve

Western Blot Conditions: No star, 100 nM PROTAC at 24 h; *1 uM PROTAC at 24 h.

Degradation: 3 = Strong (>60% degradation at 24 h); 2 = Medium (20-40% degradation at 24 h); 1 = None (<20% degradation at 24 h)

b. JAK-Directed PROTACs Potently Kill CRLF2-Rearranged ALL Cell Lines

Figure 6B:
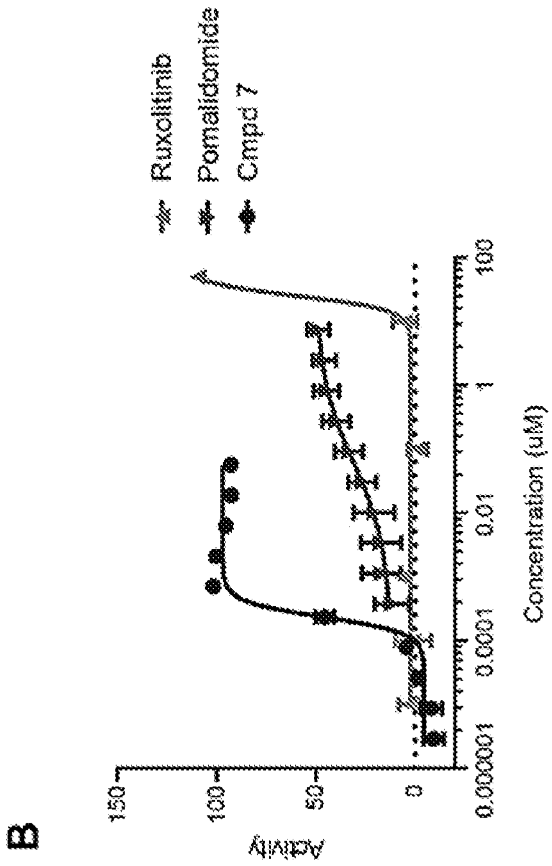
FIG. 6A-G show representative data illustrating protein degradation in MHH-CALL-4 cells treated with PROTAC compounds 5, 6, and 7.
Figure 6A:
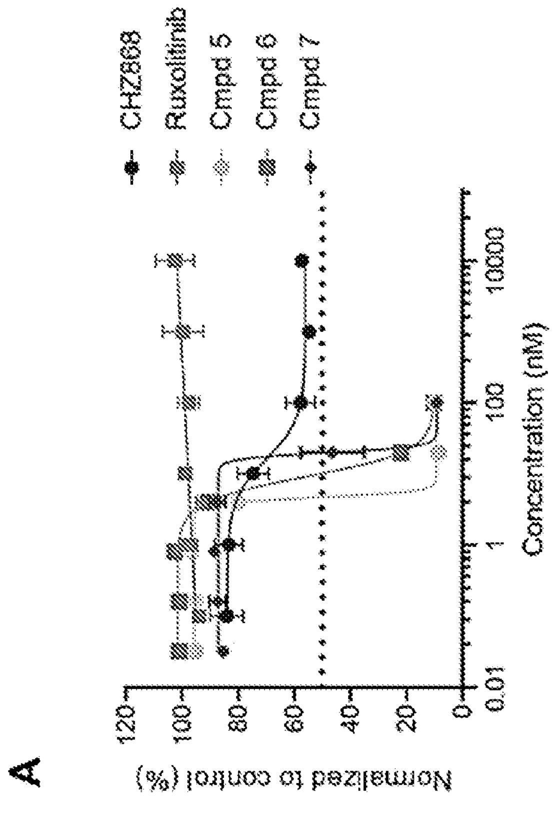
Figure 6C:
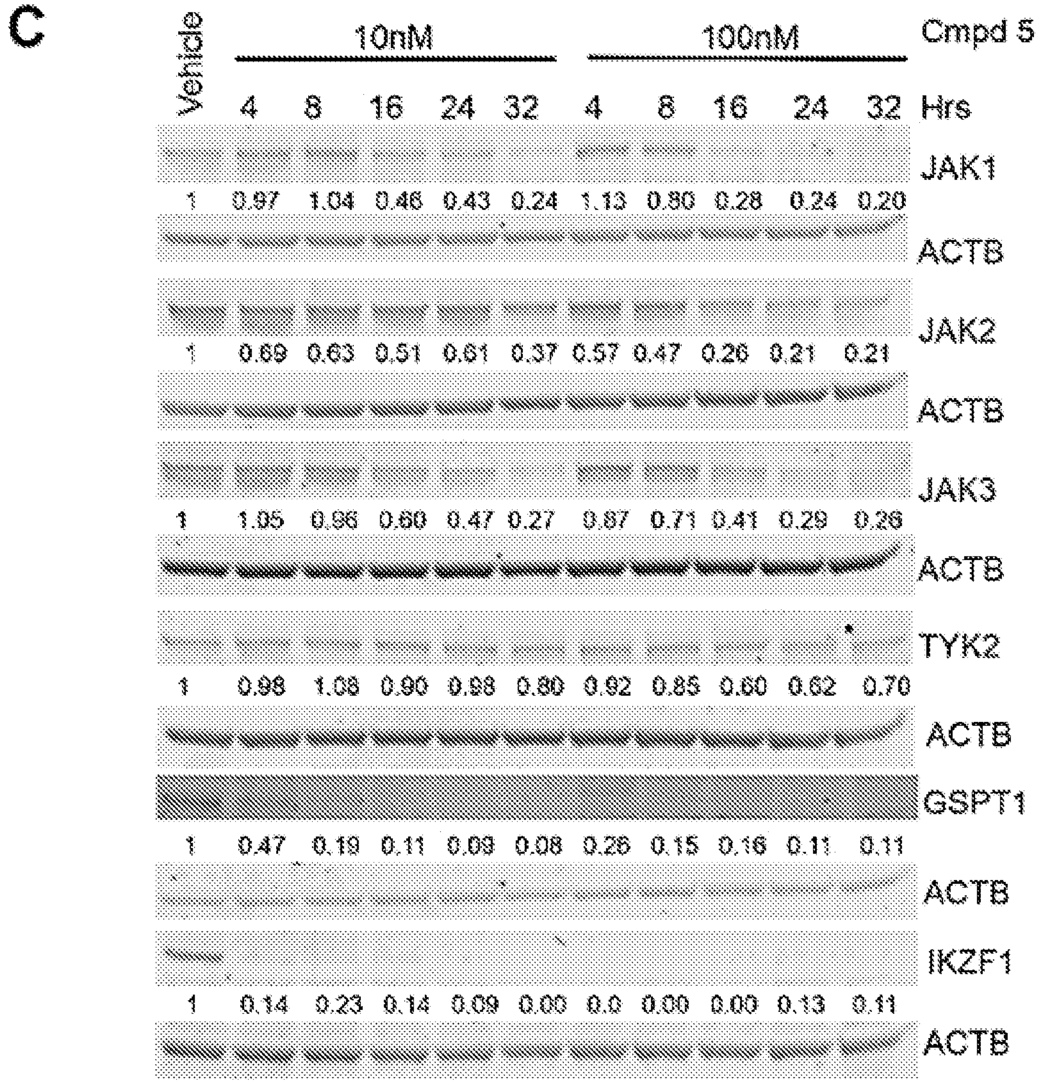
Figure 6D:
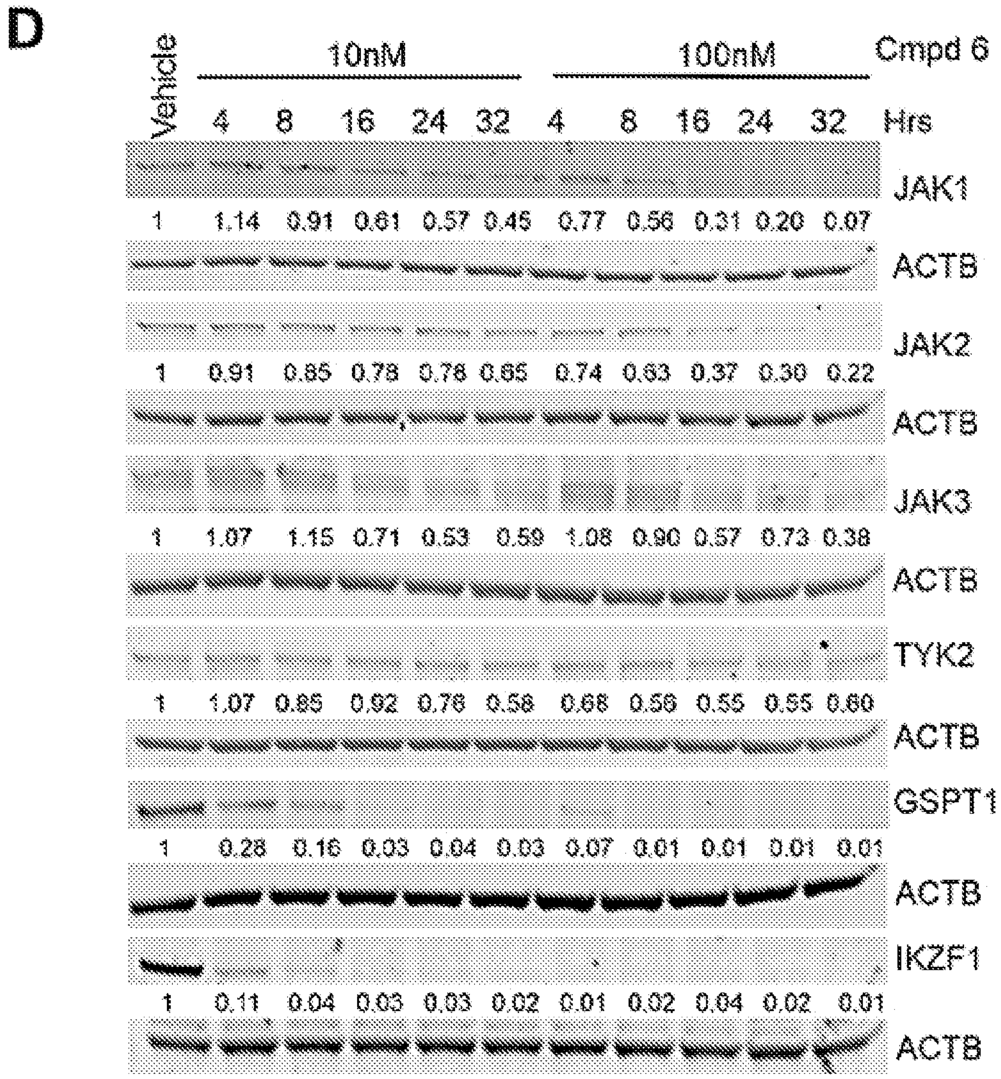
Figure 6E:
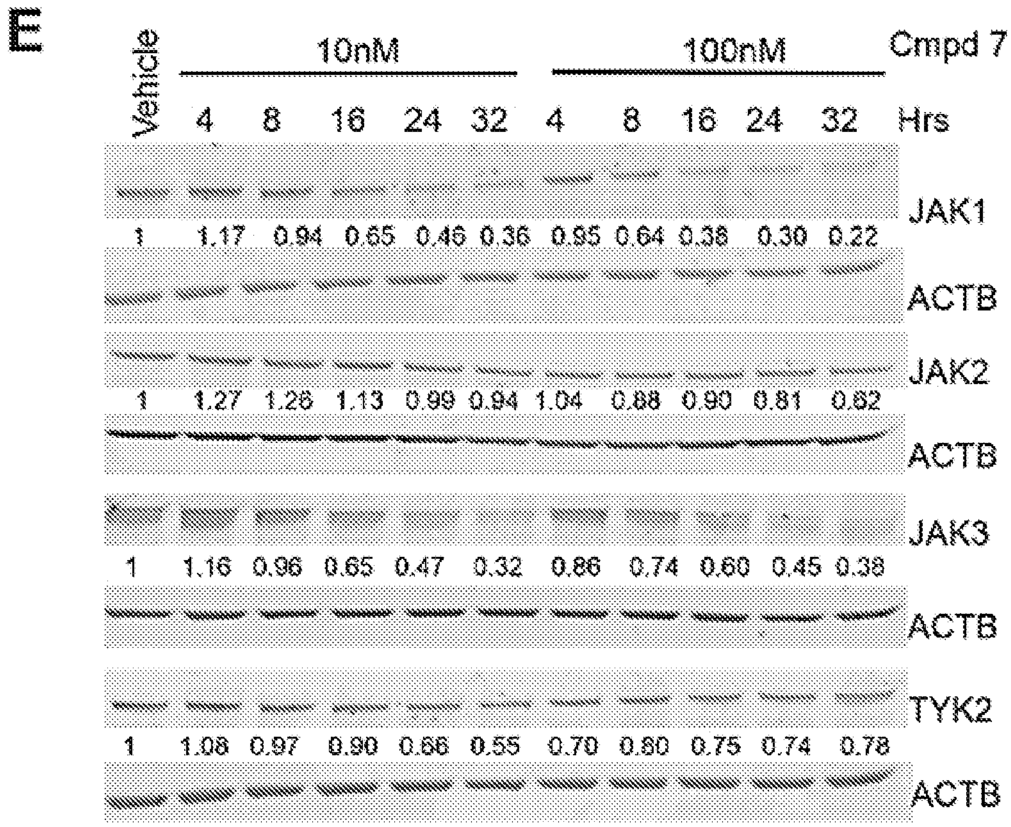
Figure 6F:
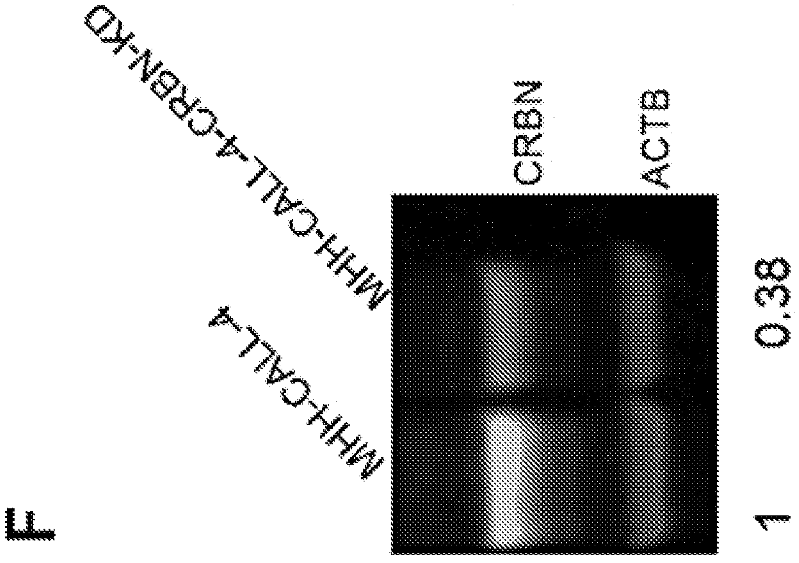
Figure 6G:
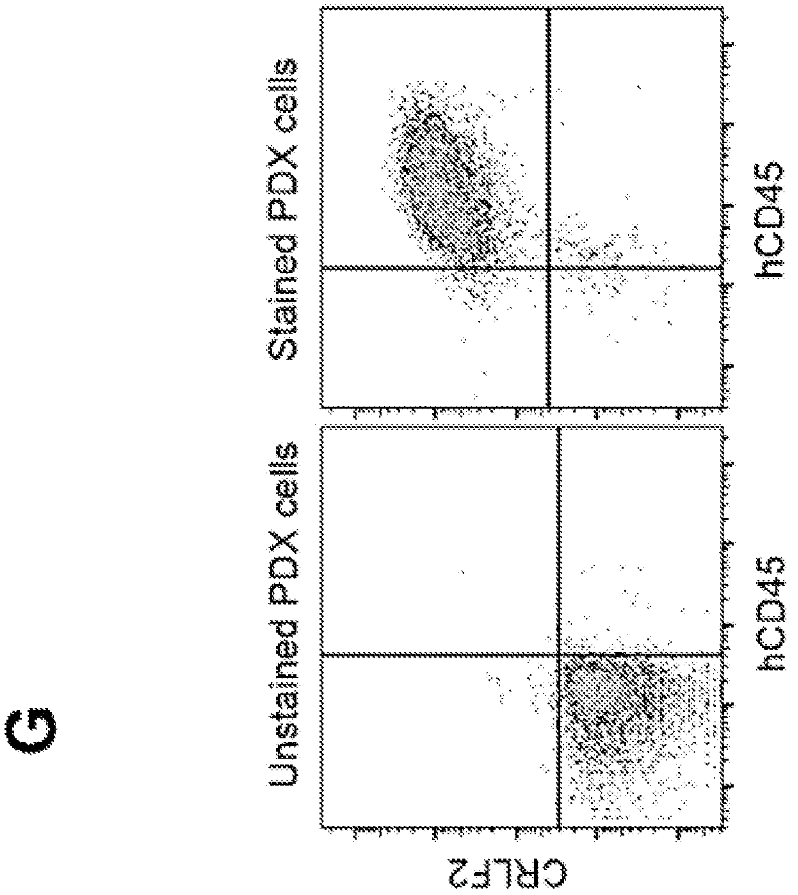

Consistent with prior data, weak activity of existing type I Janus kinase inhibitors was observed in cell line and xenograft models of CRLF2r ALL (FIG. 6A and FIG. 6G). In contrast, multiple Janus-kinase directed PROTACs exhibited potent activity, several exhibiting over 10,000-fold potency over the parent JAK inhibitor (ruxolitinib or baricitinib) or the CRBN-interacting moiety (thalidomide, lenalidomide or pomalidomide; FIG. 6B, Table 2, and Table 3). These compounds were most active in the CRLF2r cell lines MHH-CALL-4 and KOPN49, with less potency in MHH-CALL-2 (hypodiploid ALL) and KOPN75 (PAX5-ETV6) and least efficacy in 697 ($TCF_3$-PBX1) and NALM-6 (DUX4-rearranged ALL). Importantly, this activity was not attenuated by 0.6 μM of baricitinib, the parent JAK inhibitor indicating that activity was not merely due to Janus kinase inhibition (Table 2 and Table 3). In contrast, the activity of compound 7 was abolished either by co-treatment with 30 μM of lenalidomide, or CRISPR/Cas9 genome editing based knockdown of CRBN, indicating the E3 ligase activity was required for activity (Table 2 and Table 3).

Referring to FIG. 6A, PROTAC compounds 5, 6, and 7, but not Ruxolitinib and CHZ, two Jak2 inhibitors, show cytotoxicity in PDX cells ex vivo. Referring to FIG. 6B, compound 7 outcompeted Ruxolitinib and pomalidomide in a cytotoxicity assay in MHH-CALL-4 cells. Referring to FIG. 6G, a flow cytometry analysis showing overexpression of CRLF2 in hCD45+ PDX cells is shown.

c. PROTAC Activity is Influenced by Janus Kinase and GSPT1 Degradation

Figure 7B:
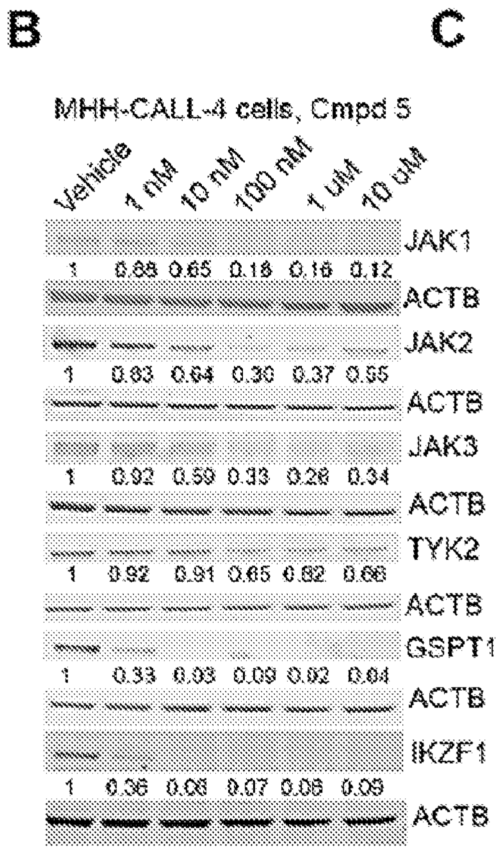
Figure 7C:
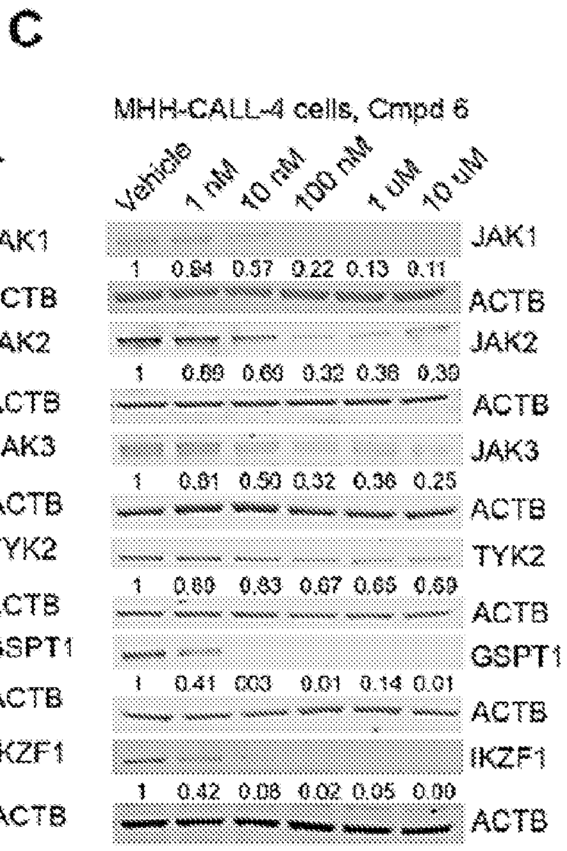
Figure 7D:
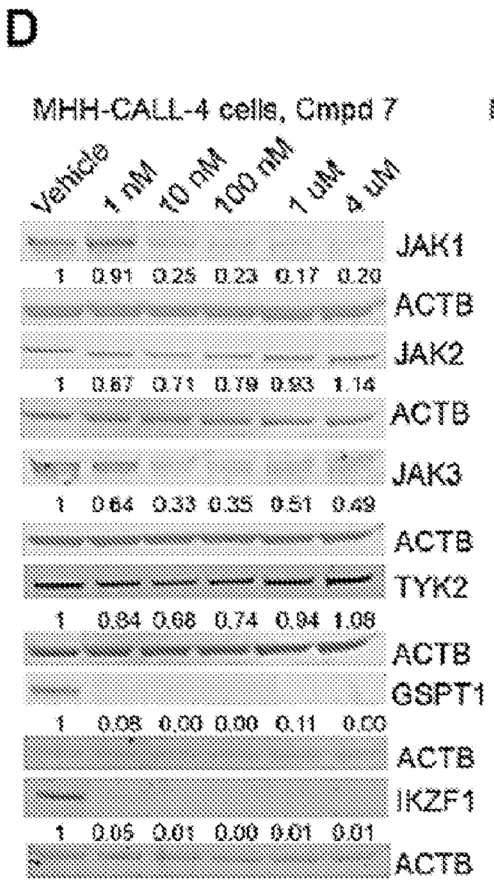
Figure 7E:
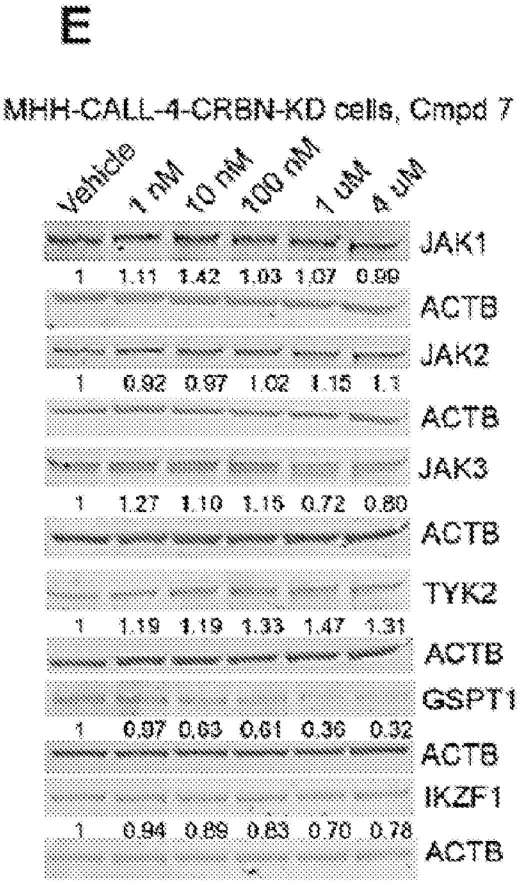
Figure 7F:
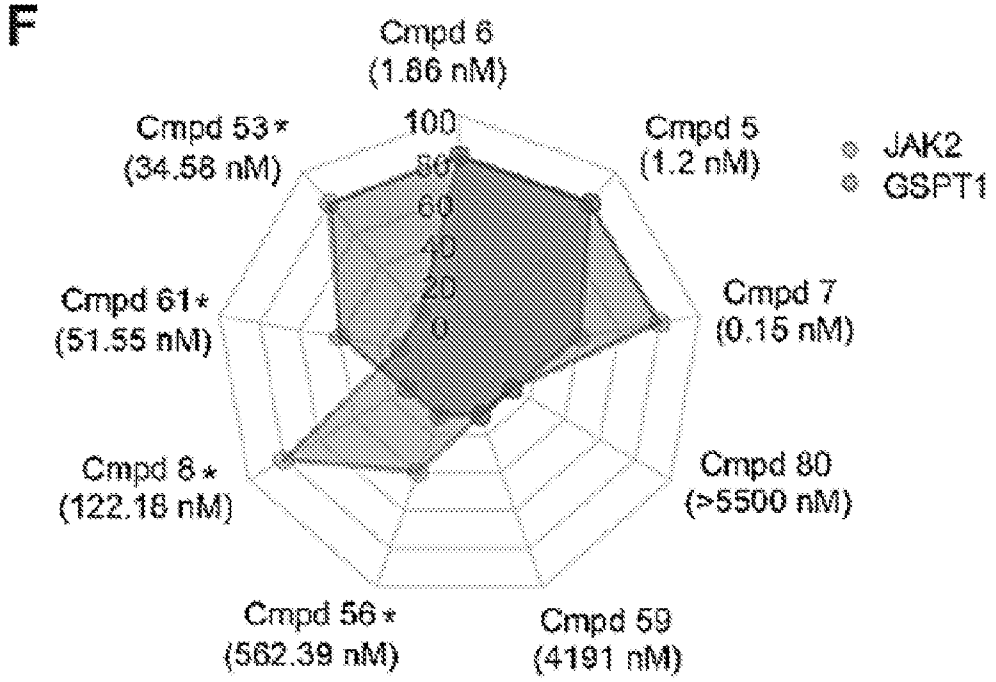
Figure 7G:
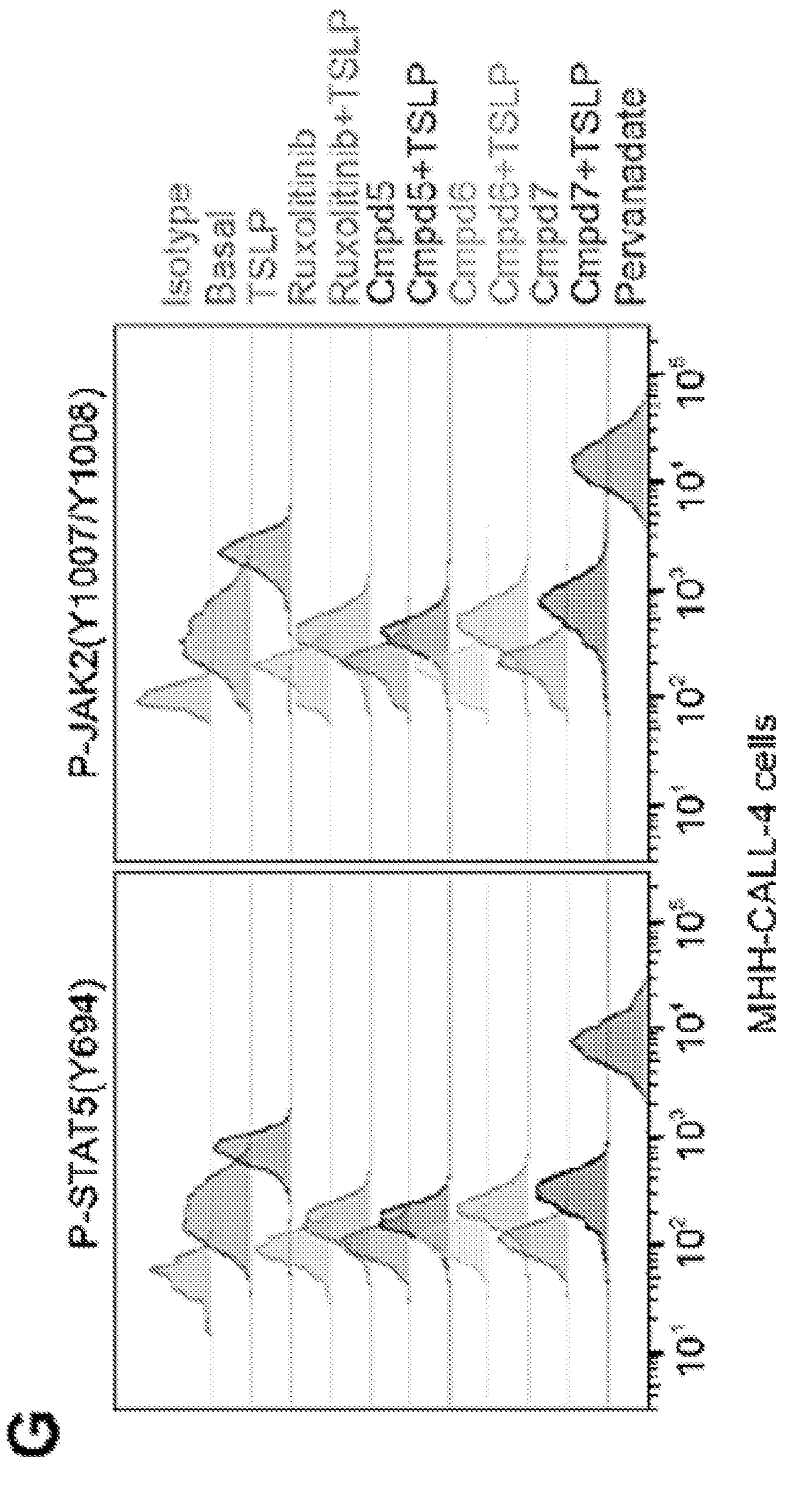
Figure 8:
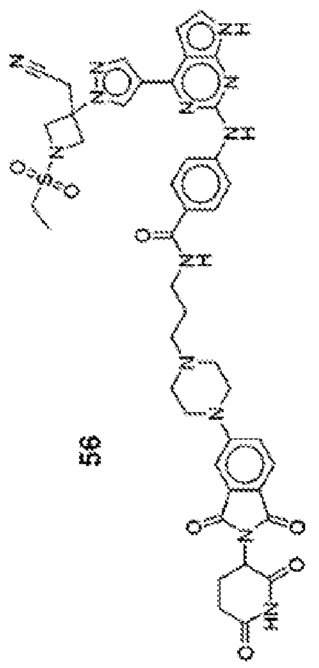
FIG. 8 shows representative structures of PROTACs 53, 56, 59, 61, and 80 described in spider chart in FIG. 7F.
Figure 8:
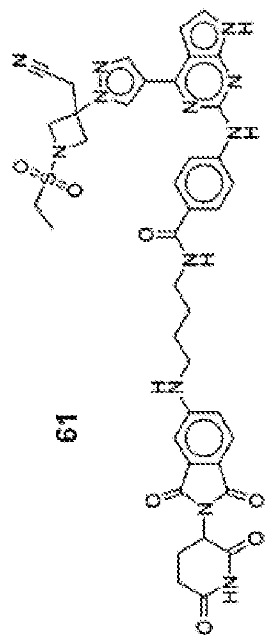
Figure 8:
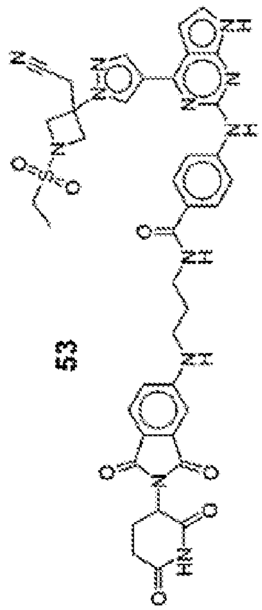
Figure 8:
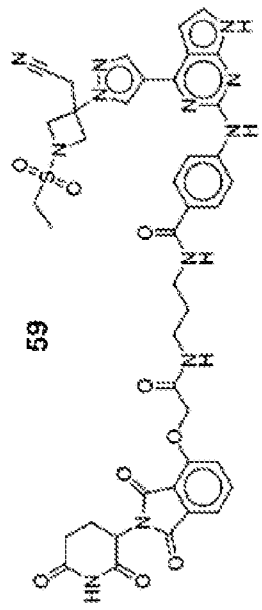
Figure 8:
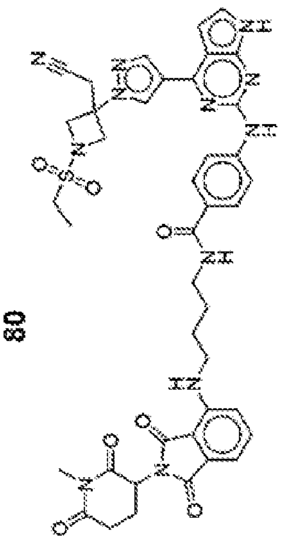

To determine the mechanistic basis of cell killing by JAK-directed PROTACs, time- and dose-dependent analysis of protein degradation was performed by immunoblotting. This demonstrated the ability of multiple PROTACs to degrade multiple Janus kinases (JAK1>JAK3>JAK2>>TYK2) that was also abolished by knockdown of CRBN (FIG. 6C, FIG. 6D, and FIG. 7B-E). In addition to Janus kinases, the known IMiD-induced CRBN neosubstrates IKZF1 and GSPT147 were degraded (FIG. 6C, FIG. 6D, and FIG. 7B-D). Thus, PROTAC-induced cell killing occurred despite loss of IKZF1, which otherwise promotes leukemic cell fitness in B-ALL (Mullighan, et al. (2008) *Nature* 453(7191): 110-114; Mullighan, et al. (2009) *N Engl J Med* 360(5): 470-480; Churchman, et al. (2015) *Cancer Cell.* 28(3): 343-356; Virely, et al. (2010) *Leukemia.* 24(6): 1200-1204; Joshi, et al. (2014) *Nat Immunol.* 15(3): 294-304). Correlative analysis of the extent of degradation of GSPT1 and JAK2 and killing of MHH-CALL-4 cells demonstrated that compounds with minimal activity on either target (e.g., 59 and 80) had relatively low activity; compounds resulting in preferential JAK2 (e.g., 8 or 56) or GSPT1 degradation (e.g., 53 or 61) were intermediately effective; and those compounds with the greatest degradation of both targets resulted in the greatest cellular cytotoxicity (FIG. 7F and FIG. 8). Phosphoflow cytometry of MHH-CALL-4 cells starved of cytokines overnight and treated with ruxolitinib or PROTAC (5, 6, or 7) for one hour before stimulation with or without administration of the CRLF2 ligand TSLP for 30 minutes showed that ruxolitinib and PROTACs resulted in comparable JAK inhibition (FIG. 7G). This is consistent with the notion that degradation, rather than simple inhibition of JAK2 activity was required for activity.

Referring to FIG. 6C-E, protein degradation in MHH-CALL-4 cells at different time (up to 32 hours) treated with 10 nM and 100 nM of compounds 5 (FIG. 6C), 6 (FIG. 6D) and 7 (FIG. 6E) are shown. Referring to FIG. 6F, cereblon (CRBN) was down regulated in MHH-CALL-4-CRBN-KD cells.

Figure 7A:
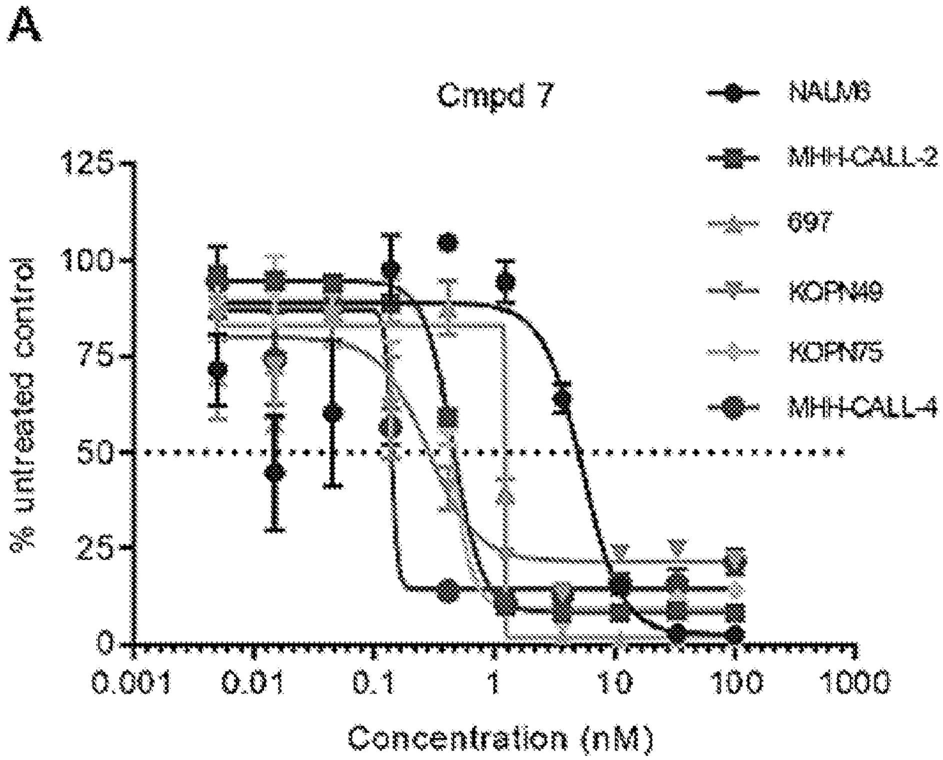
FIG. 7A-G show representative data illustrating protein degradation, cytotoxicity, and effect on JAK-STAT signaling pathway of PROTAC compounds in MHH-CALL-4 cells.

Referring to FIG. 7A, cytotoxicity of compound 7 in 6 different ALL cell lines (72 hours incubation) is shown. Referring to FIG. 7B-D, dose dependent degradation of compound 5, 6, and 7 in MHH-CALL-4 cells is shown. Referring to FIG. 7E, protein degradation by compound 7 in MHH-CALL-4 cells with CRBN knock-down is shown. Referring to FIG. 7F, a spider chart showing $EC_{50}$ data of 9 representative PROTACs and degradation of JAK2 and GSPT1 in MHH-CALL-4 cells is shown. Number in the chart is the percentage of protein degradation normalized to vehicle control. *$EC_{50}$ was determined based on partial cytotoxicity curve and additional data not shown. The structures of compounds 53, 56, 59, 61, and 80 are shown in FIG. 8. Referring to FIG. 7G, phosphoflow analysis of JAK-STAT5 signaling pathway in MHH-CALL-4 cells treated with or without 25 ng/mL of TSLP is shown. For inhibition, cells were pre-treated with 1 μM of ruxolitinib or PROTACs for one hour before TLSP stimulation.

d. In Vivo Activity of PROTACs

Figure 9A:
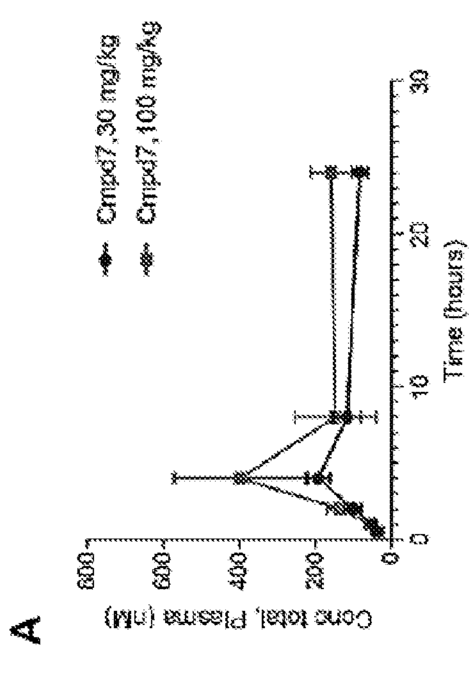
FIG. 9A-H show representative data illustrating the in vivo pharmacokinetic properties, pharmacodynamic properties, and efficacy of ruxolitinib based PROTAC compound 7.
Figure 9B:
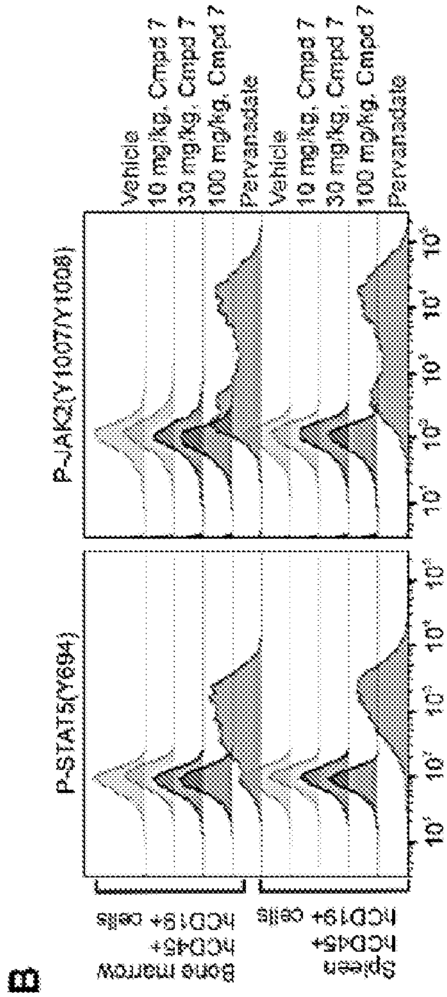
Figure 9C:
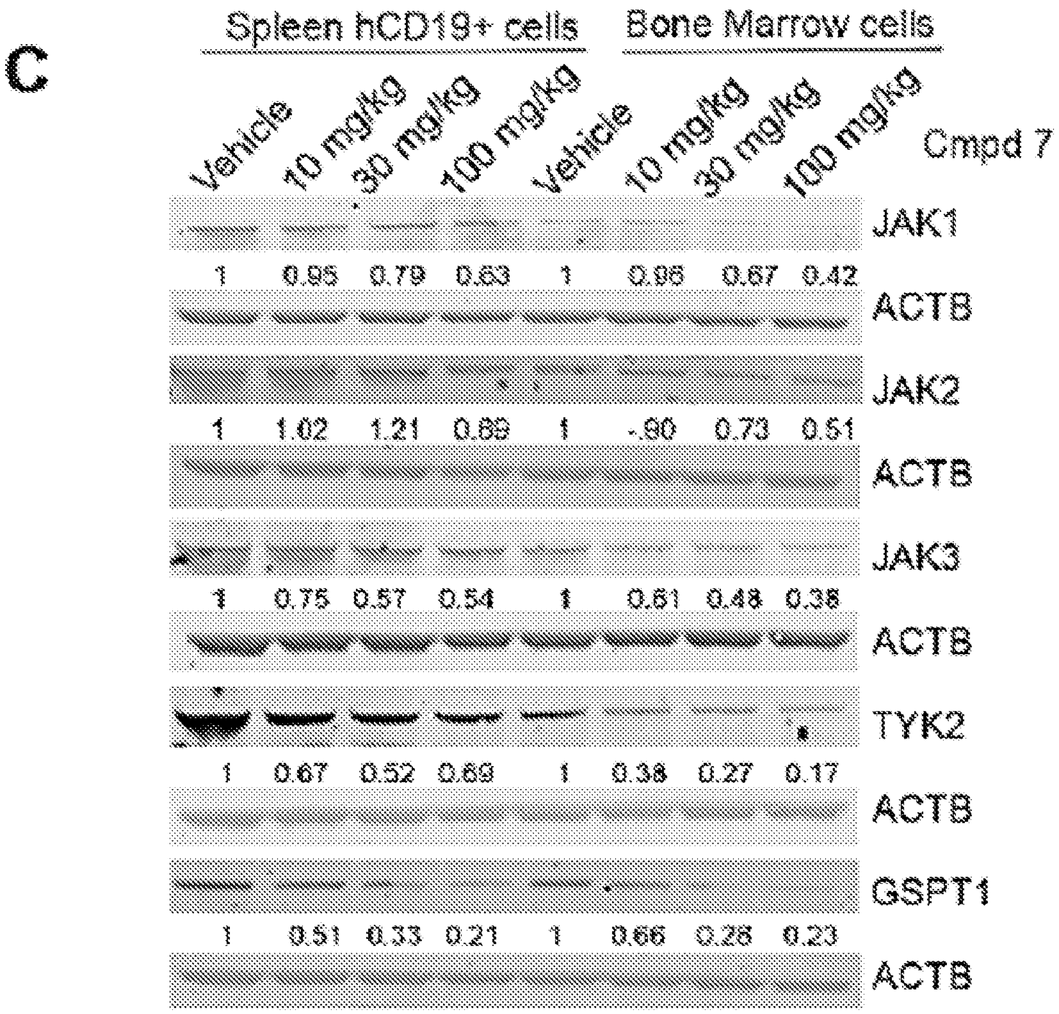
Figure 9D:
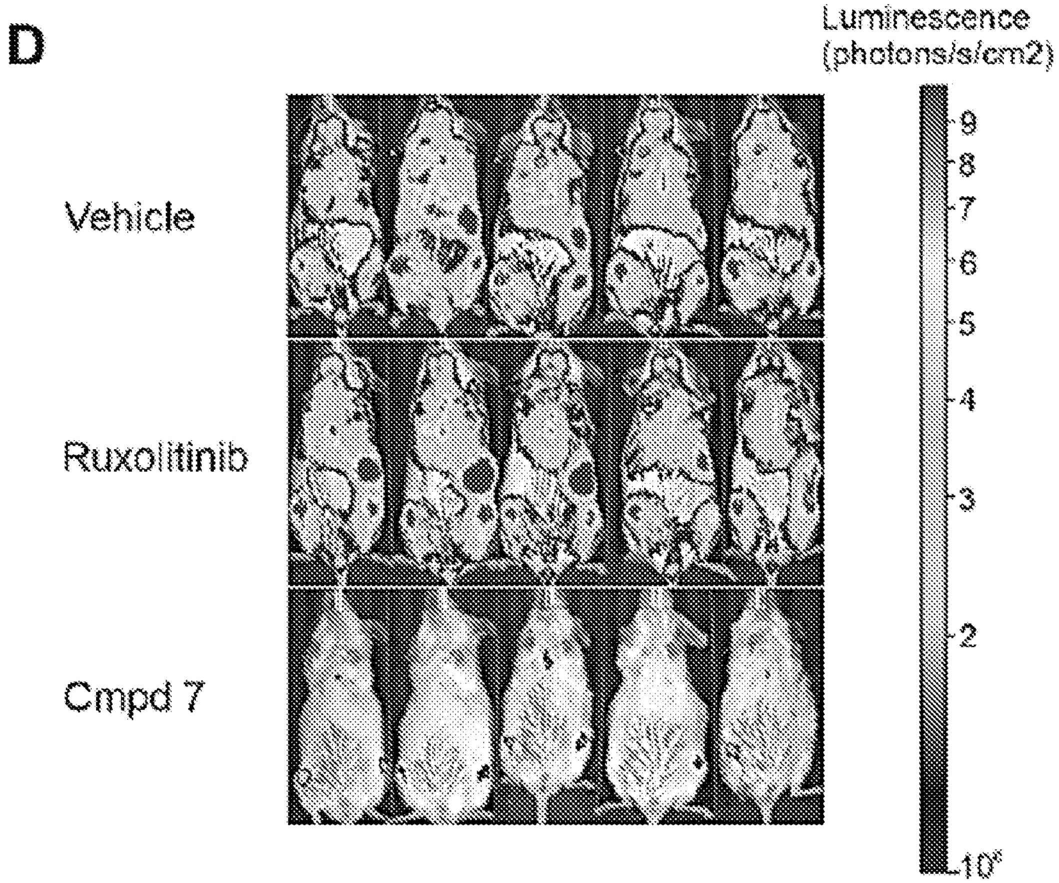
Figure 9E:
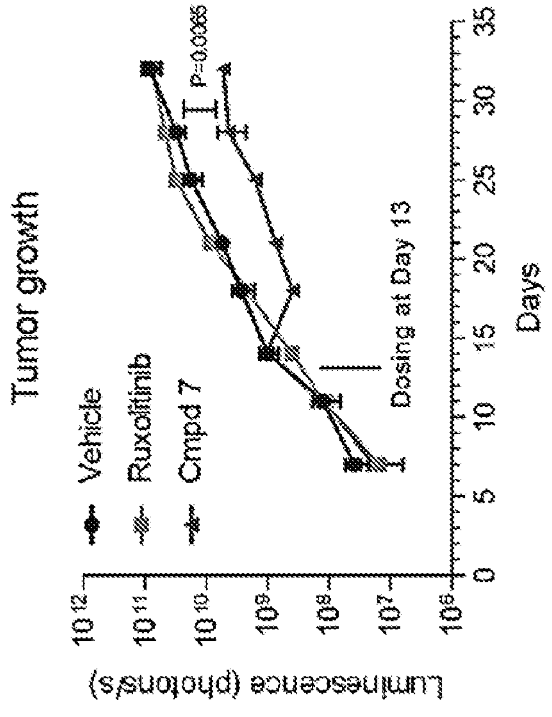
Figure 9F:
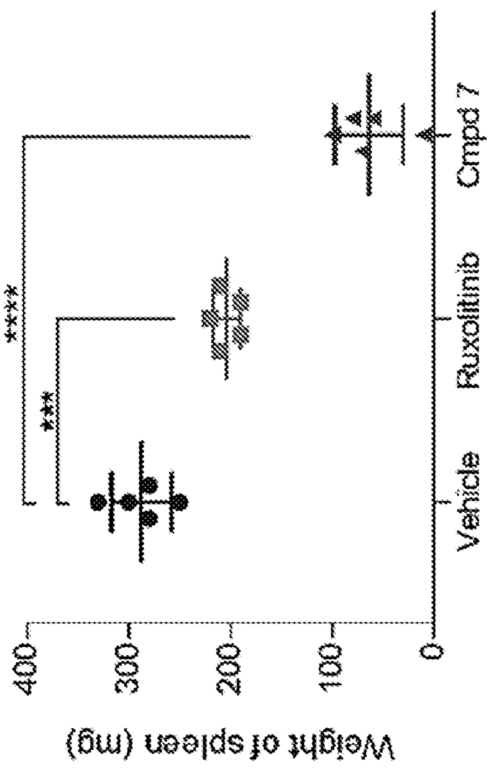
Figure 9H:
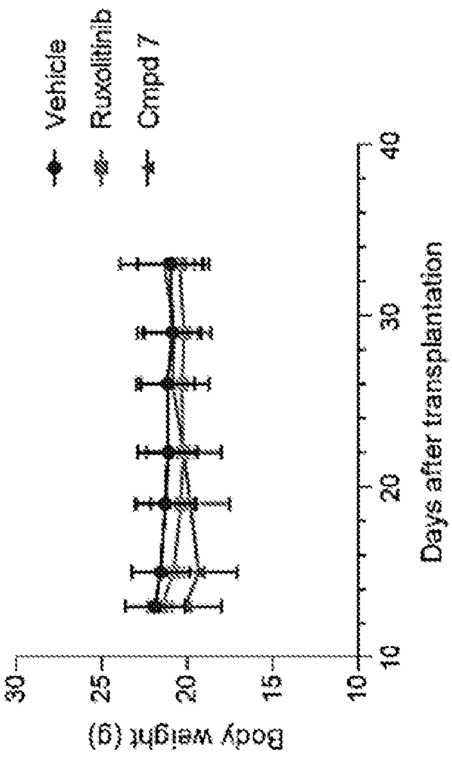

Next, the pharmacokinetics, anti-tumor activity, and pharmacodynamics of PROTACs were examined in vivo. To guide selection of an optimal in vivo dose of PROTAC compound 7, pharmacokinetic analysis was performed at 30 and 100 mg/kg doses showing that sustained in vivo exposure could be achieved after intraperitoneal dosing, with plasma concentration after 24 hours well above the compounds cellular $EC_{50}$ value (FIG. 9A and Table 7). Doses of 10, 30, and 100 mg/kg were used for pharmacodynamic studies in which leukemic cells harvested from NSG engrafted with CRLF2r leukemic cells marked with a lentiviral vector expressing yellow fluorescent protein and luciferase were subjected to phosphoflow cytometry and immunoblotting for Janus kinases and GSPT1. This showed dose dependent inhibition of JAK2 and STAT5 phosphorylation and JAK/GSPT1 degradation that was near maximal at the 30 mg/kg dose (FIG. 9B and FIG. 9C). In vivo, ruxolitinib alone did not attenuate leukemic cell proliferation of CRLF2r B-ALL xenograft. In contrast, monotherapy with compound 7 administered at 30 mg/kg intraperitoneally daily resulted in marked reduction in leukemia burden in bone marrow, blood, and spleen, and as measured by total body bioluminescent imaging over a 28-day dosing period (FIG. 9D-G and FIG. 19A-D). Administration of compound 7 was well tolerated with no weight loss or perturbation in blood counts over a 28-day period (FIG. 9H and data not shown).

Figure 9G:
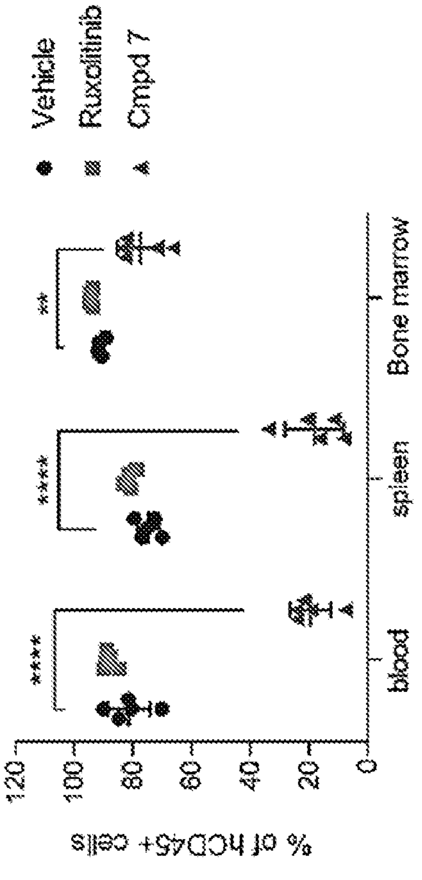
Figure 10B:
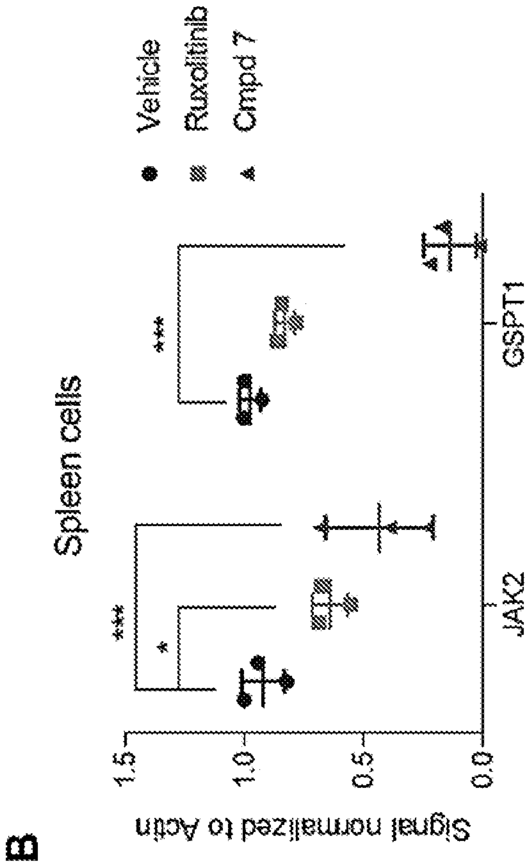
FIG. 10A-D show representative data from an ex vivo cytotoxicity assay of PROTAC compounds and the protein degradation of compound 7 used in the in vivo efficacy study.
Figure 10A:
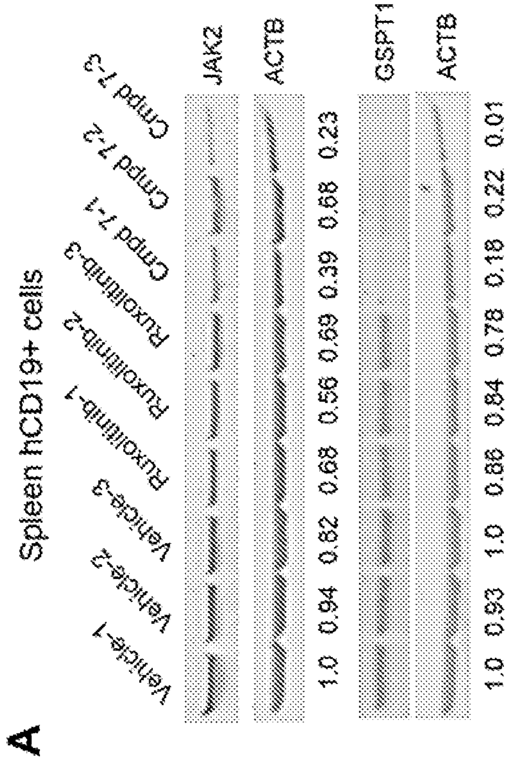
Figure 10C:
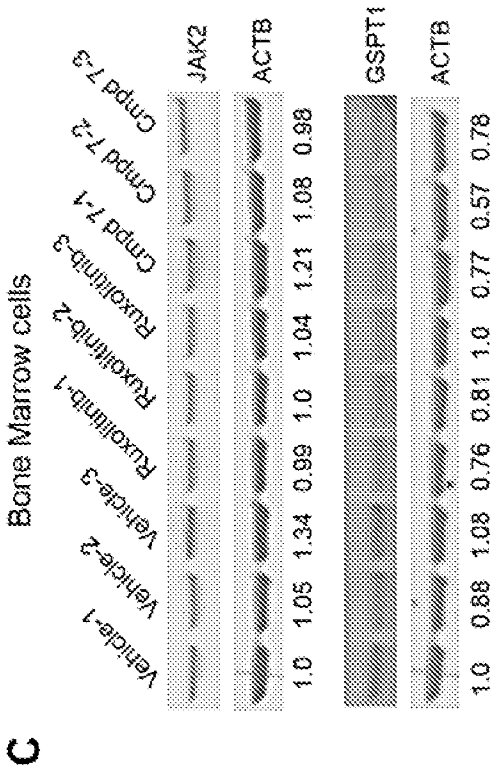
Figure 10D:
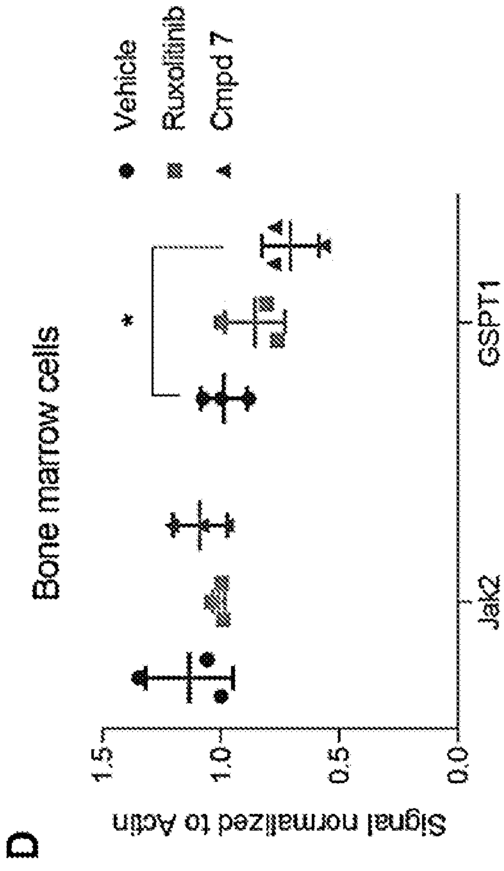

Referring to FIG. 9A, plasma concentration of compound 7 in mouse injected i.p. with single dose of compound 7 is shown. Referring to FIG. 9B, phosphoflow analysis of compound 7's effect on JAK-STAT signaling pathway in vivo is shown. Referring to FIG. 9C, degradation of JAK family kinases and GSPT1 by compound 7 in vivo is shown. Referring to FIG. 9D and FIG. 9E, compound 7 but not ruxolitinib slowed leukemia growth in PDX. Bioluminescence imaging (FIG. 9D) was taken at day 32 after transplantation, two days before end of study, with leukemia burden during the study shown in FIG. 9E. Referring to FIG. 9F and FIG. 9G, compound 7 reduced spleen size and tumor burden in PDX model. Referring to FIG. 9H, the weight of NSG mice dosed with compounds and vehicle in an in vivo efficacy study are shown. P<0.01, *P<0.001, ****P<0.0001.

TABLE 7

| Mouse ID | Dose (mg/kg) | N of samples | Cmax (ng/mL) | Tlast (hr) | Clast (ng/mL) | AUClast (hr*ng/mL) |
|---|---|---|---|---|---|---|
| 2300 | 30 | 6 | 114.7 | 24 | 45.5 | 1350 |
| 2301 | 30 | 6 | 125.8 | 24 | 53 | 1759.1 |
| 2302 | 30 | 6 | 155.3 | 24 | 74.3 | 2248.2 |
| 2303 | 100 | 6 | 233.2 | 24 | 79.1 | 2179.3 |
| 2304 | 100 | 6 | 410.5 | 24 | 152 | 4459 |
| 2305 | 100 | 6 | 181.3 | 24 | 98.1 | 1884.7 |

18. Discussion

CRLF2r ALL is the clinically most problematic form of B-ALL. CRLF2r ALL accounts for the majority of Ph-like ALL cases and is consistently associated with high risk features and poor outcome with conventional therapy (Roberts, K G (2018) *Best Pract Res Clin Haematol.* 31(4): 351-356; Tasian, et al. (2017) *Blood.* 130(19): 2064-2072; Jain, et al. (2017) *Blood.* 129(5): 572-581). In view of the extensive genetic and preclinical data indicating the importance of CRLF2 overexpression and concomitant lesions driving activation of JAK-STAT and parallel signaling pathways as drivers of leukemogenesis in this entity (Yoda, et al. (2010) *Proc Natl Acad Sci USA.* 107(1): 252-257; Russell, et al. (2009) *Blood.* 114(13): 2688-2698; Mullighan, et al. (2009) *Nat Genet.* 41(11): 1243-1246; Tasian, et al. (2012) *Blood.* 120(4): 833-842), abrogation of JAK-STAT signaling is intuitively attractive. While type I JAK inhibitors have shown promise in preclinical models, data from human models (e.g., PDX) and emerging clinical data have shown variable or poor activity of ruxolitinib in CRLF2r ALL, at least when administered as single agent (Jain, et al. (2017) *Blood.* 130(Suppl 1): 1322-1322). While the basis for this in unclear, this has been attributed to activation of JAK1/3 due to stabilization of phosphorylated JAK2 with type I inhibitors, and/or activation of PI3K and ERK signaling pathways.

Here, crystal structures of JAK inhibitors bound to the JH1 kinase domain of JAK2 were obtained to inform the rational design and synthesis of multiple series of JAK-directed PROTACs utilizing different parent JAK inhibitors, CRBN-interacting IMiDs, and their derivatives. Solute-exposed regions of JAK inhibitors were identified, along with moieties amenable for modification and attachment of linkers. PROTACs generated from ruxolitinib and baricitinib showed potent anti-leukemic efficacy. Several such compounds showed remarkable efficacy, with, e.g., compound 7 showing greater than 70,000-fold activity in CRLF2r MHH-CALL-4 cells compared to each of the parent compounds, ruxolitinib and pomalidomide. This activity requires CRBN-mediated protein degradation, as the compounds showed similar inhibition of JAK2 phosphorylation to ruxolitinib; efficacy was not abolished by competition with parent JAK inhibitor, whereas activity was abolished by genetic disruption of CRBN. These results contrast with prior efforts to design JAK-directed PROTACs that have not been tested in tumors (Shah, et al. (2020) *Bioorg Med Chem.* 28(5): 115326).

Importantly, by comparing protein degradation patterns and anti-leukemic activity of multiple series of compounds, the relative contribution of degradation of key targets, including GSPT1 as well as Janus kinases, could be examined. GSPT1 is a widely expressed translation termination factor, and a neosubstrate of CRBN upon treatment with molecular glues such as CC-885 that have shown efficacy in acute myeloid leukemia (Matyskiela, et al. (2016) *Nature.*

535(7611): 252-257). Using immunoblotting and global proteomic analysis, it was shown that PROTACs active in cellular assays resulted in degradation of multiple Janus kinases (typically, JAK1, JAK2, and JAK3 more than TYK2) as well as GSPT1 and the known CRBN neosubstrates IKZF1 and IKZF3. While IMiD or PROTAC-based degradation of IKZF1/3 is of therapeutic benefit in mature B cell malignancies such as myeloma or chronic lymphocytic leukemia, degradation in pre-B cell ALL may be expected to increase leukemic cell survival, as loss-of-function/dominant negative IKZF1/3 alterations are common initiating or cooperating leukemogenic in multiple subtypes of pre-B ALL, including Ph-like ALL (Mullighan, et al. (2008) *Nature.* 453(7191): 110-114; Mullighan, et al. (2009) *N Engl J Med* 360(5): 470-480; Holmfeldt, et al. (2013) *Nat Genet.* 45(3): 242-252). Moreover, many somatic mutant forms of IKZF1 lack the second N-terminal zinc finger that interacts with the thalidomide-CRBN-E3 ligase complex, and thus IMiD or PROTAC degraders may selectively degrade wild type, but not mutant IKZF1 observed in B-ALL. Despite these potential caveats, direct degradation of IKZF1 in ALL lines with IMiDs such as thalidomide had minimal effect on ALL cell viability. In contrast, degradation of GSPT1 was observed after treatment with the most potent PROTACs (e.g., compounds 5, 6, and 7), and chemical modification of PROTACs to attenuate GSPT1 degradation while retaining JAK2 activity resulted in reduced activity (e.g., compound 8). These results are consistent with other data that while JAK2 mutation and activation is required for transformation and induction of leukemia, inactivation of JAK2 alone is relatively dispensable for leukemic cell maintenance (Mullighan, et al. (2009) *Nat Genet.* 41(11): 1243-1246; Kim, et al. (2018) *Genes Dev.* 32(11-12): 849-864). In contrast, the data herein support the notion that combined targeting of JAK2 with other cellular vulnerabilities such as BCL25,58, PI3K11, MYC57, and in the present study, GSPT1, are required for optimal antitumor activity.

CRLF2r ALL represents only one of multiple hematopoietic malignancies that harbor JAK-STAT activating mutations, and/or are postulated to be dependent on JAK-STAT signaling. These results, which describe the structural and chemical principles for the rational design of JAK-specific PROTACs with "tunable" specificity, provides the foundation for the evaluation of such compounds across a range of potentially susceptible malignancies.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

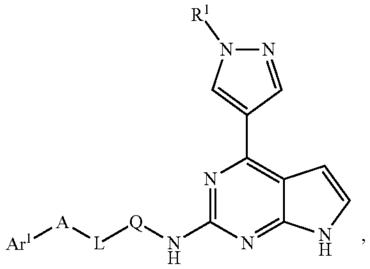

wherein A is selected from —O—, —S—, —NH—, —$CH_2$—, —O—(C1-C4 alkyl)-C(O) NH—, and a structure

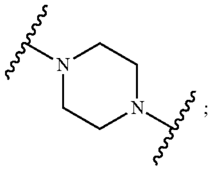

wherein L is selected from C2-C15 alkyl and —$(CH_2CH_2O)_n$(C1-C4 alkyl)-;

wherein n, when present, is selected from 1, 2, 3, 4, 5, 6, 7, and 8;

wherein Q is a structure:

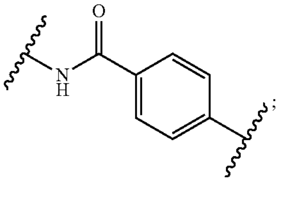

wherein $R^1$ is selected from C1-C8 alkyl, C1-C8 hydroxyalkyl, C1-C8 cyanoalkyl, C1-C8 aminoalkyl, and a structure selected from:

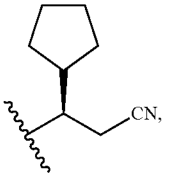
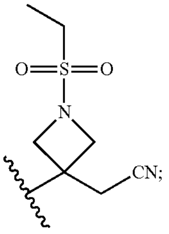 and 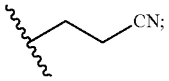

and wherein $Ar^1$ is a structure selected from:

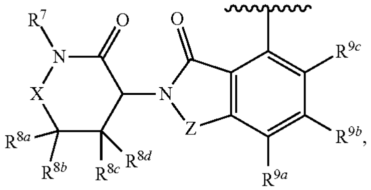
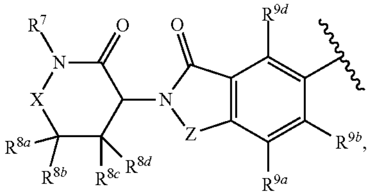
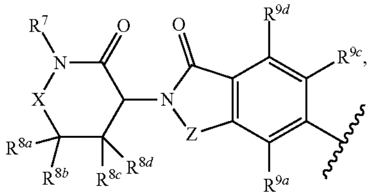 and
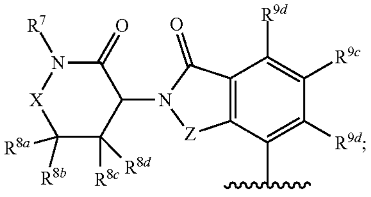

wherein X is selected from —C(O)— and —$CH_2$;

wherein Z is selected from —$CH_2$— and —C(O)—;

wherein $R^7$ is selected from hydrogen and C1-C8 alkyl;

wherein each of $R^{8a}$, $R^{8b}$, $R^{8c}$, and $R^{8d}$ is independently selected from hydrogen, halogen, —$NH_2$, —OH, —$NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4) (C1-C4) dialkylamino, and C1-C4 aminoalkyl; and wherein each of $R^{9a}$, $R^{9b}$, $R^{9c}$, and $R^{9d}$, when present, is independently selected from hydrogen, halogen, $-NH_2$, —OH, $-NO_2$, —CN, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4) (C1-C4) dialkylamino, and C1-C4 aminoalkyl, or a pharmaceutically acceptable salt thereof.

2. The compound of claim 1, wherein A is selected from —NH— and $-CH_2-$.

3. The compound of claim 1, wherein L is C2-C15 alkyl.

4. The compound of claim 1, wherein L is $-(CH_2CH_2O)_n(C1\text{-}C4\ alkyl)$-.

5. The compound of claim 1, wherein $R^1$ is C1-C8 alkyl.

6. The compound of claim 1, wherein $Ar^1$ is a structure represented by a formula:

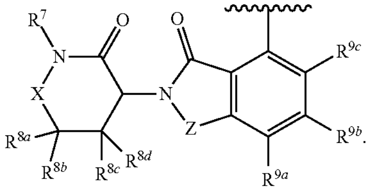

7. The compound of claim 1, wherein $Ar^1$ is a structure represented by a formula:

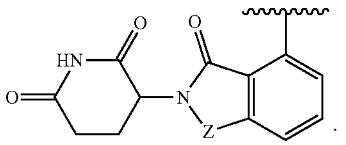

8. The compound of claim 1, wherein $Ar^1$ is a structure:

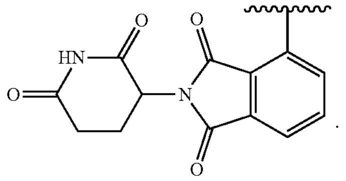 [SMILES: *c1cccc2c1C(=O)N(C1CCC(=O)NC1=O)C2=O]

9. The compound of claim 1, wherein $Ar^1$ is a structure represented by a formula:

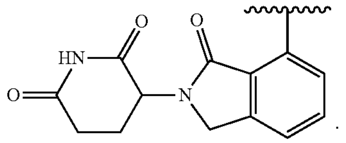 [SMILES: *c1cccc2c1C(=O)N(C1CCC(=O)NC1=O)C2]

10. The compound of claim 1, wherein Z is —C(O)—.

11. The compound of claim 1, wherein the compound is selected from:

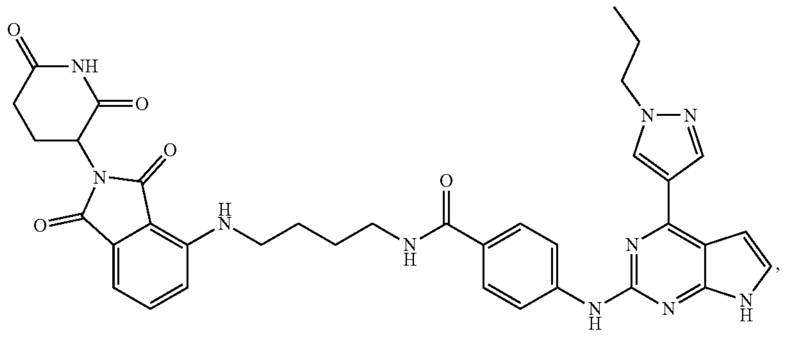

,

-continued
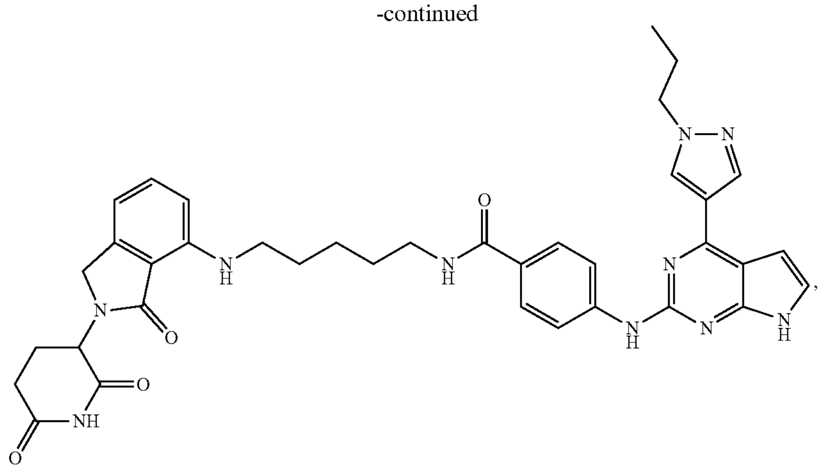
,
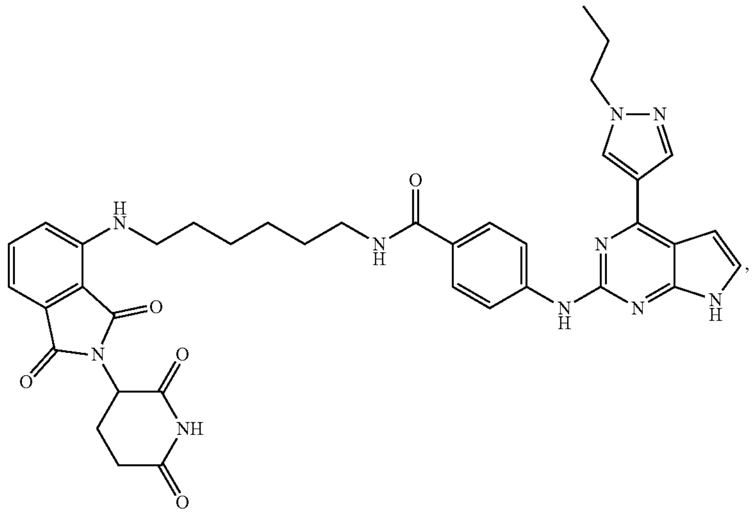
,
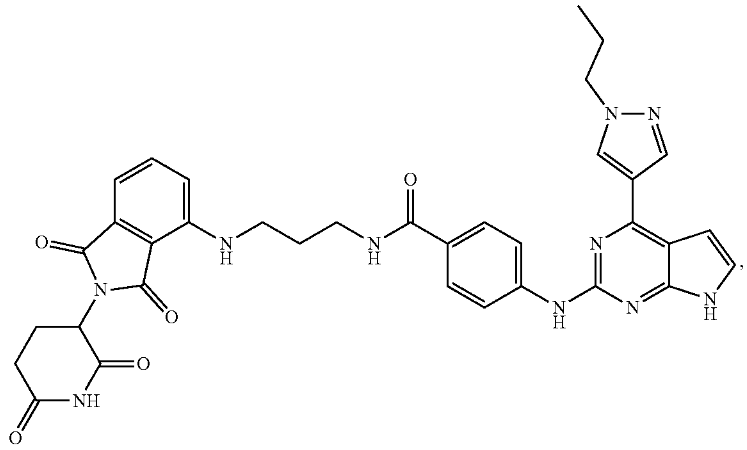
,

-continued
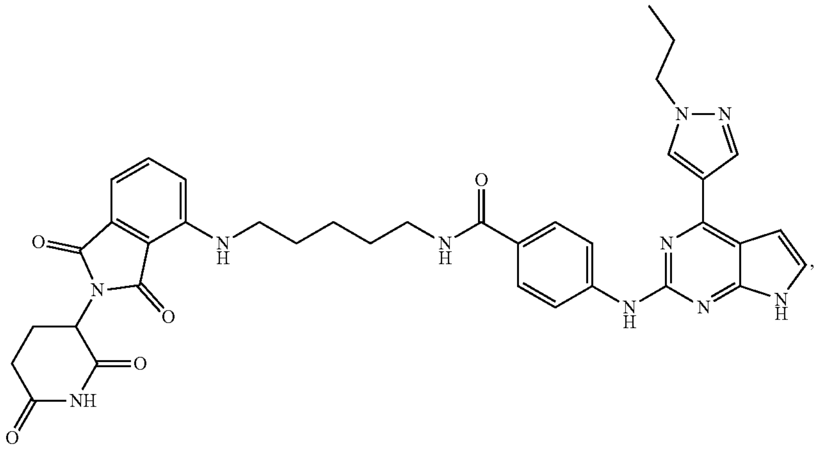
,
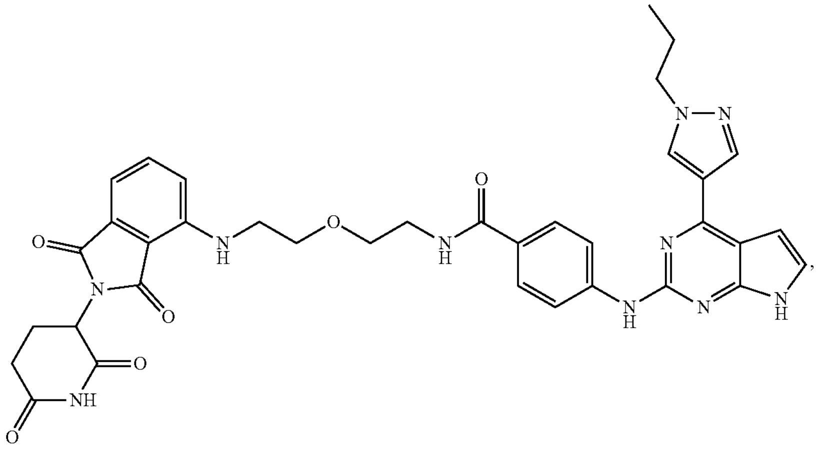
,
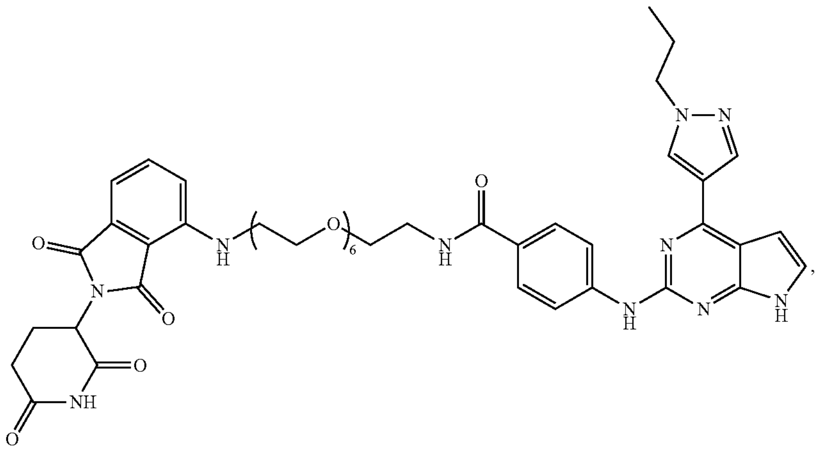
,

-continued
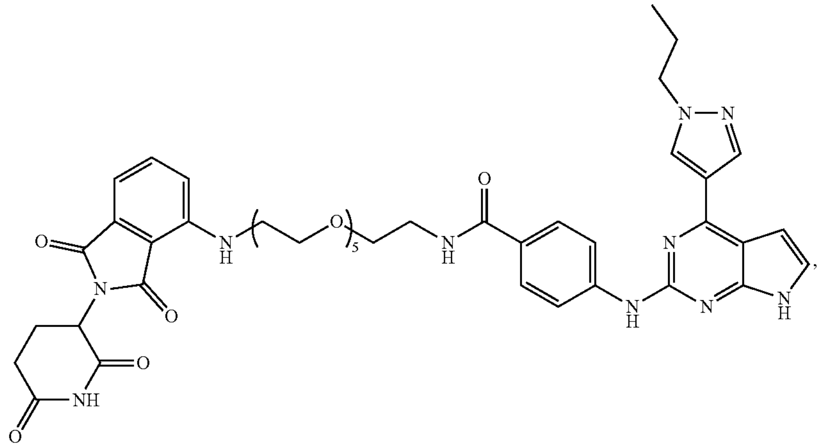
,
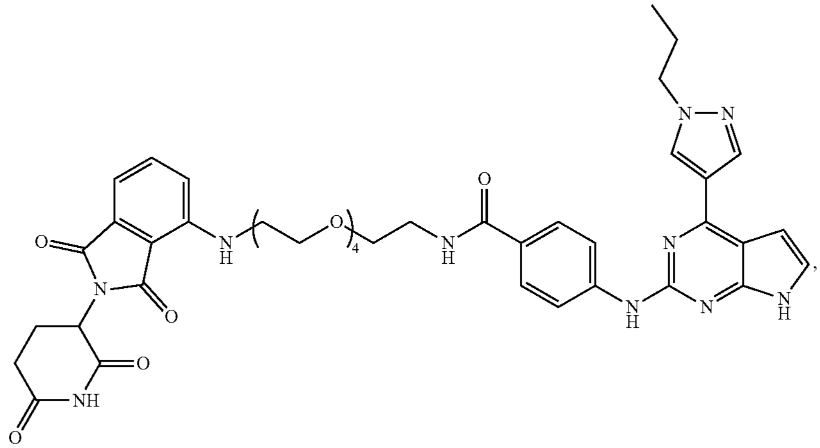
,
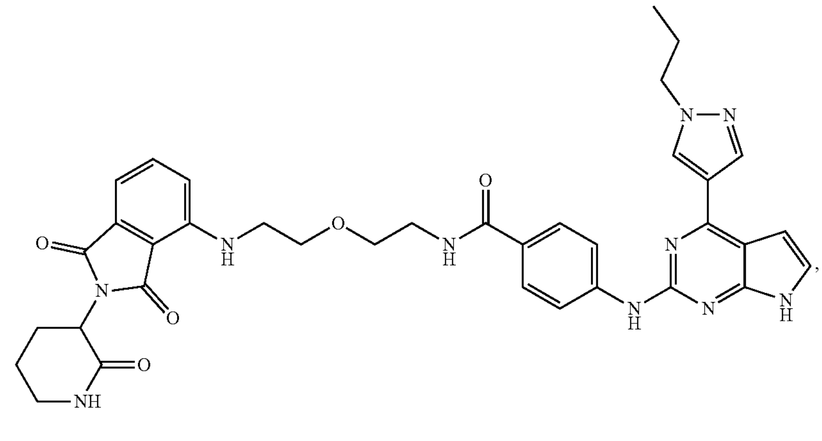
,

-continued
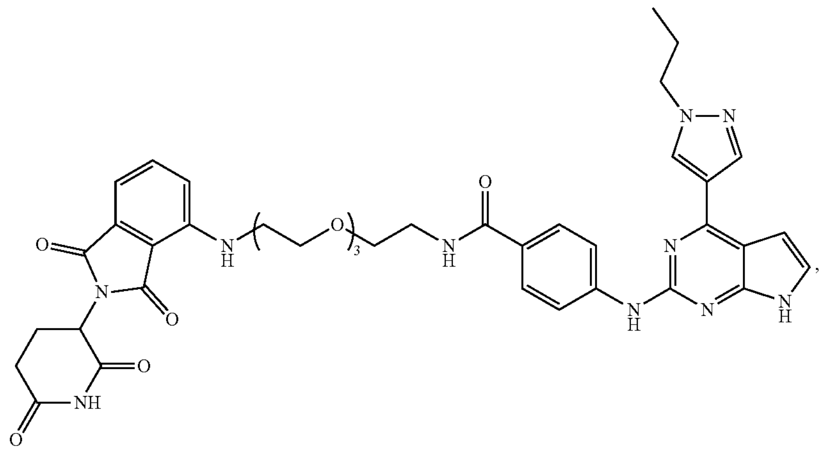
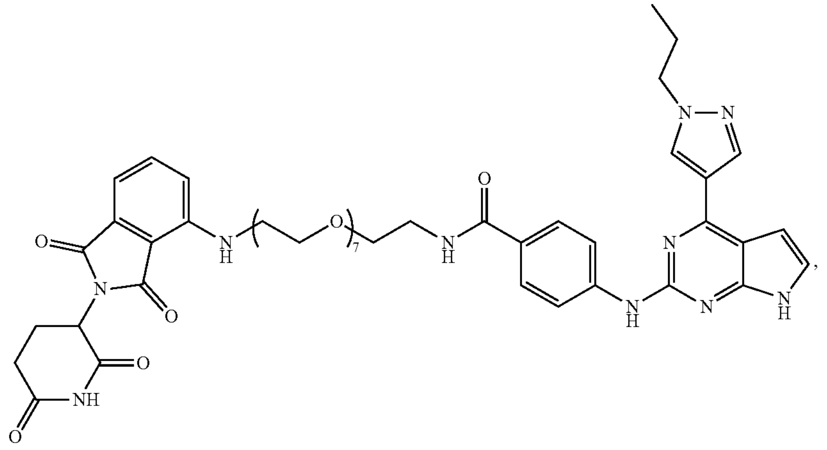
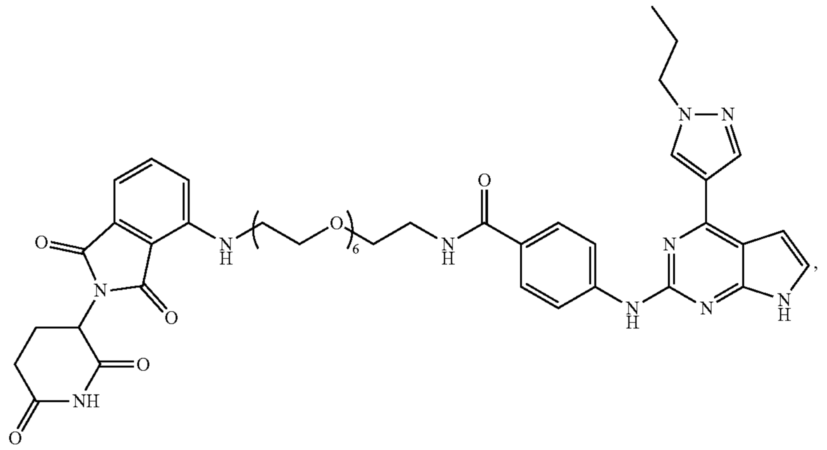

-continued
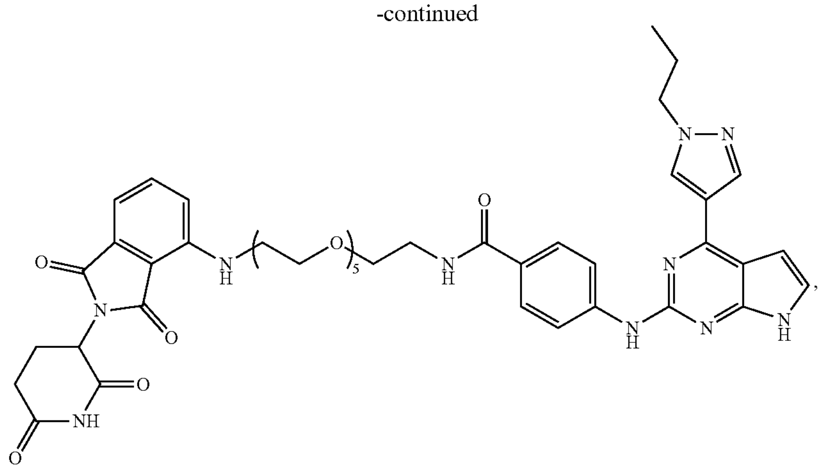
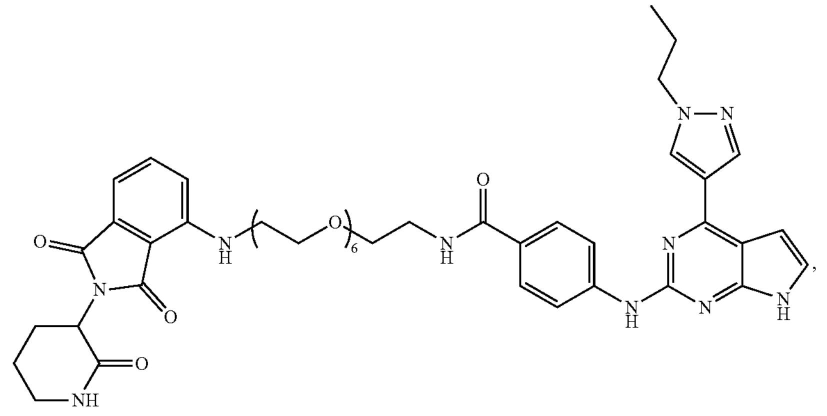
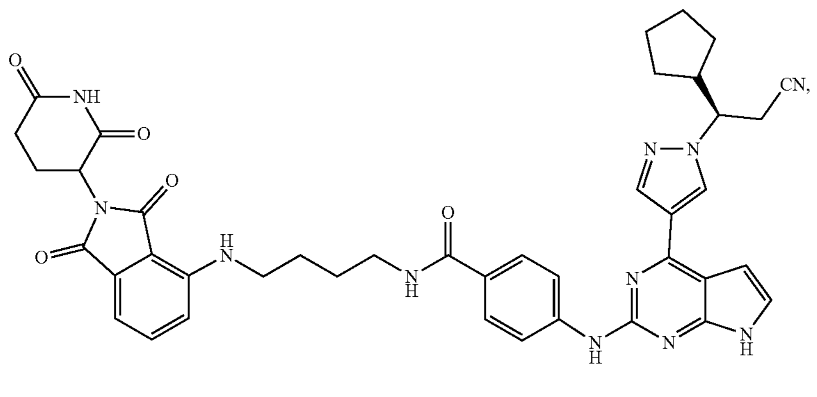

-continued
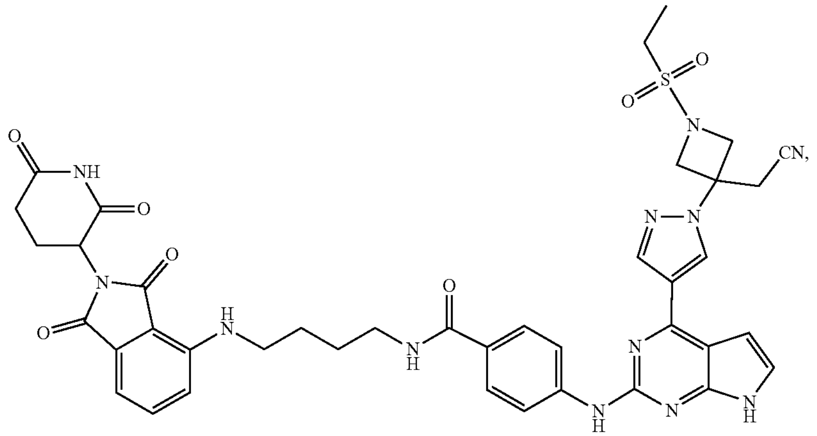
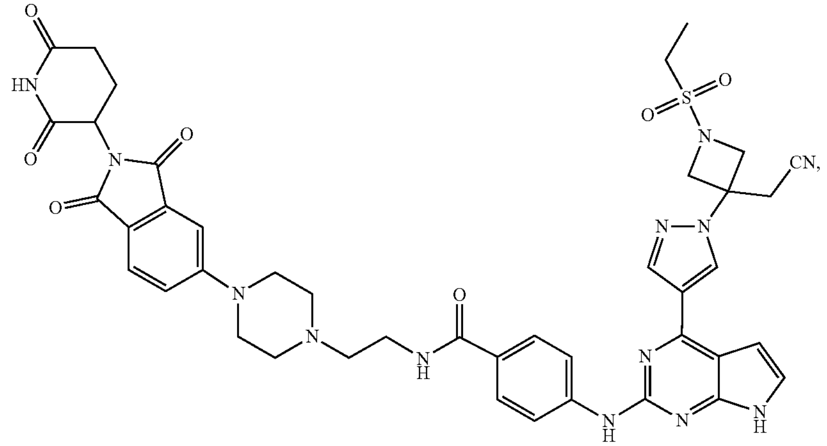
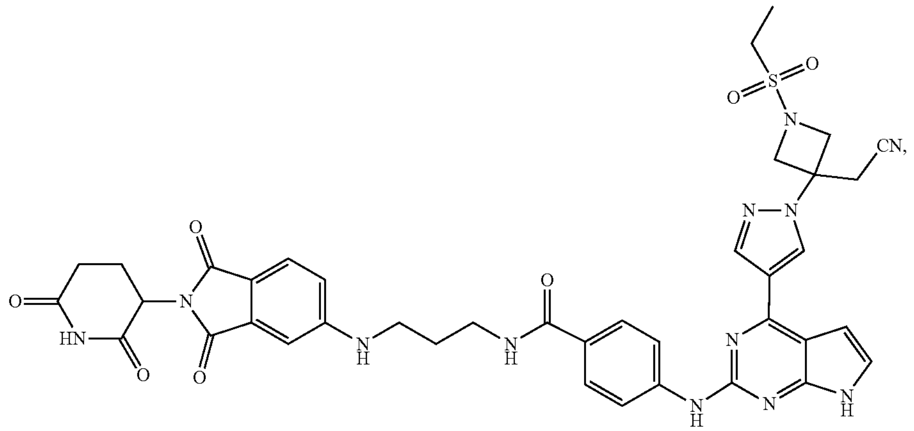

-continued
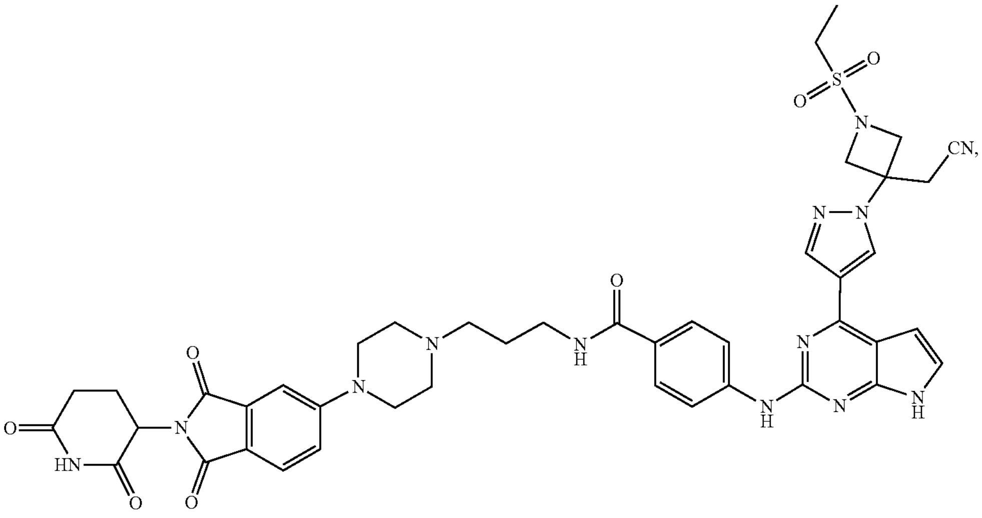
,
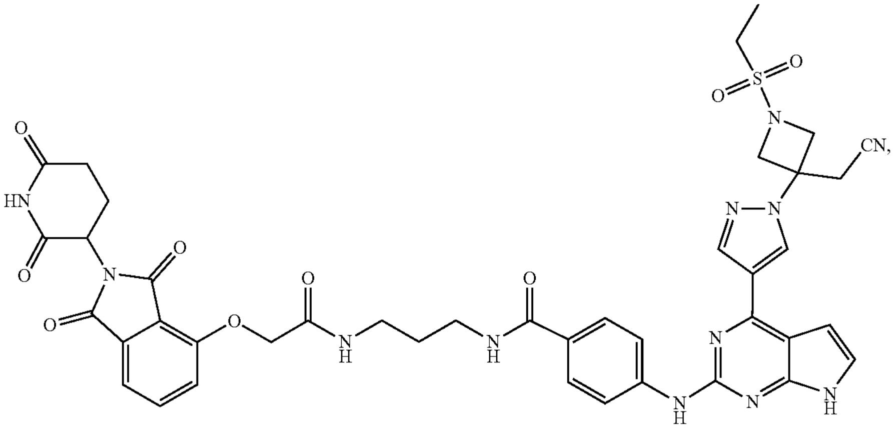
,
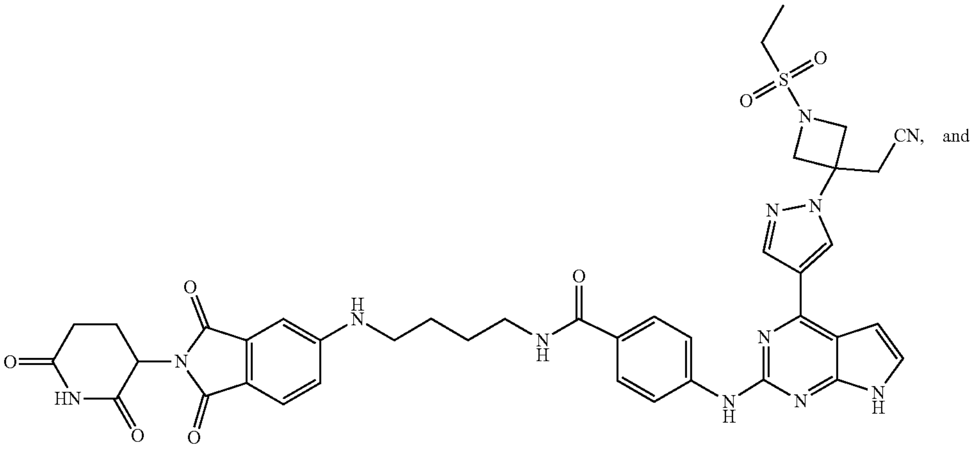
, and

-continued

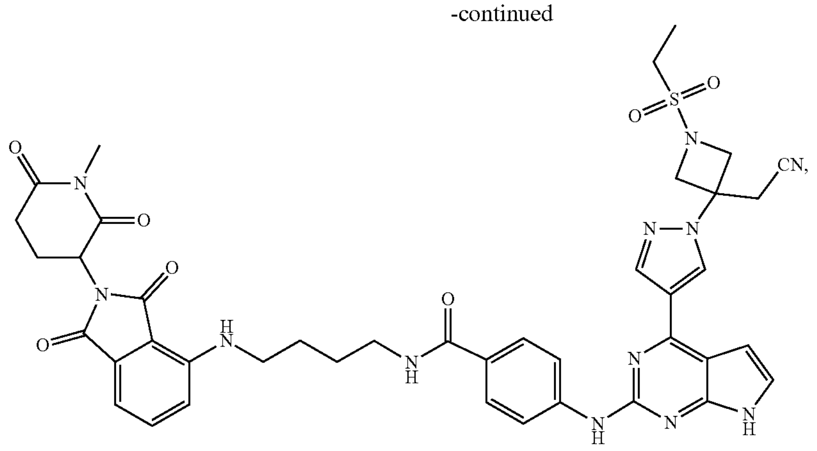

or a pharmaceutically acceptable salt thereof.

12. A pharmaceutical composition comprising a therapeutically effective amount of the compound of claim 1 and a pharmaceutically acceptable carrier.

13. A method of treating a disorder of uncontrolled cellular proliferation in a subject, the method comprising the step of administering to the subject an effective amount of the compound of claim 1.

14. The method of claim 13, wherein the subject has been diagnosed with a need for treatment of the disorder prior to the administering step.

15. The method of claim 13, further comprising the step of identifying a subject in need of treatment of the disorder.

16. The method of claim 13, wherein the effective amount is a therapeutically effective amount.

17. The method of claim 13, wherein the disorder is a cancer.

18. The method of claim 17, wherein the cancer is selected from a sarcoma, a carcinoma, a hematological cancer, a solid tumor, breast cancer, cervical cancer, gastrointestinal cancer, colorectal cancer, brain cancer, skin cancer, prostate cancer, ovarian cancer, non-small cell lung carcinoma, thyroid cancer, testicular cancer, pancreatic cancer, liver cancer, endometrial cancer, melanoma, glioma, leukemia, lymphoma, chronic myeloproliferative disorder, myelodysplastic syndrome, myeloproliferative neoplasm, and plasma cell neoplasm (myeloma).

19. The method of claim 17, wherein the cancer is acute lymphoblastic leukemia (ALL).

* * * * *